(12) United States Patent
Boge et al.

(10) Patent No.: US 7,632,651 B2
(45) Date of Patent: *Dec. 15, 2009

(54) MOLECULAR MODIFICATION ASSAYS

(75) Inventors: Annegret Boge, San Jose, CA (US); J. Richard Sportsman, Encinitas, CA (US); Elizabeth Gaudet, Menlo Park, CA (US); George G. Yi, Sunnyvale, CA (US)

(73) Assignee: MDS Analytical Technologies (US) Inc., Sunnyvale, CA (US)

( * ) Notice: Subject to any disclaimer, the term of this patent is extended or adjusted under 35 U.S.C. 154(b) by 283 days.

This patent is subject to a terminal disclaimer.

(21) Appl. No.: 11/241,872

(22) Filed: Sep. 30, 2005

(65) Prior Publication Data

US 2006/0121544 A1 Jun. 8, 2006

Related U.S. Application Data

(63) Continuation-in-part of application No. 10/746,797, filed on Dec. 23, 2003, and a continuation-in-part of application No. 11/146,553, filed on Jun. 6, 2005, now abandoned, and a continuation-in-part of application No. 10/957,332, filed on Sep. 30, 2004, now abandoned, said application No. 11/146,553 is a continuation-in-part of application No. 10/746,797, which is a continuation-in-part of application No. 09/844,655, filed on Apr. 27, 2001, now Pat. No. 7,070,921, said application No. 09/844,655 is a continuation-in-part of application No. PCT/US00/16025, filed on Jun. 9, 2000, and a continuation-in-part of application No. 09/596,444, filed on Jun. 19, 2000, now abandoned, said application No. PCT/US00/16025 is a continuation-in-part of application No. 09/349,733, filed on Jul. 8, 1999, now abandoned, said application No. 09/596,444 is a continuation-in-part of application No. 08/929,095, filed on Sep. 15, 1997, now abandoned, and a continuation-in-part of application No. PCT/US00/16025.

(60) Provisional application No. 60/615,308, filed on Sep. 30, 2004, provisional application No. 60/683,377, filed on May 20, 2005, provisional application No. 60/577,079, filed on Jun. 4, 2004, provisional application No. 60/602,712, filed on Aug. 18, 2004, provisional application No. 60/615,308, filed on Sep. 30, 2004, provisional application No. 60/436,725, filed on Dec. 26, 2002, provisional application No. 60/507,006, filed on Sep. 29, 2003, provisional application No. 60/200,594, filed on Apr. 28, 2000, provisional application No. 60/223,642, filed on Aug. 8, 2000, provisional application No. 60/241,032, filed on Oct. 17, 2000, provisional application No. 60/138,111, filed on Jun. 9, 1999, provisional application No. 60/138,438, filed on Jun. 10, 1999, provisional application No. 60/200,594, filed on Apr. 28, 2000, provisional application No. 60/507,569, filed on Sep. 30, 2003, provisional application No. 60/092,203, filed on Jul. 9, 1998.

(51) Int. Cl.
*G01N 33/573* (2006.01)
*C12Q 1/42* (2006.01)
*G01N 33/533* (2006.01)
*G01N 33/20* (2006.01)
*G01N 33/24* (2006.01)
*G01N 21/76* (2006.01)

(52) U.S. Cl. .................. 435/7.4; 435/21; 435/136; 435/142; 436/546; 436/73; 436/81; 436/172

(58) Field of Classification Search ................ 436/544, 436/546, 164, 172, 800; 435/7.1
See application file for complete search history.

(56) References Cited

U.S. PATENT DOCUMENTS

| | | | |
|---|---|---|---|
| 3,135,793 | A | 6/1964 | Bruce et al. |
| 3,214,377 | A | 10/1965 | Hotten |
| 3,485,818 | A | 12/1969 | Thompson |
| 3,504,052 | A | 3/1970 | Neuse et al. |
| 3,530,049 | A | 9/1970 | Scherzer et al. |
| 3,901,654 | A | 8/1975 | Gross |
| 3,925,162 | A | 12/1975 | Kanno |
| 3,966,556 | A | 6/1976 | Rubenstein et al. |
| 3,996,345 | A | 12/1976 | Ullman et al. |
| 4,163,780 | A | 8/1979 | Ishida et al. |
| 4,181,654 | A | 1/1980 | Weitl et al. |
| 4,199,559 | A | 4/1980 | Ullman et al. |
| 4,205,952 | A | 6/1980 | Cais |
| 4,220,722 | A | 9/1980 | Rowley et al. |

(Continued)

FOREIGN PATENT DOCUMENTS

CA 2099542 1/1994

(Continued)

OTHER PUBLICATIONS

Dadabhoy et al. Long wavelength sensitizers for europium(III) luminescence based on acridone derivatives. J. Chem. Soc., Perkin Trans., 2002, vol. 2, pp. 348-357.*

(Continued)

*Primary Examiner*—Shafiqul Haq
(74) *Attorney, Agent, or Firm*—Kolisch Hartwell, PC

(57) ABSTRACT

Systems for detecting molecular modifications and the presence and/or activity of enzymes and/or other agents involved in facilitating or otherwise regulating such modifications.

19 Claims, 40 Drawing Sheets

U.S. PATENT DOCUMENTS

| | | |
|---|---|---|
| 4,238,195 A | 12/1980 | Boguslaski et al. |
| 4,238,395 A | 12/1980 | Buckler et al. |
| 4,240,751 A | 12/1980 | Linnecke et al. |
| 4,257,774 A | 3/1981 | Richardson et al. |
| 4,277,437 A | 7/1981 | Maggio |
| 4,280,815 A | 7/1981 | Oberhardt et al. |
| 4,293,310 A | 10/1981 | Weber |
| 4,318,846 A | 3/1982 | Khanna et al. |
| 4,341,957 A | 7/1982 | Wieder |
| 4,352,395 A | 10/1982 | Sydansk |
| 4,352,751 A | 10/1982 | Wieder et al. |
| 4,363,759 A | 12/1982 | Boguslaski et al. |
| 4,372,745 A | 2/1983 | Mandle et al. |
| 4,374,120 A | 2/1983 | Soini et al. |
| 4,378,344 A | 3/1983 | Zahradnik et al. |
| 4,412,064 A | 10/1983 | Hinman |
| 4,419,453 A | 12/1983 | Dorman et al. |
| 4,421,654 A | 12/1983 | Plueddemann |
| 4,425,427 A | 1/1984 | Luderer |
| 4,432,907 A | 2/1984 | Wieder et al. |
| 4,433,061 A | 2/1984 | Chiang |
| 4,459,360 A | 7/1984 | Marinkovich |
| 4,490,216 A | 12/1984 | McConnell |
| 4,492,762 A | 1/1985 | Wang et al. |
| 4,514,508 A | 4/1985 | Hirschfeld |
| 4,542,104 A | 9/1985 | Stryer et al. |
| 4,547,527 A | 10/1985 | Ingram |
| 4,565,790 A | 1/1986 | Hemmilä et al. |
| 4,587,223 A | 5/1986 | Soini et al. |
| 4,637,988 A | 1/1987 | Hinshaw et al. |
| 4,652,440 A | 3/1987 | Paik et al. |
| 4,656,127 A | 4/1987 | Mundy |
| 4,659,839 A | 4/1987 | Nicolotti et al. |
| 4,670,572 A | 6/1987 | Hinshaw et al. |
| 4,687,732 A | 8/1987 | Ward et al. |
| 4,687,747 A | 8/1987 | Lin |
| 4,699,978 A | 10/1987 | Barton |
| 4,704,353 A | 11/1987 | Humphries et al. |
| 4,707,440 A | 11/1987 | Stavrianopoulos |
| 4,711,955 A | 12/1987 | Ward et al. |
| 4,721,669 A | 1/1988 | Barton |
| 4,724,217 A | 2/1988 | Miller |
| 4,741,900 A | 5/1988 | Alvarez et al. |
| 4,745,076 A | 5/1988 | Müller et al. |
| 4,751,190 A | 6/1988 | Chiapetta et al. |
| 4,761,481 A | 8/1988 | Hale et al. |
| 4,772,548 A | 9/1988 | Stavrianopoulos |
| 4,794,191 A | 12/1988 | Hinshaw et al. |
| 4,801,722 A | 1/1989 | Hinshaw et al. |
| 4,801,804 A | 1/1989 | Rosenthal |
| 4,806,488 A | 2/1989 | Berger, Jr. et al. |
| 4,808,541 A | 2/1989 | Mikola et al. |
| 4,822,733 A | 4/1989 | Morrison |
| 4,830,786 A | 5/1989 | Pease et al. |
| 4,837,169 A | 6/1989 | Toner |
| 4,849,330 A | 7/1989 | Humphries et al. |
| 4,851,331 A | 7/1989 | Vary et al. |
| 4,859,609 A | 8/1989 | Dull et al. |
| 4,863,849 A | 9/1989 | Melamede |
| 4,863,876 A | 9/1989 | Hevey |
| 4,876,190 A | 10/1989 | Recktenwald |
| 4,876,335 A | 10/1989 | Yamane et al. |
| 4,883,579 A | 11/1989 | Humphries et al. |
| 4,885,363 A | 12/1989 | Tweedle et al. |
| 4,894,347 A | 1/1990 | Hillyard et al. |
| 4,915,812 A | 4/1990 | Parce et al. |
| 4,920,195 A | 4/1990 | Kankare et al. |
| 4,942,127 A | 7/1990 | Wada et al. |
| 4,943,523 A | 7/1990 | Stavrianopoulos |
| 4,946,958 A | 8/1990 | Campbell et al. |
| 4,956,275 A | 9/1990 | Zuk et al. |
| 4,962,020 A | 10/1990 | Tabor et al. |
| 4,963,658 A | 10/1990 | Kung et al. |
| 4,966,917 A | 10/1990 | White |
| 4,978,608 A | 12/1990 | Kung et al. |
| 5,004,806 A | 4/1991 | Kung |
| 5,011,770 A | 4/1991 | Kung et al. |
| 5,021,567 A | 6/1991 | Johnson et al. |
| 5,030,576 A | 7/1991 | Dull et al. |
| 5,032,677 A | 7/1991 | Hale et al. |
| 5,039,512 A | 8/1991 | Kraft et al. |
| 5,055,578 A | 10/1991 | Hale et al. |
| 5,077,037 A | 12/1991 | Wallace |
| 5,086,002 A | 2/1992 | Hillyard et al. |
| 5,104,804 A | 4/1992 | Humphries et al. |
| 5,106,957 A | 4/1992 | Hale et al. |
| 5,112,134 A | 5/1992 | Chow et al. |
| 5,116,989 A | 5/1992 | Hale et al. |
| 5,120,644 A | 6/1992 | Ikenaka et al. |
| 5,124,457 A | 6/1992 | Ungemach et al. |
| 5,141,852 A | 8/1992 | Egan et al. |
| 5,143,854 A | 9/1992 | Pirrung et al. |
| 5,155,212 A | 10/1992 | Dubler et al. |
| 5,160,957 A | 11/1992 | Ina et al. |
| 5,180,828 A | 1/1993 | Ghazarossian et al. |
| 5,202,423 A | 4/1993 | Kankare et al. |
| 5,216,134 A | 6/1993 | Mukkala et al. |
| 5,219,553 A | 6/1993 | Kraft et al. |
| 5,221,605 A | 6/1993 | Bard et al. |
| 5,225,543 A | 7/1993 | Eppler et al. |
| 5,232,858 A | 8/1993 | Wolfbeis et al. |
| 5,235,039 A | 8/1993 | Heath et al. |
| 5,238,808 A | 8/1993 | Bard et al. |
| 5,245,038 A | 9/1993 | Hale et al. |
| 5,246,867 A | 9/1993 | Lakowicz et al. |
| 5,252,293 A | 10/1993 | Drbal et al. |
| 5,252,462 A | 10/1993 | Drevin et al. |
| 5,252,740 A | 10/1993 | Hale et al. |
| 5,256,535 A | 10/1993 | Ylikoski et al. |
| 5,258,512 A | 11/1993 | Heiman et al. |
| 5,260,200 A | 11/1993 | Kahn et al. |
| 5,260,441 A | 11/1993 | Heiman et al. |
| 5,270,171 A | 12/1993 | Cercek et al. |
| 5,271,929 A | 12/1993 | Hashiguchi et al. |
| 5,274,113 A | 12/1993 | Kang et al. |
| 5,278,048 A | 1/1994 | Parce et al. |
| 5,279,943 A | 1/1994 | Mathis et al. |
| 5,281,704 A | 1/1994 | Love et al. |
| 5,283,173 A | 2/1994 | Fields et al. |
| 5,302,509 A | 4/1994 | Cheeseman |
| 5,310,687 A | 5/1994 | Bard et al. |
| 5,312,986 A | 5/1994 | Simon et al. |
| 5,315,015 A | 5/1994 | Hui et al. |
| 5,316,757 A | 5/1994 | Sherry et al. |
| 5,316,909 A | 5/1994 | Xu |
| 5,324,825 A | 6/1994 | Kankare et al. |
| 5,326,692 A | 7/1994 | Brinkley et al. |
| 5,340,714 A | 8/1994 | Katsilometes |
| 5,340,716 A | 8/1994 | Ullman et al. |
| 5,341,215 A | 8/1994 | Seher |
| 5,364,613 A | 11/1994 | Sieving et al. |
| 5,369,108 A | 11/1994 | Breslow et al. |
| 5,374,531 A | 12/1994 | Jensen |
| 5,384,108 A | 1/1995 | Rajagopalan |
| 5,393,659 A | 2/1995 | Noah et al. |
| 5,403,928 A | 4/1995 | Arrhenuis |
| 5,409,666 A | 4/1995 | Nagel et al. |
| 5,409,835 A | 4/1995 | Lakowicz et al. |
| 5,424,190 A | 6/1995 | Fuller |
| 5,428,154 A | 6/1995 | Gansow et al. |
| 5,433,896 A | 7/1995 | Kang et al. |
| 5,434,088 A | 7/1995 | Ikeda et al. |
| 5,443,791 A | 8/1995 | Cathcart et al. |
| 5,445,935 A | 8/1995 | Royer |

| | | | | | |
|---|---|---|---|---|---|
| 5,446,145 A | 8/1995 | Love et al. | 5,741,714 A | 4/1998 | Liberti |
| 5,453,356 A | 9/1995 | Bard et al. | 5,741,715 A | 4/1998 | Ghoshal et al. |
| 5,457,186 A | 10/1995 | Mukkala et al. | 5,744,305 A | 4/1998 | Fodor et al. |
| 5,462,725 A | 10/1995 | Kiefer et al. | 5,744,320 A | 4/1998 | Sherf et al. |
| 5,464,607 A | 11/1995 | Anelli et al. | 5,746,974 A | 5/1998 | Massey et al. |
| 5,466,578 A | 11/1995 | Kidwell | 5,747,247 A | 5/1998 | Kowalczykowski et al. |
| 5,478,754 A | 12/1995 | Brandt et al. | 5,750,410 A | 5/1998 | Dou et al. |
| 5,482,699 A | 1/1996 | Almen et al. | 5,756,292 A | 5/1998 | Royer |
| 5,494,793 A | 2/1996 | Schindele et al. | 5,756,304 A | 5/1998 | Jovanovich |
| 5,501,956 A | 3/1996 | Wada et al. | 5,760,188 A | 6/1998 | Beaudet et al. |
| 5,512,493 A | 4/1996 | Mathis et al. | 5,762,910 A | 6/1998 | Unger et al. |
| 5,518,900 A | 5/1996 | Nikiforov et al. | 5,763,158 A | 6/1998 | Bohannon |
| 5,521,289 A | 5/1996 | Hainfeld et al. | 5,770,455 A | 6/1998 | Cargill et al. |
| 5,525,479 A | 6/1996 | Anthony et al. | 5,773,257 A | 6/1998 | Nielson et al. |
| 5,527,684 A | 6/1996 | Mabile et al. | 5,779,868 A | 7/1998 | Parce et al. |
| 5,527,688 A | 6/1996 | Mallia | 5,783,397 A | 7/1998 | Hughes et al. |
| 5,531,978 A | 7/1996 | Berg et al. | 5,783,687 A | 7/1998 | Glazer et al. |
| 5,538,858 A | 7/1996 | Mallia et al. | 5,786,139 A | 7/1998 | Burke et al. |
| 5,541,113 A | 7/1996 | Siddigi et al. | 5,798,083 A | 8/1998 | Massey et al. |
| 5,554,749 A | 9/1996 | Wallace et al. | 5,798,085 A | 8/1998 | Seaton et al. |
| 5,561,051 A | 10/1996 | Silverman | 5,800,778 A | 9/1998 | Chen et al. |
| 5,561,052 A | 10/1996 | Koike | 5,800,989 A | 9/1998 | Linn et al. |
| 5,567,302 A | 10/1996 | Song et al. | 5,800,996 A | 9/1998 | Lee et al. |
| 5,571,684 A | 11/1996 | Lawrence et al. | 5,801,149 A | 9/1998 | Shoelson |
| 5,571,897 A | 11/1996 | Takalo et al. | 5,804,395 A | 9/1998 | Schade et al. |
| 5,573,752 A | 11/1996 | Ranganathan et al. | 5,807,522 A | 9/1998 | Brown et al. |
| 5,583,219 A | 12/1996 | Subramanian et al. | 5,811,256 A | 9/1998 | Bryant |
| 5,587,285 A | 12/1996 | Cloyd et al. | 5,820,849 A | 10/1998 | Schmitt-Willich et al. |
| 5,591,581 A | 1/1997 | Massey et al. | 5,824,517 A | 10/1998 | Cleuziat et al. |
| 5,593,867 A | 1/1997 | Walker et al. | 5,824,557 A | 10/1998 | Burke et al. |
| 5,599,681 A | 2/1997 | Epstein et al. | 5,824,772 A | 10/1998 | Vincent et al. |
| 5,610,075 A | 3/1997 | Stahl-Rees | 5,827,653 A | 10/1998 | Sammes et al. |
| 5,610,287 A | 3/1997 | Nikiforov et al. | 5,830,769 A | 11/1998 | Wieder et al. |
| 5,614,368 A | 3/1997 | Ghazarossian et al. | 5,846,710 A | 12/1998 | Bajaj |
| 5,616,312 A | 4/1997 | Rosik | 5,846,722 A | 12/1998 | Kauvar et al. |
| 5,621,075 A | 4/1997 | Kahn et al. | 5,849,547 A | 12/1998 | Cleuziat et al. |
| 5,622,821 A | 4/1997 | Selvin et al. | 5,849,794 A | 12/1998 | Bianchi et al. |
| 5,624,847 A | 4/1997 | Lakowicz et al. | 5,852,191 A | 12/1998 | Karandikar et al. |
| 5,629,157 A | 5/1997 | Goodman et al. | 5,853,699 A | 12/1998 | Maier et al. |
| 5,631,127 A | 5/1997 | Sundrehagen | 5,853,992 A | 12/1998 | Glazer et al. |
| 5,631,169 A | 5/1997 | Lakowicz et al. | 5,853,999 A | 12/1998 | Olsson et al. |
| 5,632,982 A | 5/1997 | Sussman et al. | 5,854,008 A | 12/1998 | Diamandis |
| 5,637,463 A | 6/1997 | Dalton et al. | 5,858,195 A | 1/1999 | Ramsey |
| 5,637,509 A | 6/1997 | Hemmilä et al. | 5,858,671 A | 1/1999 | Jones |
| 5,639,599 A | 6/1997 | Ryder et al. | 5,858,676 A | 1/1999 | Yang et al. |
| 5,639,615 A | 6/1997 | Selvin et al. | 5,858,805 A | 1/1999 | Cheng |
| 5,641,633 A | 6/1997 | Linn et al. | 5,859,215 A | 1/1999 | Rodríguez-Ubis et al. |
| 5,641,878 A | 6/1997 | Dandliker et al. | 5,861,239 A | 1/1999 | Kleyn et al. |
| 5,645,800 A | 7/1997 | Masterson et al. | 5,861,262 A | 1/1999 | Chaudiere et al. |
| 5,646,001 A | 7/1997 | Terstappen et al. | 5,866,335 A | 2/1999 | Katsilometes et al. |
| 5,648,269 A | 7/1997 | Lakowicz et al. | 5,869,255 A | 2/1999 | Mathies et al. |
| 5,656,254 A | 8/1997 | Ramalingam et al. | 5,871,713 A | 2/1999 | Meyer et al. |
| 5,656,433 A | 8/1997 | Selvin et al. | 5,871,918 A | 2/1999 | Thorp et al. |
| 5,660,991 A | 8/1997 | Lakowicz et al. | 5,874,214 A | 2/1999 | Nova et al. |
| 5,668,110 A | 9/1997 | Barrett et al. | 5,880,096 A | 3/1999 | Barrett et al. |
| 5,670,113 A | 9/1997 | Akong et al. | 5,880,296 A | 3/1999 | Imbert et al. |
| 5,676,943 A | 10/1997 | Baetge et al. | 5,885,470 A | 3/1999 | Parce et al. |
| 5,677,196 A | 10/1997 | Herron et al. | 5,885,779 A | 3/1999 | Sadowski et al. |
| 5,677,199 A | 10/1997 | Arrhenuis | 5,888,728 A | 3/1999 | Olson et al. |
| 5,677,280 A | 10/1997 | Barrett et al. | 5,888,819 A | 3/1999 | Goelet et al. |
| 5,683,983 A | 11/1997 | Barrett et al. | 5,891,621 A | 4/1999 | Chabin et al. |
| 5,688,648 A | 11/1997 | Mathies et al. | 5,891,674 A | 4/1999 | Hillman et al. |
| 5,705,045 A | 1/1998 | Park et al. | 5,891,696 A | 4/1999 | Shaw et al. |
| 5,707,804 A | 1/1998 | Mathies et al. | 5,900,228 A | 5/1999 | Meade et al. |
| 5,707,813 A | 1/1998 | Dandliker et al. | 5,910,574 A | 6/1999 | Presta et al. |
| 5,711,915 A | 1/1998 | Siegmund et al. | 5,912,137 A | 6/1999 | Tsien et al. |
| 5,712,389 A | 1/1998 | Meyer et al. | 5,914,095 A | 6/1999 | Watson |
| 5,723,304 A | 3/1998 | Abuknesha | 5,914,230 A | 6/1999 | Liu et al. |
| 5,728,528 A | 3/1998 | Mathies et al. | 5,925,558 A | 7/1999 | Tsien et al. |
| 5,731,147 A | 3/1998 | Bard et al. | 5,945,283 A | 8/1999 | Kwok et al. |
| 5,736,410 A | 4/1998 | Zarling et al. | 5,948,620 A | 9/1999 | Hurd et al. |
| 5,738,825 A | 4/1998 | Rudigier et al. | 5,952,236 A | 9/1999 | Thompson et al. |
| 5,739,001 A | 4/1998 | Brown et al. | 5,955,605 A | 9/1999 | Axworthy et al. |

| | | | |
|---|---|---|---|
| 5,958,694 A | 9/1999 | Nikiforov |
| 5,962,243 A | 10/1999 | Brown et al. |
| 5,972,380 A | 10/1999 | Daleke |
| 5,981,180 A | 11/1999 | Chandler et al. |
| 5,981,185 A | 11/1999 | Matson et al. |
| 5,985,550 A | 11/1999 | Goodman et al. |
| 5,989,835 A | 11/1999 | Dunlay et al. |
| 6,004,744 A | 12/1999 | Goelet et al. |
| 6,005,113 A | 12/1999 | Wu et al. |
| 6,007,984 A | 12/1999 | Wang et al. |
| 6,013,431 A | 1/2000 | Söderlund et al. |
| 6,013,457 A | 1/2000 | Neuenhofer et al. |
| 6,022,708 A | 2/2000 | de Sauvage et al. |
| 6,025,129 A | 2/2000 | Nova et al. |
| 6,030,840 A | 2/2000 | Mullinax et al. |
| 6,037,136 A | 3/2000 | Beach et al. |
| 6,045,755 A | 4/2000 | Lebl et al. |
| 6,045,776 A | 4/2000 | Platzek et al. |
| 6,045,996 A | 4/2000 | Cronin et al. |
| 6,054,557 A | 4/2000 | Faure et al. |
| 6,056,939 A | 5/2000 | Desreux et al. |
| 6,071,748 A | 6/2000 | Modlin et al. |
| 6,087,107 A | 7/2000 | Sheffield et al. |
| 6,137,584 A | 10/2000 | Seidel et al. |
| 6,146,842 A | 11/2000 | Josiah et al. |
| 6,149,787 A | 11/2000 | Chow et al. |
| 6,150,520 A | 11/2000 | Argese et al. |
| 6,153,073 A | 11/2000 | Dubrow et al. |
| 6,274,713 B1 | 8/2001 | Sieving et al. |
| 6,287,774 B1 | 9/2001 | Nikiforov |
| 6,451,871 B1 | 9/2002 | Winterton et al. |
| 6,472,141 B2 | 10/2002 | Nikiforov |
| 6,632,626 B1 | 10/2003 | Brown et al. |
| 6,670,456 B2 | 12/2003 | Frank et al. |
| 6,703,498 B2 | 3/2004 | Tchaga |
| 6,709,652 B2 | 3/2004 | Reno et al. |
| RE38,506 E | 4/2004 | Breslow et al. |
| 6,770,261 B2 | 8/2004 | Meade et al. |
| 6,774,228 B1 | 8/2004 | Parker et al. |
| 6,875,419 B2 | 4/2005 | Sherry et al. |
| 6,896,874 B2 | 5/2005 | Li et al. |
| 6,972,122 B2 | 12/2005 | Haroon et al. |
| 7,070,921 B2 | 7/2006 | Huang et al. |
| 7,102,005 B2 | 9/2006 | Agnew et al. |
| 2002/0127182 A1 | 9/2002 | Sherry |
| 2002/0136692 A1 | 9/2002 | Haroon |
| 2002/0164577 A1 | 11/2002 | Tsien et al. |
| 2003/0009976 A1 | 1/2003 | Hauser et al. |
| 2003/0023050 A1 | 1/2003 | Frank |
| 2003/0129579 A1 | 7/2003 | Bornhop |
| 2003/0206865 A1 | 11/2003 | Platzek |
| 2003/0215391 A1 | 11/2003 | Rabito |
| 2003/0215898 A1 | 11/2003 | Kapeller-Libermann et al. |
| 2004/0067924 A1 | 4/2004 | Frank |
| 2004/0096923 A1 | 5/2004 | Drees et al. |
| 2007/0087452 A1 | 4/2007 | Parker et al. |

FOREIGN PATENT DOCUMENTS

| | | |
|---|---|---|
| EP | 0 137 457 A2 | 4/1985 |
| EP | 0 178 450 A2 | 4/1986 |
| EP | 0 204 109 | 4/1986 |
| EP | 0 259 386 B1 | 2/1987 |
| EP | 0 242 847 A2 | 10/1987 |
| EP | 0 278 149 A2 | 8/1988 |
| EP | 0 317 074 B1 | 10/1988 |
| EP | 0 312 897 A1 | 4/1989 |
| EP | 0 382 433 B1 | 8/1990 |
| EP | 0 178 450 B1 | 4/1991 |
| EP | 0 578 067 A1 | 6/1993 |
| EP | 0639647 | 2/1995 |
| EP | 0678581 | 10/1995 |
| EP | 0 382 433 A2 | 12/1996 |
| EP | 0774515 | 5/1997 |
| EP | 0774516 | 5/1997 |
| EP | 0457213 | 7/1997 |
| EP | 0781853 | 7/1997 |
| EP | 0 648 280 B1 | 5/1999 |
| EP | 0650521 | 3/2001 |
| GB | 2 223 096 A | 8/1989 |
| JP | 1-143874 | 6/1989 |
| JP | 1-231898 | 9/1989 |
| JP | 2-295496 | 12/1990 |
| JP | 5-123196 | 5/1993 |
| JP | 6-043159 | 2/1994 |
| JP | 6-431159 | 2/1994 |
| WO | WO81/00261 | 2/1981 |
| WO | WO81/01883 | 7/1981 |
| WO | WO87/07385 | 12/1987 |
| WO | WO88/06633 | 9/1988 |
| WO | WO90/05301 | 5/1990 |
| WO | WO91/13075 | 9/1991 |
| WO | WO92/11039 | 7/1992 |
| WO | WO92/15712 | 9/1992 |
| WO | WO93/10461 | 5/1993 |
| WO | WO93/19206 | 9/1993 |
| WO | WO93/25672 | 12/1993 |
| WO | WO95/12607 | 5/1995 |
| WO | WO95/21271 | 8/1995 |
| WO | WO96/03410 | 2/1996 |
| WO | WO97/22719 | 6/1997 |
| WO | WO97/35033 | 9/1997 |
| WO | WO97/40104 | 10/1997 |
| WO | WO97/45539 | 12/1997 |
| WO | WO97/45739 | 12/1997 |
| WO | WO98/00231 | 1/1998 |
| WO | WO98/00705 | 1/1998 |
| WO | WO98/01472 | 1/1998 |
| WO | WO98/05962 | 2/1998 |
| WO | WO98/12156 | 3/1998 |
| WO | WO98/18956 | 5/1998 |
| WO | WO98/23942 | 6/1998 |
| WO | WO98/45481 | 10/1998 |
| WO | WO98/45484 | 10/1998 |
| WO | WO98/59066 | 12/1998 |
| WO | WO99/11774 | 3/1999 |
| WO | WO99/16162 | 4/1999 |
| WO | WO99/23466 | 5/1999 |
| WO | WO99/29894 | 6/1999 |
| WO | WO99/31431 | 6/1999 |
| WO | WO99/36779 | 7/1999 |
| WO | WO99/60383 | 11/1999 |
| WO | WO99/60385 | 11/1999 |
| WO | WO00/00819 | 1/2000 |
| WO | WO00/06989 | 2/2000 |
| WO | WO00/06990 | 2/2000 |
| WO | WO00/06991 | 2/2000 |
| WO | WO00/11220 | 3/2000 |
| WO | WO00/14515 | 3/2000 |
| WO | WO00/23785 | 4/2000 |
| WO | WO00/42209 | 7/2000 |
| WO | WO00/47693 | 8/2000 |
| WO | WO00/48990 | 8/2000 |
| WO | WO00/48991 | 8/2000 |
| WO | WO00/55372 | 9/2000 |
| WO | WO00/66269 | 11/2000 |
| WO | WO00/72016 | 11/2000 |
| WO | WO00/75167 | 12/2000 |
| WO | WO00/75662 | 12/2000 |
| WO | WO00/75664 | 12/2000 |
| WO | WO0075332 | 12/2000 |
| WO | WO01/49874 | 7/2001 |

| WO | WO01/88195 | 11/2001 |

OTHER PUBLICATIONS

Rapid Protein Kinase Assay Using Phosphocellulose-Paper Absorption, Witt et al., *Analytical Biochemistry*, 66:253-258, 1975.
Intramolecular Mobility of Pepsin, Glotov et al., *Molecular Biology* (Moscow), vol. 10, No. 1, pp. 161-174, Jan.-Feb. 1976.
*Structural Concepts in Immunology and Immunochemistry*, Kabat, 2nd Ed., pp. 103-105, 1976.
Histone H1-DNA Interaction. Influence of Phosphorylation on the Interaction of Histone H1 with Linear Fragmented DNA, Glotov et al., *Nucleic Acids Research*, vol. 4, No. 4, pp. 1065-1082, Apr. 1977.
Histone H1—DNA Interaction. On the Mechanism of DNA Strands Crosslinking by Histone H1, Glotov et al., *Nucleic Acids Research*, vol. 5, No. 7, pp. 2587-2605, Jul. 1978 (abstract only included).
Isolation of Phosphorylated Peptides and Proteins on Ion Exchange Papers, Glass et al., *Analytical Biochemistry*, 87:566-575, 1978.
*Principles of Fluorescence Spectroscopy*, First Edition, Lakowicz, Sep. 1983.
Photoelectroanalytical Chemistry: Possible Interferences in Serum and the Selective Detection of Tris(2,2'-bipyridine)ruthenium(II) in the Presence of Interferents, Weber et al., *Clin. Chem.*, vol. 29, No. 9, pp. 1665-1672, 1983.
Application of the Energy Gap Law to Nonradiative, Excited-State Decay, Caspar et al., *J. Phys. Chem.*, vol. 87, pp. 952-957, 1983.
*Molecular Biology of the Cell*, Alberts et al., pp. 58-61, 1983.
Interaction of Creatine Kinase from Monkey Brain with Substrate: Analysis of Kinetics and Fluorescence Polarization. Grossman, *Journal of Neurochemistry*, vol. 41, No. 3, 729-736, 1983.
Immobilized Metal Ion Affinity Adsorption and Immobilized Metal Ion Affinity Chromatography of Biomaterials. Serum Protein Affinities for Gel-Immobilized Iron and Nickel Ions, Porath et al., *Biochemistry*, vol. 22, pp. 1621-1630, 1983.
Electrogenerated Cheniluminescent Determination of $Ru(bpy)_3^2$ at Low Levels, Ege et al., *Anal. Chem.*, vol. 56, pp. 2413-2417, 1984.
Luminescence and Redox Reactions of the Metal-to-Ligand Charge-Transfer Excited State of Tricarbonylchloro(polypyridyl)rhenium(I) Complexes, Kalyanasundaram, *J. Chem. Soc. Faraday Trans.*, vol. 82, pp. 2401-2415, 1986.
Selective Adsorption of Phosphoproteins on Gel-Immobilized Ferric Chelate, Muszynska et al., *Biochemistry*, vol. 25, No. 22, pp. 6850-6853, 1986.
Fluorescence Polarization Immunoassay to Determine Aminoglycoside Modifying Enzymes Activity, Pagani et al., *Microbiologica*, vol. 9, pp. 423-430, 1986.
A Solid-Phase Assay for the Phosphorylation of Proteins Blotted on Nitrocellulose Membrane Filters, Valtorta et al., *Analytical Biochemistry*, vol. 158, pp. 130-137, 1986.
A System for Rapid DNA Sequencing with Fluorescent Chain-Terminating Dideoxynucleotides, Prober et al., *Science*, pp. 336-341, Oct. 16, 1987.
Time-Resolved Fluorescence of Lanthanide Probes and Applications in Biotechnology, Soini et al., *CRC Critical Reviews in Analytical Chemistry*, vol. 18, No. 2, 1987.
Solid Phase DNA Sequencing Using the Biotin-Avidin System, Stahl et al., *Nucleic Acids Res.*, vol. 16, No. 7, pp. 3025-3038, Apr. 11, 1988 (abstract only).
Stratagene 1988 Catalog excerpt, 1988.
Synthetic Peptide Analogues Differentially After the Binding Affinities of Cyclic Nucleotide Dependent Protein Kinases for Nucleotide Substrates, Bhatnagar et al., *Biochemistry*, vol. 27, No. 6, pp. 1988-1994, 1988.
Direct Solid Phase Sequencing of Genomic and Plasmid DNA Using Magnetic Beads as Solid Support, Hultman et al., *Nucleic Acids Res.*, vol. 17, No. 13, pp. 4937-4946, Jul. 11, 1989 (abstract only).
The Interaction of Papain with Polycations, Mekras et al., *J. Pharm. Pharmacol.*, vol. 41, pp. 22-26, 1989.
Detection of Protein-DNA Complex Formation by Time-Resolved Fluorescence Depolarization of Bound Ethidium Bromide, Cook et al., *Analytical Biochemistry*, vol. 190, pp. 331-339, 1990.

RNA Sequencing Using Fluorescent-Labeled Dideoxynucleotides and Automated Fluorescence Detection, Bauer, *Nucleic Acids Res.*, vol. 18, No. 4, pp. 879-884, Feb. 25, 1990 (abstract only).
A Quantitative Assay for Tyrosine Sulfation and Tyrosine Phosphorylation in Peptides, Blode et al., *Biol. Chem.*, vol. 371, pp. 145-151, Feb. 1990.
Adaptation of Fluorescence Polaration Immunoassay to the Assay of Macromolecules, Urios et al., *Analytical Biochemistry*, vol. 185, No. 2, pp. 308-312, Mar. 1990.
The Unusual Origin of the Polymerase Chain Reaction, Kary B. Mullis, *Scientific American*, pp. 56-65, Apr. 1990.
A Primer-Guided Nucleotide Incorporation Assay in the Genotyping of Apolipoprotein E, Syvanen et al., *Genomics*, vol. 8, No. 4, pp. 684-692, Dec. 1990 (abstract only).
Fluorescent-Labeled Oligonucleotide Probes: Detection of Hybrid Formation in Solution by Fluorescence Polarization Spectroscopy, Murakami et al., *Nucleic Acids Research*, vol. 19, No. 15, pp. 4097-4102, Aug. 11, 1991.
Direction Observation of the Biphasic Conformational Change of DNA Induced by Cationic Polymers, Minagawa et al., *FEBS*, vol. 295, No. 1-3, pp. 67-69, Dec. 1991.
Design and Use of Peptide Substrates for Protein Kinases, Kemp et al., *Methods in Enzymology*, vol. 200, pp. 121-134, 1991.
Automated Nonisotropic Assay for Protein-Tyrosine Kinase and Protein-Tyrosine Phosphatase Activities, Babcook et al., *Analytical Biochemistry*, vol. 196, pp. 245-251, 1991.
A Brief Survey of Methods for Preparing Protein Conjugates with Dyes, Haptens, and Cross-Linking Reagents, Brinkley, *Bioconjugate Chemistry*, vol. 3, No. 1, pp. 59-70, Jan./Feb. 1992.
Chromatin Condensation: Does Histone H1 Dephosphorylation Play a Role?, Roth et al., *TIBS*, vol. 17, pp. 93-98, Mar. 1992.
Trapped-Oligonucleotide Nucleotide Incorporation (TONI) Assay, A Simple Method for Screening Point Mutations, Prezant et al., *Hum. Mutat.*, vol. 1, No. 2, pp. 159-164, 1992 (abstract only).
Model Studies on Iron(H1) Ion Affinity Chromatography, Muszynka et al., *Journal of Chromatography*, vol. 604, pp. 19-28, 1992.
Rapid Measurement of Protein Kinase and Phosphatase Activities by Slot-Filtration, Volonté et al., *BioTechniques*, vol. 12, No. 6, pp. 854-863, 1992.
Protein Phosphatase Assay Using a Modification of the P81 Paper Protein Kinase Assay Procedure, Abukhalaf et al., *J. Biochem. Biophys.*, vol. 26, pp. 95-104, May 1993 (abstract only included).
PNA Hybridizes to Complementary Oligonucleotides Obeying the Watson-Crick Hydrogen-Bonding Rules, Egholm et al., *Nature*, vol. 365, No. 6446, pp. 566-568, Oct. 7, 1993.
Time-Resolved Fluorescence of a new Europium Chelate Complex: Demonstration of Highly Sensitive Detection of Protein and DNA Samples, Saha et al., *J. Am. Chem. Soc.*, vol. 115, No. 23, pp. 11032-11033, 1993.
Luminescent Lanthanide Complexes as Photochemical Supramolecular Devices, Sabbatini et al., *Coordination Chemistry Reviews*, vol. 123, pp. 201-228, 1993.
A Transcriptionally Amplified DNA Probe Assay with Ligatable Probes and Immunochemical Detection, Carpenter et al., *Clin. Chem.*, vol. 39, No. 9, pp. 1934-1938, 1993.
Post-Translational Modification of Proteins, R. Krishna, *Advances in Enzymology*, 67:265-299, 1993.
Metal ($Fe^3$) Affinity Chromatography: Differential Adsorption of Tau Phosphoproteins, Erickson et al., *Journal of Neuroscience Methods*, vol. 46, pp. 245-249, 1993.
Protein Kinase Assay Using Tritiated Peptide Substrates and Ferric Adsorbent Paper for Phosphopeptide Binding, Toomik et al., *Analytical Biochemistry*, vol. 209, pp. 348-353, 1993.
Myelin Basic Protein Interaction with Zinc and Phosphate: Fluorescence Studies on the Water-Soluble Form of the Protein, Cavatoria et al., *Biophysical Journal*. vol. 66, pp. 1174-1179, Apr. 1994.
Accessibility of Nucleic Acid-Complexed Biomolecules to Hydroxyl Radicals Correlates With Their Conformation: A Fluorescence Polarization Spectroscopy Study, Makrigiorgos et al., *International Journal of Radiation Biology*, vol. 66, No. 3, pp. 247-257. Sep. 1994.
Time-Resolved Detection of Lanthanide Luminescence for Ultrasensitive Bioanalytical Assays. Dickson et al., *J. of Photochem. Photobiol. B; Biol.*, 27 (1995) 3-19, Oct. 28, 1994.

Processing of cDNA and Genomic Kilobase-Size Clones for Massive Screening, Mapping and Sequencing by Hybridization, Drmanac et al., *BioTechniques*, vol. 17, No. 2, pp. 328-336, 1994.

Synthesis of Squaraine-N-Hydroxysucciniamide Esters and Their Biological Application as Long-Wavelength Fluorescent Labels, Terpetschnig et al., *Anal. Chem.*, vol. 217, pp. 197-204, 1994.

Sorting Single Molecules: Application to Diagnostics and Evolutionary Biotechnology, Eigen et al., *PNAS*, vol. 91, pp. 5740-5747, 1994.

A Fluorimetric Method for the Detection of Copper-Mediated Hydroxyl Free Radicals in the Immediate Proximity of DNA, Makrigiorgos et al., *Free Radical Biology & Medicine*, vol. 18, No. 4, pp. 669-678, Apr. 1995.

Fluoresence Polarization—A New Tool for Cell and Molecular Biology, Checovich et al., *Nature*, vol. 375, pp. 254-256, May 18, 1995.

Fluorescence-Based DNA Minisequence Analysis for Detection of Known Single-Base Changes in Genomic DNA, Kobayashi et al., *Mol. Cell Probes*, vol. 9, No. 3, pp. 175-182, Jun. 1995 (abstract only).

Probing Molecular Interactions with Homogeneous Techniques Based on Rare Earth Cryplates and Fluorescence Energy Transfer, Mathis, *Clinical Chemistry*. vol. 41, No. 9, pp. 1391-1397, Sep. 1995.

Hybridization of Fluorescein-Labeled DNA Oligomers Detected by Fluorescence Anisotropy with Protein Binding Enhancement, Kumke et al., *Anal. Chem.*, vol. 67, No. 21, Nov. 1, 1995.

Gmelin: Handbook of Inorganic and Organometallic Chemistry: Ga Gallium: Supplement vol. D 3 Coordination Compounds 3, Kotowski et al., pp. 152-170, 202, 209, and 262, Nov. 1995.

Fluorescence Anisotropy Applied to Biomolecular Interactions, D.M. Jameson et al., *Methods in Enzymology*, 246:283-300, 1995.

Fluorescence Energy Transfer Immunoassay Based on a Long-Lifetime Luminescent Metal-Ligand Complex, Young et al., *Analytical Biochemistry*, vol. 232, pp. 24-30, 1995.

A Lifetime-Based Optical $CO_2$ Gas Sensor with Blue or Red Excitation and Stokes or Anti-Stokes Detection, Jeffrey Sipior et al., *Analytical Biochemistry*, 227, 309-318, 1995.

DNA Detection by Strand Displacement Amplification and Fluorescence Polarization with Signal Enhancement Using a DNA Binding Protein, Walker et al., vol. 24, No. 2, pp. 348-353, Jan. 15, 1996.

Molecular Beacons: Probes that Fluoresce Upon Hybridization, Tyagi et al., *Nature Biotechnology*, vol. 14, pp. 303-308, Mar. 1996.

Effects of Cell Cycle Dependent Histone III Phosphorylation on Chromatin Structure and Chromatin Replication, Halmer et al., *Nucleic Acids Research*, vol. 24, No. 8, pp. 1420-1427, Apr. 15, 1996.

A Homogeneous Fluorescence Polarization Assay for Detection of Antibody to Brucella Abortus, Nielsen et al., *J. Immunol. Methods*, vol. 195, pp. 161-168, Sep. 9, 1996.

BODIPY-alpha-casein, a pH-Independent Protein Substrate for Protease Assays Using Fluorescence Polarization, Schade et al., *Anal. Biochem.*, vol. 234, No. 1, pp. 1-7, Dec. 1996.

Gene Genie, Jonathan Burke, *The Red Herring*, internet pages 1-7, Dec. 1996.

Tyrosine Protein Kinase Assays, Boutin, *Journal of Chromatography B*, vol. 684, pp. 179-199, 1996.

Chemical Abstracts No. 124:160.011; abstract for Lindstroem et al., Electron transport properties in dye-sensitized nanocrystalline/nanostructured titanium dioxide films: J. Phys. Chem. vol. 100 (8), pp. 3084-3088, 1996.

Multiplex. Fluorescent. Solid-Phase Minisequencing for Efficient Screening of DNA Sequence Variation, Pastinen et al., *Clinical Chemistry*, vol. 42, No. 9, pp. 1391-1397, 1996.

Comparative Study of Fluorescence Ternary Terbium Complexes, Application in Enzyme Amplified Fluorimetric Immunoassay for a-fetoprotein, Veiopoulou et al., *Analytics Chimica Acta*, vol. 335, pp. 177-184, 1996.

Fluorescence Anisotropy: Rapid Quantitative Assay for Protein-DNA and Protein-Protein Interaction, Heyduk et al., *Methods in Enzymology*, vol. 274, pp. 492-503, 1996.

Fluorescence Polarization Analysis of Protein-DNA and Protein-Protein Interactions, Lundblad et al. *Molecular Endocrinology*, vol. 10, No. 6, pp. 607-612, 1996.

Gene Chip Breakthrough, David Stipp, *Fortune*, internet pages 1-12, Mar. 31, 1997.

Thermodynamic Analysis of Monoclonal Antibody Binding to Duplex DNA. Tanha et al., *Nucleic Acids Research*, vol. 25, No. 7, pp. 1442-1449, Apr. 1, 1997.

A Fluorescence Polarization Based Src-SH2 Binding Assay, Lynch et al., *Anal. Biochem.*, vol. 247, No. 1, pp. 77-82, Apr. 5, 1997.

Measurement of Specific Protease Activity Utilizing Fluorescence Polarization, Levine et al., *Anal. Biochem.*, vol. 247, No. 1, pp. 83-88. Apr. 5, 1997.

Dynamic Fluorescence Spectroscopy on Single Tryptophan Mutants of EII (mtl) in Detergent Micelles. Effects of Substrate Binding and Phosphorylation on the Fluorescence and Anisotropy Decay, Dijkstra et al., *Biochemistry*, vol. 36, No. 16, pp. 4860-4866, Apr. 22, 1997.

The Society for Biomolecular Screening, $3^{rd}$ Annual Conference and Exhibition, p. 59, Sep. 9, 22-25, 1997.

A Homogeneous, Fluorescence Polarization Assay for Src-Family Tyrosine Kinases, Seethala et al., *Anal. Biochem.*, vol. 253, No. 2, pp. 210-218, Nov. 15, 1997.

Fluorescence Polarization Colloid Charge Titration: Development and Application for Feed Forward Coagulant Control at Water Treatment Facilities (Thesis), Green, *University of Colorado Graduate School*, approved Dec. 11, 1997.

Electrochemiluminescence: A Technology Review internet pages, IGEN, printed Dec. 16, 1997.

A Chemiluminescent Microtier Plate Assay for Sensitive Detection of Protein Kinase Activity, Lehel et al., *Analytical Biochemistry*, vol. 244, pp. 340-346, 1997.

Chemical Abstracts No. 126:72,240: abstract for Hermann et al. "Structure of Nanocrystalline TiO2 Powders and Precursor to Their Highly Efficient Photosensitizer", Chem. Mater. vol. 9 (2), pp. 430-439, 1997.

A Homogeneous Method for Genotyping with Fluorescence Polarization, Gibson et al., *Clinical Chemistry*, vol. 43, No. 8, pp. 1336-1341, 1997.

Development of Luminescent Lanthanide Chelate Labels for Diagnostic Assays, Hemmila et al., *Journal of Alloys and Compounds*, Vo. 249, pp. 158-162, 1997.

Minisequencing: A Specific Tool for DNA Analysis and Diagnostics on Oligonucleotide Arrays, Pastinen et al., *Genome Research*, vol. 7, pp. 606-614, 1997.

Template-Directed Dye-Terminator Incorporation (TDI) Assay: A Homogeneous DNA Diagnostic Method Based on Fluorescence Resonance Energy Transfer, Chen et al., *Nucleic Acids Research*, vol. 25, No. 2, pp. 347-353, 1997.

Towards Materials with Planned Properties: Dinuclear f-f Helicates and d-f Non-Covalent Podates Based on Benzimidazole-Pyridine Binding Units, Bunzli et al., *Journal of Alloys and Compounds*, vol. 249, pp. 14-24, 1997.

Water-Soluble Neutral calyx[4]arene-Lanthanide Complexes: Synthesis and Luminescence Properties, Steemers et al., *J. Org. Chem.*, vol. 62, pp. 4229-4235, 1997.

Application of Fluorescence Polarization Assays in High-Throughput Screening, Owicki et al., *Genetic Engineering News*, vol. 17, No. 19, pp. 1-3, 1997.

*Chemistry of the Elements, Second Edition*, Greenwood et al., pp. 905-925, 1997.

A Fluorescence Polarization Competition Immunoassay for Tyrosine Kinases, Seethala et al., *Analytical Biochemistry*, vol. 255, No. 2, pp. 257-262, Jan. 15, 1998.

Multicolor Molecular Beacons for Allele Discrimination, Tyagi et al., *Nature Biotechnology*, vol. 16, pp. 49-53, Jan. 16, 1998.

*Fluorescence Polarization Applications Guide, DNA-Protein Binding Applications*, Panvera Corporation, pp. 2-1 to 2-9, Jan. 1998.

*Fluorescence Polarization Applications Guide*, PanVera Corporation, pp. 6-1 through 6-4, Jan. 1998 Edition.

GeneChip Probe Array Synthesis, Affymetric, internet pp. 1-2, Mar. 17, 1998.

Mutation Detection and Single-Molecular Counting Using Isothermal Rolling-Circle Amplification, Lizardi et al., *Nature Genetics*, vol. 19, No. 3, pp. 225-232, Jul. 1998.

Homogeneous Time-Resolved IL-2-ILRa Assay Using Fluorescence Resonance Energy Transfer, Stenroos et al., *Cytokine*, vol. 10, No. 7, pp. 495-499, Jul. 1998.

Temporally and Spectrally Resolved Imaging Microscopy of Lanthanide Chelates, Vereb et al., *Biophysical Journal*, vol. 74, pp. 2210-2222, May 1998.

Synthesis, Spectral Properties and Detection Limits of Reactive Squarylium Dyes, a New Class of Diode Laser Compatible Fluorescent Protein Labels, Oswald et al., Aug. 21, 1998.

Phosphorylation of the C-Terminal Sites of Human p53 Reduces Non-Sequence-Specific DNA Binding as Modeled with Synthetic Peptides, Hoffmann et al., *Biochemistry*, vol. 37, pp. 13755-13764, Sep. 29, 1998.

Illuminating the SNP Genomic Code, Czarnik, *Modern Drug Discovery*, pp. 49-55, Nov./Dec. 1998.

A Catalog of Reagents, Microplates and Accessories of Life Science Research, Book 2, Packard BioScience Company, Dec. 1998.

CytoFluor Fluorescence Multi-Well Plate Reader brochure, PerSeptive Biosystems, 1998.

Luc-Screen™ brochure, Tropix, Inc., 1998.

Xpress-Screen™ brochure, Tropix, Inc., 1998.

Fixed Polarizer Ellipsometry for Simple and Sensitive Detection of Thin Films Generated by Specific Molecular Interactions: Applications in Immunoassays and DNA Sequence Detection, Ostroff et al., *Clinical Chemistry*, 44:9, pp. 2031-2035, 1998.

Substrate Specificity of Mammalian Prenyl Proetein-Specific Endoprostease Activity, G.-F. Jang and M.H. Gelb. *Biochem Journal*, vol. 37, pp. 4473-4481, 1998.

A Microfabricated Devices for Sizing and Sorting DNA Molecules, Chou et al., *PNAS*, vol. 96, pp. 11-13, Jan. 1999.

Fluorescence Polarization in Homogeneous Nucleic Acid Analysis, Chen et al., *Genome Research*, vol. 9, pp. 492-498, Feb. 26, 1999.

*The Human Genome Project: Challenges and Opportunities*, Washington University in St. Louis, Mar. 5, 1999.

Homogeneous Proximity Tyrosine Kinase Assays: Scintillation Proximity Assay Versus Homogeneous Time-Resolved Fluorescence, Park et al., *Analytical Biochemistry*, vol. 269, No. 1, pp. 94-104, Apr. 1999.

Tyr'd and True: Immunochemical Reagents and Kits for Studying Tyrosine Phosphorylation, Wilkinson, *The Scientist*, vol. 13, internet printed pp. 1-9, May 10, 1999.

Everything's Great When It Sits on a Chip, Bob Sinclair, *The Scientist*, vol. 13, #11, May 24, 1999.

U.S. Appl. No. 09/321,309 File History, Sundberg et al., filed May 27, 1999.

Immobilized Gallium(III) Affinity Chromatography of Phosphopeptides, Posewitz et al., *Analytical Biochemistry*, vol. 71, No. 14, pp. 2883-2892, Jul. 15, 1999.

*Assay Miniaturization for High-Throughput Screening*, Peter Panfili, Application Note, Sep. 1999.

CyBi™-Disk brochure, CyBio AG, Oct. 1999.

PanVera Postings, Issue 5, PanVera Corporation, Oct. 1999.

SnaPshot ddNTP Primer Extension Kit product bulletin, PE Biosystems, Oct. 1999.

Handout Information, Tips and Tricks . . . Automated Liquid-Handling in the Microplate Format, CyBio AG, Nov. 1999.

Magellan, Instrument Control and Data Analysis Software brochure, Tecan AG, Nov. 1999.

Twister™, Tecan's Automated Microplate Handler brochure, Tecan AG, Nov. 1999.

A Microfabricated Fluorescence-Activated Cell Sorter, Fu et al., *Nature Biotechnology*, vol. 17, pp. 1109-1111, Nov. 1999.

Absorbance Readers brochure, Tecan AG, Dec. 1999.

Kinase Assay Based on Thiophosphorylation and Biotinylation, Jeong et al., *BioTechniques*, vol. 27, pp. 1232-1238, Dec. 1999.

ULTRA—The Solution for HTS and Assay Development brochure, Tecan Austria GmbH, Dec. 1999.

Synthesis, Time-Resolved Luminescence, NMR Spectroscopy, Circular Dichroism and Circularly Polarised Luminescence Studies of Enantiopure Macrocyclic Lanthanide Tetraamide Complexes, Dickins et al., *Chem. Eur. J.*, vol. 5, No. 3, 1999.

Mono(di)nuclear Europium(III) Complexes of Macrobi(tri)cyclic Cryptands Derived from Diazatetralactams as Luminophores in Aqueous Solution, Galaup et al., *Helvetica Chimica Acta*, vol. 82, pp. 543-560, 1999.

*Principles of Fluorescence Spectroscopy*, Joseph R. Lakowicz, Second Edition, 1999.

A Microchip-Based Enzyme Assay for Protein Kinase A, Cohen et al., *Analytical Biochemistry*, vol. 273, No. 1, abstract only, 1999.

Detection of Hybrid Formation Between Peptide Nucleic Acids and DNA by Fluorescence Polarization in the Presence of Polylysine, Nikiforov et al., *Analytical Biochemistry*, vol. 275, pp. 248-253, 1999.

Terbium and Rhodamine as Labels in a Homogeneous Time-Resolved Fluorometric Energy Transfer Assay of the β Subunit of Human Chorionic Gonadotropin in Serum, Blomberg et al., *Clinical Chemistry*, vol. 45, No. 6, pp. 855-861, 1999.

*New Fluorescent Labels for Polarization Assays and Lifetime Imaging*, Analytix, Feb. 2000.

Novel Electrochemiluminescent Assays for Drug Discovery, Kibbey et al., *JALA*, vol. 5, No. 1, pp. 45-48, Mar. 2000.

CyBi™-PlateSafe brochure, CyBio AG, May 2000.

Packarg BioScience Company Introduces the Fusion™ Universal Microplate Analyzer press release, Packard BioScience Company, Jun. 29, 2000.

*Tris(2,2'-bipyridyl)ruthenium(II)* internet pages, OMLC, printed Jul. 3, 2000.

Protein Tyrosine Kinase Assay Kits flyer, PanVera Corporation, Jul. 2000.

Protein Kinase C Assay Kits flyer, PanVera Corporation, Jul. 2000.

CoreHTS, Estrogen Receptor-α & -β Competitor Assays brochure, PanVera Corporation, Jul. 2000.

Glucocorticoid Receptor flyer, PanVera Corporation, Jul. 2000.

CoreHTS Glucocorticoid Receptor Competitor Assay Kit flyer. PanVera Corporation, Aug. 2000.

Fusion™, Universal Microplate Analyzer, Packard BioScience Company, Aug. 2000.

Linker Histone Binding and Displacement: Versatile Mechanism for Transcription Regulation, Zlatanova et al., *The FASAB Journal*, vol. 14, No. 12, pp. 1697-1704, Sep. 2000.

Fluorescence Polarization and Anisotropy in High Throughput Screening: Perspectives and Primer, Owicki, *Journal of Biomolecular Screening*, vol. 5, No. 5, pp. 297-306, Oct. 2000.

Escaping the Heat: A Host of Kinase Assay Formats Gives Nonradioactive Options to Researchers, Fitzgerald, *The Scientist*, vol. 14, internet printed pp. 1-7, Nov. 13, 2000.

Microchip-Based System for Target Validation and HTS, Sundberg et al., *Drug Discovery Today*, vol. 5, No. 12 (Suppl.), pp. S92-S103, Dec. 2000.

Development of High Throughput Screening Assays Using Fluorescence Polarization Nuclear Receptor-Ligand-Binding and Kinase Phosphatase Assays, Parker et al., *Journal of Biomolecular Screening*, vol. 5, No. 2, pp. 77-88, 2000.

Lifetime- and Color-Tailored Fluorophores in the Micro- to Millisecond Time Regime, Chen et al., *J. Am. Chem. Soc.*, vol. 122, pp. 657-660, 2000.

Luminescence and Structure of Europium Compounds, Vicentini et al., *Coordination Chemistry Reviews*, vol. 196, pp. 353-382, 2000.

Reacti-Bind™ Metal Chelate Plates flyer, Pierce Chemical Company, 2000.

Reacti-Bind™ Metal Chelate High Binding Capacity Plates flyer, Pierce Chemical Company, 2000.

Reacti-Bind™ NeutrAvidin™ High Binding Capacity (HBC) Coated Plates flyer, Pierce Chemical Company, 2000.

Reacti-Bind™ Strepavidin High Binding Capacity (HBC) Coated Plates flyer, Pierce Chemical Company, 2000.

Reacti-Bind™ NeutrAvidin™ and Streptavidin Coated Plates flyer, Pierce Chemical Company, 2000.

Spectroscopic Properties and Design of Highly Luminescent Lanthanide Coordination Complexes, de Sa et al., *Coordination Chemistry Reviews*, vol. 196, pp. 165-195, 2000.

Detection of Phosphopeptides by Fluorescence Polarization in the Presence of Cationic Polyamino Acids: Application to Kinase Assays, Coffin et al., *Analytical Biochemistry*, vol. 278, pp. 206-212, 2000.

Histone H1GenBank Search, Lamar, *Davidson College Department of Biology*, internet pp. 1-2, 2000.

Geldamanycin Abrogates ErbB2 Association with Proteasome-Resistant β-Catenin-E-Cadherin Association and Decreases β-Catenin-Sensitive Transcription, Bonvini et al., *Cancer Research*, vol. 61, pp. 1671-1677, Feb. 15, 2001.

*Application Notes: Miniaturization of LANCE Kinase Assays*, PerkinElmer Life Sciences, pp. 1-3, May 2001.

*Analysis of Potential Compound Interference of AlphaScreen Signal*, Packard BioSciences Inc., Application Note, pp. 1-4, Aug. 2001.

Use of Fluorescence Polarization to Monitor MHC-Peptide Interactions in Solution, Dedier et al., *J. Immunol. Methods*, vol. 255, pp. 57-66, Sep. 1, 2001.

Lysine[16-1]αof Protein Farnesyltransferase is Important for Both CoaX Substrate Binding Catalysis, K.E. Hightower, S. De. and C. Weinbaum, *Biochem Journal*, vol. 360, pp. 625-631, 2001.

The Crystal Structure of Human Protein Farnesyltransferase Reveals the Basis for Inhibition by CaaX Tetrapeptides and TheirMinmetics, S.B. Long, P.J. Hancock, A.M. Kral, H.W. Hellinga, and L.S. Beese, *Proc. Natl. Acad. Sci.*, vol. 98, pp. 1249-12953, 2001.

Dual Mechanisms of ABCA1 Regulation by Geranylgeranyl Pyrophosphate, X. Gun, R. Kaplan, J.G. Menke, K. MacNaul, Y. Chen, C.P. Sparrow, G. Zhou, S.D. Wright, and T.-Q. Cai, *J. Biol. Chem.*, vol. 276, 48702-48708, 2001.

Homogeneous Cell-Based Fluorescence Polarization Assay for the Direct Detection of cAMP, Prystay et al. *Journal of Biomolecular Screening*, vol. 6, No. 2, pp. 75-82, 2001.

*MAP Kinase Assay*, Pedro et al. for Packard Bioscience Inc., Application Note, pp. 1-4, Nov. 2001.

*P-Tyr-100 Insulin Receptor Tyrosine Kinase Assay*, Pedro et al. for Packard Bioscience Inc., Application Note, pp. 1-4, Nov. 2001.

A Homogeneous High Throughput Nonradioactive Method for Measurement of Functional Activity of $G_3$-Coupled Receptors in Membranes, Allen et al., *Journal of Biolecular Screening*, vol. 7, No. 1, pp. 35-44, Feb. 2002.

*What is a Coordination Compound?*, internet printouts, pp. 1-5, Jun. 9, 2002 (print date).

A Fluorescence Polarization Assay for Cyclic Nucleotide Phosphodiesterases, Huang et al., *Journal of Biolecular Screening*, vol. 7, No. 3, pp. 215-255, 2002.

*IQ Kinase Assay Products*, Pierce Biotechnology, Inc., internet printed pp. 1-8, 2002.

*Homogeneous Time-Resolved Fluorescence Product List*, CIS Bio International, 2002.

An Evaluation of Fluorescence Polarization and Lifetime Discriminated Polarization for High Throughput Screening of Serine Threonine Kinases, Fowler et al., *Analytical Biochemistry*, vol. 308, pp. 223-231, 2002.

Mobility Shift Screening Assays for Protein Kinase Targets, Kotturi et al., *American Laboratory*, pp. 32, 34, 36, and 38-39, Feb. 2003.

A Homogeneous Fluorescence Polarization Assay Adoptable for a Range of Protein Serine/Threonine and Tyrosine Kinases, Gaudet et al., *Journal of Biomolecular Screening*, vol. 8, No. 2, pp. 164-175, Apr. 2003.

IQ® Assay Platform Technical, Pierce Biotechnology, Inc., Aug. 2003.

*Analyst® GT Multimode Reader*, Molecular Devices Corporation, brochure, pp. 1-2, 2003.

Profiling Substrate Phosphorylation at the Phosphopeptide Level, Gatti, *Analytical Biochemistry*, vol. 312, pp. 40-47, 2003.

Acumen Explorer brochure, Acumen, undated.

Protein Kinase C (PKC) tech specs, PanVera Corporation, undated.

PW 384 brochure, PanVera Corporation, undated.

Analyst® Gt Multimode Reader, Molecular Devices Corporation, brochure, pp. 1-2, 2003.

Bretonniere et al., Ratiometric Probes for Hydrogencarbonate Analysis in Intramolecular or Extracellular Environments Using Europium Luminescence, Chem. Commun., vol. 17, pp. 1930-1931 (2002).

Liu et al., Interaction of the copper(II) macrocyclic complexes with DNA studied by fluorescence quenching of ethidium, Journal of Inorganic Biochemistry, vol. 71, pp. 1-6 (1998).

Stables et al., A Bioluminescent Assay for Agonist Activity at Potentially Any G-Protein Coupled Receptor, Analytical Biochemistry, vol. 252, pp. 115-126 (1997), abstract only.

Waga et al., Micro-trap Phosphorylation Assay of Mitogen-activated Protein (MAP) Kinases to Detect Their Activation by Lipopolysaccharides, Journal of Immunological Methods, vol. 190, No. 1, pp. 71-77 (1996).

Yu et al., Synthesis of a Europium Complex for Anion-Sensing Involving Regioselective Substitution of Cylcen, Eur. J. Org. Chem., pp. 4249-4252 (2005).

Zhou et al., Detection and Sequencing of Phosphopeptides Affinity Bound to Immobilized Metal Ion Beads by Matrix-Assisted Laser Desorption/Ionization Mass Spectrometry, Journal American Society for Mass Spectrometry, vol. 11, pp. 273-282 (2000).

Yu et al., Synthesis of a Europium Complex doe Anion-Sensing Involving Regioselective Substitution of Cylcen, Europ. J. Org. Chem., pp. 4249-4252.

* cited by examiner

SIGNALING CELLS  SIGNAL SUBSTANCES  TARGET CELLS

G-PROTEIN-LINKED RECEPTOR MECHANISM

ENZYME-LINKED RECEPTOR MECHANISM

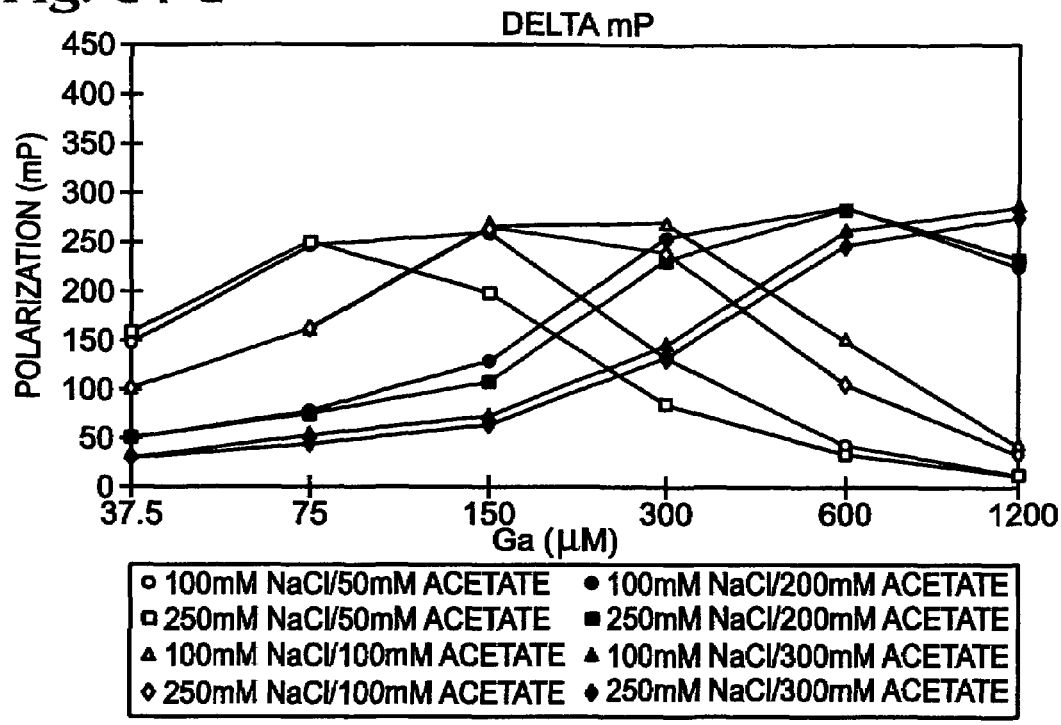
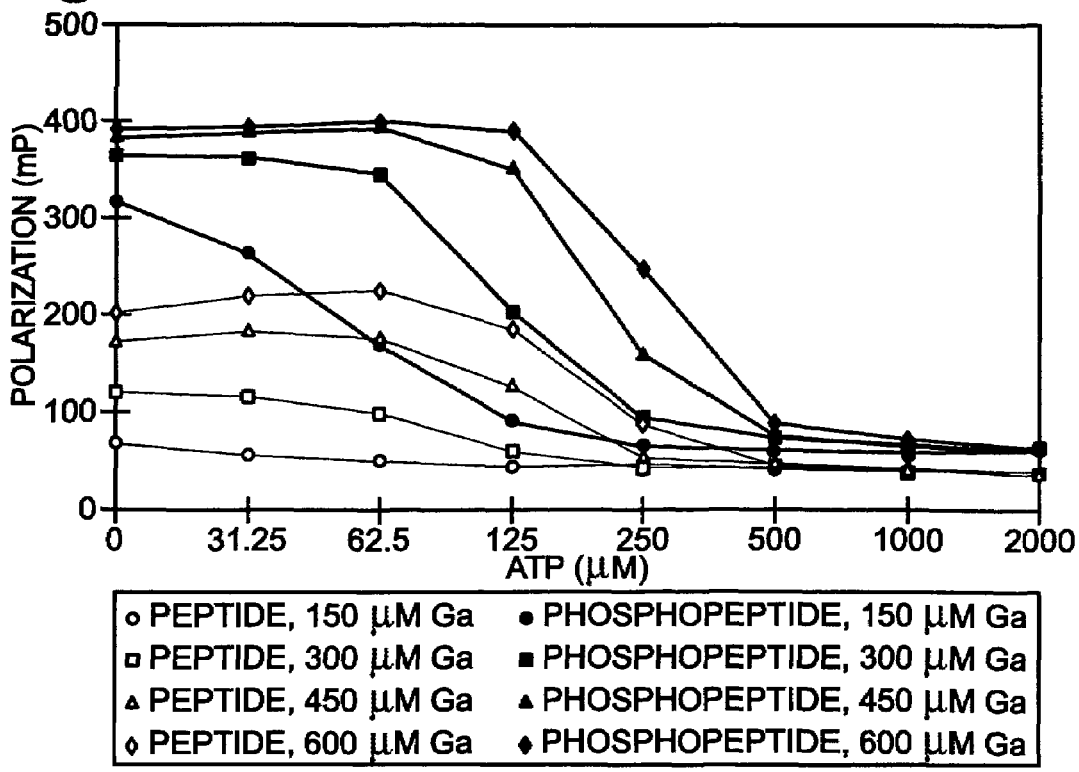

TR-FRET Assay with IMAP Binding Reagent

TR-FRET Assay with IMAP Binding Reagent

Figure 43
Exemplary Tb(III) chelates
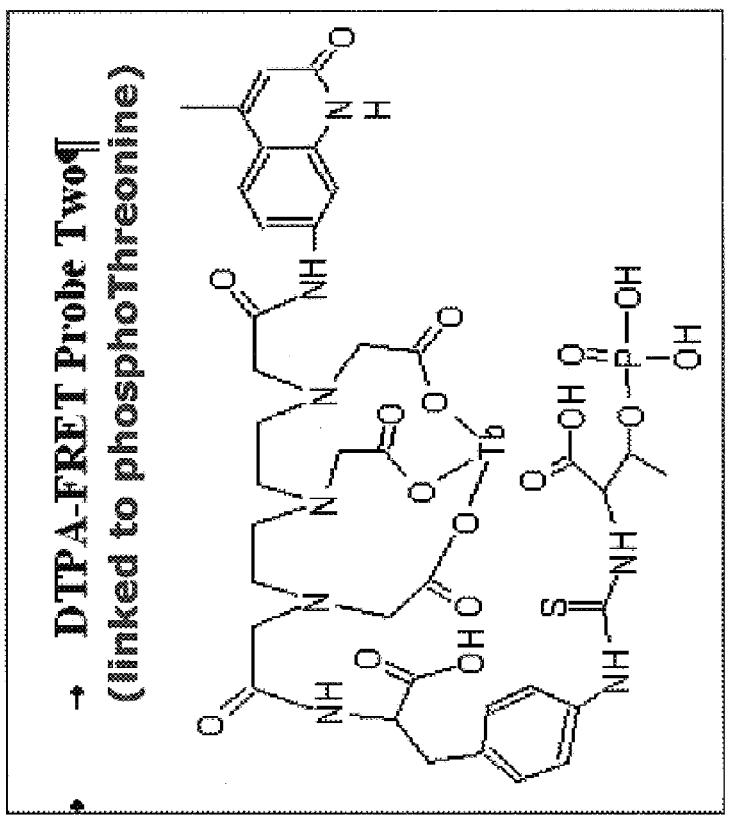
DTPA-FRET Probe Two
(linked to phosphoThreonine)
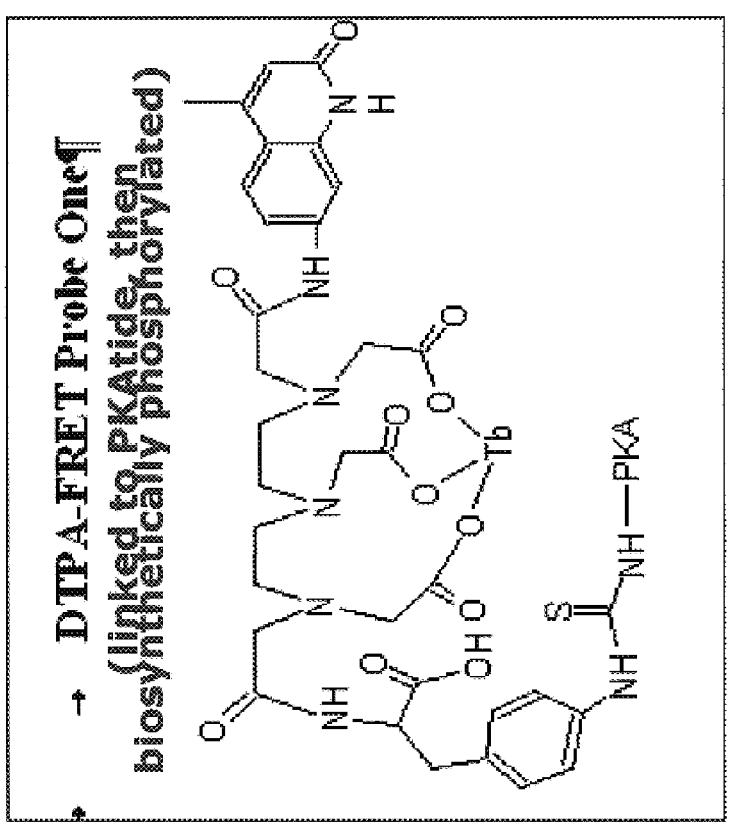
DTPA-FRET Probe One
(linked to PKAtide, then biosynthetically phosphorylated)

Terbium and Fluorescein Spectra (Analyst Filters)

Terbium and Rhodamine (similar to TAMRA) Spectra
(Analyst Filters)

IMAP TR-FRET Assay Detects Phosphorylation

IMAP CDK2/Cyclin A TR-FRET Assay

IMAP CDK2/Cyclin A Assay (FAM): TR-FRET vs. FP

IMAP CDK2/Cyclin A Assays (TAMRA): TR-FRET vs. FP

SEQUENCE LISTING

<160> NUMBER OF SEQ ID NOS: 25

<210> SEQ ID NO 1
<211> LENGTH: 7
<212> TYPE: PRT
<213> ORGANISM: Artificial
<220> FEATURE:
<223> OTHER INFORMATION: Artificial sequence is synthesized
<220> FEATURE:
<221> NAME/KEY: MOD_RES
<222> LOCATION: (1)..(1)
<223> OTHER INFORMATION: Fluorescein Conjugation

<400> SEQUENCE: 1

Leu Arg Arg Ala Ser Leu Gly
1               5

<210> SEQ ID NO 2
<211> LENGTH: 12
<212> TYPE: PRT
<213> ORGANISM: Artificial
<220> FEATURE:
<223> OTHER INFORMATION: Artificial sequence is synthesized
<220> FEATURE:
<221> NAME/KEY: MOD_RES
<222> LOCATION: (1)..(1)
<223> OTHER INFORMATION: Fluorescein Conjugation
<220> FEATURE:
<221> NAME/KEY: MOD_RES
<222> LOCATION: (12)..(12)
<223> OTHER INFORMATION: AMIDATION

<400> SEQUENCE: 2

Lys Lys Gly Glu Ala Ile Tyr Ala Ala Pro Phe Ala
1               5                   10

<210> SEQ ID NO 3
<211> LENGTH: 20
<212> TYPE: PRT
<213> ORGANISM: Artificial
<220> FEATURE:
<223> OTHER INFORMATION: Artificial sequence is synthesized
<220> FEATURE:
<221> NAME/KEY: MOD_RES
<222> LOCATION: (1)..(1)
<223> OTHER INFORMATION: Fluorescein Conjugation

<400> SEQUENCE: 3

Val Ser Arg Ser Gly Leu Tyr Arg Ser Pro Ser Met Pro Glu Asn Leu
1               5                   10                  15

Asn Arg Pro Arg
            20

<210> SEQ ID NO 4
<211> LENGTH: 15
<212> TYPE: PRT
<213> ORGANISM: Artificial
<220> FEATURE:
<223> OTHER INFORMATION: Artificial sequence is synthesized
<220> FEATURE:
<221> NAME/KEY: MOD_RES
<222> LOCATION: (1)..(1)
<223> OTHER INFORMATION: Fluorescein Conjugation
<220> FEATURE:
<221> NAME/KEY: MOD_RES
<222> LOCATION: (15)..(15)
<223> OTHER INFORMATION: AMIDATION

<400> SEQUENCE: 4

-continued

```
Ala Leu Lys Leu Val Arg Tyr Pro Ser Phe Val Ile Thr Ala Lys
1               5                   10                  15

<210> SEQ ID NO 5
<211> LENGTH: 14
<212> TYPE: PRT
<213> ORGANISM: Artificial
<220> FEATURE:
<223> OTHER INFORMATION: Artificial sequence is synthesized
<220> FEATURE:
<221> NAME/KEY: MOD_RES
<222> LOCATION: (1)..(1)
<223> OTHER INFORMATION: Fluorescein Conjugation
<220> FEATURE:
<221> NAME/KEY: MOD_RES
<222> LOCATION: (14)..(14)
<223> OTHER INFORMATION: AMIDATION

<400> SEQUENCE: 5

Ala Met Arg Leu Glu Arg Gln Asp Ser Ile Phe Tyr Pro Lys
1               5                   10

<210> SEQ ID NO 6
<211> LENGTH: 11
<212> TYPE: PRT
<213> ORGANISM: Artificial
<220> FEATURE:
<223> OTHER INFORMATION: Artificial sequence is synthesized
<220> FEATURE:
<221> NAME/KEY: MOD_RES
<222> LOCATION: (1)..(1)
<223> OTHER INFORMATION: Fluorescein Conjugation

<400> SEQUENCE: 6

Gly Arg Pro Arg Thr Ser Ser Phe Ala Glu Gly
1               5                   10

<210> SEQ ID NO 7
<211> LENGTH: 11
<212> TYPE: PRT
<213> ORGANISM: Artificial
<220> FEATURE:
<223> OTHER INFORMATION: Artificial sequence is synthesized
<220> FEATURE:
<221> NAME/KEY: MOD_RES
<222> LOCATION: (1)..(1)
<223> OTHER INFORMATION: Fluorescein Conjugation
<220> FEATURE:
<221> NAME/KEY: MOD_RES
<222> LOCATION: (7)..(7)
<223> OTHER INFORMATION: PHOSPHORYLATION

<400> SEQUENCE: 7

Gly Arg Pro Arg Thr Ser Ser Phe Ala Glu Gly
1               5                   10

<210> SEQ ID NO 8
<211> LENGTH: 12
<212> TYPE: PRT
<213> ORGANISM: Artificial
<220> FEATURE:
<223> OTHER INFORMATION: Artificial sequence is synthesized
<220> FEATURE:
<221> NAME/KEY: MOD_RES
<222> LOCATION: (1)..(1)
<223> OTHER INFORMATION: Fluorescein Conjugation
<220> FEATURE:
<221> NAME/KEY: MOD_RES
<222> LOCATION: (12)..(12)
<223> OTHER INFORMATION: AMIDATION
```

```
<400> SEQUENCE: 8

Lys Lys Lys Lys Glu Glu Ile Tyr Phe Phe Phe Gly
1               5                   10

<210> SEQ ID NO 9
<211> LENGTH: 15
<212> TYPE: PRT
<213> ORGANISM: Artificial
<220> FEATURE:
<223> OTHER INFORMATION: Artificial sequence is synthesized
<220> FEATURE:
<221> NAME/KEY: MOD_RES
<222> LOCATION: (15)..(15)
<223> OTHER INFORMATION: Fluorescein Conjugation

<400> SEQUENCE: 9

Leu Val Glu Pro Leu Thr Pro Ser Gly Glu Ala Pro Asn Gln Lys
1               5                   10                  15

<210> SEQ ID NO 10
<211> LENGTH: 15
<212> TYPE: PRT
<213> ORGANISM: Artificial
<220> FEATURE:
<223> OTHER INFORMATION: Artificial sequence is synthesized
<220> FEATURE:
<221> NAME/KEY: MOD_RES
<222> LOCATION: (1)..(1)
<223> OTHER INFORMATION: Fluorescein Conjugation
<220> FEATURE:
<221> NAME/KEY: MOD_RES
<222> LOCATION: (1)..(1)
<223> OTHER INFORMATION: PHOSPHORYLATION
<220> FEATURE:
<221> NAME/KEY: MOD_RES
<222> LOCATION: (12)..(12)
<223> OTHER INFORMATION: PHOSPHORYLATION
<220> FEATURE:
<221> NAME/KEY: MOD_RES
<222> LOCATION: (12)..(12)
<223> OTHER INFORMATION: AMIDATION

<400> SEQUENCE: 10

Tyr Thr Gly Leu Ser Thr Arg Asn Gln Glu Thr Tyr Glu Thr Leu
1               5                   10                  15

<210> SEQ ID NO 11
<211> LENGTH: 10
<212> TYPE: PRT
<213> ORGANISM: Artificial
<220> FEATURE:
<223> OTHER INFORMATION: Artificial sequence is synthesized
<220> FEATURE:
<221> NAME/KEY: MOD_RES
<222> LOCATION: (1)..(1)
<223> OTHER INFORMATION: Fluorescein Conjugation

<400> SEQUENCE: 11

Lys Lys Leu Asn Arg Thr Leu Ser Val Ala
1               5                   10

<210> SEQ ID NO 12
<211> LENGTH: 10
<212> TYPE: PRT
<213> ORGANISM: Artificial
<220> FEATURE:
<223> OTHER INFORMATION: Artificial sequence is synthesized
<220> FEATURE:
<221> NAME/KEY: MOD_RES
<222> LOCATION: (1)..(1)
<223> OTHER INFORMATION: Rhodamine Conjugation
```

```
<400> SEQUENCE: 12

Lys Lys Leu Asn Arg Thr Leu Ser Val Ala
1               5                   10

<210> SEQ ID NO 13
<211> LENGTH: 13
<212> TYPE: PRT
<213> ORGANISM: Artificial
<220> FEATURE:
<223> OTHER INFORMATION: Artificial sequence is synthesized
<220> FEATURE:
<221> NAME/KEY: MOD_RES
<222> LOCATION: (1)..(1)
<223> OTHER INFORMATION: Fluorescein Conjugation

<400> SEQUENCE: 13

Gly Gly Gly Pro Ala Thr Pro Lys Lys Ala Lys Lys Leu
1               5                   10

<210> SEQ ID NO 14
<211> LENGTH: 11
<212> TYPE: PRT
<213> ORGANISM: Artificial
<220> FEATURE:
<223> OTHER INFORMATION: Artificial sequence is synthesized
<220> FEATURE:
<221> NAME/KEY: MOD_RES
<222> LOCATION: (1)..(1)
<223> OTHER INFORMATION: Fluorescein Conjugation
<220> FEATURE:
<221> NAME/KEY: MOD_RES
<222> LOCATION: (11)..(11)
<223> OTHER INFORMATION: AMIDATION

<400> SEQUENCE: 14

Gly Arg His Asp Ser Gly Leu Asp Ser Met Lys
1               5                   10

<210> SEQ ID NO 15
<211> LENGTH: 13
<212> TYPE: PRT
<213> ORGANISM: Artificial
<220> FEATURE:
<223> OTHER INFORMATION: Artificial sequence is synthesized
<220> FEATURE:
<221> NAME/KEY: MOD_RES
<222> LOCATION: (1)..(1)
<223> OTHER INFORMATION: Fluorescein Conjugation
<220> FEATURE:
<221> NAME/KEY: MOD_RES
<222> LOCATION: (13)..(13)
<223> OTHER INFORMATION: AMIDATION

<400> SEQUENCE: 15

Lys Lys Ser Arg Gly Glu Tyr Met Thr Met Gln Ile Gly
1               5                   10

<210> SEQ ID NO 16
<211> LENGTH: 13
<212> TYPE: PRT
<213> ORGANISM: Artificial
<220> FEATURE:
<223> OTHER INFORMATION: Artificial sequence is synthesized
<220> FEATURE:
<221> NAME/KEY: MOD_RES
<222> LOCATION: (1)..(1)
<223> OTHER INFORMATION: Fluorescein Conjugation
<220> FEATURE:
<221> NAME/KEY: MOD_RES
<222> LOCATION: (13)..(13)
```

```
<223> OTHER INFORMATION: AMIDATION

<400> SEQUENCE: 16

Glu Phe Pro Ile Tyr Asp Phe Leu Pro Ala Lys Lys Lys
1               5                   10

<210> SEQ ID NO 17
<211> LENGTH: 13
<212> TYPE: PRT
<213> ORGANISM: Artificial
<220> FEATURE:
<223> OTHER INFORMATION: Artificial sequence is synthesized
<220> FEATURE:
<221> NAME/KEY: MOD_RES
<222> LOCATION: (1)..(1)
<223> OTHER INFORMATION: Fluorescein Conjugation
<220> FEATURE:
<221> NAME/KEY: MOD_RES
<222> LOCATION: (13)..(13)
<223> OTHER INFORMATION: AMIDATION

<400> SEQUENCE: 17

Lys Val Glu Lys Ile Gly Glu Gly Thr Tyr Gly Val Val
1               5                   10

<210> SEQ ID NO 18
<211> LENGTH: 13
<212> TYPE: PRT
<213> ORGANISM: Artificial
<220> FEATURE:
<223> OTHER INFORMATION: Artificial sequence is synthesized
<220> FEATURE:
<221> NAME/KEY: MOD_RES
<222> LOCATION: (1)..(1)
<223> OTHER INFORMATION: Fluorescein Conjugation
<220> FEATURE:
<221> NAME/KEY: MOD_RES
<222> LOCATION: (10)..(10)
<223> OTHER INFORMATION: PHOSPHORYLATION
<220> FEATURE:
<221> NAME/KEY: MOD_RES
<222> LOCATION: (13)..(13)
<223> OTHER INFORMATION: AMIDATION

<400> SEQUENCE: 18

Lys Val Glu Lys Ile Gly Glu Gly Thr Tyr Gly Val Val
1               5                   10

<210> SEQ ID NO 19
<211> LENGTH: 18
<212> TYPE: PRT
<213> ORGANISM: Artificial
<220> FEATURE:
<223> OTHER INFORMATION: Artificial sequence is synthesized
<220> FEATURE:
<221> NAME/KEY: MOD_RES
<222> LOCATION: (1)..(1)
<223> OTHER INFORMATION: Fluorescein Conjugation
<220> FEATURE:
<221> NAME/KEY: MOD_RES
<222> LOCATION: (14)..(14)
<223> OTHER INFORMATION: PHOSPHORYLATION
<220> FEATURE:
<221> NAME/KEY: MOD_RES
<222> LOCATION: (18)..(18)
<223> OTHER INFORMATION: AMIDATION

<400> SEQUENCE: 19

Leu Asp Val Pro Ile Pro Gly Arg Phe Asp Arg Arg Val Ser Val Ala
1               5                   10                  15

Ala Glu
```

<210> SEQ ID NO 20
<211> LENGTH: 9
<212> TYPE: PRT
<213> ORGANISM: Artificial
<220> FEATURE:
<223> OTHER INFORMATION: Artificial sequence is synthesized
<220> FEATURE:
<221> NAME/KEY: MOD_RES
<222> LOCATION: (1)..(1)
<223> OTHER INFORMATION: Fluorescein Conjugation
<220> FEATURE:
<221> NAME/KEY: MOD_RES
<222> LOCATION: (9)..(9)
<223> OTHER INFORMATION: AMIDATION

<400> SEQUENCE: 20

Gly Arg Thr Gly Arg Arg Asn Ser Ile
1               5

<210> SEQ ID NO 21
<211> LENGTH: 11
<212> TYPE: PRT
<213> ORGANISM: Artificial
<220> FEATURE:
<223> OTHER INFORMATION: Artificial sequence is synthesized
<220> FEATURE:
<221> NAME/KEY: MOD_RES
<222> LOCATION: (1)..(1)
<223> OTHER INFORMATION: Fluorescein Conjugation

<400> SEQUENCE: 21

Ala Lys Arg Arg Arg Leu Ser Ser Leu Arg Ala
1               5                   10

<210> SEQ ID NO 22
<211> LENGTH: 10
<212> TYPE: PRT
<213> ORGANISM: Artificial
<220> FEATURE:
<223> OTHER INFORMATION: Artificial sequence is synthesized
<220> FEATURE:
<221> NAME/KEY: MOD_RES
<222> LOCATION: (1)..(1)
<223> OTHER INFORMATION: Fluorescein Conjugation
<220> FEATURE:
<221> NAME/KEY: MOD_RES
<222> LOCATION: (10)..(10)
<223> OTHER INFORMATION: AMIDATION

<400> SEQUENCE: 22

Leu Arg Arg Arg Leu Ser Asp Ala Asn Phe
1               5                   10

<210> SEQ ID NO 23
<211> LENGTH: 11
<212> TYPE: PRT
<213> ORGANISM: Artificial
<220> FEATURE:
<223> OTHER INFORMATION: Artificial sequence is synthesized
<220> FEATURE:
<221> NAME/KEY: MOD_RES
<222> LOCATION: (1)..(1)
<223> OTHER INFORMATION: Fluorescein Conjugation
<220> FEATURE:
<221> NAME/KEY: MOD_RES
<222> LOCATION: (11)..(11)
<223> OTHER INFORMATION: AMIDATION

<400> SEQUENCE: 23

Ala Leu Gln Lys Asp Tyr Glu Asn Val Gly Val

```
<210> SEQ ID NO 24
<211> LENGTH: 11
<212> TYPE: PRT
<213> ORGANISM: Artificial
<220> FEATURE:
<223> OTHER INFORMATION: Artificial sequence is synthesized
<220> FEATURE:
<221> NAME/KEY: MOD_RES
<222> LOCATION: (1)..(1)
<223> OTHER INFORMATION: Fluorescein Conjugation
<220> FEATURE:
<221> NAME/KEY: MOD_RES
<222> LOCATION: (11)..(11)
<223> OTHER INFORMATION: AMIDATION

<400> SEQUENCE: 24

Ala Leu Glu Lys Asp Tyr Glu Asp Val Gly Val
1               5                   10

<210> SEQ ID NO 25
<211> LENGTH: 12
<212> TYPE: PRT
<213> ORGANISM: Artificial
<220> FEATURE:
<223> OTHER INFORMATION: Artificial sequence is synthesized
<220> FEATURE:
<221> NAME/KEY: MOD_RES
<222> LOCATION: (1)..(1)
<223> OTHER INFORMATION: Fluorescein Conjugation

<400> SEQUENCE: 25

Arg Arg Arg Ala Asp Asp Ser Asp Asp Asp Asp
1               5                   10
```

MOLECULAR MODIFICATION ASSAYS

CROSS-REFERENCES TO PRIORITY APPLICATIONS

This application is a continuation-in-part of the following U.S. patent applications: Ser. No. 10/746,797, filed Dec. 23, 2003; Ser. No. 11/146,553, filed Jun. 6, 2005; now abandoned and Ser. No. 10/957,332, filed Sep. 30, 2004 now abandoned. This application also is based upon and claims the benefit under 35 U.S.C. § 119(e) of the following U.S. provisional patent applications: Ser. No. 60/615,308, filed Sep. 30, 2004; and Ser. No. 60/683,377, filed May 20, 2005.

U.S. patent application Ser. No. 11/146,553, in turn, is a continuation-in-part of U.S. patent application Ser. No. 10/746,797, filed Dec. 23, 2003. This application also is based upon and claims the benefit under 35 U.S.C. § 119(e) of the following U.S. provisional patent applications: Ser. No. 60/577,079, filed Jun. 4, 2004; Ser. No. 60/602,712, filed Aug. 18, 2004; and Ser. No. 60/615,308, filed Sep. 30, 2004.

U.S. patent application Ser. No. 10/746,797, in turn, is a continuation-in-part of U.S. patent application Ser. No. 09/844,655, filed Apr. 27, 2001 now U.S. Pat. No. 7,070,921. U.S. patent application Ser. No. 10/746,797 also is based upon and claims the benefit under 35 U.S.C. § 119(e) of the following U.S. provisional patent applications: Ser. No. 60/436,725, filed Dec. 26, 2002; and Ser. No. 60/507,006, filed Sep. 29, 2003.

U.S. patent application Ser. No. 09/844,655, in turn, is a continuation-in-part of the following patent applications: PCT Patent Application Serial No. PCT/US00/16025, filed Jun. 9, 2000; and U.S. patent application Ser. No. 09/596,444, filed Jun. 19, 2000 now abandoned. U.S. patent application Ser. No. 09/844,655 also is based upon and claims the benefit under 35 U.S.C. § 119(e) of the following U.S. provisional patent applications: Ser. No. 60/200,594, filed Apr. 28, 2000; Ser. No. 60/223,642, filed Aug. 8, 2000; and Ser. No. 60/241,032, filed Oct. 17, 2000.

PCT Patent Application Serial No. PCT/US00/16025, in turn, is a continuation-in-part of U.S. patent application Ser. No. 09/349,733, filed Jul. 8, 1999 now abandoned. PCT Patent Application Serial No. PCT/US00/16025 also is based upon and claims the benefit under 35 U.S.C. § 119(e) of the following U.S. provisional patent applications: Ser. No. 60/138,311, filed Jun. 9, 1999; Ser. No. 60/138,438, filed Jun. 10, 1999; and Ser. No. 60/200,594, filed Apr. 28, 2000.

U.S. patent application Ser. No. 09/596,444, in turn, is a continuation-in-part of the following patent applications: U.S. patent application Ser. No. 08/929,095, filed Sep. 15, 1997; now abandoned and PCT Patent Application Ser. No. PCT/US00/16025, with priority claims as indicated above.

U.S. patent application Ser. No. 09/349,733, in turn, is based upon and claims the benefit under 35 U.S.C. § 119(e) of U.S. Provisional Patent Application Ser. No. 60/092,203, filed Jul. 9, 1998.

U.S. patent application Ser. No. 10/957,332, in turn, is based upon and claims the benefit under 35 U.S.C. § 119(e) of U.S. Provisional Patent Application Ser. No. 60/507,569, filed Sep. 30, 2003.

Each of the above-identified U.S., PCT, and provisional patent applications is incorporated herein by reference in its entirety for all purposes.

CROSS-REFERENCES TO OTHER MATERIALS

This application incorporates by reference the following U.S. Pat. No. 5,843,378, issued Dec. 1, 1998; U.S. Pat. No. 6,965,381, issued Oct. 12, 1999; U.S. Pat. No. 6,071,748, issued Jun. 6, 2000; and U.S. Pat. No. 6,097,025, issued Aug. 1, 2000.

This application also incorporates by reference the following U.S. patent applications: Ser. No. 08/840,553, filed Apr. 14, 1997; Ser. No. 09/118,141, filed Jul. 16, 1998; Ser. No. 09/144,578, filed Aug. 31, 1998; Ser. No. 09/156,318, filed Sep. 18, 1998; Ser. No. 09/478,819, filed Jan. 5, 2000; Ser. No. 09/626,208, filed Jul. 26, 2000; Ser. No. 09/643,221, filed Aug. 18, 2000; Ser. No. 09/710,061, filed Nov. 10, 2000; Ser. No. 09/722,247, filed Nov. 24, 2000; Ser. No. 09/733,370, filed Dec. 8, 2000; Ser. No. 09/759,711, filed Jan. 12, 2001; Ser. No. 09/765,869, filed Jan. 19, 2001; Ser. No. 09/765,874, filed Jan. 19, 2001; Ser. No. 09/766,131, filed Jan. 19, 2001; Ser. No. 09/767,316, filed Jan. 22, 2001; Ser. No. 09/767,434, filed Jan. 22, 2001; Ser. No. 09/767,579, filed Jan. 22, 2001; Ser. No. 09/767,583, filed Jan. 22, 2001; Ser. No. 09/768,661, filed Jan. 23, 2001; Ser. No. 09/768,742, filed Jan. 23, 2001; Ser. No. 09/768,765, filed Jan. 23, 2001; Ser. No. 09/770,720, filed Jan. 25, 2001; Ser. No. 09/770,724, filed Jan. 25, 2001; Ser. No. 09/777,343, filed Feb. 5, 2001; Ser. No. 09/813,107, filed Mar. 19, 2001; Ser. No. 09/815,932, filed Mar. 23, 2001; and Ser. No. 09/836,575, filed Apr. 16, 2001.

This application also incorporates by reference the following PCT patent applications: Ser. No. PCT/US98/23095, filed Oct. 30, 1998; Ser. No. PCT/US99/01656, filed Jan. 25, 1999; Ser. No. PCT/US99/03678, filed Feb. 19, 1999; and Ser. No. PCT/US99/08410, filed Apr. 16, 1999.

This application also incorporates by reference the following U.S. provisional patent applications: Ser. No. 60/092,203, filed Jul. 9, 1998; Ser. No. 60/094,275, filed Jul. 27, 1998; Ser. No. 60/094,276, filed Jul. 27, 1998; Ser. No. 60/094,306, filed Jul. 27, 1998; Ser. No. 60/100,817, filed Sep. 18, 1998; Ser. No. 60/100,951, filed Sep. 18, 1998; Ser. No. 60/104,964, filed Oct. 20, 1998; Ser. No. 60/114,209, filed Dec. 29, 1998; Ser. No. 60/116,113, filed Jan. 15, 1999; Ser. No. 60/117,278, filed Jan. 26, 1999; Ser. No. 60/119,884, filed Feb. 12, 1999; Ser. No. 60/121,229, filed Feb. 23, 1999; Ser. No. 60/124,686, filed Mar. 16, 1999; Ser. No. 60/125,346, filed Mar. 19, 1999; Ser. No. 60/126,661, filed Mar. 29, 1999; Ser. No. 60/130,149, filed Apr. 20, 1999; Ser. No. 60/132,262, filed May 3, 1999; Ser. No. 60/132,263, filed May 3, 1999; Ser. No. 60/135,284, filed May 21, 1999; Ser. No. 60/136,566, filed May 28, 1999; Ser. No. 60/138,737, filed Jun. 11, 1999; Ser. No. 60/138,893, filed Jun. 11, 1999; Ser. No. 60/142,721, filed Jul. 7, 1999; Ser. No. 60/178,026, filed Jan. 26, 2000; Ser. No. 60/222,222, filed Aug. 1, 2000; Ser. No. 60/244,012, filed Oct. 27, 2000; Ser. No. 60/250,681, filed Nov. 30, 2000; Ser. No. 60/250,683, filed Nov. 30, 2000; Ser. No. 60/267,639, filed Feb. 10, 2001; Ser. No. 60/369,704, filed Apr. 2, 2002; and Ser. No. 60/554,766, filed Mar. 19, 2004.

This application also incorporates by reference the following publications: Richard P. Haugland, *Handbook of Fluorescent Probes and Research Chemicals* (6$^{th}$ ed. 1996); Joseph R. Lakowicz, *Principles of Fluorescence Spectroscopy* (2$^{nd}$ Edition 1999); and Bob Sinclair, *Everything's Great When It Sits on a Chip: A Bright Future for DNA Arrays,* 13 THE SCIENTIST, May 24, 1999, at 18.

BACKGROUND

The physiological modification of molecules and supramolecular assemblies plays a major role in the structure and regulation of biological systems. These modifications may include "local" modifications, such as phosphorylation, cyclization, prenylation, carboxylation, glycosylation, acylation, and/or sulfonation of amino acids, nucleotides, and/or lipids, among others, as well as the reversal of these modifications. These modifications also may include "global" modifications, among others, such as cleavage and/or ligation of proteins, nucleic acids, and/or lipids, in which molecules are split into two or more fragments or spliced to one or more other molecules, respectively.

The prevalence and significance of molecular modifications make it particularly likely that errors in modifications and/or errors in the regulation of such modifications will lead to disease and/or other pathologies. Therefore, there is intense interest both in characterizing molecular modifications and in understanding their regulation. There also is intense interest in identifying and/or characterizing activating and/or inhibitory drugs to modulate molecular modifications. This interest, in turn, has created a demand for assays of molecular modifications and/or their effects. Unfortunately, standard assays have a number of shortcomings, including the use of radioactive labels (with their attendant safety issues), binding partners that are excessively specific to the substrate or product (making them difficult to use with more than one or unknown substrates or products), and/or slow time courses and unstable endpoints (that require precise timing of assay readouts), among others. Thus, there is a significant need for molecular modification assays that are both safe and simple.

SUMMARY

The present teachings relate to systems for detecting molecular modifications and the presence and/or activity of enzymes and/or other agents involved in facilitating or otherwise regulating such modifications.

BRIEF DESCRIPTION OF THE DRAWINGS

FIG. 38 is a graph showing binding results from binding reactions performed with a p38 substrate peptide or product phosphopeptide as binding target, as a function of ATP concentration and with various gallium concentrations, in accordance with aspects of the present teachings.

FIG. 43 are schematics showing exemplary terbium chelates, which may be used as suitable members of a donor/acceptor pair, in accordance with aspects of the present teachings.

DEFINITIONS

Figure 1:
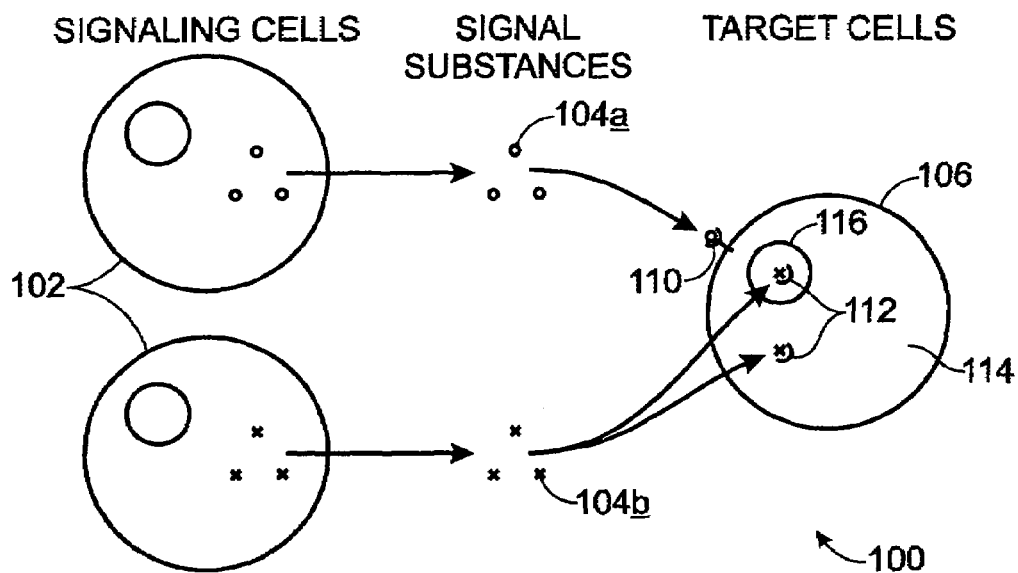
FIG. 1 is a schematic view of a cell-signaling pathway.

The various technical terms used herein generally have the meanings that are commonly recognized by those skilled in the art. However, some terms may have additional and/or alternative meanings, as described below, and/or as described in the Definitions sections of the patents and patent applications listed above under Cross-References, which are incorporated herein by reference, particularly Ser. No. 10/746,797, filed Dec. 23, 2003 (e.g., for phosphate modifications); Ser. No. 60/554,766, filed Mar. 19, 2004 (e.g., for protease and ligation modifications); Ser. No. 10/957,332, filed Sep. 30, 2004 (e.g., for prenyl transfer modifications); and Ser. No. 11/146,553, filed Jun. 6, 2005 (e.g., for lipid modifications):

Association—a detectable connection, proximity, and/or binding between a first partner (a moiety, molecule, or group of molecules) and a second partner (moiety, molecule, or group of molecules). The association may include covalent linkages, higher affinity (e.g., specific) binding, lower affinity binding, and/or relatively nonspecific binding, among others.

Cyclization/decyclization—the formation or degradation of a ring connecting a phosphate group and a nucleoside in a nucleotide. A common cyclization forms cAMP and cGMP from ATP and GTP, respectively, by removing two phosphate groups from the nucleotide triphosphates and joining the "free" end of the remaining phosphate group to the sugar in the remaining nucleotide monophosphate. A common decyclization reaction degrades the ring to form noncyclized AMP and noncyclized GMP from cAMP and cGMP, respectively.

Immunoglobulin—a group of typically large glycoproteins secreted by plasma cells in vertebrates that function as antibodies in the immune response by binding to specific antigens.

Luminescent—capable of, suitable for, or exhibiting luminescence, which is the emission of light by sources other than a hot, incandescent body. Luminescence is caused by electronic transitions within a luminescent substance (or luminophore) from more energetic to less energetic states. Among several types are chemiluminescence, electrochemiluminescence, electroluminescence, photoluminescence, and triboluminescence, which are produced by chemical reactions, electrochemical reactions, electric discharges, absorption of light, and the rubbing or crushing of crystals, respectively. Molecules may be intrinsically and/or extrinsically luminescent, meaning that they are luminescent on their own or luminescent due to covalent and/or noncovalent association with another molecule that is luminescent. Exemplary luminescent molecules and mechanisms for producing luminescent molecules, as well as exemplary energy transfer pairs, are described in U.S. patent application Ser. No. 09/815,932, filed Mar. 23, 2001; and in Richard P. Haugland, *Handbook of Fluorescent Probes and Research Chemicals* (6$^{th}$ ed. 1996), each of which is incorporated herein by reference.

Nucleotide—a compound comprising a nucleoside and a phosphate group, some of which function as cell regulators and some of which function as the basic constituent of DNA and RNA. A nucleoside in turn is a compound comprising a sugar, such as ribose or deoxyribose, and a purine or pyrimidine base, such as adenine, cytosine, guanine, thymine, or uracil. Nucleotides are named according to the identities of their constituent bases and sugars, the number of their constituent phosphates, and the presence or absence of cyclization. Suitable nucleotides are listed in the following table:

TABLE 1

| Nucleotide | Abbreviation |
| --- | --- |
| Adenosine cyclic monophosphate | cAMP |
| Cytidine cyclic monophosphate | cCMP |
| Guanosine cyclic monophosphate | cGMP |
| Thymidine cyclic monophosphate | cTMP |
| Uridine cyclic monophosphate | cUMP |
| Adenosine monophosphate | AMP |
| Cytidine monophosphate | CMP |
| Guanosine monophosphate | GMP |
| Thymidine monophosphate | TMP |
| Uridine monophosphate | UMP |

Phosphorylation/dephosphorylation—the introduction or removal of a phosphate group to or from an organic molecule such as a polypeptide. Phosphorylation is a versatile post-translational modification that is a recurrent theme for regulation of enzyme activity and signal transduction pathways.

Polypeptide—a polymer comprising two or more amino acid residues linked together by covalent bonds, typically from amino end to carboxyl end by peptide bonds, and/or modifications or complexes thereof. Polypeptides generally include peptides, proteins, and/or protein segments, among others. Here, peptide generally refers to smaller polypeptides (e.g., less than about 100, 50, 20, or 10 amino acids, among others), and protein generally refers to larger polypeptides, and/or complexes thereof, possibly modified by other organic or inorganic conjugated chemical groups, such as phosphates, sugars, luminescent labels, and/or so on. Polypeptides may include unbranched chains and/or branched chains, among others. Exemplary amino acids are listed in Table 2:

TABLE 2

| Amino acid | Three-letter abbreviation | One-letter abbreviation |
| --- | --- | --- |
| Alanine | Ala | A |
| Arginine | Arg | R |
| Asparagine | Asn | N |
| Aspartic acid | Asp | D |
| Asparagine or aspartic acid | Asx | B |
| Cysteine | Cys | C |
| Glutamine | Gln | Q |
| Glutamic acid | Glu | E |
| Glutamine or glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Specific binding—binding to a specific partner to the general exclusion of binding to most other potential partners. Specific binding can be characterized by a dissociation constant. Generally, dissociation constants for specific binding range from $10^{-4}$ M to $10^{-12}$ M and lower, and preferred dissociation constants for specific binding range from $10^{-8}$ or $10^{-9}$ M to $10^{-12}$ M and lower.

DETAILED DESCRIPTION

The present teachings relate to systems for detecting molecular modifications and the presence and/or activity of enzymes and/or other agents involved in facilitating or otherwise regulating such modifications. The modifications may include, among others, (1) phosphate modifications such as the phosphorylation and dephosphorylation of molecules such as polypeptides and lipids, and the cyclization and decyclization of molecules such as nucleotides, (2) prenyl modifications such as the prenylation and deprenylation of molecules such as polypeptides, and/or (3) the cleavage and/or degradation of molecules such as polypeptides and lipids. The enzymes may include, among others, enzymes involved in performing and/or regulating phosphorylation, dephosphorylation, prenylation, cyclization, decyclization, cleavage, and ligation modifications, such as kinases, phosphatases, prenyl transferases, cyclases, phosphodiesterases (PDEs), proteases, and ligases, respectively. The systems may include, among others, luminescence assays, such as assays detecting luminescence energy transfer, luminescence polarization, and/or luminescence intensity. The systems provided by the present teachings may be useful in a variety of applications, including, without limitation, life science research, drug research, accelerated drug discovery, assay development, and high-throughput screening.

Further aspects of the present teachings are described in the following sections, including, among others, (I) cell-signaling pathways, (II) overview, (III) assays, and (IV) examples.

I. CELL-SIGNALING PATHWAYS

The systems described herein may be used for any suitable purpose(s), including, among others, (1) detection of the presence and/or state of modification of a composition, such as an enzyme substrate or enzyme product, (2) the presence and/or activity of an enzyme, for example, that might act on an enzyme substrate to generate an enzyme product, and/or (3) the presence and/or activity of a modulator of enzyme activity. These assays may be performed on any suitable system(s), including biological systems, which may be studied in vitro and/or in vivo. This section describes, without limitation, exemplary cell-signaling pathways that are suitable for analysis using the disclosed assays.

FIG. 1 is a schematic view of a representative cell-signaling pathway 100. Here, signaling cells 102 produce signal substances 104a,b that interact with target cells 106 to effect a response in the target cells. These responses may be short term, such as glycogen breakdown or muscle contraction, among others. These responses also may be long term, such as growth, differentiation, reproduction, and/or apoptosis, among others. Generally, these responses are brought about by increasing, decreasing, and/or maintaining enzyme activity in the target cells.

Signaling cells 102 are cells capable of producing a signal (substance) that can effect a specific response in another (target) cell. The signaling cells may be components of an endocrine, paracrine, or nervous system. The endocrine system is an organism-wide control system that regulates body function using hormones released by endocrine organs into the bloodstream. The endocrine organs include the pituitary gland, thyroid gland, parathyroid glands, adrenal glands, thymus gland, pineal body, pancreas, ovaries, testes, and kidneys. The paracrine system is a local control system that regulates nearby cells using local mediators released into the extracellular medium. The nervous system is a specialized control system that regulates specific cells using electrical impulses and neurotransmitters.

Signal substances 104a,b are substances through which a signaling cell may communicate with target cells, evoking a specific response. Signal substances may act as hormones, local mediators, and/or neurotransmilters, among others. Signal substances may take the form of proteins, small peptides, amino acids, nucleotides, steroids (e.g., cortisol, steroid sex hormones, vitamin D), retinoids, fatty acid derivatives, and dissolved gases (e.g., nitric oxide (NO) and carbon monoxide (CO)), among others.

Target cells 106 are cells capable of responding to a specific signal substance produced by a signaling cell. The ability to respond may depend on the cell and on the signal substance. For example, the signal substance thyroxine from the thyroid gland may evoke a response in nearly all cells, whereas the signal substance progesterone from the ovary may evoke a response only in specific cells in the lining of the uterus. The target response may include kinase activity, GTP binding, and/or cyclic nucleotide production.

The ability of a cell to respond to a given signal substance generally is determined by whether the cell includes a receptor for the signal substance. Here, a receptor is any molecule or supramolecular assembly capable of specifically binding a signal substance and initiating a response in a target cell. Representative receptors include cell-surface receptors 110 located on the surface of the target cell and intracellular receptors 112 located within the cytosol 114 or nucleus 116 of the target cell.

The nature of the response initiated by binding of a signal substance is determined by the intracellular machinery to which the receptor is operatively coupled. For example, binding of the neurotransmitter acetylcholine to identical receptors in heart muscle cells and secretory cells causes muscle relaxation in the heart muscle cells and secretion in the secretory cells, due to differences in the associated intracellular machinery.

The remainder of this section examines (1) the receptor mechanisms that cells use to bind signal substances and to communicate this binding to the cell interior, (2) the intracellular pathways that cells use for regulation, (3) the effects of errors in cell-signaling pathways, and (4) selected shortcomings of current cell-signaling assays.

I.A Receptor Mechanisms

Target cells generally have receptors capable of specifically binding specific signal substances, including cell-surface receptors and/or intracellular receptors, as described above. Cell-surface receptors are more common and include (A) G-protein-linked receptors, (B) enzyme-linked receptors, and (C) ion-channel-linked receptors. These receptors typically bind large and/or water-soluble signal substances, such as many peptide hormones. Intracellular receptors are less common and include (A) guanylyl cyclase and (B) ligand-activated gene regulatory proteins. These receptors typically bind small and/or water-insoluble signal substances, such as steroid hormones, thyroid hormones, retinoids, vitamin D, and NO.

Figure 2:
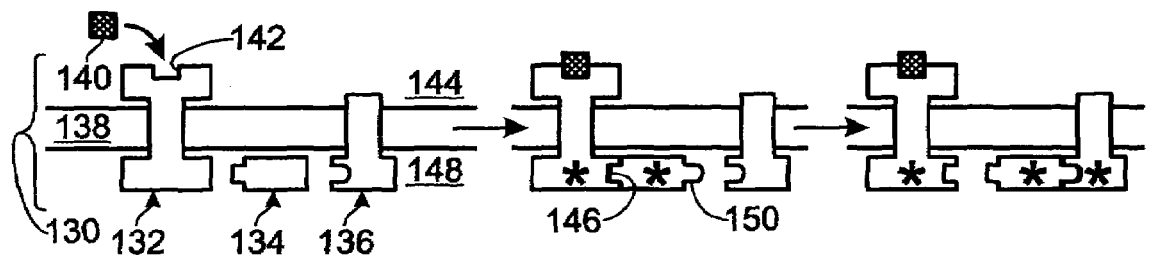
FIG. 2 is a schematic view of a G-protein-linked cell-surface receptor mechanism that includes a receptor protein, a G-protein, and a target protein, all associated with the plasma membrane of a target cell.

FIG. 2 is a schematic view of a representative G-protein-linked cell-surface receptor mechanism 130 that includes a receptor protein 132, a G-protein 134, and a target protein 136. These proteins may be positioned on or within the plasma membrane 138 of a target cell. In use, a specific signal substance 140 binds to a signal-substance binding site 142 on the extracellular side 144 of the receptor protein and thereby creates, exposes, or otherwise activates (*) a G-protein binding site 146 on the intracellular side 148 of the receptor protein. The G-protein then binds to the G-protein binding site on the receptor protein and thereby creates, exposes, or otherwise activates (*) a target-protein binding site 150 on the G-protein. The G-protein then dissociates from the receptor protein, binds (via the target-protein binding site) to the target protein, and activates (*) the target protein. Activation and deactivation of the G-protein may involve binding of a guanosine triphosphate (GTP) molecule and dephosphorylation of the GTP molecule, respectively. The receptor protein may belong to a large superfamily of homologous, seven-pass transmembrane proteins. These seven-pass proteins consist of a single polypeptide chain that crosses the membrane seven times, with an extracellular signal-substance binding portion and an intracellular catalytic portion. The G-protein may be trimeric, consisting of three polypeptide chains—α, β, and γ—that associate and dissociate during signaling. The target protein may consist of an enzyme or ion channel, among others. In particular, the target protein may be an enzyme that modulates the presence or activity of second messengers within the cell. These second messengers (also known as intracellular messengers or intracellular mediators) may bind allosterically to specific cellular proteins to alter their conformation and hence their activity. These second messengers include adenosine 3',5'-cyclic monophosphate (cAMP) and calcium ($Ca^{2+}$).

In the cAMP pathway, the target protein may be adenylyl cyclase (also known as adenylate cyclase), and the G-protein may be a stimulatory G-protein ($G_s$) that activates the adenylyl cyclase to make cAMP, or an inhibitory G protein ($G_i$) that inhibits the adenylyl cyclase to prevent it from making cAMP. The cAMP produced by the adenylyl cyclase activates cAMP-dependent protein kinase (A-kinase), which is a serine/threonine kinase that in turn activates or inhibits other enzymes to effect a physiological response. For example, in connection with glycogen metabolism, A-kinase may inhibit glycogen synthase to shut down glycogen synthesis, and simultaneously activate phosphorylase kinase that in turn activates glycogen phosphorylase to break down glycogen. A variety of signal substances use cAMP as a second messenger, including calcitonin, chorionic gonadotropin, corticotropin, epinephrine, follicle-stimulating hormone, glucagon, luteinizing hormone, lipotropin, melanocyte-stimulating hormone, norepinephrine, parathyroid hormone (PTH), thyroid-stimulating hormone, and vasopressin. The level of cAMP may be reduced by phosphodiesterases (PDEs), and the activity of kinases may be reversed by phosphatases, as described below.

In the $Ca^{2+}$ pathway, the target protein may be a phospholipase with specificity for a phosphoinositide (i.e., inositol phospholipid), and the G-protein may be $G_q$, which activates the phospholipase to cleave the phosphoinositide to produce an intermediate that releases $Ca^{2+}$ from the endoplasmic reticulum. For example, the phospholipase phosphoinositide-specific phospholipase C (phospholipase C-β) cleaves the phosphoinositide phosphatidylinositol 4,5-bisphosphate ($PIP_2$) to produce the second messengers inositol triphosphate ($IP_3$) and diacylglycerol. The inositol triphosphate is water soluble and diffuses to the endoplasmic reticulum (ER), where it releases $Ca^{2+}$ from the ER by binding to $IP_3$-gated $Ca^{2+}$-release channels in the ER membrane. The diacylglycerol is membrane bound and may be cleaved to form the second messenger arachidonic acid or may activate the $Ca^{2+}$-dependent serine/threonine kinase protein kinase C that in turn activates or inhibits other enzymes to effect a response. A variety of signal substances use $Ca^{2+}$ as a second messenger, including acetylcholine, thrombin, and vasopressin.

Figure 3:
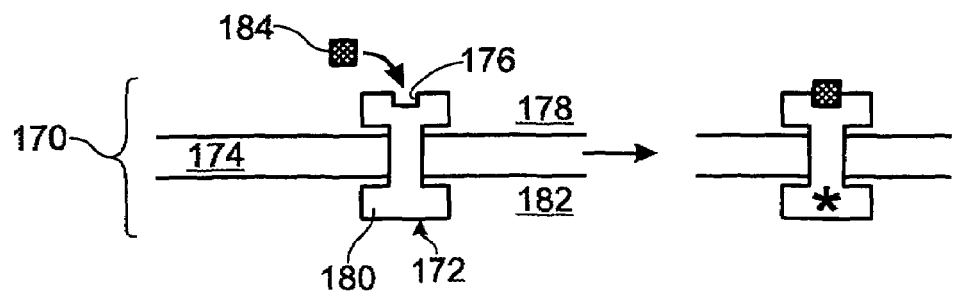
FIG. 3 is a schematic view of an enzyme-linked cell-surface receptor mechanism that includes a receptor protein positioned across the plasma membrane of a target cell.

FIG. 3 is a schematic view of a representative enzyme-linked cell-surface receptor mechanism 170 that includes a receptor protein 172 positioned across the plasma membrane 174 of a target cell. The receptor protein includes a signal-substance binding site 176 on the extracellular side 178 of the membrane and a catalytic portion 180 on the intracellular side 182 of the membrane. (In some cases, the catalytic portion of the receptor may be replaced or augmented by a separate enzyme directly associated with the receptor protein.) In use, a specific signal substance 184 binds to the signal-substance binding site, initiating a series of events (such as dimerization and concomitant autophosphorylation of the receptor proteins) that activates (*) the catalytic portion of the receptor. The receptor protein may belong to one of at least five classes -of single-pass transmembrane proteins: (A) receptor guanylyl cyclases, which catalyze the production of guanosine 3',5'-cyclic monophosphate (cGMP) in the cytosol; (B) receptor tyrosine kinases, which phosphorylate specific tyrosine residues on some intracellular proteins, (C) tyrosine-kinase-associated receptors, which associate with proteins that phosphorylate specific tyrosine residues on some intracellular proteins; (D) receptor tyrosine phosphatases, which dephosphorylate specific tyrosine residues on some intracellular proteins, and (E) receptor serine/threonine kinases, which phosphorylate specific serine or threonine residues on some intracellular proteins. Some of these receptors are described below in more detail.

The signal substance also may bind to intracellular receptors, such as guanylyl cyclase. This enzyme produces cGMP from GTP, which then acts as a second messenger much like cAMP. As described above, cGMP also may be produced by enzyme-linked cell-surface receptors. cGMP is present in most tissues at levels 1/10 to 1/100 those of cAMP. A variety of compounds increase cGMP levels in cells, including (1) the hormones acetylcholine, insulin, and oxytocin, (2) the guanylate cyclase stimulators (and vasodilators) nitroprusside, nitroglycerin, sodium nitrate, and nitric oxide, (3) chemicals such as serotonin and histamine, and (4) peptides such as atrial natriuretic peptide (ANP) that relax smooth muscle.

The level of cyclic nucleotides such as cAMP and cGMP may be controlled by specialized enzymes known as phosphodiesterases (PDEs). These enzymes catalyze the hydrolysis of the 3'-ester bond of cAMP and/or cGMP to form the corresponding noncyclized nucleotide monophosphates AMP and GMP, respectively. More than 30 human PDEs are known, and there is great interest in the pharmaceutical industry in finding inhibitors for PDEs for a broad range of potential therapeutic applications. A selective inhibitor of PDE-5 has been commercialized as the drug Viagra™ (i.e., Sildenafil) for the treatment of male erectile dysfunction. Moreover, several PDE-4 inhibitors are in clinical trials as anti-inflammatory drugs for the treatment of diseases such as asthma I.B Intracellular Signaling Pathways Target cells may have intracellular signaling pathways capable of specifically binding signal substances, including cell-surface receptors and intracellular receptors, as described above. These pathways may include (1) a phosphorylation pathway involving ATP/ADP, and (2) a GTP-binding pathway involving GTP/GDP.

FIG. 4A is a schematic view of a representative portion of a phosphorylation pathway. Phosphorylation is the predominant mechanism used to regulate protein activity in eucaryotic cells. In phosphorylation, a phosphate group (P) is reversibly attached to the side chain of an amino acid in a protein. The attached phosphate group may cause structural changes in the protein, for example, due to electrostatic interactions between the negative charges on the phosphate group and positive charges on the side chains of nearby amino acids. These structural changes may affect the activity of the phosphorylated protein, enhancing or inhibiting its function.

Specialized enzymes control phosphorylation in cells. In particular, protein kinase enzymes transfer phosphate groups to proteins, and protein phosphatase enzymes remove phosphate groups from proteins. Protein kinases and protein phosphatases are found in great variety in eucaryotic cells: a single cell may contain more than 100 different kinases, and one percent of genes may code for kinases.

There are two major categories of protein kinases: (1) serine/threonine (S/T) kinases, and (2) tyrosine kinases. The S/T kinases function by selectively phosphorylating serine and threonine side chains on substrate proteins or peptides. These kinases include cyclic AMP-dependent kinase (A-kinase), cyclic GMP-dependent kinase (G-kinase), protein kinase C (C-kinase), $Ca^{2+}$-calmodulin-dependent kinase (CaM-kinase), phosphorylase kinase, MAP kinase, and TGF-β receptor, among others. The S/T kinases are predominantly cytosolic. The tyrosine kinases function by selectively phosphorylating tyrosine side chains on substrate proteins or peptides. These kinases include the receptor kinases for epidermal growth factor (EGF), platelet-derived growth factor (PDGF), fibroblast growth factors (FGFs), hepatocyte growth factor (HGF), insulin, insulin-like growth factor-1 (IGF-1), nerve growth factor (NGF), vascular endothelial growth factor (VEGF), and macrophage colony stimulating factor (M-CSF). These kinases also include the nonreceptor kinases associated with the tyrosine-kinase-associated receptors, such as the Src family (Src, Yes, Fgr, Fyn, Lck, Lyn, Hck, and Blk) and Janus family (JAK1, JAK2, and Tyk2) kinases. The tyrosine kinases are predominantly membrane bound. A few kinases function by selectively phosphorylating threonine and tyrosine side chains on substrate proteins or peptides. These kinases include the mitogen-activated protein (MAP) kinase-kinase.

FIG. 4B is a schematic of a representative portion of a GTP-binding pathway. The GTP-binding pathway generally resembles the phosphorylation pathway in that each pathway involves transfer of a phosphate group to a protein. However, in the GTP-binding pathway, the protein gains a phosphate group by exchanging a bound GDP for a bound GTP, whereas in the phosphorylation pathway, the protein gains a phosphate group by covalent addition of the phosphate group to a serine, threonine, or tyrosine by a kinase enzyme. The binding of a GTP to a GTP-binding protein may cause structural changes in the protein that in turn affect the activity of the protein. Examples of GTP-binding proteins include the trimeric G-proteins described above and the Ras superfamily of monomeric GTPases. The Ras proteins are activated by release of bound GDP and binding of GTP stimulated by guanine-nucleotide releasing proteins (GNRPs). The Ras proteins are inactivated by hydrolysis of the bound GTP by GTPase-activating proteins (GAPs).

Figure 4:
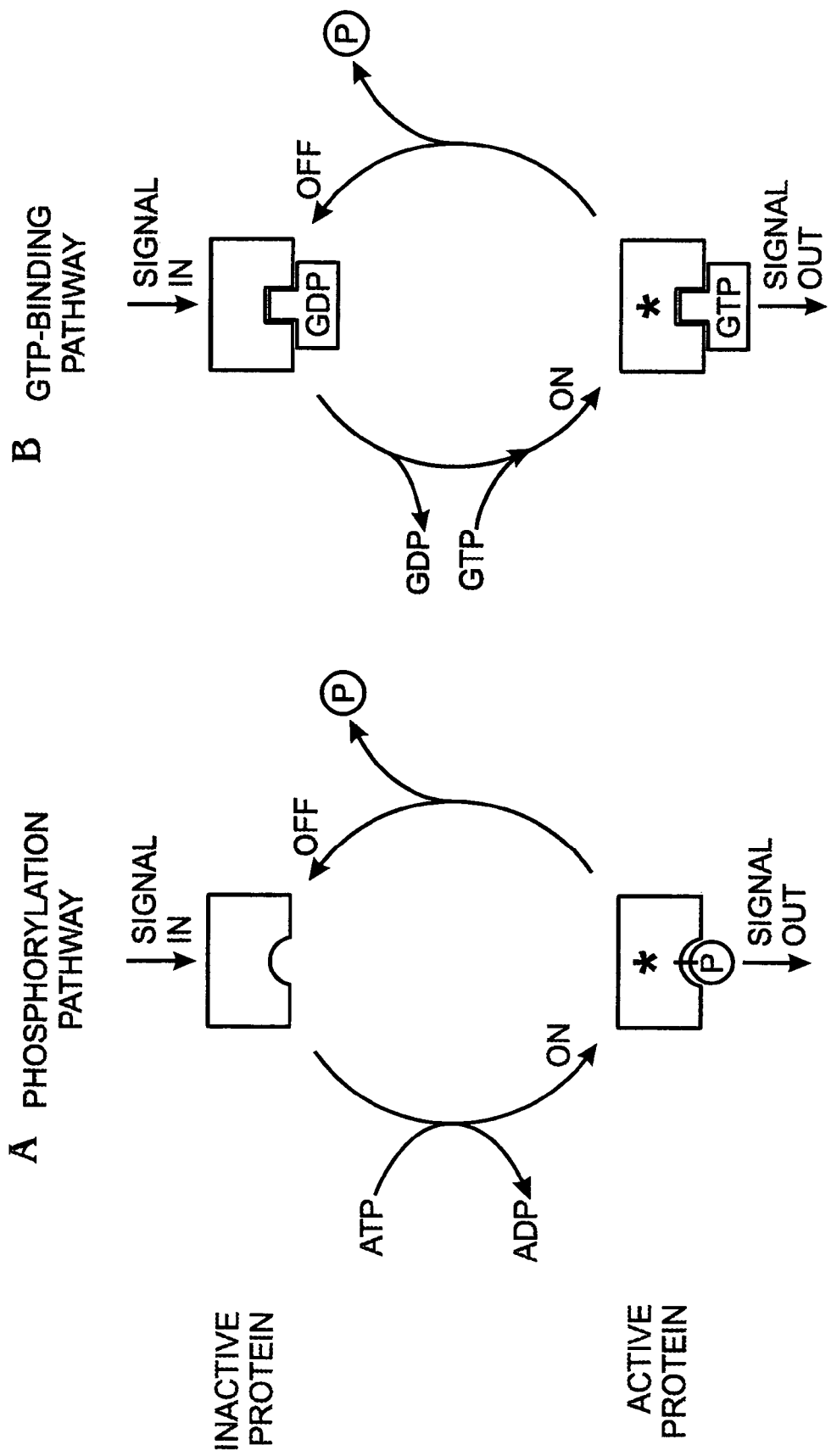
FIG. 4 is a schematic view of two common intracellular signaling pathways: (A) a phosphorylation pathway involving ATP/ADP, and (B) a GTP-binding pathway involving GTP/GDP.
Figure 5:
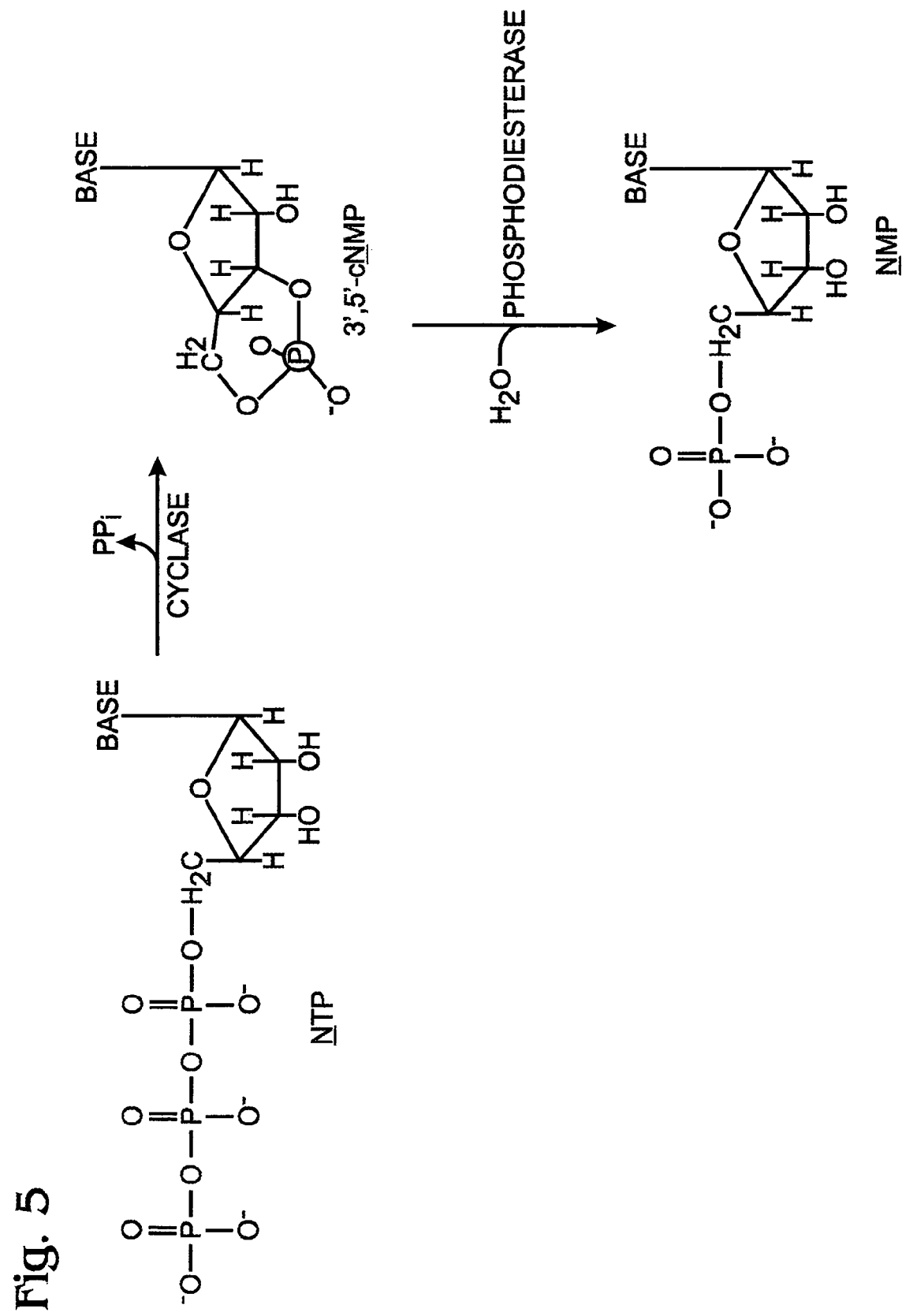
FIG. 5 is a schematic view of a representative portion of a second messenger pathway that may follow the receptor activation shown in FIG. 4.

FIG. 5 is a schematic view of a representative portion of a second messenger pathway that may follow the receptor activation shown in FIG. 4. Specifically, FIG. 5 shows the production of cyclic nucleotides by activated receptor cyclases such as adenylyl cyclase and guanylyl cyclase and the degradation of cyclic nucleotides to form the corresponding non-cyclized nucleotide monophosphates by phosphodiesterases and/or other mechanisms.

A physiological response may require stimulation by only a single type of signal substance, or may require stimulation by two or more types of signal substances. The latter mechanism permits finer tuning of the physiological response through signal integration. For example, a protein may be activated only by phosphorylation by two different kinases, themselves activated by binding of two different signal substances to two different receptors. Alternatively, a protein may be activated only by concurrent phosphorylation and GTP binding, or by binding of two subunits whose binding is contingent on phosphorylation by separately activated kinases.

I.C Effects of Errors

Errors in the signal transduction and regulation pathways described above can cause cancer and other diseases. Indeed, a primary cause of cancer is a mutation that makes a stimulatory gene product hyperactive, converting a proto-oncogene into an oncogene. The primary classes of known proto-oncogenes include the following cell-signaling proteins: (1) growth-factor receptors acting via tyrosine kinases, (2) GTP binding proteins, (3) membrane/cytoskeleton-associated tyrosine kinases, (4) cytoplasmic tyrosine kinases, (5) steroid-type growth-factor receptors, and (6) S/T kinases. Consequently, cell-signaling proteins have become important subjects of research and drug development.

II. OVERVIEW

Figure 6:
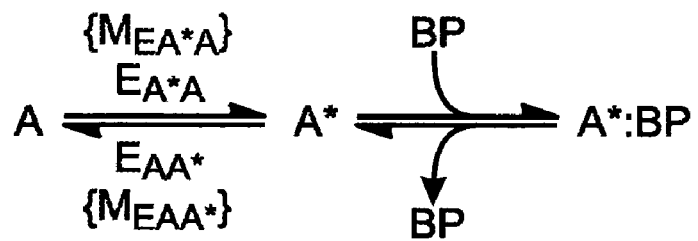
FIG. 6 is a schematic view of species and/or reactions that may be analyzed using assays provided by the aspects of the present teachings.

FIG. 6 shows exemplary species and/or reactions that may be analyzed using assays provided by the present teachings. Additional and/or alternative exemplary species and/or reactions are shown and described in the patents and patent applications listed above under Cross-References, which are incorporated herein by reference, including Ser. No. 10/746,797, filed Dec. 23, 2003 (e.g., particularly for phosphate modifications); Ser. No. 60/554,766, filed Mar. 19, 2004 (e.g., particularly for protease and ligation modifications); Ser. No. 10/957,332, filed Sep. 30, 2004 (e.g., particularly for prenyl transfer modifications); and Ser. No. 11/146,553, filed Jun. 6, 2005 (e.g., particularly for lipid modifications). The species include reactant and product A and A*, respectively, enzymes $E_{AA}$ and $E_{A*A}$, and/or enzyme modulators $M_{EAA*}$ and $M_{EA*A}$, among others. The assays may be used to analyze the presence and/or quantity of a binding target, A and/or A*. Alternatively, or in addition, the assays may be used to analyze the presence, quantity, and/or activity of $E_{AA*}$, $E_{A*A}$, $M_{EAA*}$, and/or $M_{EA*A}$. Quantity refers generally to amount, which may be defined intrinsically and/or extrinsically, for example, using concentration and/or number or mass, respectively. Activity refers generally to rate, which may be defined as the rate of substrate consumption and/or product formation per time. Here, quantity and/or amount may be used so as to encompass the simple presence of components, and activity and/or rate may be used so as to encompass the simple presence of activity.

Binding targets A and A* generally comprise any two species related by a modification (denoted by the presence or absence of *). A and A* may include molecules and assemblies of molecules such as polypeptides and/or nucleotides, among others. The modification may include phosphate modifications such as phosphorylation, dephosphorylation, cyclization, and/or decyclization, among others, and nonphosphate modifications such as nonphosphate posttranslational modifications of polypeptides, among others. A and A* may be related as substrate and product in a reaction, such as an enzyme-catalyzed reaction. Thus, depending on the direction of the reaction, A and A* in a phosphate modification may be a phosphorylated polypeptide, a nonphosphorylated polypeptide, a cyclized nucleotide, or a noncyclized nucleotide, among others. In some embodiments, A and/or A* may include components intended to facilitate detection of binding between A or A* and BP, such as a luminophore, a quencher, an energy transfer partner, and the like.

BP generally comprises any binding partner capable of binding specifically to binding target A or A* (i.e., the modified species or the unmodified species) but not to both. BP may include any binding partner having the specified binding properties. In some examples, BP may not include a polypeptide and/or an immunoglobulin, and/or a functional portion or fragment thereof.

BP may include a metal. In some examples, the metal may be a metal ion. The metal may be configured to form a metal-ligand coordination complex with the binding target, in which one or more electrons are shared between the metal and the binding target. For example, the metal may be a Lewis acid and particularly a strong Lewis acid. In exemplary embodiments, the metal is a Lewis acid that shares electrons with a Lewis base, such as a phosphate. Accordingly, binding between BP and the binding target may be a covalent interaction and/or may be a charge-charge interaction, among others. Exemplary metals that may be suitable as part (or all) of the binding partner include aluminum, chromium, europium, gallium, iridium, iron, manganese, osmium, platinum, rhenium, ruthenium, scandium, strontium, terbium, titanium, vanadium, yttrium, and/or zirconium, among others. In some examples, the metals may be aluminum, gallium, and/or iron. Alternatively, or in addition, the metals may be strontium, europium, terbium, and/or zirconium.

The metal may be in ionic form. Accordingly, BP may be, include, and/or be formed from a metal salt. BP may include one or more metal ions, including dicationic, tricationic, tetracationic, and/or other polycationic metal ions, among others. Suitable dicationic metal ions may include europium ($Eu^{2+}$), iridium ($Ir^{2+}$), osmium ($Os^{2+}$), platinum ($Pt^{2+}$), rhenium ($Re^{2+}$), ruthenium ($Ru^{2+}$), and/or strontium ($Sr^{2+}$), among others. Suitable tricationic metal ions may include aluminum ($Al^{3+}$), chromium ($Cr^{3+}$), europium ($Eu^{3+}$), gallium ($Ga^{3+}$), iron ($Fe^{3+}$), manganese ($Mn^3+$), scandium ($Sc^{3+}$), terbium ($Tb^{+3}$), titanium ($Ti^{3+}$), vanadium ($V^{3+}$), and/or yttrium ($Y^{3+}$), among others. Suitable tetracationic metal ions may include zirconium ($Zr^{4+}$).

A metal or metal ion may be a binding species of BP required for interaction with the modification on binding target A or A*, for example,. the phosphate group on a phosphorylated protein or a noncyclized nucleotide. BP may bind to a substrate such as A or A* only if it is phosphorylated, where the binding between the substrate and the binding partner is substantially nonspecific with respect to the structure of the substrate aside from any phosphate groups. Thus, the binding may occur substantially without regard to the target amino acid or surrounding amino acid sequence in a phosphorylation/dephosphorylation assay, or the base or nucleoside in a cyclization/decyclization assay.

In some examples, BP may include a distinct structure to which the metal is connected or otherwise associated. The distinct structure may be a macromolecule (a protein, nucleic acid, polysaccharide, polymer, and/or the like) and/or an associated solid support (or solid phase). The solid support may be a particle, a membrane, and/or a sample holder (such as a microplate), among others. Here, particles include nanoparticles and microparticles, among others, where nanoparticles are particles with at least one dimension less than about 100 nm, and microparticles are particles with dimensions between about 100 nm and about 10 μm. The metal may be associated with (or "tethered") to the macromolecule and/or solid support using any suitable linkage mechanism, including hydrogen bonding, ionic bonding, electrostatic binding, hydrophobic interactions, Van der Waals interactions, and/or covalent attachment, among others. Alternatively, or in addition, the metal may be "untethered," that is, not connected to a distinct structure substantially lacking the metal. However, an untethered metal may be included in a metal-based complex, particularly a macromolecular complex, such as an aggregate, microcrystal, and/or a metal hydroxide/oxide, among others. In some embodiments, the complex may form from a metal (or metal salt) when the metal (or metal salt) is placed in a suitable aqueous environment. The suitable aqueous environment may include buffer components (including pH-modifying components such as an acid or base). In some embodiments, BP may include components intended to facilitate detection of binding between BP and A or A*, such as a luminophore, a quencher, an energy transfer partner, and the like.

Metal salts forming a metal-based complex included in the binding partner may have any suitable formula weight. As used herein, the formula weight is the mass of the smallest repeating unit of the metal salt. The formula weight generally is defined with the metal salt in an anhydrous or hydrated crystalline form, that is, before placed in a liquid. With this definition, water-mediated reactions that produce bridged compounds, hydroxides/oxides, aggregates, etc. are ignored in calculating the formula weight. For example, the metal salt gallium chloride may form larger complexes in certain aqueous environments (see, e.g., Example 23 of Section IV), but has a formula weight (anhydrous) of about 176 grams/mole. In some embodiments, the metal salt may have a formula weight of less than about $10^5$, $10^4$, $10^3$, or 400 grams/mole. Alternatively, or in addition, the metal salt may have a formula weight that is less than the formula or molecular weight of the binding target (for example, the substrate or product), or less than about ten-fold or one-hundred fold the formula or molecular weight of the binding target.

$E_{AA*}$ and $E_{A*A}$ generally comprise any enzymes or other catalysts capable of facilitating reactions converting A to A* and A* to A, respectively. $E_{AA*}$ and $E_{A*A}$ may include, among others, enzymes such as kinases and phosphatases, which catalyze the addition and removal of phosphate groups to and from polypeptides, respectively. $E_{AA*}$ and $E_{A*A}$ also may include enzymes such as cyclases and phosphodiesterases, which catalyze the cyclization and decyclization of nucleotides, respectively, to produce cyclized and noncyclized nucleotides.

$M_{EAA*}$ and $M_{EA*A}$ generally comprise any modulators or other agents capable of modulating or otherwise affecting the activity of $E_{AA*}$ and $E_{A*A}$, respectively. The modulator may be a change in environmental condition, such as a change in sample temperature, but more typically is an enzyme or other reagent added to the sample. The modulator may be a chemical reagent, such as an acid, base, metal ion, organic solvent, and/or other substance intended to effect a chemical change in the sample. Alternatively, or in addition, the modulator may have or be suspected to have a biological activity or type of interaction with a given biomolecule, such as an enzyme, drug, oligonucleotide, nucleic acid polymer, peptide, protein, and/or other biologically active molecule. The modulator may include an agonist or inhibitor capable of promoting or inhibiting, respectively, the activity of the modulated enzyme. For example, in a cyclic nucleotide assay, preferred agonists include magnesium and calmodulin, and preferred inhibitors include isobutylmethylxanthine and Zaprinast.

III. ASSAYS

Figure 7:
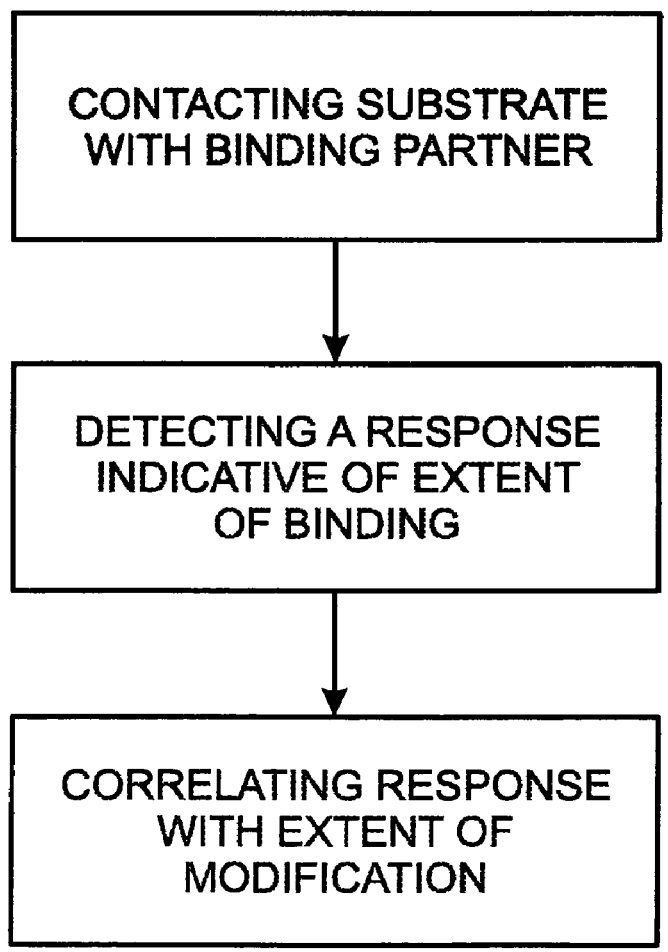
FIG. 7 is a flowchart showing steps that may be used alone, together, or in combination with other steps to construct assays according to various aspects of the present teachings.

FIG. 7 shows several exemplary steps that may be used alone, together, or in combination with other steps to construct assays according to various aspects of the present teachings. Additional and/or alternative exemplary steps are shown and described in the patents and patent applications listed above under Cross-References, which are incorporated herein by reference, including Ser. No. 10/746,797, filed Dec. 23, 2003 (e.g., particularly for phosphate modifications); Ser. No. 60/554,766, filed Mar. 19, 2004 (e.g., particularly for protease and ligation modifications); Ser. No. 10/957,332, filed Sep. 30, 2004 (e.g., particularly for prenyl transfer modifications); and Ser. No. 11/146,553, filed Jun. 6, 2005 (e.g., particularly for lipid modifications). These steps may include (a) contacting at least one member of a pair of molecules or other entities related by a modification as described above with a binding partner capable of binding one of the pair of molecules but not the other as described above, (b) detecting a response indicative of the extent of binding between the at least one member of the pair and the binding partner, and (c) correlating the response with the extent of modification, or with the activity of an enzyme that affects the modification. The extent of binding or modification, or the activity, as used herein, are intended to include the presence or absence of binding or modification, and the presence or absence of activity. The assays further may include contacting the at least one member with the enzyme before and/or after the steps of contacting, detecting, and correlating. The assays further may include contacting the at least one member and the enzyme with a candidate compound such as a putative modulator before and/or after the step of contacting the at least one member with the enzyme, and determining the ability of the candidate compound to promote or inhibit the modification by its effects on the extent of binding. Alternatively, or in addition, the assays further may include washing the sample including the at least one member and the binding partner to remove any member of the pair not bound to the binding partner prior to the step of detecting the extent of binding. In some embodiments, the assays may include repeating the steps of contacting, detecting, and/or correlating for the same sample and/or a plurality of different samples. For example, the assays may involve providing a sample holder having a plurality of sample sites supporting a corresponding plurality of samples, and sequentially and/or simultaneously repeating the steps of contacting, detecting, and/or correlating for the plurality of samples. The remainder of this section describes in more detail the steps of (a) contacting, (b) detecting, and (c) correlating.

III.A Contacting

The step of contacting assay components such as enzymes, enzyme modulators, substrates, products, and/or binding partners with one another and/or with other species generally comprises any method for bringing any specified combination of these components into functional and/or reactive contact. A preferred method is by mixing and/or forming the materials in solution, although other methods, such as attaching one or more components such as the binding partner to a bead or surface, also may be used, as long as the components retain at least some function, specificity, and/or binding affinity following such attachment. Exemplary apparatus having fluidics capability suitable for contacting or otherwise preparing assay components are described in the following U.S. patent applications, which are incorporated herein by reference: Ser. No. 09/777,343, filed Feb. 5, 2001; and Ser. No. 10/061,416, filed Feb. 1, 2002.

One or more of the assay components may comprise a sample, which typically takes the form of a solution containing one or more biomolecules that are biological and/or synthetic in origin. The sample may be a biological sample that is prepared from a blood sample, a urine sample, a swipe, or a smear, among others. Alternatively, the sample may be an environmental sample that is prepared from an air sample, a water sample, or a soil sample, among others. The sample typically is aqueous but may contain biologically compatible organic solvents, buffering agents, inorganic salts, and/or other components known in the art for assay solutions.

The assay components and/or sample may be supported for contact and/or analysis by any substrate or material capable of providing such support. Suitable substrates may include microplates, PCR plates, biochips, and hybridization chambers, among others, where features such as microplate wells and microarray (i.e., biochip) sites may comprise assay sites. Suitable microplates are described in the following U.S. patent applications, which are incorporated herein by reference: Ser. No. 08/840,553, filed Apr. 14, 1997, now abandoned; and Ser. No. 09/478,819, filed Jan. 5, 2000, now U.S. Pat. No. 6,488,892. These microplates may include 96, 384, 1536, or other numbers of wells. These microplates also may include wells having small ($\leqq 50$ µL) volumes, elevated bottoms, and/or frusto-conical shapes capable of matching a sensed volume. Suitable PCR plates may include the same (or a similar) footprint, well spacing, and well shape as the preferred microplates, while possessing stiffness adequate for automated handling and thermal stability adequate for PCR. Suitable microarrays include nucleic acid and polypeptide microarrays, which are described in Bob Sinclair, *Everything's Great When It Sits on a Chip: A Bright Future for DNA Arrays*, 13 THE SCIENTIST, May 24, 1999, at 18, which is incorporated herein by reference: Suitable hybridization chambers are described in U.S. Pat. No. 6,486,947, issued Nov. 26, 2002, which is incorporated herein by reference.

III.B Detecting

The step of detecting a response indicative of the extent of binding generally comprises any method for effectuating such detection, including detecting and/or quantifying a change in, or an occurrence of, a suitable parameter and/or signal. The method may include luminescence and/or nonluminescence methods, and heterogeneous and/or homogeneous methods, among others. The method also may include combining two or more detection methods on a single composition, for example, combining luminescence energy transfer and luminescence polarization, among others. Exemplary systems, including apparatus and methods, for combining two or more detection modes are described in U.S. Pat. No. 6,825,921, issued Nov. 30, 2004, which is incorporated herein by reference.

Luminescence and nonluminescence methods may be distinguished by whether they involve detection of light emitted by a component of the sample. Luminescence assays involve detecting light emitted by a luminescent compound (or luminophore) and using properties of that light to understand properties of the compound and its environment. A typical luminescence assay may involve (1) exposing a sample to a condition capable of inducing luminescence from the sample, and (2) measuring a detectable luminescence response indicative of the extent of binding between the member of interest and a corresponding binding partner. Most luminescence assays are based on photoluminescence, which is luminescence emitted in response to absorption of suitable excitation light. However, luminescence assays also may be based on chemiluminescence, which is luminescence emitted in response to chemical excitation, and electrochemiluminescence, which is luminescence emitted in response to electrochemical energy. Suitable luminescence assays include, among others, (1) luminescence intensity, which involves detection of the intensity of luminescence, (2) luminescence polarization, which involves detection of the polarization of light emitted in response to excitation by polarized light, and/or (3) luminescence energy transfer. Luminescence energy transfer involves detection of energy transfer between a luminescent donor and a suitable acceptor (a donor-acceptor energy transfer pair). Such energy transfer may occur with or without the emission of a photon. Generally the efficiency of the energy transfer is dependent on the distance between the donor and acceptor. Accordingly, the amount of energy transfer detected relates, at least partially, to the proximity of the energy donor and acceptor, and thus may be correlated with conversion of substrate to product in an assay. In particular, the energy donor and acceptor may be placed in (or out of) proximity by the enzyme reaction itself, or by selective association of a substrate or product of the enzyme with an association partner. These and other luminescence assays are described below in Example 14 and materials cited therein. Nonluminescence assays involve using a detectable response other than light emitted by the sample, such as absorption, scattering, and/or radioactivity, among others. These and other nonluminescence assays are described in the following materials, which are incorporated herein by reference: U.S. Pat. No. 6,466,316, issued Oct. 15, 2002; and Joseph R. Lakowicz, *Principles of Fluorescence Spectroscopy* ($2^{nd}$ ed. 1999).

The detectable luminescence response generally comprises a change in, or an occurrence of, a luminescence signal that is detectable by direct visual observation and/or by suitable instrumentation. Typically, the detectable response is a change in a property of the luminescence, such as a change in the intensity, polarization, energy transfer, lifetime, and/or excitation or emission wavelength distribution of the luminescence. For example, energy transfer may be measured as a decrease in donor luminescence, an increase (often from zero) in acceptor luminescence, and/or a decrease in donor luminescence lifetime, among others. The detectable response may be simply detected, or it may be quantified. A response that is simply detected generally comprises a response whose existence merely is confirmed, whereas a response that is quantified generally comprises a response having a quantifiable (e.g., numerically reportable) value such as an intensity, polarization, and/or other property. In luminescence assays, the detectable response may be generated directly using a luminophore associated with an assay component actually involved in binding such as A* or BP, or indirectly using a luminophore associated with another (e.g., reporter or indicator) component. Suitable methods and luminophores for luminescently labeling assay components are described in the following materials, which are incorporated herein by reference: Richard P. Haugland, *Handbook of Fluorescent Probes and Research Chemicals* (6$^{th}$ ed. 1996); U.S. patent application Ser. No. 09/813,107, filed Mar. 19, 2001; and U.S. patent application Ser. No. 09/815,932, filed Mar. 23, 2001.

Heterogeneous and homogeneous methods may be distinguished by whether they involve sample separation before detection. Heterogeneous methods generally require bulk separation of bound and unbound species. This separation may be accomplished, for example, by washing away any unbound species following capture of the bound species on a solid phase, such as a bead or microplate surface labeled with a tricationic metal ion or other suitable binding partner. The extent of binding then can be determined directly by measuring the amount of captured bound species and/or indirectly by measuring the amount of uncaptured unbound species (if the total amount is known). Homogeneous methods, in contrast, generally do not require bulk separation but instead require a detectable response such as a luminescence response that is affected in some way by binding or unbinding of bound and unbound species without separating the bound and unbound species. Alternatively, or in addition, enzyme activity may result in increased or decreased energy transfer between a donor and acceptor of an energy transfer pair, based on whether the acceptor quenches or not, and based on whether enzyme activity in the assay results in increased or decreased proximity of the donor and acceptor. Homogeneous assays typically are simpler to perform but more complicated to develop than heterogeneous assays.

III.C Correlating

The step of correlating generally comprises any method for correlating the extent of binding with the extent of modification of the assay component being analyzed, and/or with the presence and/or activity of an enzyme that affects the modification. The nature of this step depends in part on whether the detectable response is simply detected or whether it is quantified. If the response is simply detected, it typically will be used to evaluate the presence of a component such as a substrate, product, and/or enzyme, or the presence of an activity such as an enzyme or modulator activity. In contrast, if the response is quantified, it typically will be used to evaluate the presence and/or quantity of a component such as a substrate, product, and/or enzyme, or the presence and/or activity of a component such as an enzyme or modulator.

The correlation generally may be performed by comparing the presence and/or magnitude of the response to another response (e.g., derived from a similar measurement of the same sample at a different time and/or another sample at any time) and/or a calibration standard (e.g., derived from a calibration curve, a calculation of an expected response, and/or a luminescent reference material). Thus, for example, in a polarization assay for cyclic nucleotide concentration, the cyclic nucleotide concentration in an unknown sample may be determined by matching the polarization measured for the unknown with the cyclic nucleotide concentration corresponding to that polarization in a calibration curve generated under similar conditions by measuring polarization as a function of cyclic nucleotide concentration. More generally, the following table shows representative qualitative changes in the indicated detectable luminescence response upon binding between A* and BP following a forward reaction A→A*.

TABLE 3

| Label on A* | Label on BP | Intensity (Luminophore) | Intensity (Acceptor) | FP (Luminophore) | ET (Lum. → Acc.) |
|---|---|---|---|---|---|
| Luminophore | — | | | Increases | |
| — | Luminophore | | | Increases | |
| Luminophore | Quencher | Decreases | | | |
| Quencher | Luminophore | Decreases | | | |
| Luminophore | Acceptor | Decreases | Increases | Decreases | Increases |
| Acceptor | Luminophore | Decreases | Increases | | Increases |

This reaction is representative of a phosphorylation reaction performed by a kinase or a decyclization reaction performed by a PDE, assuming that the binding partner binds to the (noncyclized) phosphorylated species. Similarly, the following table shows representative qualitative changes in the indicated detectable luminescence response upon binding of A* and BP following the reverse reaction A*→A.

TABLE 4

| Label on A* | Label on BP | Intensity (Luminophore) | Intensity (Acceptor) | FP (Luminophore) | ET (Lum. → Acc.) |
|---|---|---|---|---|---|
| Luminophore | — | | | Decreases | |
| — | Luminophore | | | Decreases | |
| Luminophore | Quencher | Increases | | | |
| Quencher | Luminophore | Increases | | | |
| Luminophore | Acceptor | Increases | Decreases | Increases | Decreases |
| Acceptor | Luminophore | Increases | Decreases | | Decreases |

This reaction is representative of a dephosphorylation reaction performed by a phosphatase or a cyclization reaction performed by a cyclase, assuming again that the binding partner binds to the (noncyclized) phosphorylated species.

IV. EXAMPLES

The following examples describe, without limitation, further aspects of the present teachings. These aspects include (1) the ability of binding partners such as tricationic metal ions to bind specifically to phosphorylated species such as phosphopeptides and nucleotides, and (2) the use of such binding in assays for enzymes and other agents involved in phosphorylation and dephosphorylation (e.g., kinases and phosphatases, respectively) and cyclization and decyclization (e.g., cyclases and PDEs, respectively), among others. The aspects also include (3) experiments comparing metal ions with and without associated beads as phosphate-binding partners in binding assays, (4) experiments testing the effect of other solution components on the ability of a metal salt in the absence of beads to serve as a phosphate-binding partner in binding assays, and (5) experiments testing hypotheses for the action of a metal salt, without associated beads, as a binding partner in the binding assays, and (6) experiments testing the effects of different assay conditions-substrates, buffers, salt concentrations, gallium concentrations, ATP concentrations, etc.—on assay performance. These aspects are applicable to a wide variety of enzymes and enzyme substrates and products.

Example 1

This example describes a macromolecular trapping system for use in luminescence polarization and/or energy transfer assays, among others, in accordance with aspects of the present teachings. In this system, $Ru^{2+}$ is entrapped in small (~20-30 kDa) synthetic polymer macromolecules (MM), which are obtained from PreSens Precision Sensing (Neuburg/Donau, Germany). These macromolecules are relatively hydrophilic, with carboxyl groups on their surfaces for activation. The MM with the entrapped $Ru^{2+}$ is used as a support to immobilize tricationic metal cations, including $Fe^{3+}$ and $Ga^{3+}$. Specifically, the chelator imidodiacetic (IDA) acid is linked to the MM using the secondary amine group of IDA and a carboxyl group on the MM. Afterwards, the MM-IDA is incubated with either $FeCl_3$ or $GaCl_3$. The $FeCl_3$ quenches the luminescence of $Ru^{2+}$, whereas the $GaCl_3$ does not. The macromolecule loaded with $Fe^{3+}$ or $Ga^{3+}$ is denoted MM-Fe or MM-Ga, respectively.

The macromolecular trapping system may be used in a variety of kinase, phosphatase, phosphodiesterase, and/or cyclase assays, as described below in Examples 3-5 and 7-9. In an exemplary assay, a kinase enzyme phosphorylates a luminescently labeled kinase substrate, which binds to the metal cations immobilized on the MM. Binding is detected using polarization and/or energy transfer methods, among others, for example, using apparatus and methods as described herein. Binding is detectable using polarization because binding leads to a decrease in substrate mobility and a concomitant increase in the polarization of light emitted by luminophores bound to the substrate. Similarly, binding is detectable using energy transfer because binding leads to a decrease in separation between the luminophores bound to the substrate and the $Ru^{2+}$ immobilized in the MM, and a concomitant increase in energy transfer from the $Ru^{2+}$ (donor) to the luminophore (acceptor).

This approach may be extended by various modifications and/or substitutions. For example, in polarization assays, the $Ru^{2+}$ may be omitted, if desired. In energy transfer assays, the $Ru^{2+}$ may be replaced by any energy transfer partner, as long as the energy transfer partner supported by the MM is capable of energy transfer to or from a complementary energy transfer partner supported by the species binding to the MM. Exemplary energy transfer partners are described in U.S. patent application Ser. No. 09/815,932, filed Mar. 23, 2001, which is incorporated herein by reference. Also, the $Ru^{2+}$ or its analog does not need to be encapsulated in the MM. A luminescent species may be attached directly to a suitable $Fe^{3+}$ or $Ga^{3+}$ chelate. In a heterogeneous assay, phosphorylated proteins bound via $Ga^{3+}$ or $Fe^{3+}$ to microplates, particles, or inner surfaces of microfluidic devices may be detected after a wash by measuring luminescence intensity. Such detection can take place either directly on the surfaces or in the solution phase by adding an elution solution such as a phosphate buffer. With other detection methods, such as the laser-scanning method used in fluorometric microvolume assay technology (FMAT™) technology (PE Biosystems, Foster City, Calif.), the bound phosphoproteins can be detected directly on the beads, without the need for washing or separation. Other labels such as enzymes also may be used in the heterogeneous format.

Potential difficulties with this system include (1) interference from compounds (e.g., ATP, free phosphate, EDTA, and possibly primary/secondary amines) that may compete with or otherwise affect the interaction between the metal and the phosphorylated protein, and (2) difficulty in maintaining a pH that preserves the affinity and selectivity of the binding between the metal and phosphorylated protein.

Example 2

This example describes assays for the presence, activity, substrates, and/or products of kinases in accordance with aspects of the present teachings. Similar assays may be used to analyze phosphatases in which the substrates and products of the kinase reaction become the products and substrates of the phosphatase reaction, respectively.

Kinases catalyze the addition of phosphate groups to appropriate substrates, as shown below:

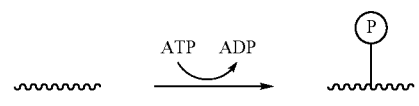

Thus, the presence and/or activity of a kinase may be detected by a decrease in the concentration of a nonphosphorylated (e.g., polypeptide) substrate and/or by an increase in the concentration of a corresponding phosphorylated product, among others. (The presence and/or activity of a phosphatase may be detected similarly by a decrease in the concentration of a phosphorylated substrate and/or an increase in the concentration of a nonphosphorylated product.) The present teachings provide among others kinase assays that involve contacting a sample containing a candidate kinase (and optionally a modulator thereof) with a luminescently labeled nonphosphorylated polypeptide having at least one amino acid subject to phosphorylation (such as a tyrosine, serine, and/or threonine) and a binding partner that binds specifically to the phosphorylated polypeptide but not to the nonphosphorylated polypeptide. These assays further involve detecting a response indicative of the extent of binding between the polypeptide and the binding partner such as luminescence intensity, polarization, and/or energy transfer, and correlating the response with the extent of phosphorylation or nonphosphorylation of the polypeptide, and thus with the activity of the candidate kinase. The binding partner may include a metal ion such as a tricationic metal ion that interacts with the phosphate group on the phosphorylated polypeptide to facilitate the binding reaction. The binding partner also may include a macromolecule, a nanoparticle, a solid phase portion, a quencher, and/or an energy transfer partner complementary to the luminophore on the polypeptide, depending in part on the detection scheme.

Example 3

This example describes experiments to characterize binding between MM-Ga and a fluorescein-labeled di-phosphotyrosine 15-amino-acid peptide tracer denoted tyrosine kinase 1 (TK-1) tracer. These experiments show the utility of the MM-Ga system for detection of phosphorylated tyrosine and the presence and/or activity of tyrosine kinases and phosphatases.

Figure 8:
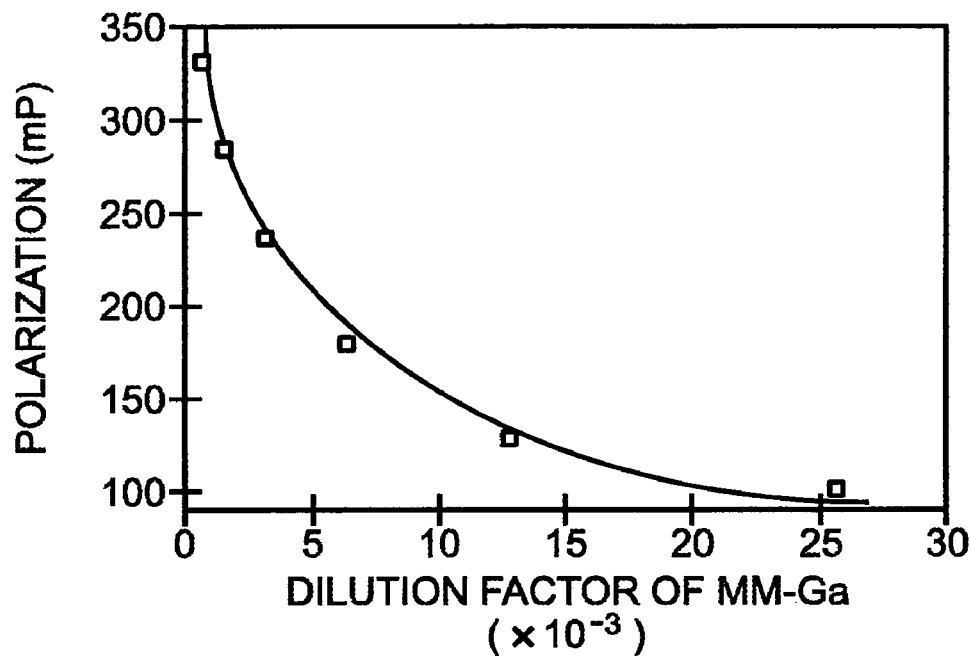
FIG. 8 is a graph showing the effects of incubating 10 nM TK-1 tracer with different concentrations of MM-Ga.

FIG. 8 shows the effects of incubating 10 nM TK-1 tracer with different concentrations of MM-GA (total volume=50 µL; incubation time=60 min). These experiments show that the maximum polarization change is more than 200 mP, at least when the MM-Ga and TK-1 tracer are incubated in MES buffer (0.1 M MES, pH 5.5, 1.0 M NaCl). This polarization change is at least sufficient for most polarization assays.

Figure 9:
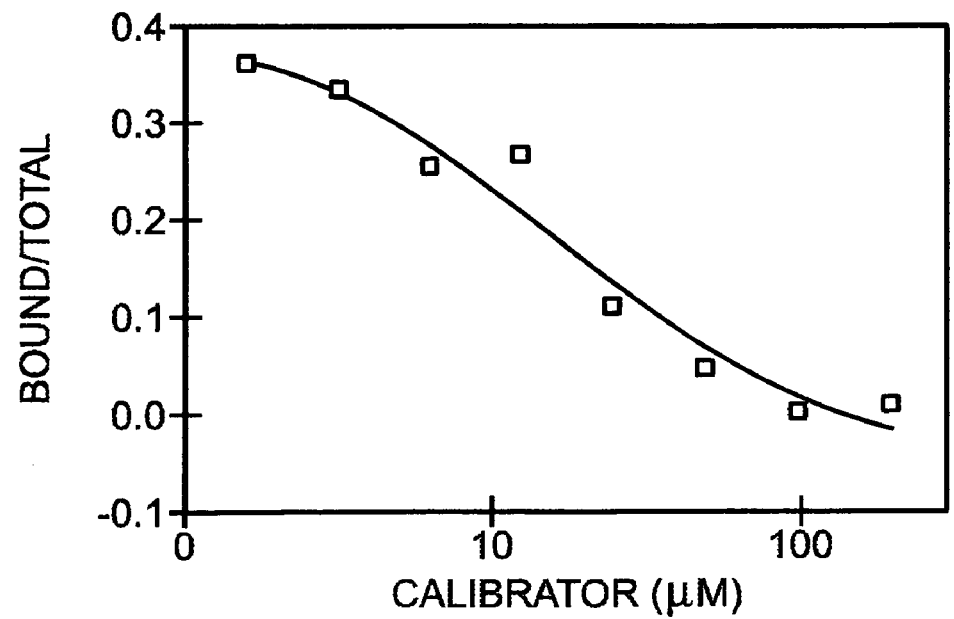
FIG. 9 is a graph showing a dose-response curve for TK-1 calibrator, with 10 nM TK-1 tracer and 1.6 nM (estimated) MM-Ga.

FIG. 9 shows a dose-response curve for TK-1 calibrator, with 10 nM TK-1 tracer and 1.6 nM (estimated) MM-Ga. The TK-1 calibrator is the same as the TK-1 tracer, without a fluorescein label. The bound/total ratio is calculated as in FIG. 8. These experiments show that the IC50 for the TK-1 calibrator also is around 10 µM. The IC50 (inhibitory concentration 50%) is the concentration of inhibitor required for 50% inhibition. More generally, the IC50 (or EC50 (effective concentration 50%)) is the drug concentration at which an associated response has decreased (increased) to 50% of the initial response, assuming that the response is a decreasing (increasing) function of drug concentration.

Example 4

This example describes experiments to characterize binding between MM-Ga and the following mono-serine fluorescein-labeled peptide tracer:

fluorescein-Leu-Arg-Arg-Ala-Ser-Leu-Gly (SEQ ID NO:1)

This peptide is termed a "Kemptide," and the fluorescein-labeled peptide is termed a "fluo-Kemptide." These experiments use cAMP-dependent protein kinase A (PKA, Promega) as the enzyme and fluo-Kemptide (SEQ ID NO:1) as the substrate. These experiments show the utility of the MM-Ga system for detection of phosphorylated serine and the presence and/or activity of serine/threonine kinases and phosphatases.

Figure 10:
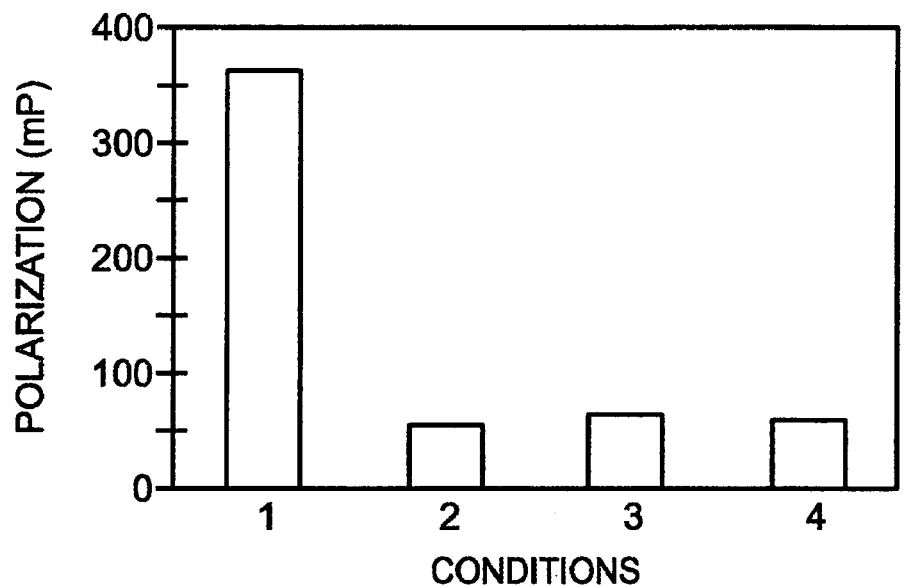
FIG. 10 is a bar graph showing results from an endpoint assay for PKA activity with MM-Ga under the following conditions: (1) reaction with enzyme, with MM-Ga; (2) reaction with enzyme, without MM-Ga; (3) reaction without enzyme, with MM-Ga; and (4) reaction without enzyme, without MM-Ga.

FIG. 10 shows an endpoint assay for PKA activity with MM-Ga under the following conditions: (1) reaction with enzyme, with MM-Ga; (2) reaction with enzyme, without MM-Ga; (3) reaction without enzyme, with MM-Ga; and (4) reaction without enzyme, without MM-Ga. The assay is performed as follows. First, a mixture is prepared of 20 mM $MgCl_2$, 0.2 mM ATP, 2 mM $NaVO_4$, and 100 µM fluo-Kemptide (SEQ ID NO:1) in a total of 50 µL 40 mM Tris-HCl (pH 7.4). Second, the reaction is initiated by adding 1.0 µL of the enzyme PKA to the mixture; for a control reaction, no PKA is added. Third, the reaction is run overnight at room temperature. Fourth, the reaction and control are diluted 1:1000, and 1 µL of the diluted solution is added to a volume of 49 µL of MM-Ga solution (approximately 30 nM MM-Ga) in a MES buffer (pH 5.5) in a 384-well plate. Fifth, the plate is incubated at room temperature for 60 min. Finally, the luminescence polarization is measured using an ANALYST™ light-detection platform (Molecular Devices Corporation, Sunnyvale, Calif.). These experiments show that the phosphorylated peptide and the MM-Ga bind to one another specifically, i.e., that the phosphorylated Kemptide and the MM-Ga bind together strongly and that the nonphosphorylated Kemptide and the MM-Ga do not bind together appreciably.

Figure 11:
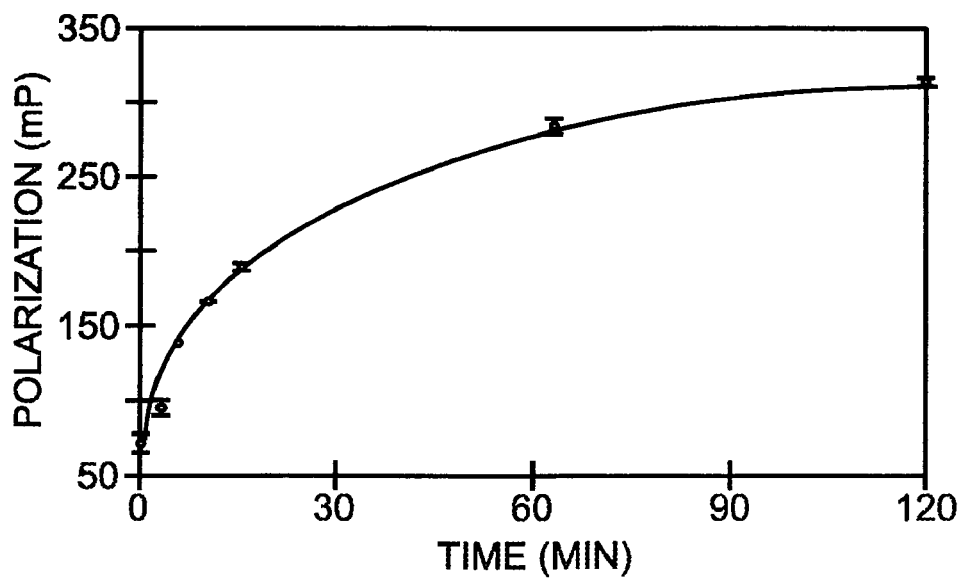
FIG. 11 is a graph showing a time-course assay of PKA activity with MM-Ga performed under the reaction conditions of FIG. 10.

FIG. 11 shows a time-course assay for PKA activity, with MM-Ga, performed under the reaction conditions of FIG. 10. At each time point, 1 µL of reaction mixture is taken out from the reaction and immediately diluted into a volume of 1000 µL of MES buffer. Afterwards, 1 µL of each diluted sample is added to a volume of 49 µL of MM-Ga solution, and an assay is conducted as described above.

Example 5

Examples 3 and 4 describe homogeneous assays in which metal ions (e.g., $Ga^{3+}$) immobilized on macromolecules system bind selectively to phosphorylated peptides generated in a kinase reaction. These assays may be used to monitor the time course and/or end point of a kinase (and/or phosphatase) reaction using various luminescence methods, including luminescence polarization.

This example describes a heterogeneous kinase assay in accordance with aspects of the present teachings. Here, the feasibility of using metal-coated plates in the development of generic kinase assays is demonstrated with a commercial $Ni^{2+}$-coated plate (Pierce, Rockford, Ill.), in which the $Ni^{2+}$ is replaced with $Ga^{3+}$. Specifically, 200 µL of a 0.5 M EDTA-containing solution is added to each well of a 96-well $Ni^{2+}$-coated plate, and the plate is incubated at room temperature for 1 hour. The process is repeated two more times to remove at least substantially all of the $Ni^{2+}$ from the plate. The plate then is washed 3 times with 10 mM Tris buffer (pH 7.4). Next, 200 µL of a 0.1 M $GaCl_3$ solution is added to each well of the plate, and the plate is incubated overnight at room temperature. The plate is washed three times before being used in a kinase assay. This procedure effectively converts the walls of the plate into assay surfaces capable of binding a phosphorylated substrate but not a nonphosphorylated substrate.

Figure 12:
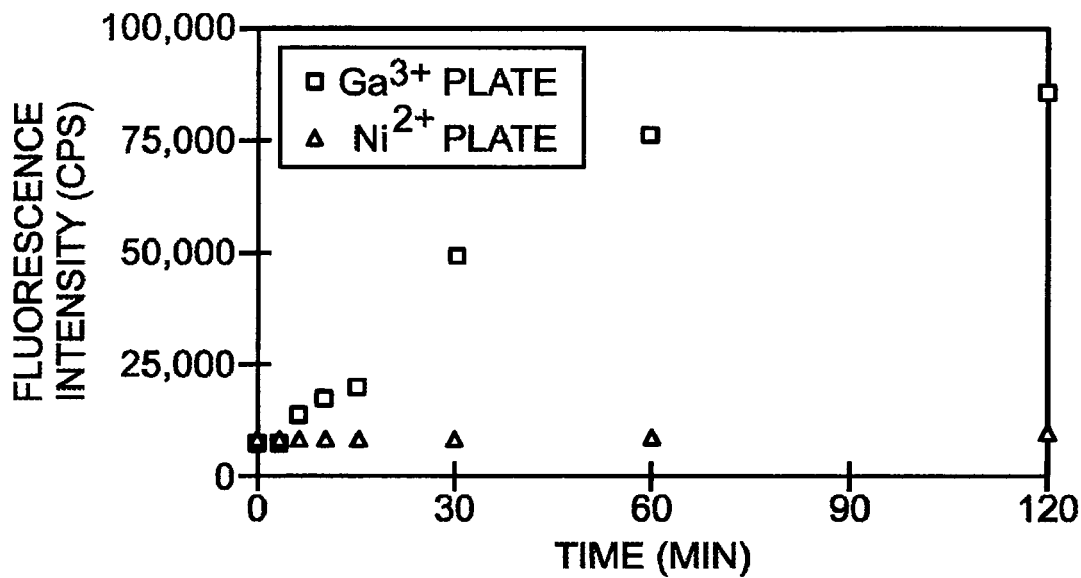
FIG. 12 is a graph showing a time-course assay of PKA activity with a $Ga^{3+}$-coated plate.

FIG. 12 shows results from a kinase assay and an associated control assay. The kinase reaction is set up as described previously, using PKA as the enzyme and fluorescein-Kemptide (SEQ ID NO:1) as the substrate. At each time point, 1 µL is taken from the reaction and diluted into 1000 µL of MES buffer. Later, a volume of 100 µL of each diluted solution is added to the $Ga^{3+}$-coated plate or (as a control) an unmodified $Ni^{2+}$-coated plate and incubated for 1 hour at room temperature. Then, the plate is washed three times, and 100 µL of a 1 M $KH_2PO_4$ solution is added to elute the bound phosphorylated Kemptide from the plate. The luminescence intensity is measured using an ANALYST™ light-detection platform (Molecular Devices Corporation, Sunnyvale, Calif.), which is set in fluorescence intensity mode and fitted with a medium attenuator. The luminescence may be measured from above and/or below the sample, for example, from below the sample by detecting through a lower surface of the sample well that transmits light. In some embodiments, a blocking reagent such as a quencher may be added to the sample to reduce luminescence (and hence background) from unbound components of the sample.

These experiments show the viability of a heterogeneous assay format and the specificity of binding to the tricationic versus dicationic metal ion. The heterogeneous assay format offers many of the advantages of the homogenous assays, including its applicability in principle to any kinase regardless of its substrate specificity. This may save assay developers 3 to 6 months of time and effort in making antibodies that recognize specifically a phosphorylated version of an amino acid sequence. The lack of availability of such special antibodies often is the major obstacle in the development of nonradioactive kinase assays. The heterogeneous assay format also allows for simple detection using luminescence intensity, without requiring polarizers or selection of complementary energy transfer pairs.

Example 6

This example describes assays for the presence, activity, substrates, and/or products of phosphodiesterases in accordance with aspects of the present teachings. Similar assays may be used to analyze cyclases in which the substrate of the phosphodiesterase reaction becomes the product of the cyclase reaction.

Phosphodiesterases (PDEs) catalyze the decyclization of cyclic nucleotides to the corresponding noncyclized nucleotide monophosphate, as shown below:

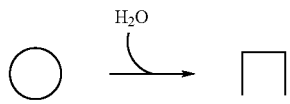

Thus, the presence and/or activity of a PDE may be detected by a decrease in the concentration of a cyclic nucleotide (cNMP) substrate and/or by an increase in the concentration of a corresponding noncyclized nucleotide monophosphate (NMP) product. (The presence and/or activity of a cyclase may be detected similarly by a decrease in the concentration of a nucleotide triphosphate substrate and/or by an increase in the concentration of a corresponding cyclic nucleotide.) The present teachings provide among others PDE assays that involve contacting a sample containing a candidate PDE (and optionally a modulator thereof) with a luminescently labeled cyclic nucleotide and a binding partner that binds specifically to the corresponding noncyclized nucleotide monophosphate but not to the cyclic nucleotide. The binding partner may include one or more of the attributes described above, such as a tricationic metal $M^{3+}$ (e.g., $Al^{3+}$, $Ga^{3+}$, and/or $Fe^{3+}$) capable of binding a noncyclized phosphate group but not a cyclized phosphate group, and optionally an energy transfer partner and/or quencher. PDE activity may be detected by an increase in NMP binding using any technique capable of measuring such an increase, including luminescence polarization, luminescence resonance energy transfer, luminescence intensity, and/or nonluminescence and/or heterogeneous techniques, among others. For example, PDE activity may be detected following NMP binding by (1) an increase in luminescence polarization (assuming that the lifetime and rotational correlation time of the binding partner are selected so that binding of the NMP to the binding partner measurably decreases the rotational correlation time of the NMP), (2) an increase in luminescence resonance energy transfer (assuming that the binding partner is associated with a suitable energy transfer partner), and/or (3) a decrease in luminescence intensity (assuming that the binding partner is associated with a suitable luminescence quencher).

The assays may include (1) contacting a sample containing a candidate PDE (and/or other cell-signaling component) with a luminescently labeled cyclic nucleotide and a binding partner capable of distinguishing between the cyclic nucleotide and the corresponding nucleotide monophosphate, (2) illuminating the sample with light capable of inducing luminescence in the sample, (3) measuring a property of the luminescence transmitted from the sample, and (4) correlating the property with the presence and/or activity of the cyclic nucleotide and/or the corresponding nucleotide monophosphate and hence the presence and/or activity of an associated enzyme.

The present teachings also provide methods for identifying modulators such as agonists and inhibitors of receptors and/or enzymes involved in the production and/or regulation of cell-signaling molecules, such as the hydrolysis of cyclic nucleotides. The methods may include looking for the effects of a modulator by conducting a method for determining the concentration of a cyclic nucleotide and/or the corresponding nucleotide monophosphate in both the presence and absence of the putative modulator. For example, in a polarization assay in which PDE activity leads to an increase in polarization, a decrease in the measured extent of polarization of the emitted light in the presence of the putative modulator identifies the putative modulator as an inhibitor of the receptor or enzyme, and an increase in the measured extent of polarization in the presence of the putative modulator identifies the putative modulator as an agonist of the receptor or enzyme.

Example 7

This example describes end-point and time-course assays for PDE 5 in accordance with aspects of the present teachings, showing in part the utility of the MM-Ga system in PDE assays. These assays use the following components, among others: (1) cGMP-specific PDE (type V, Calbiochem, La Jolla, Calif.), (2) N-methylanthraniloyl (MANT) cGMP substrate (Molecular Probes, Eugene, Oreg.), and (3) MM-Ga, as described in Example 1. MANT is a compact blue-fluorescing luminophore that attaches to the cGMP via the ribose ring of the cGMP. These assays show the utility of the MM-Ga system for detection of noncyclized GMP and the presence and/or activity of cGMP-specific PDEs.

Figure 13:
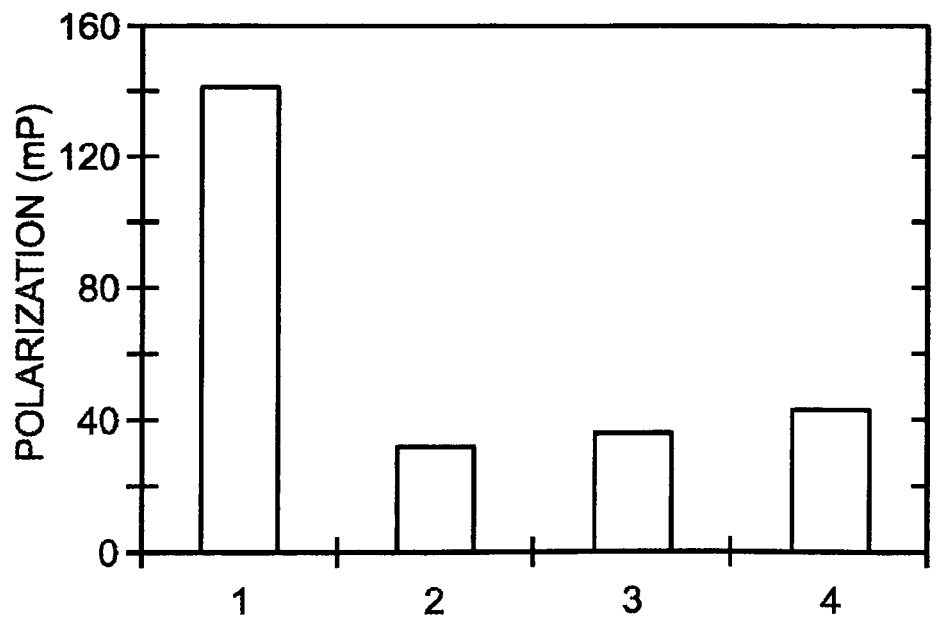
FIG. 13 is a bar graph showing results from an end-point study for CGMP PDE activity using MANT-CGMP and MM-Ga under the following conditions: (1) reaction with enzyme, with MM-Ga, (2) reaction with enzyme, without MM-Ga (3) reaction without enzyme, with MM-Ga (4) reaction without enzyme, without MM-Ga.

FIG. 13 shows results of an end-point assay. Here, 1 µL (50 units) of cGMP specific PDE is added to 50 µL of 5 µM MANT-cGMP in a HEPES buffer (pH 7.5). The tube is incubated at room temperature for 60 minutes. Then, 10 µL of the reaction mixture is added to 40 µL of MES/BSA buffer (pH 5.5) containing approximately 0.8 µM MM-Ga. The resulting mixture is incubated at room temperature for 30 minutes. Then, the luminescence polarization is measured (for MANT, excitation 360 nm, emission 480 nm) using an ANALYST™ light-detection platform (Molecular Devices Corporation, Sunnyvale, Calif.). Results correspond to the following conditions: (1) reaction with enzyme, with MM-Ga, (2) reaction with enzyme, without MM-Ga (3) reaction without enzyme, with MM-Ga, and (4) reaction without enzyme, without MM-Ga. These experiments show that the cyclic GMP and the MM-Ga bind to one another specifically.

Figure 14:
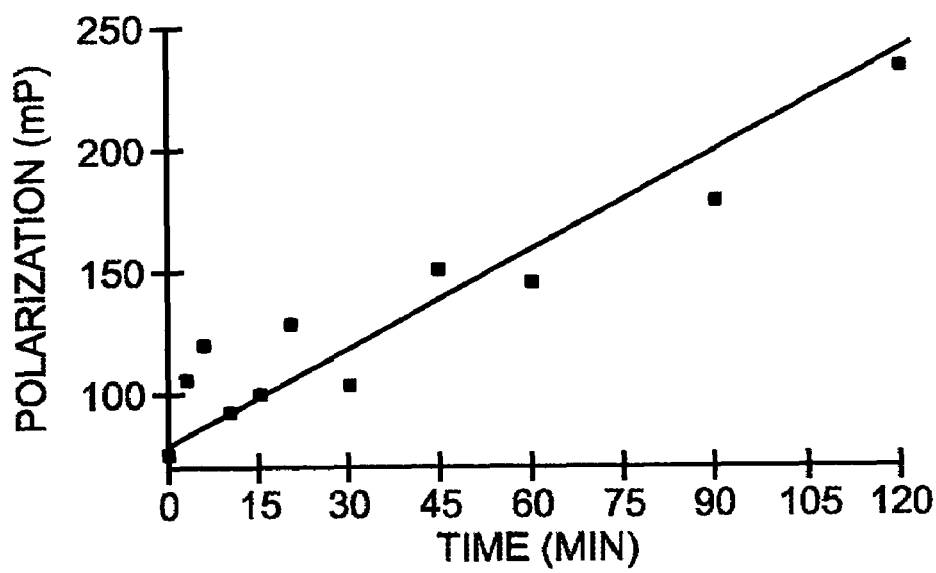
FIG. 14 is a graph showing results from a time-course study conducted using the system of FIG. 13.

FIG. 14 shows results of a time-course assay. Here, a 50-µL solution containing 100 µM MANT-cGMP and 100 units of PDE in HEPES buffer (pH 7.5) is incubated at room temperature. At each time point, 2 µL of reaction mixture is removed from the tube and diluted into 200 μL of MES/BSA buffer (pH 5.5). After 2 hours, 45 μL of each diluted reaction solution is mixed with 5 μL of MM-Ga (approx. 6.4 μM) and incubated at room temperature for 30 minutes before the fluorescence polarization is measured.

Example 8

This example describes alternative PDE assays in accordance with aspects of the present teachings. These assays are presented in a homogenous, nonradioactive format using a carboxyfluorescein labeled CGMP substrate. The assay also may be used in a heterogeneous format and/or with an alternative luminescent cGMP and/or cAMP. These assays further show the utility of the MM-Ga system for detection of non-cyclized GMP and the presence and/or activity of cGMP-specific PDEs, including the use of a different luminophore than the MANT of Example 7.

Figure 15:
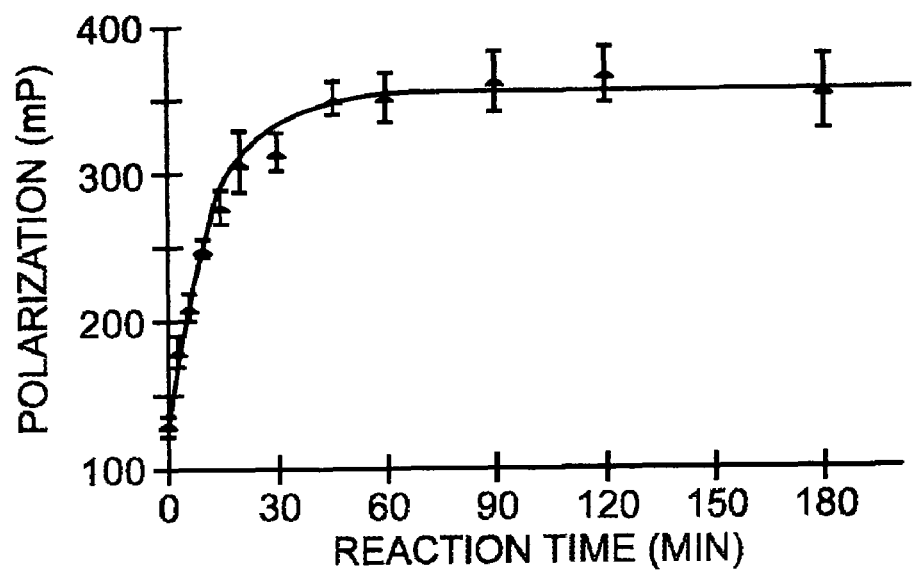
FIG. 15 is a graph showing results from a time-course study for cGMP PDE activity using fluorescein-cGMP and MM-GA.

FIG. 15 shows results of a time-course assay conducted using fluorescein-cGMP and the PDE and binding partner of Example 7. Here, 2.0 μM fluorescein-cGMP is incubated with 0.5 unit of PDE (V) in a buffer containing 40 mM MOPS (pH 7.5), 0.5 mM EDTA, 15 mM $MgCl_2$, and 0.15 mg/mL BSA in a total volume of 50 μL. At each time point, 1 μL of the reaction mixture is removed and diluted into 200 μL of MES buffer (pH 5.5), and the diluted solution is placed on ice. After the reaction, 25 μL of the diluted solution is mixed with an equal volume of a MM-Ga solution, and incubated at room temperature for 30 minutes before the luminescence polarization value is measured.

Figure 16:
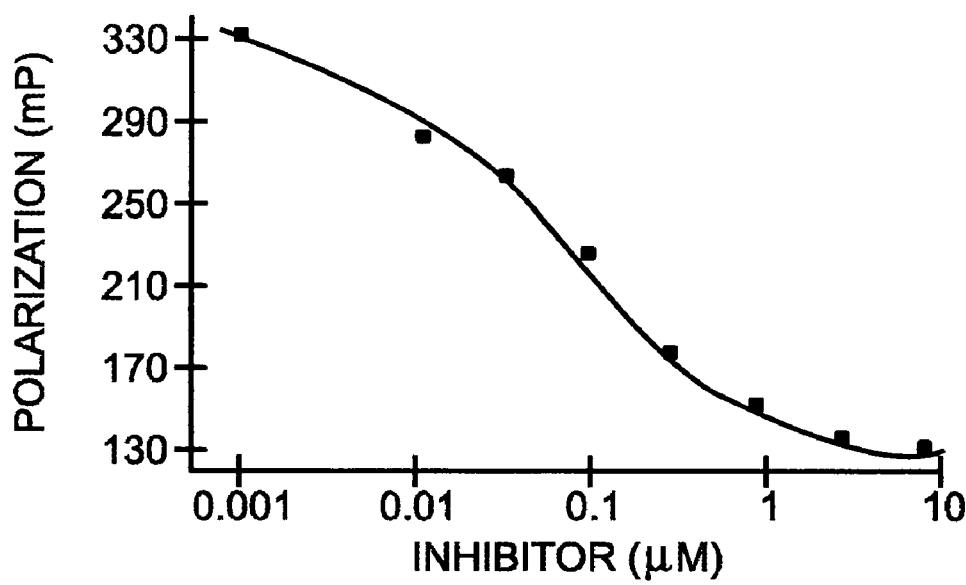
FIG. 16 is a graph showing an IC50 measurement of Zaprinast using the system of FIG. 15.

FIG. 16 shows results of an inhibition assay using the components of FIG. 15. Here, the assay was used to measure the IC50 of the known PDE (V) inhibitor, Zaprinast, using 0.5 μM fluorescein-cGMP and a reaction time of 30 min. These experiments show that the IC50 is about 0.1 μM, in reasonable agreement with the literature value of about 0.3 μM determined using a radioactive assay with $^3$H-cGMP as the substrate.

Example 9

This example describes several aspects of the present teachings, including (1) use of $Ga^{3+}$-coated nanoparticles as the binding component in the assay, (2) applications to the detection of PDE 4 enzyme, with fluorescein-labeled cAMP as substrate, and (3) applications to the detection of PDE 1 enzyme, with both fluorescein-labeled cAMP and fluorescein-labeled cGMP as substrates.

As discussed in Example 1, synthetic polymer macromolecules (MM) can be substituted with other materials that have a high molecular weight and that tricationic cations (i.e., $Fe^{3+}$, $Ga^{3+}$) can be immobilized on. Here, we use selected nanoparticles, including polystyrene nanoparticles having an average diameter of about 40 nm. The nanoparticles are from Bangs Laboratory (Fisher, Ind.), and are modified after acquisition from the vendor to attach $Ga^{3+}$ on the surfaces of the particles.

Figure 17:
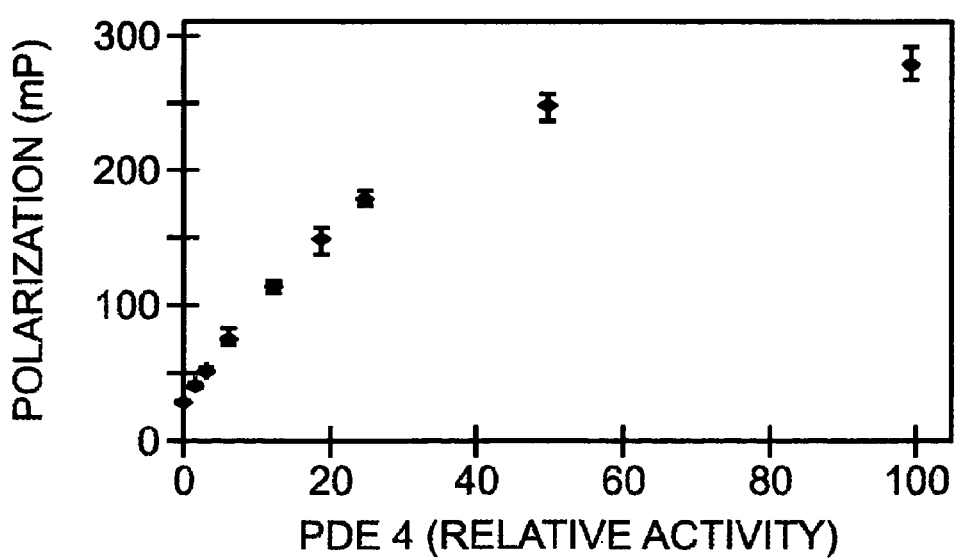
FIG. 17 is a graph showing the detection of PDE 4 activity using a fluorescein-labeled cAMP substrate.

FIG. 17 shows the detection of PDE 4 activity using a fluorescein-labeled cAMP (FL-cAMP) substrate. PDE 4 was obtained from Dr. Macro Conti at Stanford University. In this assay, 10 μL of a solution containing 40 nM of FL-cAMP is mixed with 10 μL of a series of solutions containing various concentrations of PDE 4 in a black 384-well plate. The mixture is incubated at room temperature for 45 min, and then 60 μL of a solution containing 0.16 mg/mL of the modified nanoparticles is added. The new mixture is incubated for 30 min, and then the luminescence polarization is measured.

Figure 18:
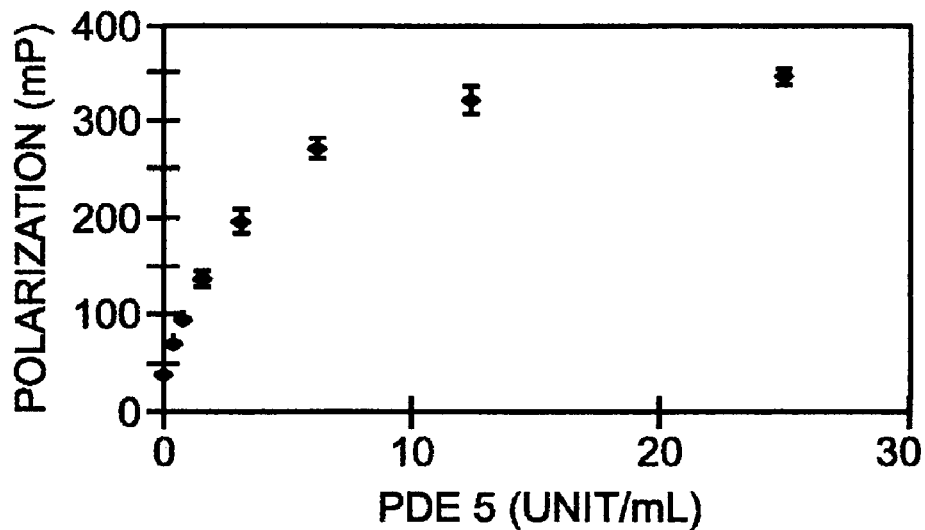
FIG. 18 is a graph showing the detection of PDE 5 activity using a fluorescein-labeled cGMP substrate using the conditions of FIG. 17.

FIG. 18 shows similar results using PDE 5 (Calbiochem, La Jolla, Calif.) as the enzyme and a fluorescein-labeled cGMP (FL-cGMP) as the substrate under the conditions of FIG. 17.

Figure 19:
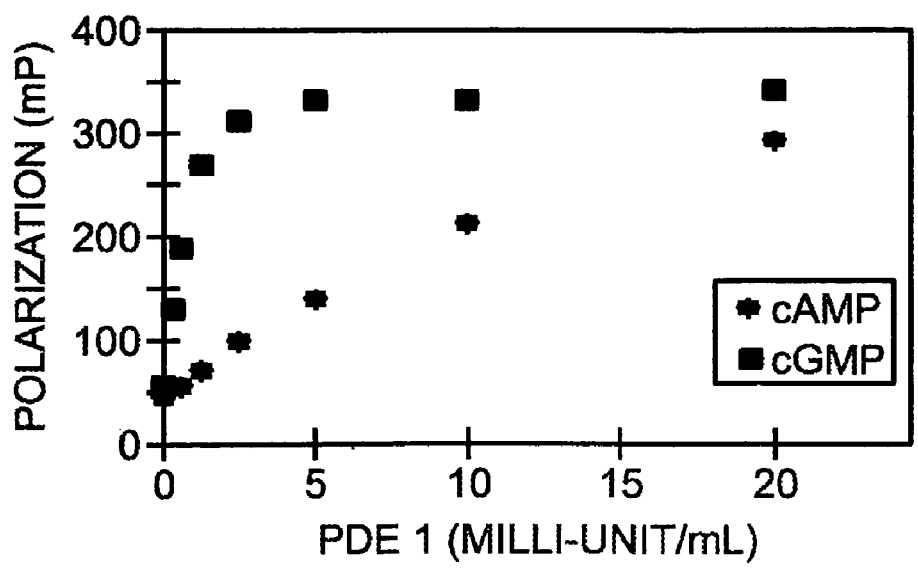
FIG. 19 is a graph showing the detection of PDE 1 activity using fluorescein-labeled cAMP and fluorescein-labeled cGMP substrates under the conditions of FIG. 17.

FIG. 19 shows similar results using PDE 1 (Sigma, St. Louis, Mo.) as the enzyme and both FL-cAMP and FL-cGMP as substrates under the conditions of FIG. 17. PDE 1 is another isozyme in the PDE family of enzymes, which acts on both FL-cAMP and FL-cGMP. The PDE 1 used here is activated according to the vendor's instructions.

Example 10

This example shows representative tracers for use in cyclic nucleotide assays, particularly luminescence-polarization-based cyclic nucleotide assays. General structures for such tracers are shown below for (A) cAMP and (B) cGMP:

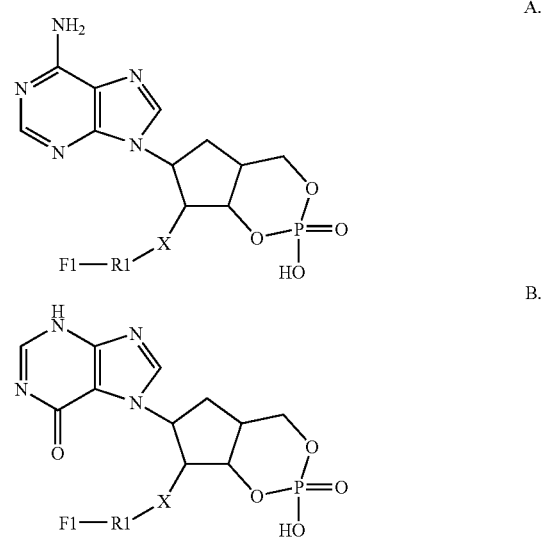

Here, X and R1 represent linkers, which optionally and independently may be present or absent, and Fl represents a reporter species. X may include among others any alkyl, allyl, or aryl linker with ester or ether bonds to the cyclic nucleotide, including —OC(=O)—$CH_2CH_2$C(=O)—. R1 may be any linker joining FL to the nucleotide, directly, or indirectly through X, including a rigid linker having (two) reactive groups for coupling, one to FL and one to the nucleotide. For example, R1 may be a diamino-alkyl, -cycloalkyl, -aryl, or -allyl group, or a dihydroxy group that forms an amide or ester, respectively, with the groups X and Fl. Fl may include any suitable reporter species, such as a luminophore for luminescence assays or an isotope for radioassays. For example, Fl may include a fluorescein or rhodamine that forms a thiourea, ester, or amide bond with the group X. Preferred structures include 1,2 and 1,4-diaminocyclohexyl-linked tracers, as described in U.S. patent application Ser. No. 09/768,661, filed Jan. 23, 2001, which is incorporated herein by reference.

Example 11

This example describes methods and kits for detecting phosphate modifications and/or associated enzymes and modulators in whole cells. The methods generally comprise growing cells under desired conditions, lysing the cells, incubating the cells before and/or after lysis with one or more reagents, and detecting the presence, quantity, and/or activity of species and/or reactions of interest. The kits generally comprise collections of reagents and/or other materials of interest, including substrates, binding partners, and/or lysis buffers, among others. The methods and kits are described greater detail in the context of cyclic nucleotide assays for adherent and suspended cells in Examples 8 and 9 of U.S. patent application Ser. No. 09/768,661, filed Jan. 23, 2001, which is incorporated herein by reference.

Example 12

This example describes miscellaneous applications and other uses for the various assays described herein.

The applications include detecting any of the modifications, enzymes, and/or modulators identified herein and/or in the following U.S. patent applications, which are incorporated herein by reference: Ser. No. 09/768,661, filed Jan. 23, 2001; and Ser. No. 09/596,444, filed Jun. 19, 2000. The modifications include phosphorylation, dephosphorylation, cyclization, and/or decyclization, among others, as described above. The enzymes include kinases, phosphatases, cyclases, and/or phosphodiesterases, among others, including variants such as isoenzymes thereof. For example, the cyclases include adenylyl cyclase and guanylyl cyclase, among others, and the phosphodiesterases include PDE 1 through PDE 10, among others. The modulators include modulators of these enzymes, among others. For example, the cyclase modulators include forskolin and ODQ, among others, and the phosphodiesterase modulators include cilostamide, dipyridamole, EHNA hydrochloride, etazolate hydrochloride, MBCQ, MMPX, MY-5445, Ro 20-1724, rolipram, siguazodan, vinpocetine, and Zaprinast, among others.

The applications also include combining assays for different modifications, enzymes, and/or modulators to form integrated assays, for example, by combining a phosphorylation assay and a cyclization assay to study signaling mechanisms involving multiple cell-signaling pathways.

Example 13

This example describes kits for use in performing assays in accordance with aspects of the present teachings. The kits may include substrates and/or binding partners for performing the assays described herein. These substrates and/or binding partners may include luminophores, quenchers, and/or energy transfer partners, among others. The kits also may include sample holders such as microplates or biochips that have been treated to act as binding partners. The kits optionally may include additional reagents, including but not limited to buffering agents, luminescence calibration standards, enzymes, enzyme substrates, nucleic acid stains, labeled antibodies, or other additional luminescence detection reagents. The substrates, binding partners, and/or additional reagents optionally are present in pure form, as concentrated stock solutions, or in predituted solutions ready for use in the appropriate energy transfer assay. Typically, the kit is designed for use in an automated and/or high-throughput assay, and so is designed to be fully compatible with microplate readers, microfluidic methods, and/or other automated high-throughput methods.

The kit may include various reagents for performing binding assays. The reagents may include a binding reagent and/or one or more binding buffers. The binding reagent may include particles (such as beads). Alternatively, or in addition, the binding reagent may include one or more metals (or metal ions), particularly a strong Lewis acid and/or a metal salt. Exemplary metals or metal ions that may be included are described elsewhere in the present teachings. The binding reagent may be provided in a liquid, particularly an aqueous liquid of any suitable pH. In some examples, the binding reagent may be supplied in an aqueous buffer and/or in an acidic or basic aqueous liquid. The acidic liquid may include any suitable acid, such as hydrochloric acid. The binding reagent may be provided as a concentrated stock configured to be diluted to a lower concentration, for example, in a binding buffer, for use in binding assays. The binding buffer(s) may be provided to be used directly or supplied as a concentrated stock to be diluted any suitable amount. In some embodiments, the binding buffer may be a set of two or more distinct binding buffers configured to be used individually or combined at one or more different ratios according to an aspect of the binding assay to be performed. In some examples, a ratio of the binding buffers (or diluted versions thereof), or one of a set of binding buffers, may be selected (and the binding buffers mixed), according to an aspect of the binding target used in the binding assay. The aspect of the binding target may be its size, structure, charge (predicted, known, or measured, among others), sequence, molecular weight, and/or the like.

Each binding buffer may include any suitable composition. For example, a binding buffer may include a buffering agent (such as acetate, propionate, morpholinoethane-sulfonic acid (MES), etc.), a salt (such as sodium chloride, potassium chloride, etc.), a detergent(s) (ionic or nonionic), and/or the like. In some examples, the kit may include two or more binding buffers of different composition. The two or more binding buffers may be different in pH, buffering agent, buffer concentration, salt identity or concentration, etc. Such binding buffers may be used separately in different binding assays (e.g., selected according to an aspect of the binding reaction and/or binding target) or may be used in combination.

Example 14

This example describes exemplary luminescence assays. Further aspects of these assays as well as additional luminescence assays and apparatus for performing luminescence assays are described in the following materials, which are incorporated herein by reference: U.S. Pat. No. 6,097,025, issued Sep. 24, 1998; U.S. patent application Ser. No. 09/349,733, filed Jul. 8, 1999; U.S. Provisional Patent Application Ser. No. 60/267,639, filed Feb. 10, 2001; and Joseph R. Lakowicz, *Principles of Fluorescence Spectroscopy* ($2^{nd}$ ed. 1999).

Luminescence, as defined above, is the emission of light from excited electronic states of atoms or molecules, including photoluminescence, chemiluminescence, and electrochemiluminescence, among others. Luminescence may be used in a variety of assays, including (A) intensity assays, (B) polarization assays, and (C) energy transfer assays, among others.

A. Intensity Assays

Luminescence intensity assays involve monitoring the intensity (or amount) of light emitted from a composition. The intensity of emitted light will depend on the extinction coefficient, quantum yield, and number of luminescent analytes in the composition, among others. These quantities, in turn, will depend on the environment of the analyte, among others, including the proximity and efficacy of quenchers and energy transfer partners. Thus, luminescence intensity assays may be used to study binding reactions, among other applications.

B. Polarization Assays

Luminescence polarization assays involve the absorption and emission of polarized light. Here, polarization refers to the direction of the light's electric field, which generally is perpendicular to the direction of the light's propagation. In a luminescence polarization assay, specific molecules within a composition are labeled with one or more luminophores. The composition then is illuminated with polarized excitation light, which preferentially excites luminophores having absorption dipoles aligned parallel to the polarization of the excitation light. These molecules subsequently decay by preferentially emitting light polarized parallel to their emission dipoles. The extent of polarization of the total emitted light depends on the extent of molecular reorientation during the time interval between luminescence excitation and emission, which is termed the luminescence lifetime, $\tau$. In turn, the extent of molecular reorientation depends on the luminescence lifetime and the size, shape, and environment of the reorienting molecule. Thus, luminescence polarization assays may be used to quantify binding reactions and enzymatic activity, among other applications. In particular, molecules commonly rotate (or "tumble") via diffusion, with a rotational correlation time $\tau_{rot}$ that is proportional to their volume, or the cube of their radius of gyration. (This cubic dependence on radius makes polarization assays very sensitive to binding.) Thus, during their luminescence lifetime, relatively large molecules will not reorient significantly, so that their total luminescence will be relatively polarized. In contrast, during the same time interval, relatively small molecules will reorient significantly, so that their total luminescence will be relatively unpolarized.

The relationship between polarization and intensity is expressed by the following equation:

$$P = \frac{I_\parallel - I_\perp}{I_\parallel + I_\perp} \quad (1)$$

Here, P is the polarization, $I_\parallel$ is the intensity of luminescence polarized parallel to the polarization of the excitation light, and $I_\perp$ is the intensity of luminescence polarized perpendicular to the polarization of the excitation light. P generally varies from zero to one-half for randomly oriented molecules (and zero and one for aligned molecules). If there is little rotation between excitation and emission, $I_\parallel$ will be relatively large, $I_\perp$ will be relatively small, and P will be close to one-half. (P may be less than one-half even if there is no rotation; for example, P will be less than one-half if the absorption and emission dipoles are not parallel.) In contrast, if there is significant rotation between absorption and emission, $I_\parallel$ will be comparable to $I_\perp$, and P will be close to zero. Polarization often is reported in milli-P units (1000×P), which for randomly oriented molecules will range between 0 and 500, because P will range between zero and one-half.

Polarization also may be described using other equivalent quantities, such as anisotropy. The relationship between anisotropy and intensity is expressed by the following equation:

$$r = \frac{I_\parallel - I_\perp}{I_\parallel + 2I_\perp} \quad (2)$$

Here, r is the anisotropy. Polarization and anisotropy include the same information, although anisotropy may be more simply expressed for systems containing more than one luminophore. In the description and claims that follow, these terms may be used interchangeably, and a generic reference to one should be understood to imply a generic reference to the other.

The relationship between polarization and rotation is expressed by the Perrin equation:

$$\left(\frac{1}{P} - \frac{1}{3}\right) = \left(\frac{1}{P_0} - \frac{1}{3}\right) \cdot \left(1 + \frac{\tau}{\tau_{rot}}\right) \quad (3)$$

Here, $P_0$ is the polarization in the absence of molecular motion (intrinsic polarization), $\tau$ is the luminescence lifetime (inverse decay rate) as described above, and $\tau_{rot}$ is the rotational correlation time (inverse rotational rate) as described above.

The Perrin equation shows that luminescence polarization assays are most sensitive when the luminescence lifetime and the rotational correlation time are similar. Rotational correlation time is proportional to molecular weight, increasing by about 1 nanosecond for each 2,400 dalton increase in molecular weight (for a spherical molecule). For shorter lifetime luminophores, such as fluorescein, which has a luminescence lifetime of roughly 4 nanoseconds, luminescence polarization assays are most sensitive for molecular weights less than about 40,000 daltons. For longer lifetime probes, such as $Ru(bpy)_2dcbpy$ (ruthenium 2,2'-dibipyridyl 4,4'-dicarboxyl-2,2'-bipyridine), which has a lifetime of roughly 400 nanoseconds, luminescence polarization assays are most sensitive for molecular weights between about 70,000 daltons and 4,000,000 daltons.

Luminescence polarization assays may be used in a variety of formats. In one format, the concentration of an analyte in solution can be measured by supplying a labeled tracer that competes with the analyte for a binding moiety, particularly a binding moiety larger than the labeled tracer. In this "competitive" format, the concentration of the analyte is inversely correlated with the enhancement of luminescence polarization in the light emitted by the tracer when it competitively binds the common moiety. In another format, the concentration of a target can be measured by supplying a labeled tracer that is capable of binding the target. In this case, the enhancement of polarization is a direct measure of the concentration of target. The target further may be, for example, an activated receptor, where activation can be indirectly measured by the directly measured concentration of a generated molecule or by its binding to labeled tracer per se.

C. Energy Transfer Assays

Energy transfer is the transfer of luminescence energy from a donor luminophore to an acceptor without emission by the donor. In energy transfer assays, a donor luminophore is excited from a ground state into an excited state by absorption of a photon. If the donor luminophore is sufficiently close to an acceptor, excited-state energy may be transferred from the donor to the acceptor, causing donor luminescence to decrease and acceptor luminescence to increase (if the acceptor is luminescent). The transfer may occur if the absorption spectrum of the acceptor overlaps the emission spectrum of the donor (matching electron vibrational levels). The efficiency of this transfer is very sensitive to the separation R between donor and acceptor, decaying as $1/R^{-6}$. Thus, the separation between donor and acceptor in energy transfer assays may be very small, typically about 1-10 μm. The efficiency of this transfer also is sensitive to the relative orientations of the donor and acceptor; for example, the donor and acceptor transition dipole orientations should be approximately parallel for optimal energy transfer. Energy transfer assays use energy transfer to monitor the proximity of donor and acceptor, which in turn may be used to monitor the presence or activity of an analyte, among others.

Energy transfer assays may focus on an increase in energy transfer as donor and acceptor are brought into proximity. These assays may be used to monitor binding, as between two molecules X and Y to form a complex X:Y. Here, colon (:) represents a noncovalent interaction. In these assays, one molecule is labeled with a donor D, and the other molecule is labeled with an acceptor A, such that the interaction between X and Y is not altered appreciably. Independently, D and A may be covalently attached to X and Y, or covalently attached to binding partners of X and Y.

Energy transfer assays also may focus on a decrease in energy transfer as donor and acceptor are separated. These assays may be used to monitor cleavage, as by hydrolytic digestion of doubly labeled substrates (peptides, nucleic acids). In one application, two portions of a polypeptide are labeled with D and A, so that cleavage of the polypeptide by a protease such as an endopeptidase will separate D and A and thereby reduce energy transfer. In another application, two portions of a nucleic acid are labeled with D and A, so that cleave by a nuclease such as a restriction enzyme will separate D and A and thereby reduce energy transfer.

Energy transfer between D and A may be monitored in various ways. For example, energy transfer may be monitored by observing an energy-transfer induced decrease in the emission intensity of D and increase in the emission intensity of A (if A is a luminophore). Energy transfer also may be monitored by observing an energy-transfer induced decrease in the lifetime of D and increase in the apparent lifetime of A.

In a preferred mode, a long-lifetime luminophore is used as a donor, and a short-lifetime luminophore is used as an acceptor. Suitable long-lifetime luminophores include metal-ligand complexes containing ruthenium, osmium, etc., and lanthanide chelates containing europium, terbium, etc. In time-gated assays, the donor is excited using a flash of light having a wavelength near the excitation maximum of D. Next, there is a brief wait, so that electronic transients and/or short-lifetime background luminescence can decay. Finally, donor and/or acceptor luminescence intensity is detected and integrated. In frequency-domain assays, the donor is excited using time-modulated light, and the phase and/or modulation of the donor and/or acceptor emission is monitored relative to the phase and/or modulation of the excitation light. In both assays, donor luminescence is reduced if there is energy transfer, and acceptor luminescence is observed only if there is energy transfer.

Example 15

This example shows assays with improved signals, signal-to-noise ratios, and/or signal-to-background ratios.

Signal may be enhanced in several ways, including (1) using a high color temperature light source, such as a xenon arc lamp, in a continuous illumination mode, (2) using a dichroic or multi-dichroic beamsplitter, and/or (3) using a sample holder whose shape is "matched" to the shape of the optical beam of the instrument, especially if the sample holder is elevated to bring the sample closer to a detector. The high color temperature light source increases the number of usable photons, which is important because the lower limit of the signal-to-noise ratio is set by the square root of the total number of photons collected in the measurement. These enhancements are described in more detail in the following U.S. Patent Applications, which are incorporated herein by reference: Ser. No. 09/349,733, filed Jul. 8, 1999; Ser. No. 09/478,819, filed Jan. 5, 2000; and Ser. No. 09/494,407, filed Jan. 28, 2000.

Signal-to-noise ratios can be enhanced at least in part by increasing signals, for example, by using the techniques described in the previous paragraph.

Signal-to-background ratios can be enhanced in several ways, including (1) using confocal optical systems having a sensed volume to avoid luminescence from the microplate walls, (2) selecting a microplate or other substrate that increases the signal and reduces the luminescent background from materials in the microplate, (3) selecting the light sources, luminescence filters, optics, signal collection electronics, and mechanical system used in the luminescence detection optical system for maximum signal-to-background ratio, and (4) utilizing signal processing, background subtraction, and luminescence lifetime techniques, particularly FLAMe™ methodology for background reduction, as described below. These enhancements are described in more detail in the following U.S. patent and U.S. patent applications, which are incorporated herein by reference: U.S. Pat. No. 6,071,748, issued Apr. 17, 1998; Ser. No. 09/349,733, filed Jul. 8, 1999; Ser. No. 09/478,819, filed Jan. 5, 2000; and Ser. No. 09/494,407, filed Jan. 28, 2000.

Example 16

This example shows mechanisms for increasing the change in polarization that accompanies a change in binding, so that the change in binding can be measured more easily. These mechanisms may be used in any of the assays described here involving luminescently labeled species, such as labeled cyclic nucleotides and labeled nonhydrolyzable GTP analogs, among others.

The change in polarization upon binding can be increased by making any linker between the luminophore and the labeled species (e.g., the cyclic nucleotide or GTP analog) as short and/or rigid as possible, while maintaining relevant substrate properties for the enzymes involved in the assay. Short and/or rigid linkers will restrict luminophore motion relative to the labeled species, reducing the "propeller effect" so that the luminophore more accurately reports the motion of both the free and bound labeled species. The rigidity of the linker may be increased by avoiding using hexanoic acid linkers, which typically are long and flexible, and by using cyclic linkers and amide groups in place of methylene groups, among other mechanisms.

The change in polarization upon binding also can be increased by including an appropriately positioned energy transfer acceptor on the binding partner, so that energy transfer will occur from the luminophore to the acceptor upon incorporation. Such energy transfer will shorten the lifetime of the luminophore, thereby increasing its polarization (because polarization varies inversely with lifetime, all else being equal).

The change in polarization upon binding also can be increased by decreasing the mobility of the binding partner for the labeled species. Mobility can be decreased by increasing the size of the binding partner, either directly or by forming a complex with a mass label. Suitable mass labels include other molecules and beads, among others.

The use of mass labels is described in detail in U.S. patent application Ser. No. 09/768,742, filed Jan. 23, 2001, which is incorporated herein by reference. Mobility also can be decreased by attaching the binding partner to a surface, such as the surface of a sample holder. Attachment to other molecules, beads, and/or surfaces may be accomplished using any of a number of well-known reactive groups.

The assays provided by the present teachings may have advantages over prior assays for detecting molecular modifications. The existence and/or identity of these advantages will depend on such as (but not always requiring) one or more of the following. First, they may be used without radioactivity. Second, they may be homogenous, so that they do not require physical separation steps or wash steps. Third, they may have stable endpoints, so that results are relatively insensitive to the timing of any measurement or detection steps. Fourth, they may be sensitive, so that picomolar amounts of cyclic nucleotides may be detected. Fifth, they may be used with solution and cell-based samples.

Example 17

This example lists exemplary peptides and phosphopeptides that may be used in molecular modification assays according to the present teachings, and exemplary uses for these peptides and phosphopeptides; see Tables 5 and 6. A number of these peptides/phosphopeptides are used in subsequent Examples for exemplary binding assays.

TABLE 5

| Sequence Identifier | Peptide sequence |
| --- | --- |
| SEQ ID NO:2 | 5FAM-Lys-Lys-Gly-Glu-Ala-Ile-Tyr-Ala-Ala-Pro-Phe-Ala-CONH₂ |
| SEQ ID NO:3 | 5FAM-Val-Ser-Arg-Ser-Gly-Leu-Tyr-Arg-Ser-Pro-Ser-Met-Pro-Glu-Asn-Leu-Asn-Arg-Pro-Arg |
| SEQ ID NO:4 | 5FAM-Ala-Leu-Lys-Leu-Val-Arg-Tyr-Pro-Ser-Phe-Val-Ile-Thr-Ala-Lys-CONH₂ |
| SEQ ID NO:5 | 5FAM-Ala-Met-Arg-Leu-Glu-Arg-Gln-Asp-Ser-Ile-Phe-Tyr-Pro-Lys-CONH₂ |
| SEQ ID NO:6 | 5FAM-Gly-Arg-Pro-Arg-Thr-Ser-Ser-Phe-Ala-Glu-Gly |
| SEQ ID NO:7 | 5FAM-Gly-Arg-Pro-Arg-Thr-Ser-pSer-Phe-Ala-Glu-Gly |
| SEQ ID NO:8 | 5FAM-Lys-Lys-Lys-Lys-Glu-Glu-Ile-Tyr-Phe-Phe-Phe-Gly-CONH₂ |
| SEQ ID NO:9 | Leu-Val-Glu-Pro-Leu-Thr-Pro-Ser-Gly-Glu-Ala-Pro-Asn-Gln-Lys-5FAM-COOH |
| SEQ ID NO:10 | 5FAM-pTyr-Thr-Gly-Leu-Ser-Thr-Arg-Asn-Gln-Glu-Thr-pTyr-Glu-Thr-Leu-CONH₂ |
| SEQ ID NO:11 | 5FAM-Lys-Lys-Leu-Asn-Arg-Thr-Leu-Ser-Val-Ala |
| SEQ ID NO:12 | 5TAMRA-Lys-Lys-Leu-Asn-Arg-Thr-Leu-Ser-Val-Ala |
| SEQ ID NO:13 | 5FAM-Gly-Gly-Gly-Pro-Ala-Thr-Pro-Lys-Lys-Ala-Lys-Lys-Leu |
| SEQ ID NO:14 | 5FAM-Gly-Arg-His-Asp-Ser-Gly-Leu-Asp-Ser-Met-Lys-CONH₂ |
| SEQ ID NO:15 | 5FAM-Lys-Lys-Ser-Arg-Gly-Glu-Tyr-Met-Thr-Met-Gln-Ile-Gly-CONH₂ |
| SEQ ID NO:16 | 5FAM-Glu-Phe-Pro-Ile-Tyr-Asp-Phe-Leu-Pro-Ala-Lys-Lys-Lys-CONH₂ |

TABLE 5-continued

| Sequence Identifier | Peptide sequence |
| --- | --- |
| SEQ ID NO:17 | 5FAM-Lys-Val-Glu-Lys-Ile-Gly-Glu-Gly-Thr-Tyr-Gly-Val-Val-CONH₂ |
| SEQ ID NO:18 | 5FAM-Lys-Val-Glu-Lys-Ile-Gly-Glu-Gly-Thr-pTyr-Gly-Val-Val-CONH₂ |
| SEQ ID NO:19 | 5FAM-Leu-Asp-Val-Pro-Ile-Pro-Gly-Arg-Phe-Asp-Arg-Arg-Val-pSer-Val-Ala-Ala-Glu-CONH₂ |
| SEQ ID NO:20 | 5FAM-Gly-Arg-Thr-Gly-Arg-Arg-Asn-Ser-Ile-CONH₂ |
| SEQ ID NO:21 | 5FAM-Ala-Lys-Arg-Arg-Arg-Leu-Ser-Ser-Leu-Arg-Ala |
| SEQ ID NO:22 | 5FAM-Leu-Arg-Arg-Arg-Leu-Ser-Asp-Ala-Asn-Phe-CONH₂ |
| SEQ ID NO:23 | 5FAM-Ala-Leu-Gln-Lys-Asp-Tyr-Glu-Asn-Val-Gly-Val-CONH₂ |
| SEQ ID NO:24 | 5FAM-Ala-Leu-Glu-Lys-Asp-Tyr-Glu-Asp-Val-Gly-Val-CONH₂ |
| SEQ ID NO:25 | 5-FAM-Arg-Arg-Arg-Ala-Asp-Asp-Ser-Asp-Asp-Asp-Asp-Asp |

Notes for Table 5:
5FAM is 5-carboxyfluorescein;
5TAMRA is 5-carboxytetramethylrhodamine;
pSer is phosphorylated serine (phosphoserine);
pTyr is phosphorylated tyrosine (phosphotyrosine);
and
CONH2 is an amidated C-terminus on the peptide (otherwise the C-terminus includes a free carboxy group).

Each sequence identifier (and peptide sequence) of Table 5 is correlated below, in Table 6, with a peptide name (and/or source protein), an exemplary enzyme(s) assayed with the peptide, and the number of carboxy groups in the peptide.

TABLE 6

| Sequence Identifier | Peptide Name | Exemplary Enzyme Assays | #COOHs |
| --- | --- | --- | --- |
| SEQ ID NO: 2 | Abl/Arg Substrate Peptide | Abl Arg | 1 |
| SEQ ID NO: 3 | Cdc25C-derived peptide | PRK2 | 2 |
| SEQ ID NO: 4 | CHK1tide | CHK1 | 0 |
| SEQ ID NO: 5 | CHK2tide | CHK2 | 2 |
| SEQ ID NO: 6 | Crosstide | Akt1 Akt2 Akt3 MSK1 MSK2 SGK1 | 2 |
| SEQ ID NO: 7 | Phospho-Crosstide | PP2A PP1 | 2 |
| SEQ ID NO: 8 | CSKtide | CSK | 2 |
| SEQ ID NO: 9 | EGFR-derived Peptide | p38 (α, β, γ, δ isoforms) | 3 |
| SEQ ID NO: 10 | FcεRI γ-chain ITAM-derived | PTP1B | 2 |
| SEQ ID NO: 11 | Fluorescein-Labeled Glycogen Synthase-Derived Peptide | MAPKAP K2 PRAK CaM KII | 1 |
| SEQ ID NO: 12 | TAMRA-Labeled Glycogen | MAPKAP K2 PRAK | 1 |

TABLE 6-continued

| Sequence Identifier | Peptide Name | Exemplary Enzyme Assays | #COOHs |
|---|---|---|---|
| | Synthase-derived peptide | CaM KII | |
| SEQ ID NO: 13 | CDKtide; Histone H1-derived peptide | CDK1/Cyclin B CDK2/Cyclin A CDK5/p35 | 1 |
| SEQ ID NO: 14 | IκBα-derived peptide | IKKβ IKKα | 2 |
| SEQ ID NO: 15 | IRS1-derived peptide | Insulin Receptor IGF1-R | 1 |
| SEQ ID NO: 16 | Lyn/Blk Phage Display-derived Peptide | Blk Lyn | 2 |
| SEQ ID NO: 17 | P34$^{cdc2}$-derived Peptide | Src Fyn Lck Yes | 2 |
| SEQ ID NO: 18 | P34$^{cdc2}$-derived phosphopeptide | Src Fyn Lck | 2 |
| SEQ ID NO: 19 | PKA regulatory subunit-derived phosphopeptide | Calcineurin | 3 |
| SEQ ID NO: 20 | PKAtide | PKA | 0 |
| SEQ ID NO: 21 | S6 Ribosomal Protein-derived Peptide | ROCK-II Rsk2 | 1 |
| SEQ ID NO: 22 | Synapsin I-derived peptide | CaMK IV | 1 |
| SEQ ID NO: 23 | alpha-Tubulin-derived Peptide | Syk Zap 70 | 2 |

Example 18

Figure 20:
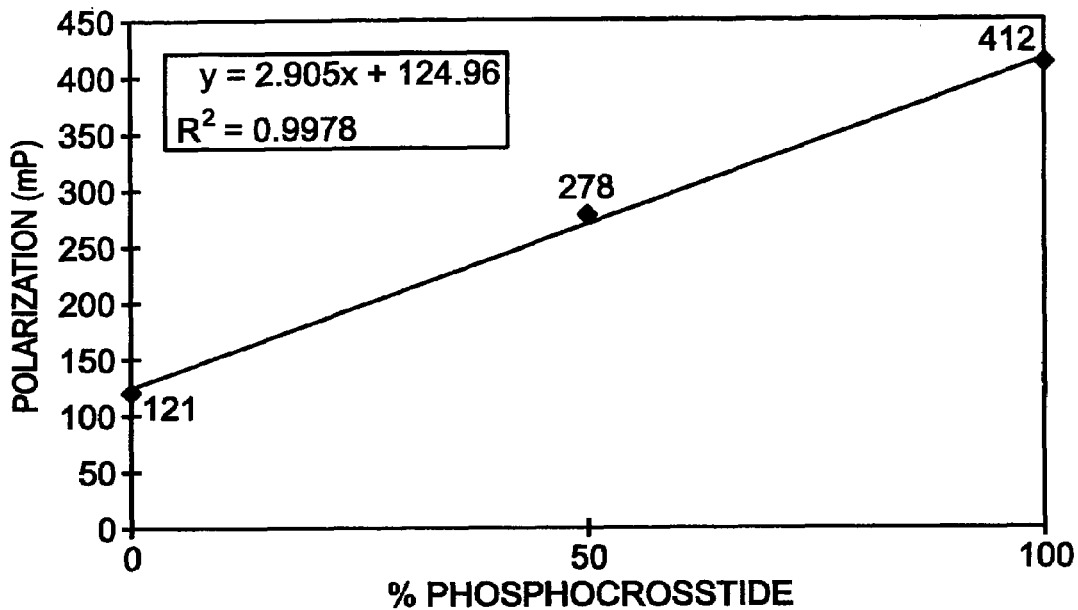
FIG. 20 is a graph showing results from binding assays using a metal salt without associated beads to provide the binding partner for phosphorylated or nonphosphorylated binding targets, in accordance with aspects of the present teachings.

This example describes an experiment to test if a metal salt, gallium chloride, in the absence of associated beads, can serve as a phosphate-binding partner to distinguish between phosphorylated and nonphosphorylated forms of a peptide in a binding assay; see FIG. 20.

The binding assay was carried out by preparing a set of binding reactions having different ratios of fluorescein-labeled (FL) Crosstide and Phosphocrosstide peptides (SEQ ID NOS:6 and 7, respectively). The total peptide concentration before dilution with binding partner was 100 nM in binding buffer (20 μL/well). Each binding reaction included gallium chloride as the binding partner. Gallium chloride was prepared as a concentrated solution at 300 mM in 0.1 M HCl. The concentrated solution was diluted to 300 μM in binding buffer, and 60 μL was added to each binding reaction. Fluorescence polarization (mP) was measured. (Binding buffers are described in more detail below in Example 22.)

FIG. 20 shows the results of the binding reactions in graphical form. The graph plots fluorescence polarization (a measure of binding) as a function of percentage FL-Phosphocrosstide. The standard curve produced, which has a maximum change in fluorescence polarization of 291 mP, is similar to one generated using gallium ions associated with beads.

Example 19

Figure 21:
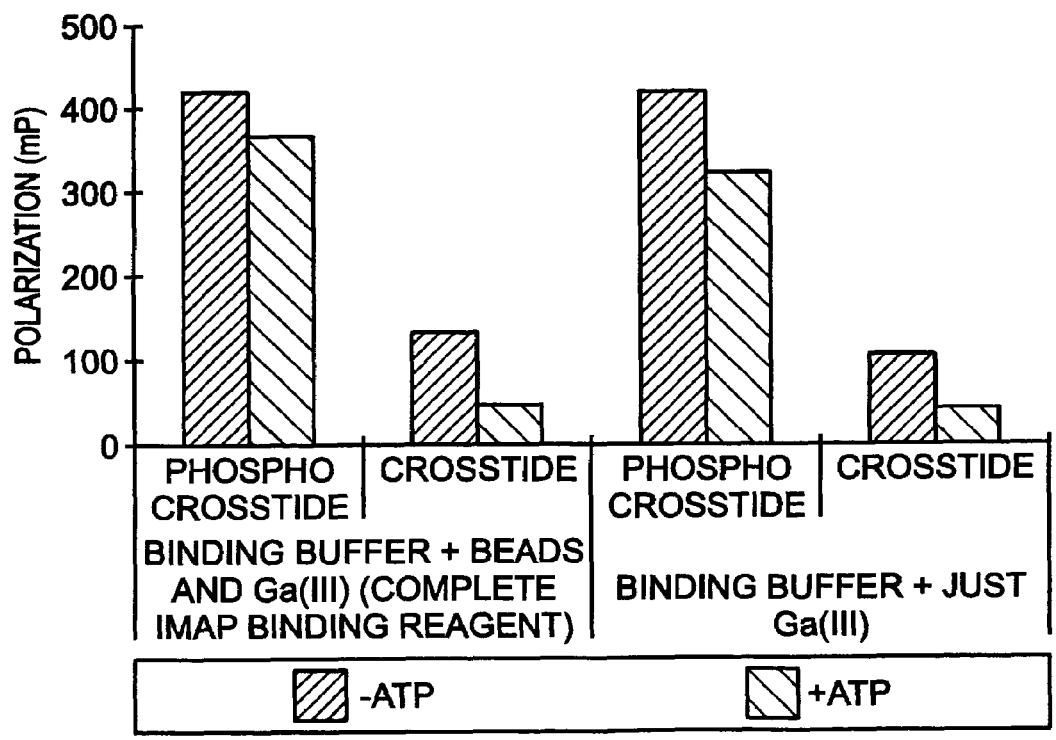
FIG. 21 is a bar graph showing results from binding assays conducted with an untethered metal ("no beads") or a particle-associated derivative thereof ("beads") as the binding partner for peptide binding targets, in the presence or absence of an ATP challenge, in accordance with aspects of the present teachings.

This example describes experiments comparing peptide binding in binding assays that include a gallium salt without beads or associated with beads; see FIG. 21.

Each binding reaction initially included fluorescein labeled ("FL") Crosstide or Phosphocrosstide (SEQ ID NOS:6 and 7, respectively) at 100 nM in 20 μL of binding buffer. Solutions of gallium chloride were prepared as described in Example 18, with or without associated beads. The gallium chloride solutions were diluted 1:400 in binding buffer, and 60 μL were added to the binding reactions. A subset of the binding reactions also included 100 μM ATP. Fluorescence polarization was measured.

FIG. 21 shows a bar graph of the results. The bar graph plots the measured fluorescence polarization (binding) as a function of the composition of each binding assay. Composition variables include presence or absence of ATP, presence of Phosphocrosstide or Crosstide as binding target, and use of gallium chloride alone (right side) or gallium chloride associated with beads (left side). The results indicate that ATP affects binding substantially the same when the binding partner is gallium chloride alone or gallium chloride associated with beads.

Example 20

Figure 22:
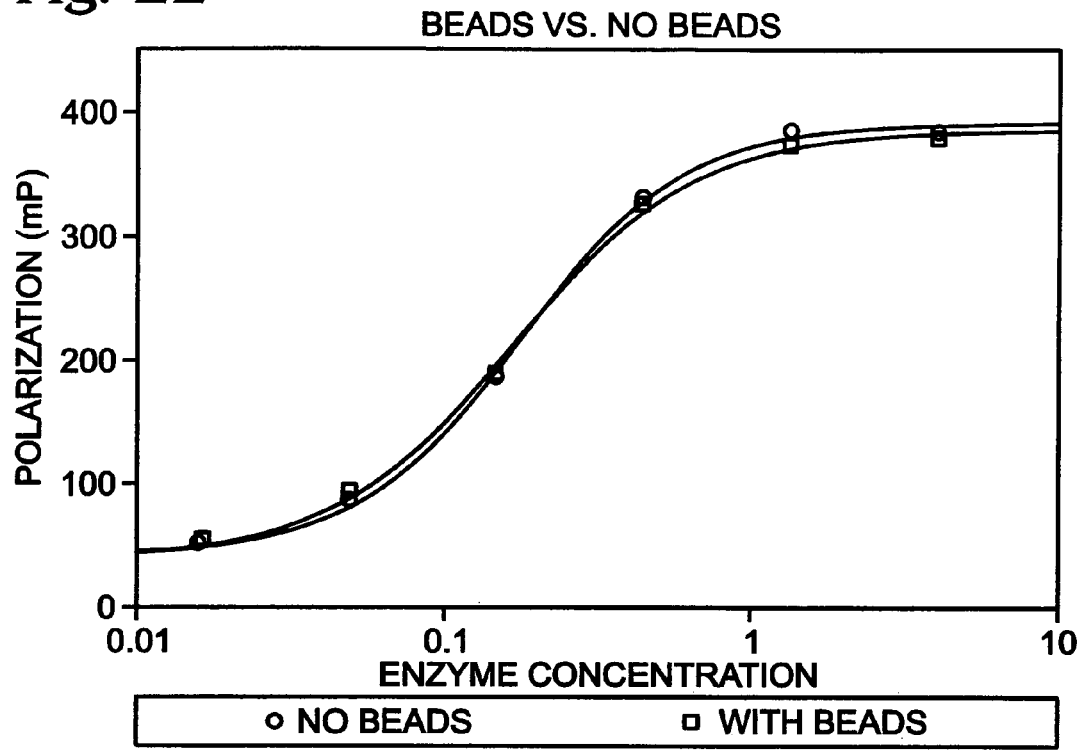
FIG. 22 is graph showing results from binding assays conducted using a tethered or untethered metal to measure the kinase activity of MAPKAP Kinase 2, in accordance with aspects of the present teachings.

This example describes experiments to test the ability of an untethered metal salt ("no beads") to act as a phosphate-specific binding partner in a kinase assay; see FIG. 22.

Kinase reactions with MAPKAP Kinase 2 enzyme were performed in 20 μL using 100 nM substrate (SEQ ID NO:11) and 10 μM ATP, as described generally in Appendices A and B of U.S. Provisional Patent Application Ser. No. 60/436,725, filed Dec. 26, 2002, which is incorporated herein by reference. Duplicate sets of reactions were prepared with a range of amounts of MAPKAP Kinase 2 enzyme and were reacted for about 60 minutes and then stopped with acid (low pH solution). After the reaction was stopped, the reaction products of each set were incubated with a binding solution (60 μL) for 30 minutes at room temperature. The binding solutions for one set included gallium ions associated with beads ("beads") and for the other set included 300 μM gallium chloride without beads ("no beads"). After incubation with the binding solutions, fluorescence polarization was measured.

FIG. 22 shows the results of the binding assays. The results are presented as a graph of measured fluorescence polarization (y-axis) as a function of enzyme concentration (x-axis) on a log scale. The curves generated with gallium chloride in the presence or absence of beads in the binding solution are essentially identical. Accordingly, metal ions not associated with beads, as binding partners in enzyme assays, may be as effective as corresponding bead-associated metal ions.

Example 21

Figure 23:
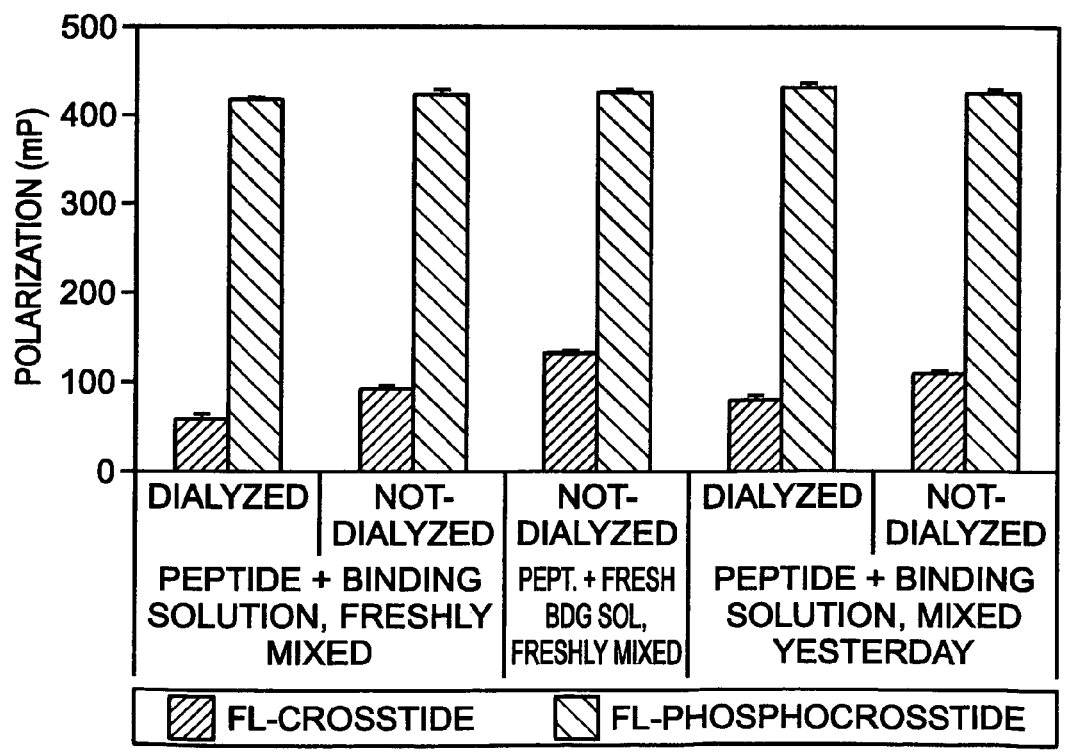
FIG. 23 is a bar graph showing results from binding assays conducted with dialyzed or nondialyzed forms of an untethered metal (not associated with beads), in accordance with aspects of the present teachings.

This example explores possible hypotheses for the ability of a metal salt, in the absence of beads, to affect fluorescence polarization substantially, and describes experiments to distinguish between these hypotheses; see FIG. 23.

A number of hypotheses may account for the ability of a "beadless" metal salt to produce the observed change in fluorescence polarization as a binding partner in the experiments of Examples 18-20. Two of these hypotheses are considered here in more detail. Hypothesis 1: interaction between the metal salt, binding target (phosphopeptide), and possibly other components in the binding reaction shortens the fluorescence lifetime of the fluorophore, producing a corresponding increase in fluorescence polarization. Hypothesis 2: a macromolecular complex forms from the metal salt in solution in situ, and the binding target binds to that complex. Furthermore, if a macromolecular complex forms in solution, the complex may form, for example, (a) before addition to the binding reaction, or (b) after addition to the binding reaction.

a. Experiments for Hypothesis 1

Hypothesis 1 postulates that interactions between components of the assay shorten the fluorescence lifetime of the fluorophore, thereby increasing fluorescence polarization. This hypothesis was tested by measuring the effect of a beadless metal salt on fluorescence lifetime of a peptide-conjugated fluorescein fluorophore (FL-Crosstide/Phosphocrosstide). The fluorescence lifetimes of FL-Crosstide and FL-Phosphocrosstide were measured on a FLARe™ instrument in a buffer that includes or lacks gallium chloride.

The following table shows the results of these measurements. The fluorescence lifetime of FL-Crosstide (± gallium) and FL-Phosphocrosstide (no gallium) was measured as 3.7 nsec. (As described earlier, each of these conditions showed a low FP signal and thus little binding to gallium(III).) By contrast, FL-Phosphocrosstide in the presence of gallium chloride showed a slight increase in fluorescence lifetime, a value of 4.3 nsec. However, this increase in fluorescence lifetime should produce a decrease in fluorescence polarization, an effect opposite to that observed in Examples 18-20. Accordingly, Hypothesis 1 is not supported by these results.

TABLE 7

Compiled Results of Fluorescein Lifetime Measurements in Binding Reactions

| 300 μM | Ga(III) | Lifetime Tau1 (n = 4) average | Sd | Lifetime Tau2 (n = 4) average | sd | % of Tau1 average | sd | % of Tau2 (100 − Tau1) |
|---|---|---|---|---|---|---|---|---|
| Fluorescein in Binding buffer | minus | 1.253 | 0.052 | 3.730 | 0.008 | 5.7 | 0.3 | 94.3 |
|  | plus | 1.276 | 0.109 | 3.751 | 0.013 | 6.8 | 0.5 | 93.2 |
| no Peptide in Binding buffer | minus | 0.280 | 0.021 | 4.950 | 0.182 | 53.5 | 1.0 | 46.5 |
|  | plus | 0.369 | 0.004 | 4.958 | 0.069 | 46.2 | 0.8 | 53.8 |
| Fl-crosstide in Binding buffer | minus | 1.488 | 0.010 | 3.779 | 0.015 | 13.1 | 0.4 | 86.9 |
|  | plus | 1.363 | 0.067 | 3.878 | 0.027 | 13.0 | 1.1 | 87.0 |
| Fl-Phosphocrosstide in Binding buffer | minus | 1.367 | 0.099 | 3.744 | 0.029 | 12.2 | 1.6 | 87.8 |
|  | plus | 1.188 | 0.046 | 4.338 | 0.004 | 6.4 | 0.1 | 93.6 |
|  |  | Buffer artifact |  | Fluorescein |  |  |  |  | b. Experiments for Hypothesis 2

Hypothesis 2 postulates that a large (macromolecular) complex of the binding partner is produced by gallium chloride in solution. Such a complex would be large enough to produce a substantial change in fluorescence polarization by slowing rotation of the binding target. In addition, such a complex may be large enough to be retained by a size exclusion matrix, such as a dialysis membrane. This hypothesis was tested using a variety of dialysis experiments that test for the presence of a large complex of Ga(III) and the time point in the binding protocol at which such a complex may be produced; see FIG. 23.

i. Experiment 1

Gallium chloride in binding buffer was tested as a binding partner, with or without overnight dialysis before the binding assay. A solution of 300 μM gallium chloride was prepared in binding buffer (see Example 18). The solution was divided into two portions and placed at room temperature. The first portion was incubated overnight without dialysis. In contrast, the second portion was dialyzed against the buffer overnight using a membrane with an exclusion limit of 12-14 kDa. This dialysis should remove Ga(III) that is not in a complex large enough to exceed the exclusion limit. After overnight incubation, each binding solution was added to a binding reaction, prepared as described in Example 18, with a binding target of either FL-Crosstide or FL-Phosphocrosstide.

FIG. 23 (left side) shows fluorescence polarization measured for dialyzed and nondialyzed binding solutions of gallium chloride that were freshly mixed with the indicated binding target. Similar increases in fluorescence polarization were measured whether the gallium chloride solution had been dialyzed or not. Thus, dialysis did not reduce the ability of the gallium chloride to provide an effective binding partner for the phosphorylated form of the binding target in the assay, suggesting that the gallium chloride in binding buffer is producing a complex large enough to remain trapped by the dialysis membrane, even in the absence of phosphopeptide or peptide.

ii. Experiment 2

Additional dialysis experiments were performed using a pre-mixed binding reaction that included either FL-Crosstide or FL-Phosphocrosstide. The ratios and concentrations used were as described for the binding reaction of Example 18 above, but in a larger volume to allow dialysis. Each pre-mixed binding reaction then was aliquoted to provide duplicate portions that were incubated overnight, either with or without dialysis against a binding buffer lacking Crosstide and gallium chloride.

FIG. 23 (center and right side) shows a bar graph of the binding assay results. Fluorescence polarization of each pre-mixed binding reaction was measured after the overnight incubation (right side). These pre-mixed binding reactions were compared with the fluorescence polarization signal produced by a freshly mixed, nondialyzed set of control binding reactions (center). The comparison showed that the pre-mixed binding reaction involving the gallium binding partner and FL-Phosphocrosstide was stable overnight during dialysis. In addition, the pre-mixed binding reaction involving gallium binding partner and FL-Crosstide showed a drop in fluorescence intensity (results not shown). This drop is consistent with the peptide not being bound to the binding partner and thus small enough to be removed by dialysis.

c. Summary

These results, taken together, suggest that the gallium is forming and/or involved in forming a large complex (larger than the exclusion limits of the dialysis membrane) in the binding solution. This complex appears to form before addition of binding target or other components of the binding reaction. Moreover, the complex appears stable, because the complex still was effective in binding assays following dialysis overnight.

Example 22

Figure 24:
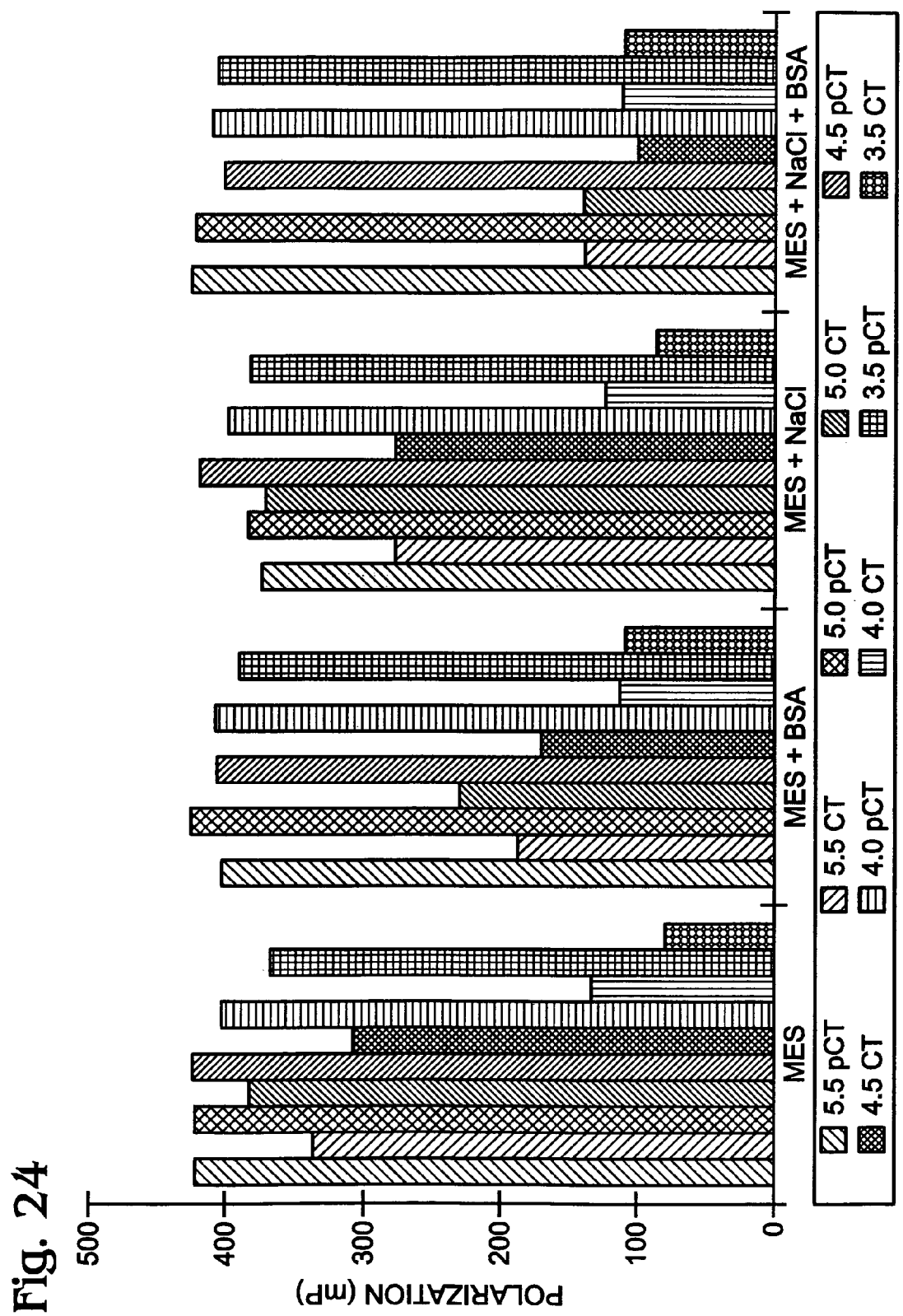
FIG. 24 is a bar graph showing results from binding assays conducted using an untethered metal in a set of binding buffers at a range of pH values, in accordance with aspects of the present teachings.
Figure 25:
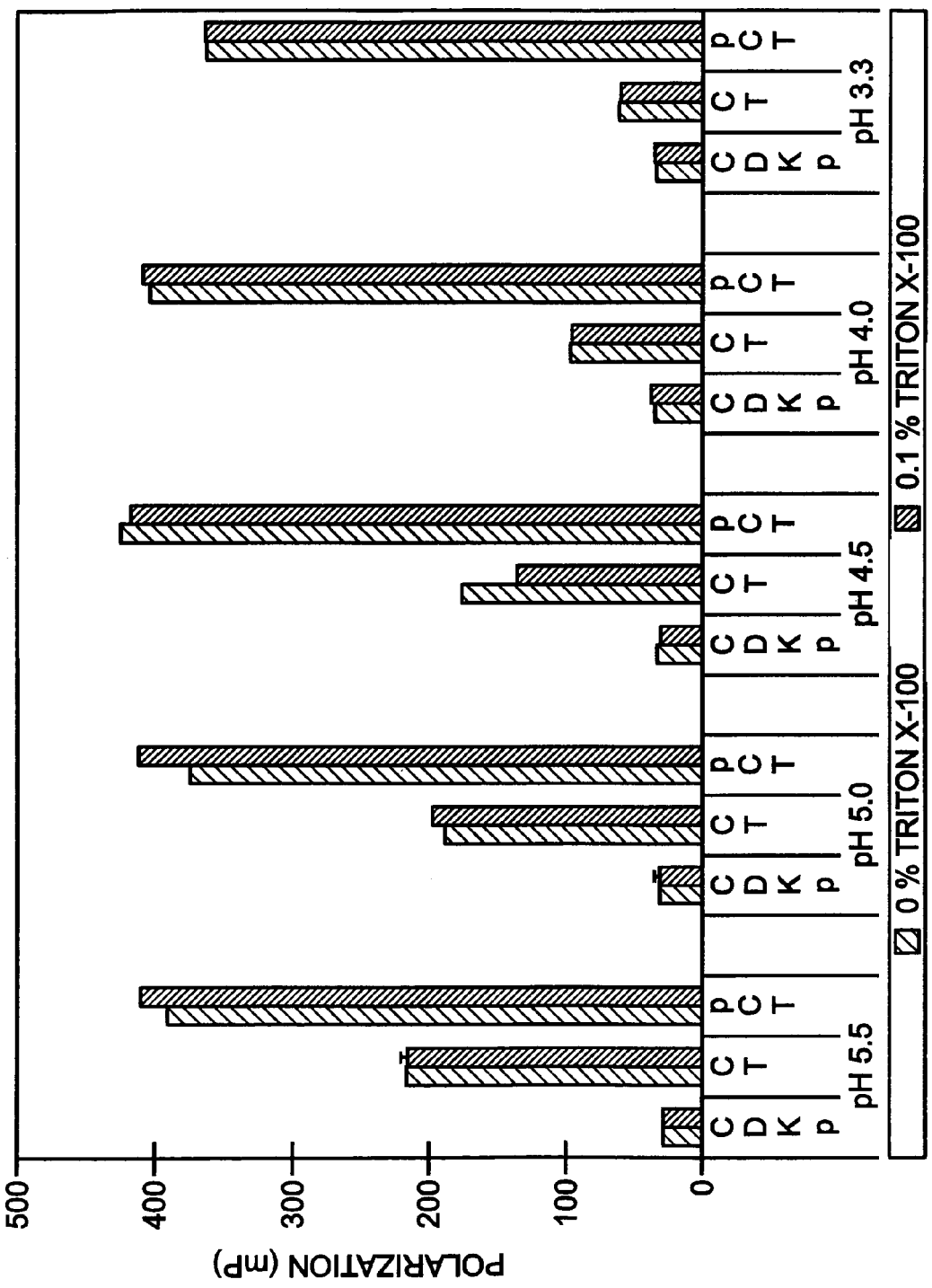
FIG. 25 is a bar graph showing results from binding reactions conducted using an untethered metal with various binding buffers and pH values and in the presence or absence of a nonionic detergent, in accordance with aspects of the present teachings.

This example describes experiments that identify components of the binding buffer that contribute to the formation of macromolecular, phosphate-binding structures; see FIGS. 24 and 25.

a. Buffer Set 1: Salt, BSA, and pH Effects

Experiments were performed using a first set of binding buffers, based on MES 2-(4-morpholino)-ethane sulfonic acid (MES), which differed in salt concentration, BSA (bovine serum albumen) concentration, and/or pH. These binding buffers had one of the following four buffer, salt, and protein compositions:

1) 50 mM MES;
2) 50 mM MES, 500 mM NaCl;
3) 50 mM MES, 0.1% BSA; or
4) 50 mM MES, 500 mM NaCl, 0.1% BSA.

In addition, for each composition, these binding buffers had one of the following five different pH values: 5.5, 5.0, 4.5, 4.0, and 3.5.

The resulting twenty different binding buffers each were used to dilute a concentrated stock solution of gallium chloride to 300 µM (see Example 18), to produce corresponding binding solutions. In turn, each binding solution was tested in a binding reaction at a 3:1 ratio with binding buffer alone, binding buffer with 100 nM FL-Crosstide, or binding buffer with 100 nM FL-Phosphocrosstide (see Example 18).

FIG. 24 graphically presents the fluorescence polarization signal produced by each binding assay. The complete binding buffer (50 mM MES, 500 mM NaCl, 0.1 % BSA) shows little pH dependence (see rightmost set of bar graphs), working almost equally well at each of the five pH values. In contrast, the other three buffer compositions (lacking BSA, salt, or both, relative to the complete binding buffer) show a stronger pH dependence (see remaining sets of bar graphs), with the highest signal-to-noise ratios at the lowest pH tested. Lowering the pH may avoid non-specific interactions.

b. Buffer Set 2: Detergent and pH Effects

Additional experiments were performed using a second set of binding buffers, based on acetate, which differed in detergent concentration and pH. These binding buffers were prepared with either 50 mM acetate alone or 50 mM acetate with 0.1% Triton X-100, each at five pH values: 5.5, 5.0, 4.5, 4.0, and 3.5.

The resulting ten different binding buffers each were used to dilute a concentration stock solution of gallium chloride to 300 µM (see Example 18), to produce corresponding binding solutions. In turn, each binding solution was tested in a binding reaction at a 3:1 ratio with binding buffer with 100 nM FL-CDK peptide (SEQ ID NO:13), 100 nM FL-Crosstide (SEQ ID NO:6), or 100 nM FL-Phosphocrosstide (SEQ ID NO:7).

FIG. 25 graphically presents the fluorescence polarization signal measured from each binding assay, as a function of pH, detergent (0% or 0.1%), and peptide identity. The binding results show a dependence on pH similar to that in FIG. 24 and no dependence on Triton X-100.

c. Conclusions

These experiments show that the ability to form a specific phosphate-binding complex from gallium chloride is independent of buffer identity, ionic strength, the presence or absence of BSA, and the presence or absence of detergent, under the range of conditions tested. However, the extent of nonspecific interaction between gallium chloride and the nonphosphorylated peptide is affected by these buffer components.

Example 23

This example describes, without limitation, exemplary models for the structure of Ga(III) in buffer or water. The precise nature or origin of the structure is not important to the efficacy of the assay; however, an understanding of the mechanism may help to improve or optimize assay conditions and results.

In aqueous solution, gallium ions may form amphoteric hydroxides and/or oxo ions that have a solubility minimum around pH 3-5. Due to this solubility minimum, microcrystalline structures or an amorphous complex may be produced at acidic pH. For example, Avivi et al. presents the following equation (J. Am. Soc (1999) 121, 4196-4199):

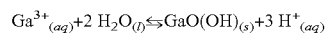

$$Ga^{3+}_{(aq)} + 2\,H_2O_{(l)} \leftrightharpoons GaO(OH)_{(s)} + 3\,H^+_{(aq)}$$

Accordingly, a solid may be formed as GaO(OH) in binding reactions. Other equations that may explain the formation of a larger complex from gallium ions in solution are as follows:

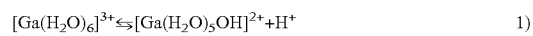

$$[Ga(H_2O)_6]^{3+} \leftrightharpoons [Ga(H_2O)_5OH]^{2+} + H^+ \qquad 1)$$

$$[Ga(H_2O)_5OH]^{2+} \leftrightharpoons + [(H_2O)_5GaOGa(H_2O)_5]^{4+} + H_2O \qquad 2)$$

Accordingly, bridged networks of gallium hydroxides/oxides may be formed by extending these equations to produce larger structures.

Example 24

This example describes additional aspects of the assays.

Suitable or preferred assay conditions for beadless (or untethered binding partner) assays may vary, depending on the enzyme (e.g., kinase versus phosphatase, specific type of kinase, etc.) and/or other reaction component(s). For example, because interactions in the different binding buffers appear to be peptide specific, suitable assays conditions for tyrosine kinases (especially receptor kinases), which preferentially interact with peptide substrates having a high content of carboxy amino acids, may differ from suitable assay conditions for other kinases, which preferentially interact with different peptide substrates. Further aspects of the effect, on binding assays, of the number of carboxy groups in a binding target, and exemplary buffer adjustments to improve binding assays based on the number of carboxy groups, are presented in the Examples below.

Assays may be performed in any suitable format. Thus, in some embodiments, microtiter plates or other solid phases (e.g., a chip or array) could be plated with Ga-oxide or hydroxides to create a phosphate binding surface, which could be used in phosphorylation assays (substrate-, auto-) together with any suitable detection modality, such as quenching. (Quenching can be performed using any suitable energy transfer pairs, for example, using quantum dots and/or suitable pairs disclosed in Richard P. Haugland, *Handbook of Fluorescent Probes and Research Chemicals* (6th ed. 1996), which is incorporated herein by reference. Suitable no-wash assays can employ a quenched product that unquenches when bound to a (Ga-coated) surface, or a quenching (masking) dye in the supernatant, so that only the product bound to the surface is observable.) Alternatively, or in addition, different metals, such as Ga(III) and Tb(III) or other lanthanides, among others, could be co-precipitated to create a mixed structure that binds phosphate. The mixed structure may be useful, for example, in time-resolved fluorescence resonance energy transfer (TR-FRET).

Example 25

This example describes exemplary parameters that may affect the sensitivity and/or reproducibility of molecular modification assays.

The molecular modification assays described herein are intended to work well under a variety of assay conditions. However, despite their great flexibility, these assays may be affected by a variety of specific factors, including (A) instability of the binding solution, (B) the structure/sequence of the substrate, and (C) sensitivity to ATP concentration. Thus, there is a need for assay components and conditions that increase the stability of the binding solution, that increase the number of different substrates that can be used (e.g., by decreasing sequence specificity), and/or that increase ATP tolerance, among others.

1. Instabilities in the Binding Solution

The binding solution (binding buffer mixed with binding reagent (binding partner such as Ga(III))) may lose binding capacity over time (although this loss may not be apparent except with kinase substrates having no or one acidic residues). This instability may be addressed in several ways. First, the binding solution may be mixed fresh, close to the time of use. Second, the binding solution may be added in two steps: (1) add binding buffer to reduce pH, and (2) add binding reagent in water (which may be generally stable). However, this introduces an additional step. Third, binding solution may be kept cool (e.g., on ice), since this slows the loss of binding sites. Fourth, gallium may be added to make up for lost binding capacity. However, above a certain concentration, added gallium may cause precipitation in the binding solution. Thus, these approaches all have shortcomings, especially for high-throughput screening.

2. Sequence Specificities of the Substrate

The choice of enzyme substrate may be limited by various factors, including sequence specificities. For example, substrates with too few acidic residues may -be sensitive to losses in buffer binding capacity, as mentioned above, and substrates with too many acidic residues may give high backgrounds. These sequence specificities may be addressed in several ways. First, substrates with good (low) Km's may be selected, for example, by choosing substrates with few acidic residues and/or by changing acidic residues to nonacidic residues (e.g., by amidation). This approach may be especially useful with known substrates (such as an alpha-tubulin derived peptide as a substrate for Zap-70 and Syk). Second, assay results simply may be accepted with higher backgrounds (e.g., for a Blk/Lyn substrate peptide). However, neither approach is ideal.

3. Sensitivities to ATP Concentration

The choice of enzymes may be limited by the number of binding sites, due to sensitivities to ATP concentrations. These limitations are greater for enzymes with high Km's for ATP (such as CDK). These limitations may be addressed, for example, by increasing ATP concentration as high as possible without losing signal, especially for enzymes with high Km's.

Example 26

Figure 26:
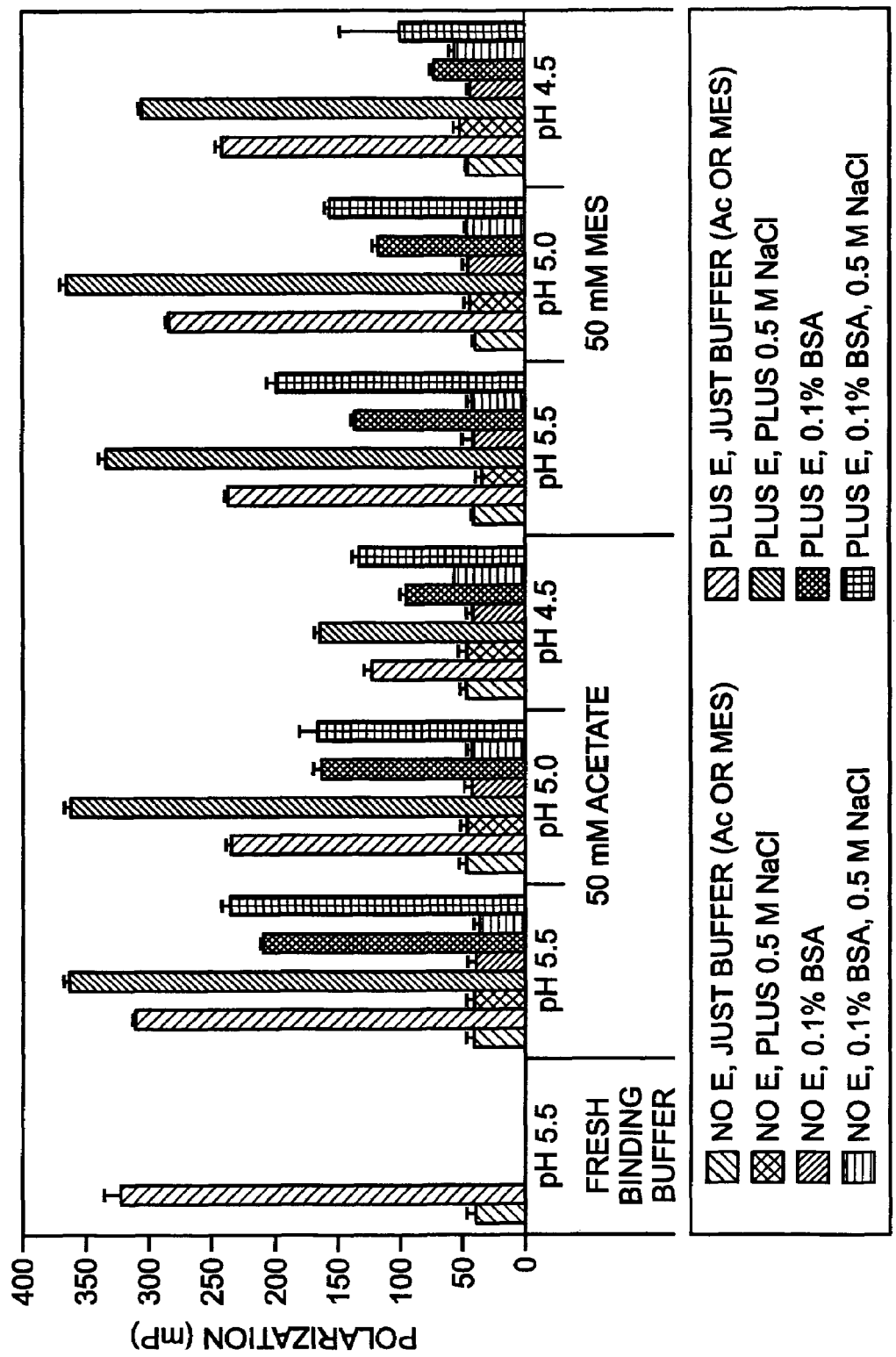
FIG. 26 is a bar graph showing results from binding reactions performed as PKA assays and testing the stability of binding solutions with various solution compositions, in accordance with aspects of the present teachings.

This example describes experiments testing the influence of various solution components on the stability of binding solutions for molecular modification assays; see FIG. 26.

The associated experiments were performed by varying the identity and/or concentration of components in a standard binding buffer (50 mM MES, 500 mM NaCl, 0.1% BSA, pH 5.0) to assess their effects on the stability of the binding solution. Stability was assessed by diluting binding reagent (120 mM gallium chloride) 1:400 (to 300 µM) in each of the indicated buffers, and then incubating 23 hours before performing a binding assay to measure PKA activity. As a control, the binding reagent was diluted 1:400 to create a binding solution and then used immediately ("fresh") to measure PKA activity. The components that were varied include buffer (sodium acetate (NaAc) or 2-(4-morpholino)-ethane sulfonic acid (MES)), salt (500 mM NaCl), and protein (bovine serum albumin; BSA). The assay system included or lacked a protein kinase A (PKA) enzyme ("plus E" and "no E", respectively). The assay system included a corresponding phosphorylation substrate, PKAtide (SEQ ID NO:20). Fluorescence polarization (mP) was measured 30 minutes after addition of the binding solution to the enzyme reaction.

These experiments show that BSA lowers the stability of the binding solution and the "active" concentration of gallium (possibly by complexing gallium). These experiments also show that NaCl has a beneficial effect on the total signal in this system.

Example 27

Figure 27A:
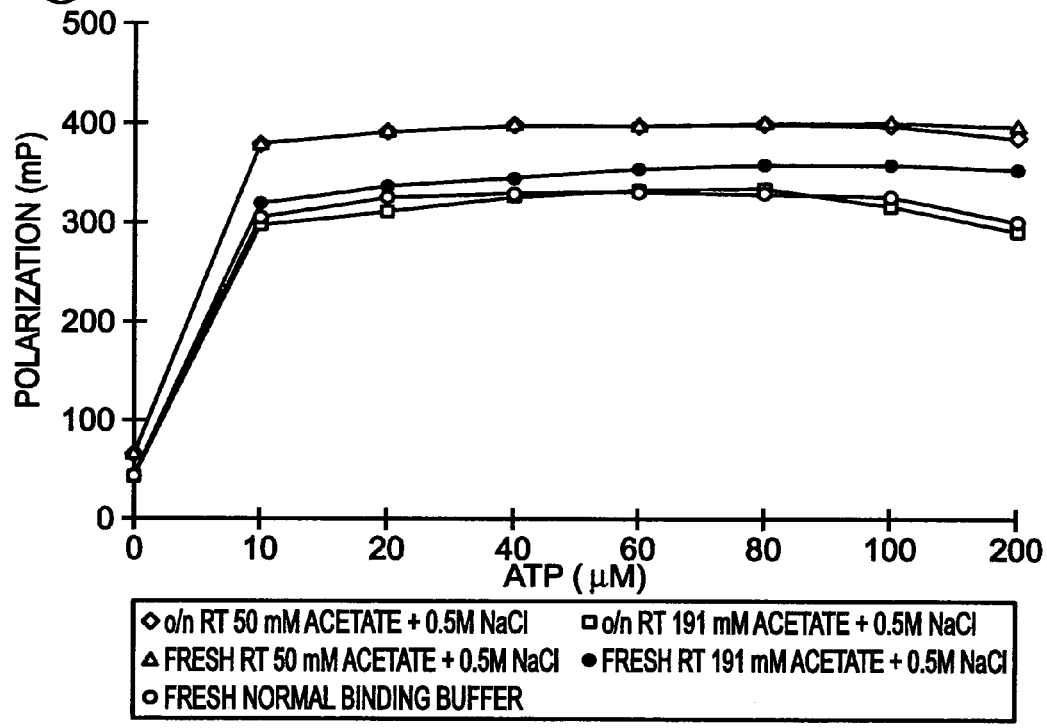
FIG. 27 is a pair of graphs showing results from binding reactions performed as CDK-2 and PKA assays, respectively, using binding solutions including various ATP, gallium, and acetate buffer concentrations, in accordance with aspects of the present teachings.
Figure 27B:
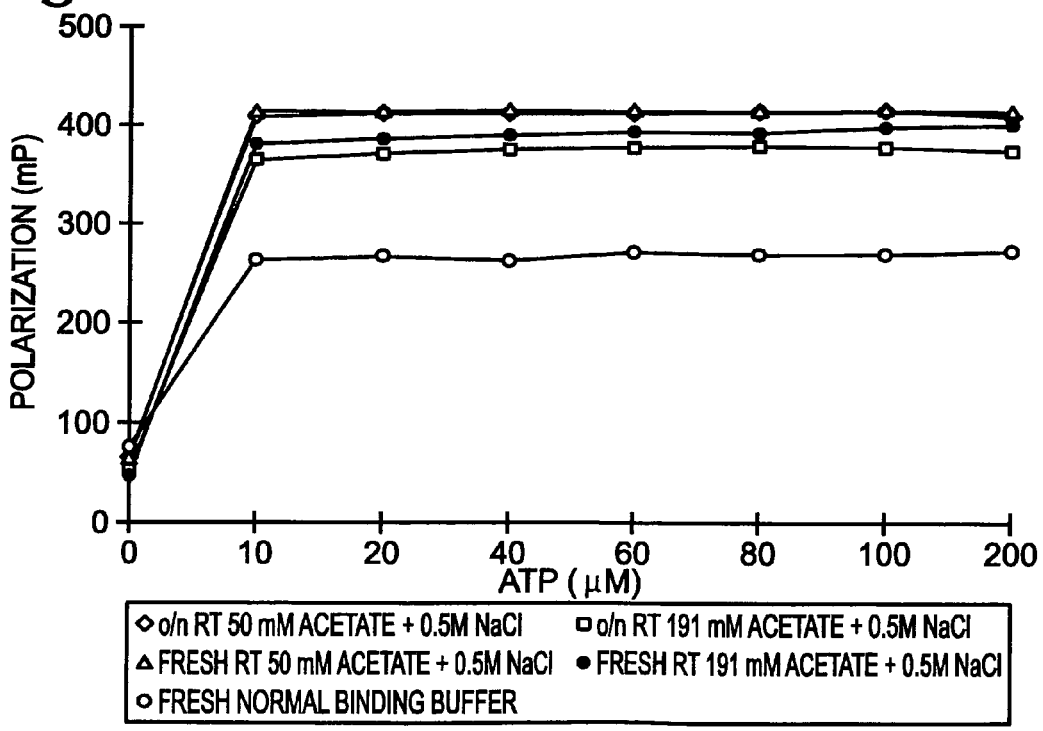

This example describes the influence of various binding solutions on fluorescence polarization in molecular modification assays involving peptide substrates with no carboxy groups; see FIGS. 27 and 28. Exemplary peptides in this group include PKAtide (SEQ ID NO:20), CDKtide (SEQ ID NO:13), and Rock II peptide (SEQ ID NO:21), which are substrates for PKA, cyclin-dependent kinase (CDK), and rho-associated kinase II (Rock II), respectively. CDK has a high Km for ATP.

Peptide substrates that lack carboxy groups may have lower affinities for a binding partner, such as gallium ions (Ga(III)), than peptide substrates having one or more carboxy groups. Thus, to engineer assays so that approximately equal percentages of both "low" and "high" affinity substrates (including fewer and more carboxy groups, respectively) bind to the binding partner, it may be helpful to use higher concentrations of binding sites with lower-affinity substrates. Specifically, it may be helpful to increase the number of (or flood the system with) binding sites of a binding partner to compensate for lower affinity peptides and/or (in the case of CDK) the need for higher concentrations of ATP. Unfortunately, although BSA may be the main cause of precipitation in the binding solution, high bead concentrations (e.g., to 1:100) also may lead to slight precipitation, especially with acetate-based buffer systems. Therefore, to have a relatively high concentration of gallium but to maintain a relatively low concentration of beads, the composition of the system may be adjusted by maintaining the same bead and detergent (e.g., Brij-35) concentrations, while increasing (e.g., by about four-fold in some embodiments) the gallium concentration.

FIG. 27 shows the effects of different binding solutions on exemplary CDK-2 (panel A) and PKA (panel B) assays. Here, system components were selected as shown (with 1.2 mM gallium in 50 mM or 191 mM NaAc, pH 5.0, with 500 mM NaCl; or "normal" or "kit" binding buffer with 50 mM MES, 500 mM NaCl, 0.1% BSA, and 300 µM gallium chloride, pH 5.5). The CDK2/cyclinA and PKA reactions were run using fixed enzyme concentrations (0.1 U/mL and 0.02 U/mL, respectively) and various concentrations of ATP, as indicated on each graph. Assays were performed using (1) binding solution that was prepared fresh ("fresh"), and (2) binding solution that had been prepared and allowed to sit overnight ("o/n"). Assay results were quantified by fluorescence polarization at 30 minutes after binding solution addition. The resulting data show (a) no significant difference between NaAc binding buffers prepared fresh or allowed to incubate overnight, (b) a wide ATP resilience, and (c) an increase in the separation between pre- and post-reaction polarizations, relative to normal binding buffer (which lacked the enhanced gallium concentration). The binding of both phosphorylated product peptides was sensitive to elevated acetate concentrations, with a 70-100 mP reduction in signal going from 50 mM NaAc to 191 mM NaAc. Additional experiments showed that increasing salt concentration from 0 mM NaCl to 500 mM NaCl doubled the assay window.

Figure 28A:
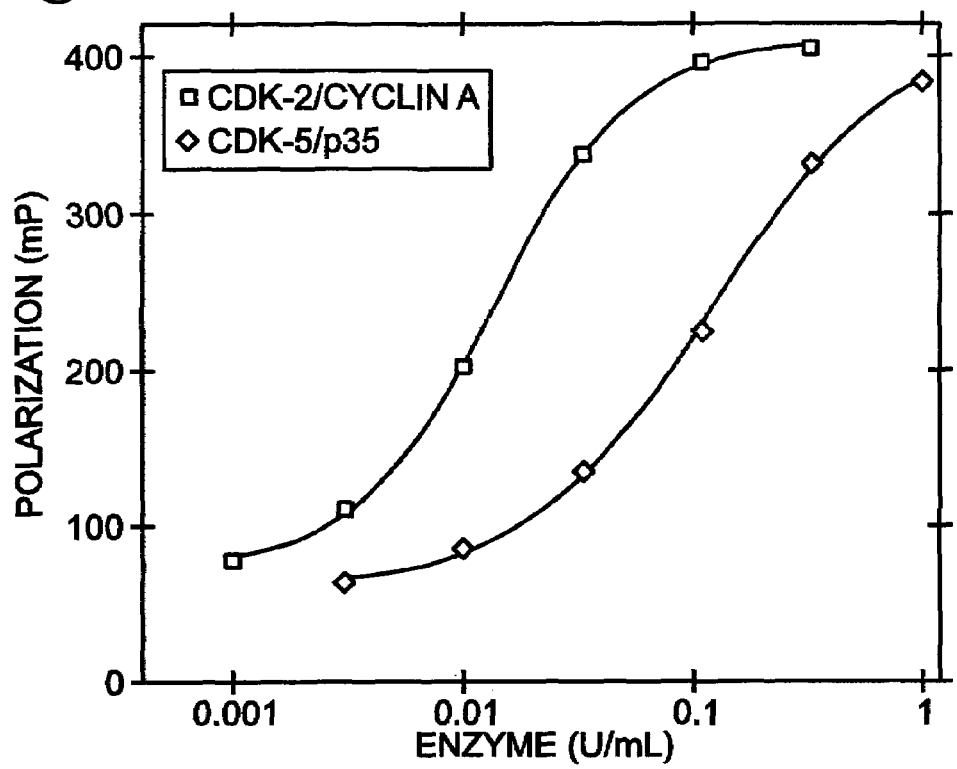
FIG. 28 is a pair of graphs showing results from binding reactions performed as CDK-2 and CKD-5 assays and comparing reconfigured (panel A) and original (panel B) binding conditions, in accordance with aspects of the present teachings.
Figure 28B:
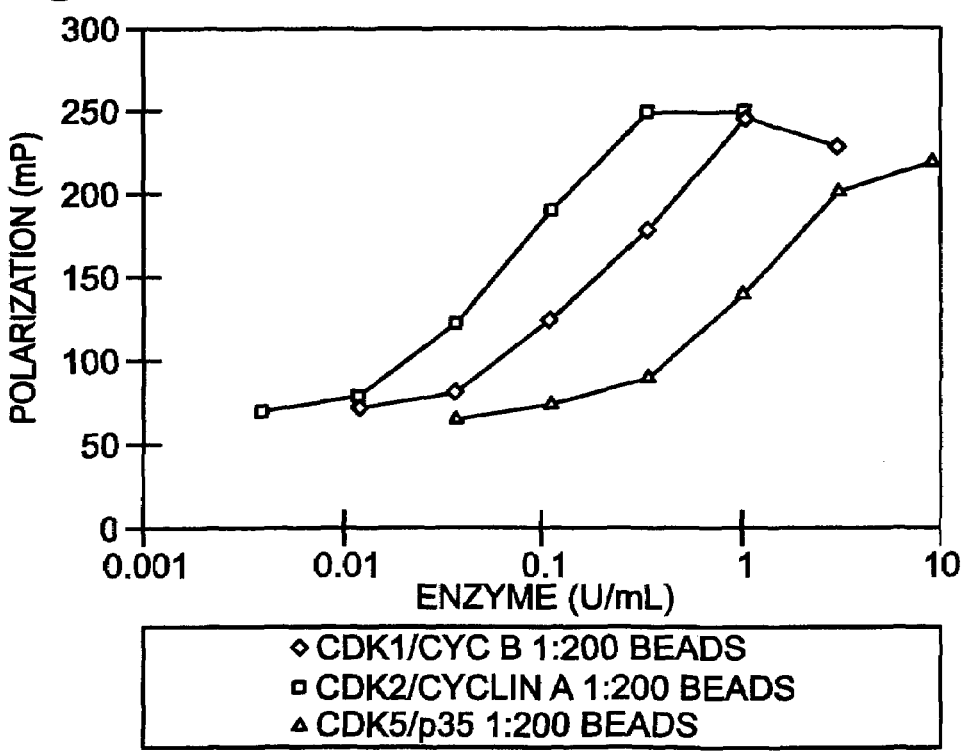

FIG. 28 shows the effects of various binding reaction conditions (including different ATP concentrations) on exemplary CDK-2/cyclin A and CDK-5/p35 assays using 100 nm of CDKtide peptide (SEQ ID NO:13) as substrate. The binding reactions to measure enzyme activity were performed under reconfigured (FIG. 28A) and original (FIG. 28B) conditions. Reconfigured conditions included 50 mM sodium acetate, 500 mM sodium chloride, 1.2 mM gallium chloride, 50 µM ATP, at pH 5.0. Original conditions included the "normal" binding buffer described in relation to FIG. 27, 10 µM ATP, a 1:200 dilution of beads, and a 60-minute incubation in binding solution before measurement of fluorescence polarization. The reconfigured conditions led to a significant increase in the assay window and a left shift in the curves (due to the increased ATP concentration) relative to the original conditions of FIG. 28B.

Example 28

Figure 29:
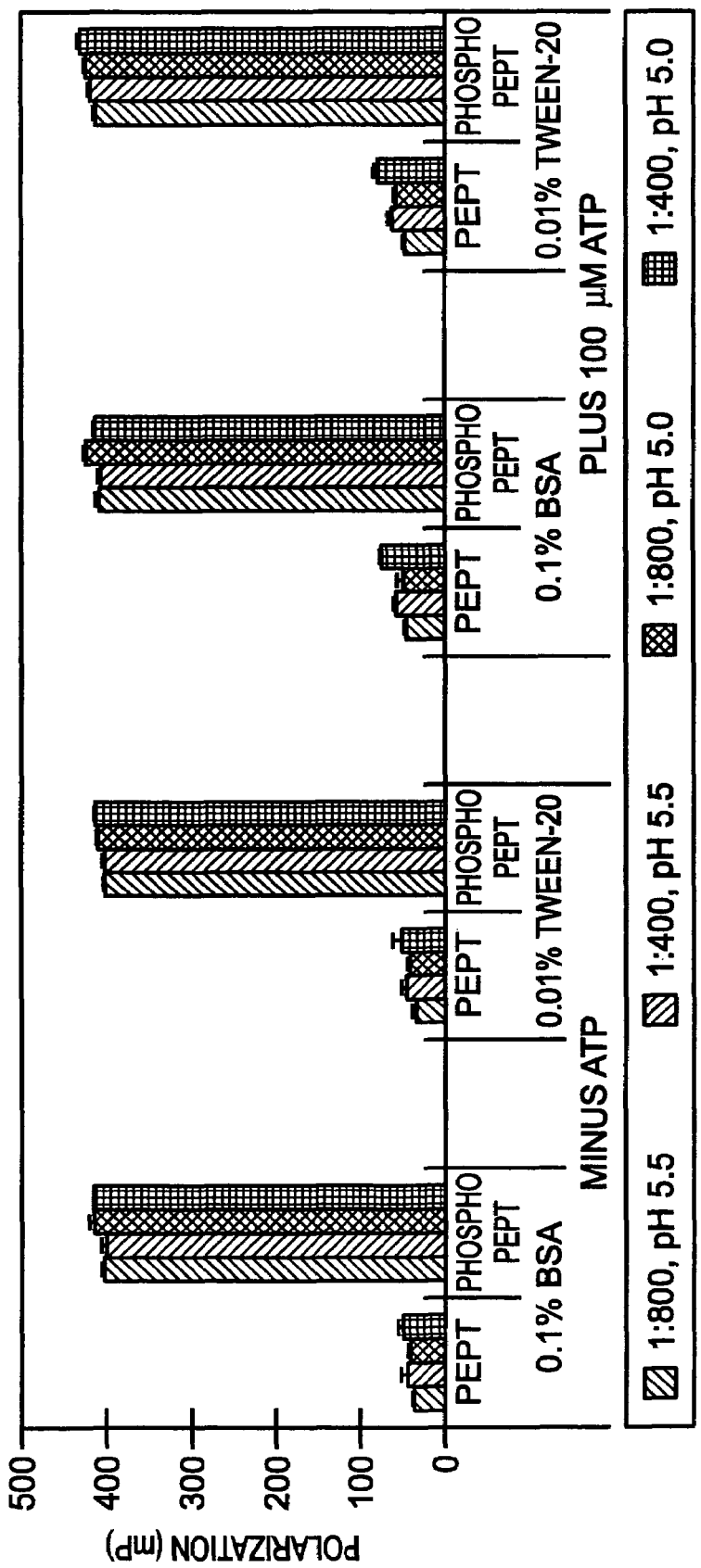
FIG. 29 is a bar graph showing results from binding reactions performed on a MAPKAP Kinase 2 substrate peptide (derived from glycogen synthase) under different binding conditions, particularly, the presence or absence of ATP, with BSA or Tween-20, and at two different gallium concentrations, in accordance with aspects of the present teachings.
Figure 30:
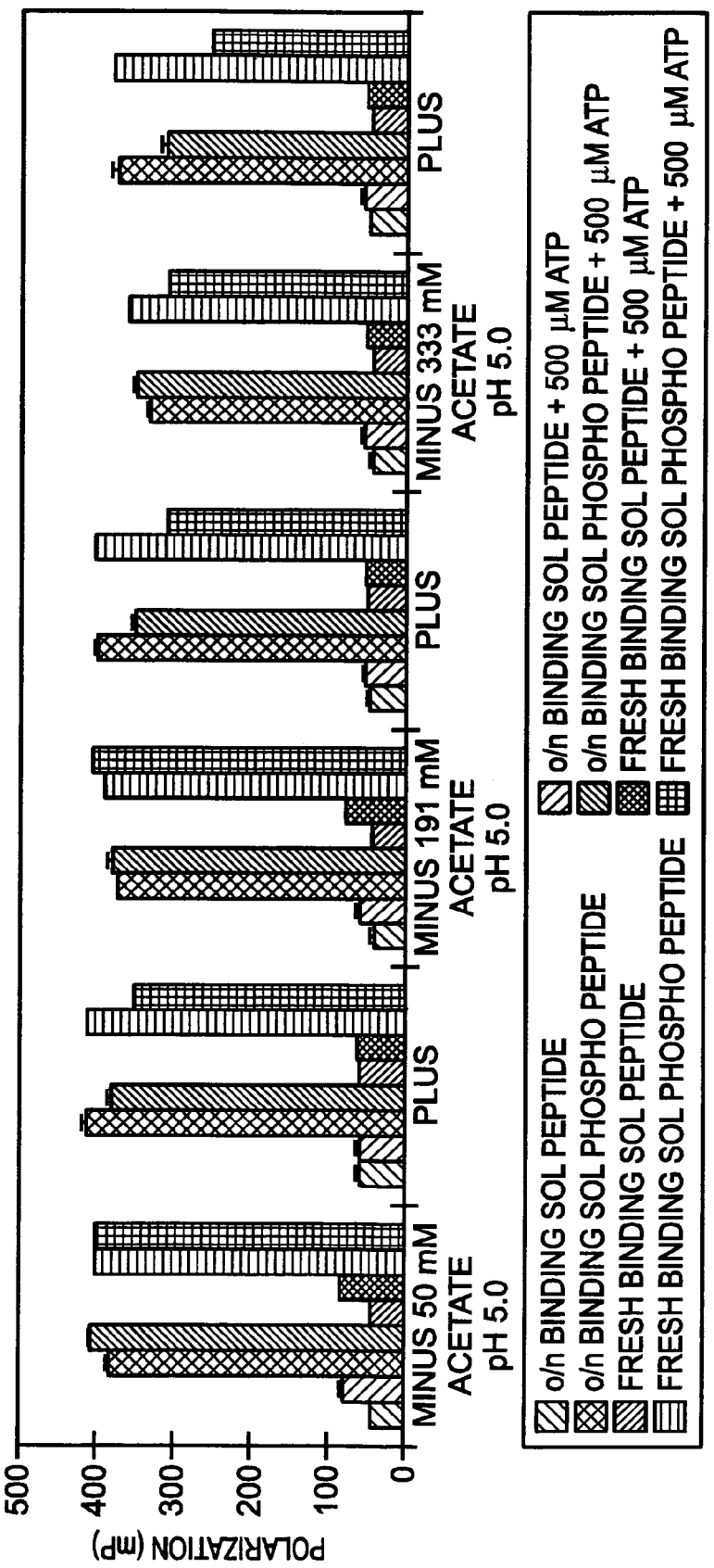
FIG. 30 is a bar graph showing results from binding reactions performed with the MAPKAP Kinase 2 substrate peptide (FIG. 29) or a corresponding product phosphopeptide as binding target under various conditions of acetate, sodium chloride, ATP, and time of binding solution preparation, in accordance with aspects of the present teachings.

This example describes the influence of various binding solutions on fluorescence polarization in molecular modification assays involving peptide substrates with one carboxy group; see FIGS. 29-31. Exemplary peptides in this group include the MAPKAP Kinase 2 substrate peptides (SEQ ID NOS: 11 and 12) and the amidated Crosstide peptide (SEQ ID NO: 6). This group of peptides, similar to the peptides of Example 27, do not show significantly increased background in response to gallium.

FIG. 29 shows the effects of various buffer conditions on binding to the glycogen synthase-derived peptide (or phosphopeptide) with one carboxy group (SEQ ID NO: 11) in the presence and absence of 100 µM ATP. The binding solution included 50 mM acetate and 500 mM NaCl, 0.1% BSA or 0.01% Tween-20, at pH 5.0 or pH 5.5, as indicated. Gallium chloride was diluted to a final concentration of 1.2 mM (1:400) or 600 µM (1:800) in the binding solution. Fluorescence polarization (y-axis) was measured 30 minutes after addition of the binding solution to the peptide system. There was no appreciable effect due to (1) ATP, (2) 1.2 mM (1:400) versus 600 µm (1:800) gallium, (3) pH 5.0 versus pH 5.5, (4) or BSA versus Tween-20. Based on these observations, it was concluded that the main negative effect of BSA in the binding solution is on the stability of the binding buffer.

FIG. 30 shows the results of binding reactions using the MAPKAP Kinase 2 substrate peptide or product phosphopeptide as binding target with various binding solutions. The fluorescence polarization of the binding mixture was plotted as a function of the binding solution used. In particular, the binding solutions varied in ATP (0 or 500 µM), acetate buffer pH 5.0 (50, 191, or 333 mM), time of binding solution preparation (fresh or the day before), and absence ("minus") or presence ("plus") of 500 mM NaCl. The results show that the fluorescence polarization signal (the binding signal) is only minimally affected by NaCl. Specifically, the signal at 191 mM NaAc is about the same as with 50 mM NaAc, while the signal at 333 mM is lowered by about 50 mP. With this higher acetate concentration, NaCl may stabilize the signal somewhat for binding solutions prepared the day before relative to prepared fresh.

Figure 31A:
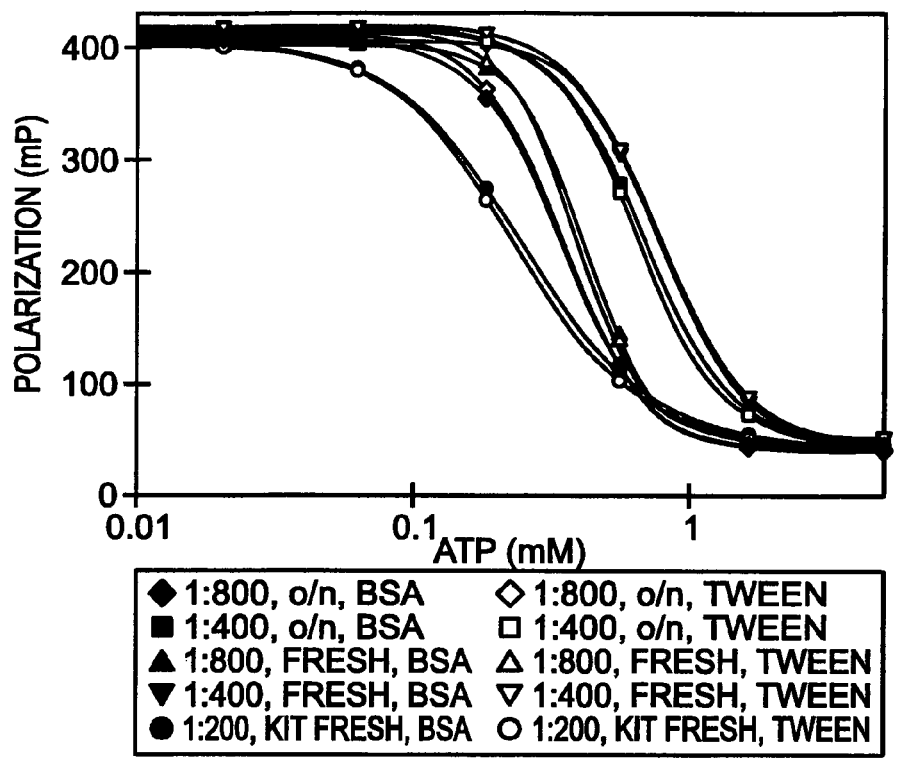
FIG. 31 is a pair of graphs showing results from binding reactions performed with the MAPKAP Kinase 2 product phosphopeptide (FIG. 30) under a range of ATP concentrations, in the presence of BSA or Tween-20, and with different gallium concentrations, in accordance with aspects of the present teachings.
Figure 31B:
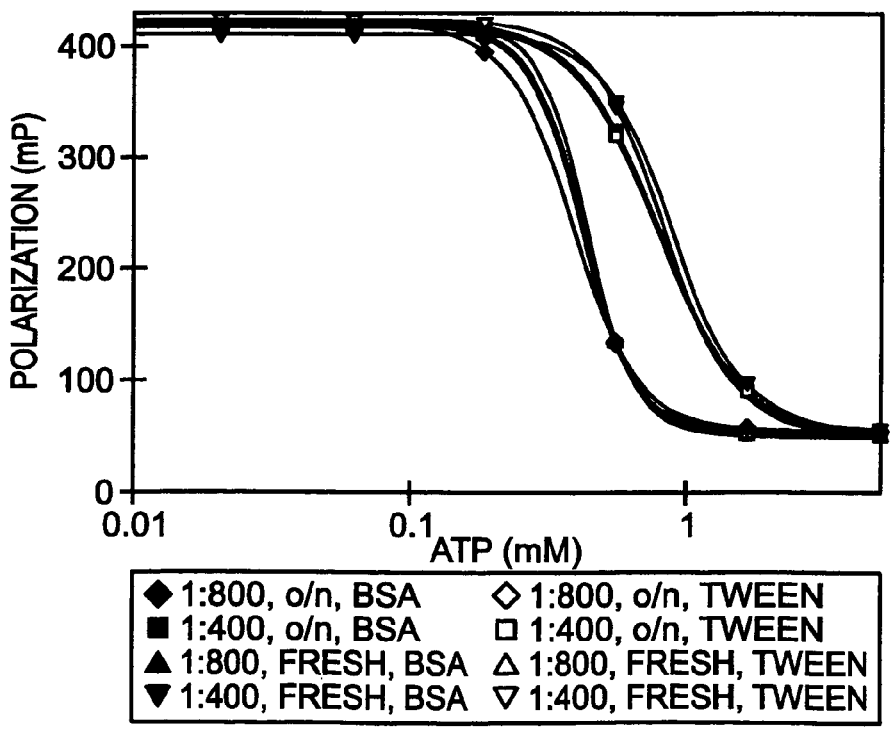

FIG. 31 shows the results of binding reactions performed with the MAPKAP Kinase 2 phosphopeptide under a range of ATP concentrations. Fluorescence polarization measured after 40 minutes of binding was plotted as a function of ATP concentration. Binding reactions included 500 mM NaCl and 0.1% BSA or 0.01% Tween-20, as indicated, and 1.2 mM (1:400) or 600 µM (1:800) gallium chloride. The experiments in FIG. 31A were run in acetate-buffered binding solutions at pH 5.5, and the experiments in FIG. 31B were run in acetate-buffered binding solutions at pH 5.0. The graph of FIG. 31A also shows binding reactions performed with the "normal" binding buffer of Example 27, here termed "kit," at a binding reagent dilution of 1:200 (600 µM gallium chloride). The two graphs further include a comparison of binding solutions made fresh versus binding solutions that are about 24 hours old. The results show that using 1.2 mM gallium chloride versus the "kit" solution shifts the IC50 for ATP from 250 µM (at 600 µM gallium chloride) to 750 µM (at 1.2 mM gallium chloride), at pH 5.5, and to 850 µM (1.2 mM gallium chloride) at pH 5.0. The stability of the 24-hour-old binding solution looked better at pH 5.0. Thus, the pH of binding buffers was selected to be pH 5.0 for subsequent assays. This selection is supported by the pKa of acetate (4.75), which is closer to 5.0 and has a better buffering capacity for acetate at that pH. The fluorescence intensities were lower at 5.0; however, this is a minor consideration, especially for dye labels that are red, which have less interference.

Example 29

This example describes the influence of various binding solutions binding signals in molecular modification assays involving peptide substrates with two carboxy groups; see FIGS. 32-36. Exemplary peptides in this group include the Src substrate peptide (SEQ ID NO:17) and Crosstide (SEQ ID NO:6, but with an amidated C-terminus). Peptides having two free carboxy groups in the sequence may be the most variable among the substrates in terms of background as a function of gallium concentration. In particular, some are very sensitive to higher gallium concentrations, and some are not.

To address the issue of peptides producing a high background in binding assays, experiments were performed to test the hypothesis that if the high background is due to nonspecific interaction of the substrate carboxy groups (acidic residues) with the binding partner, then it might be possible to lower that non-specific interaction by flooding the system with carboxy groups. This should be possible simply by raising the acetate concentration or by using another carboxy-containing buffer.

Figure 32A:
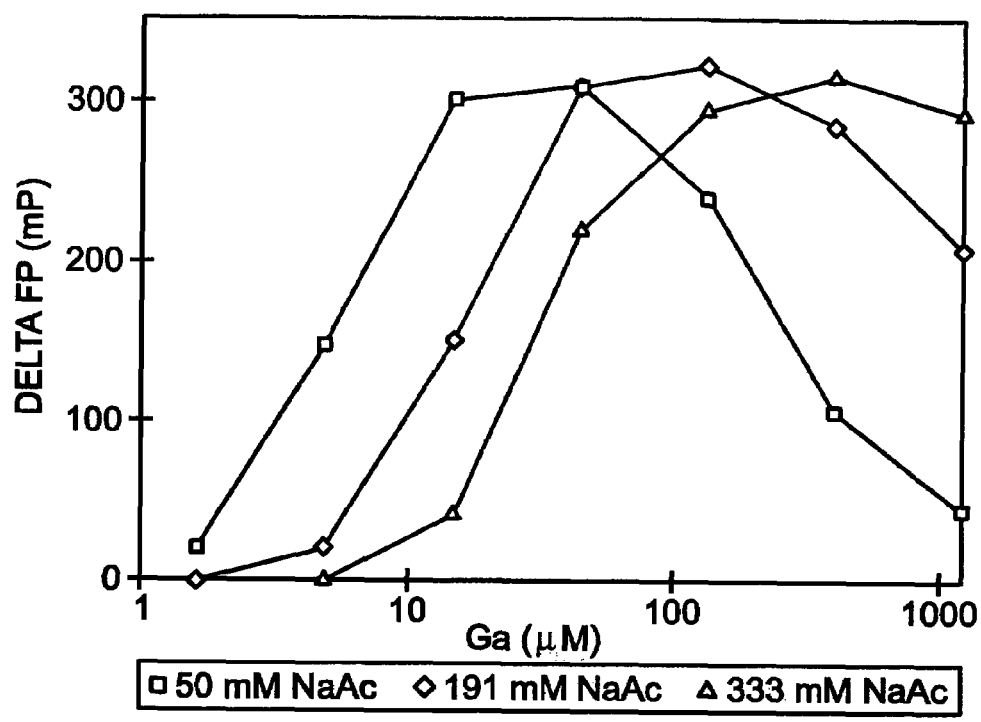
FIG. 32 is a pair of graphs showing the change in polarization produced in binding reactions with Phosphocrosstide relative to Crosstide as a function of gallium concentrations and using different acetate buffer concentrations, in accordance with aspects of the present teachings.
Figure 32B:
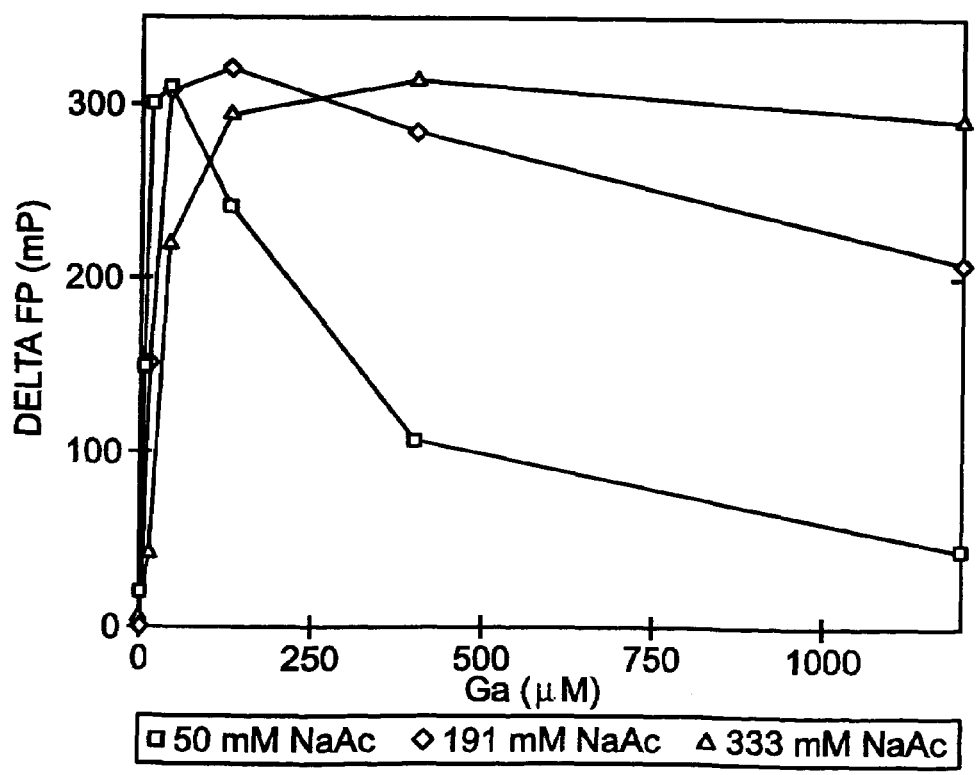

FIG. 32 shows graphs of the net fluorescence polarization signal of binding reactions with Phosphocrosstide relative to Crosstide in 50, 191, and 333 mM NaAc as a function of gallium concentration. The data are plotted on a log scale (FIG. 32A) and a linear scale (FIG. 32B) for the gallium concentration in each binding reaction. The graph of FIG. 32A indicates that for each acetate concentration there is an optimal gallium concentration. FIG. 32B indicates that the background is less sensitive to the absolute amount of gallium in the presence of high acetate compared to low acetate.

Figure 33A:
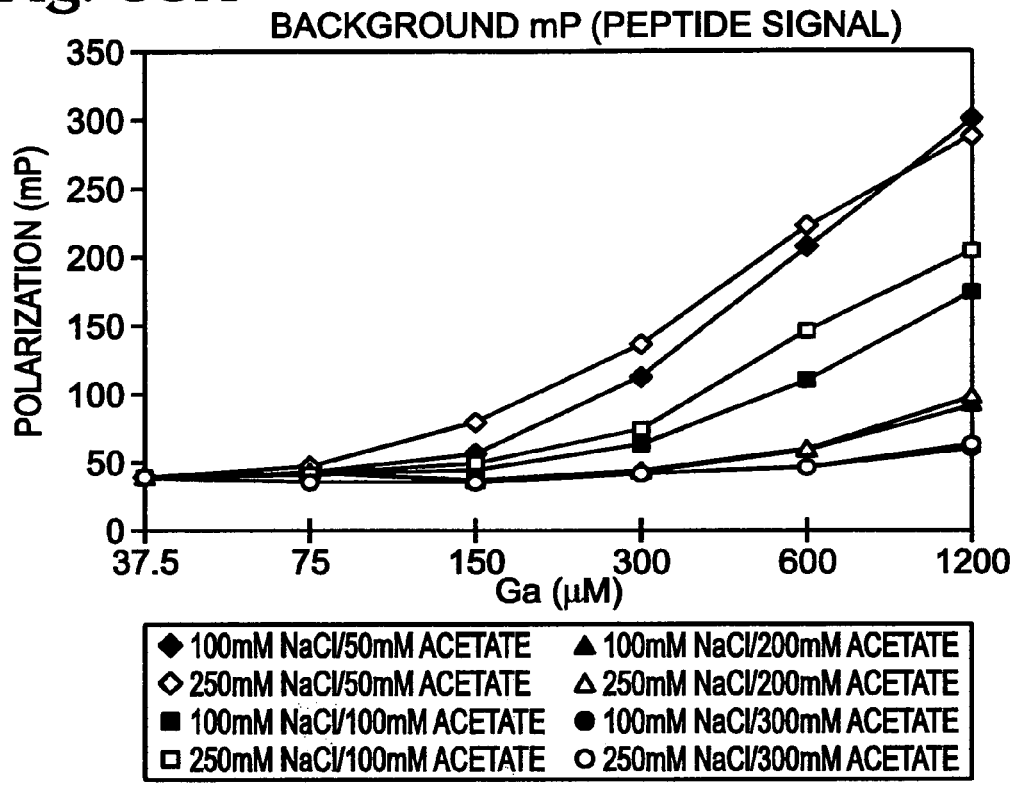
FIG. 33 is a series of graphs showing results from binding reactions with Crosstide (panel A), Phosphocrosstide (panel B), and the net binding signal defined by the difference between these two peptides (panel C), as a function of gallium concentration and with various conditions of acetate and sodium chloride in the binding reactions, in accordance with aspects of the present teachings.
Figure 33B:
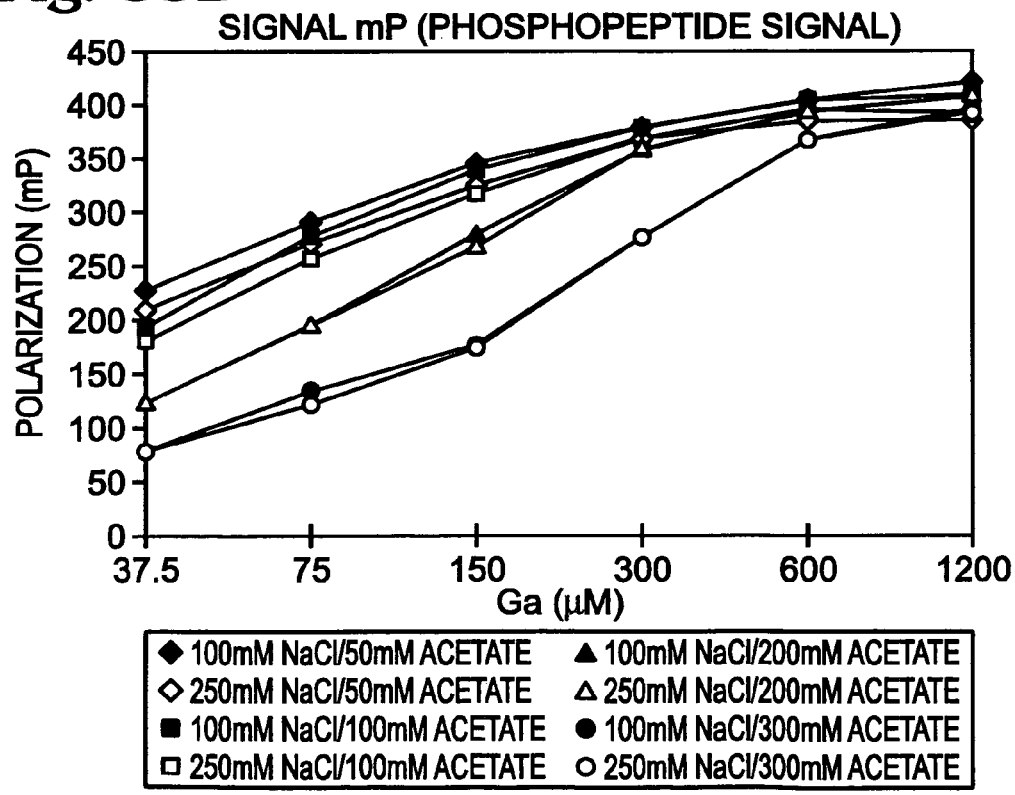
Figure 33C:
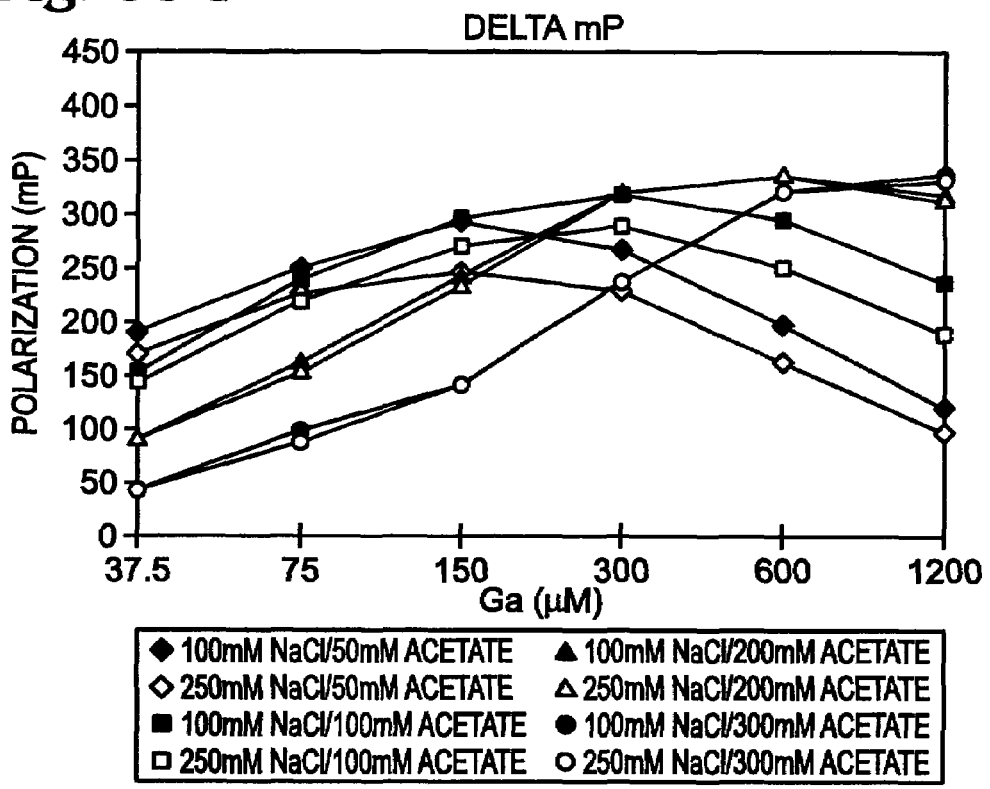
Figure 34A:
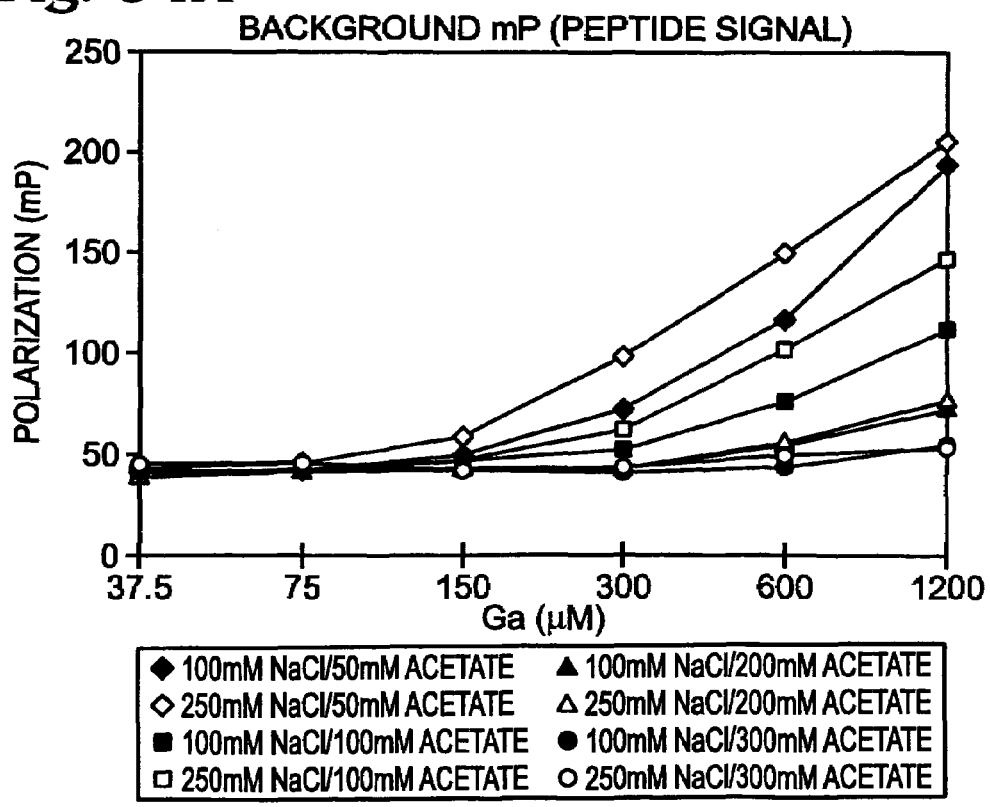
FIG. 34 is a series of graphs showing results from binding reactions with a Src substrate peptide (panel A), a Src product phosphopeptide (panel B), and a net binding signal defined by the difference of these two peptides (panel C), as a function of gallium concentration and with various conditions of acetate and sodium chloride in the binding reactions, in accordance with aspects of the present teachings.
Figure 34B:
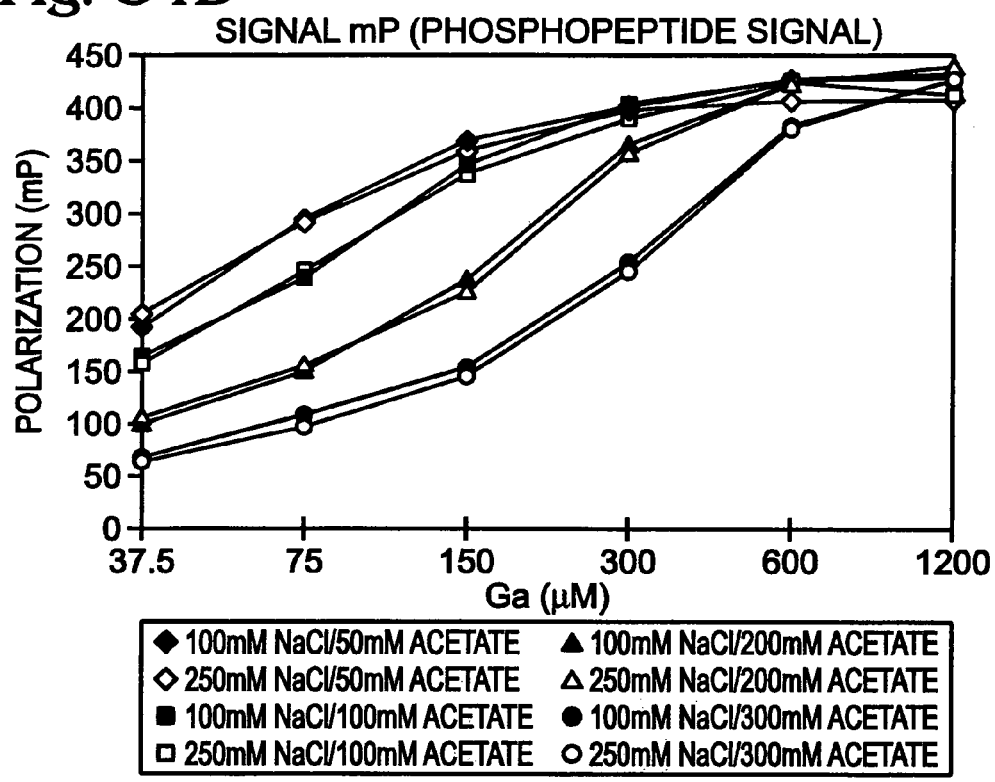
Figure 34C:
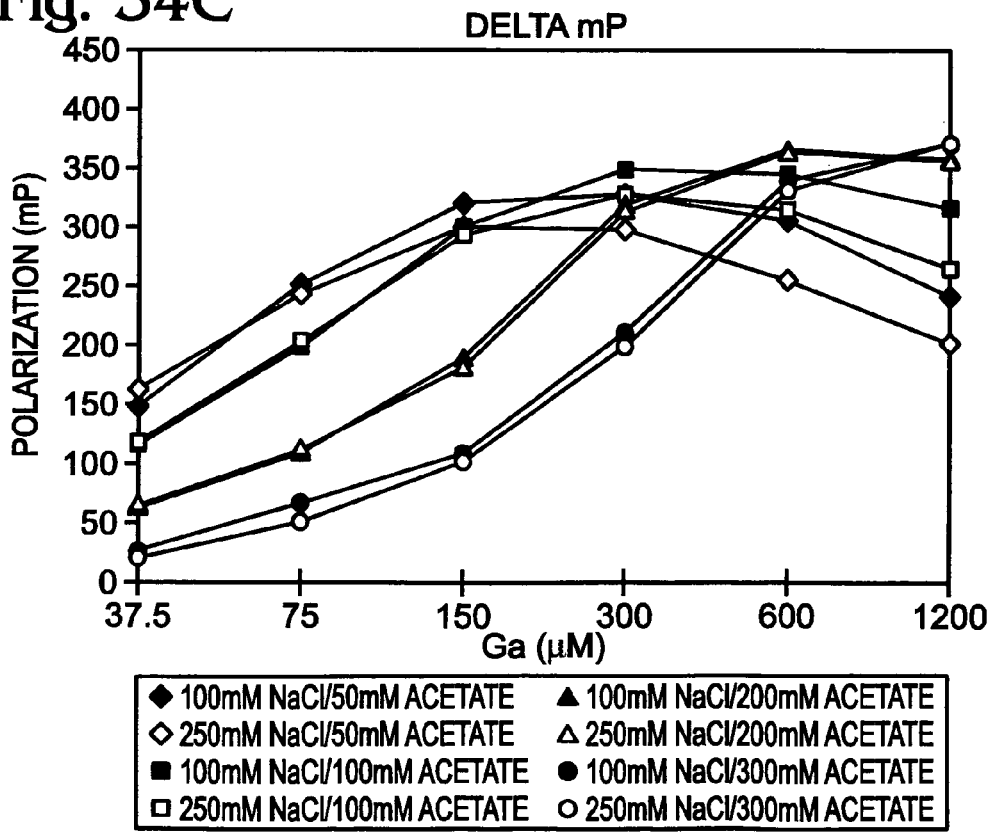

FIGS. 33 and 34 show data from binding reactions with Crosstide and Phosphocrosstide (SEQ ID NOS: 6 and7) in FIG. 33, and Src substrate peptide or product phosphopeptide (SEQ ID NOS:17 and 18) in FIG. 34. The binding reactions were performed with a range of gallium, acetate, and sodium chloride concentrations. Peptide (background) signal (panel A in each), phosphopeptide signal (panel B in each), and the delta fluorescence polarization between phosphopeptide and peptide (panel C in each) were plotted against gallium concentration for set of binding reactions. No effect of sodium chloride was detected under these conditions.

Figure 35:
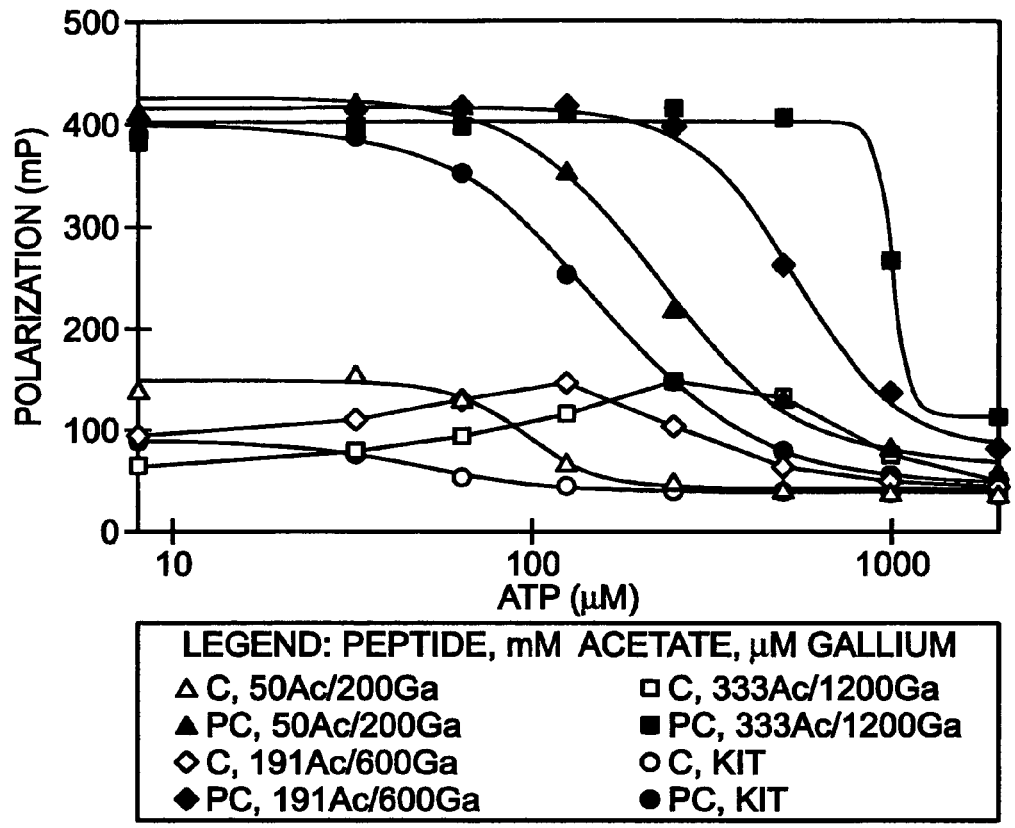
FIG. 35 is a graph showing binding results with Crosstide or Phosphocrosstide as binding target, as a function of ATP concentration and with different acetate/gallium ratios, in accordance with aspects of the present teachings.

FIG. 35 shows a graph of the fluorescence polarization signal of Crosstide ("C")/Phosphocrosstide ("PC") binding reactions as a function of ATP concentration and with different acetate/gallium ratios in the binding solutions. Resistance to adverse affects of higher ATP concentrations on the binding signal may be a measure of the absolute number of binding sites (of the binding partner) in solution. One issue is whether increasing the gallium and the acetate concentrations elevates the number of binding sites or simply reduces the number of binding sites per gallium concentration by binding of gallium to acetate. These experiments show that using higher acetate concentrations in combination with higher gallium concentrations can increase the binding capacity and thus the amount ATP that can be used. This experiment also revealed a bell shaped elevation of the signal of non-phosphorylated peptide (C) in combination with ATP that turned out to be ATP dependent.

Figure 36A:
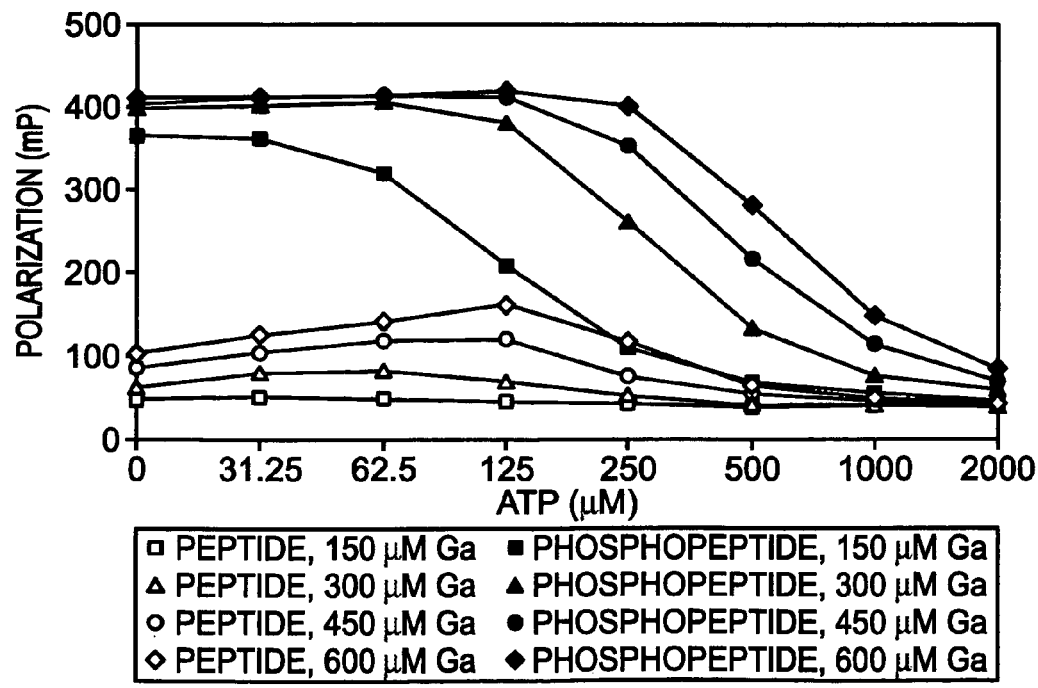
FIG. 36 is a series of graphs showing binding results from binding reactions performed to address optimization of ATP, acetate, and gallium for Crosstide, Src substrate peptide, and a p38 substrate peptide, in accordance with aspects of the present teachings.
Figure 36B:
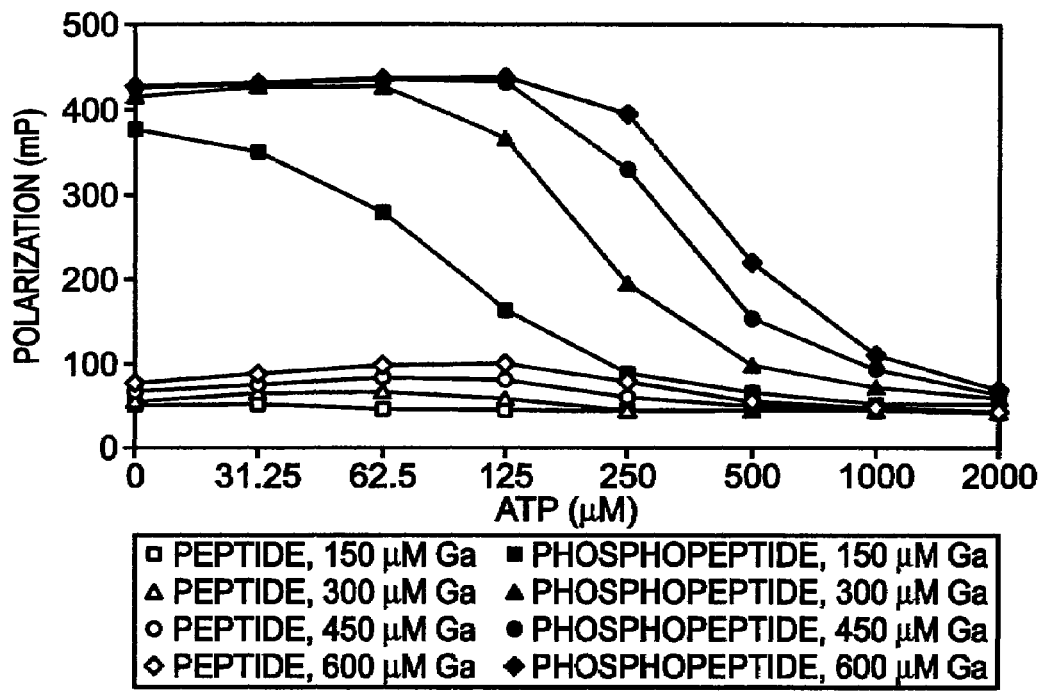
Figure 36C:
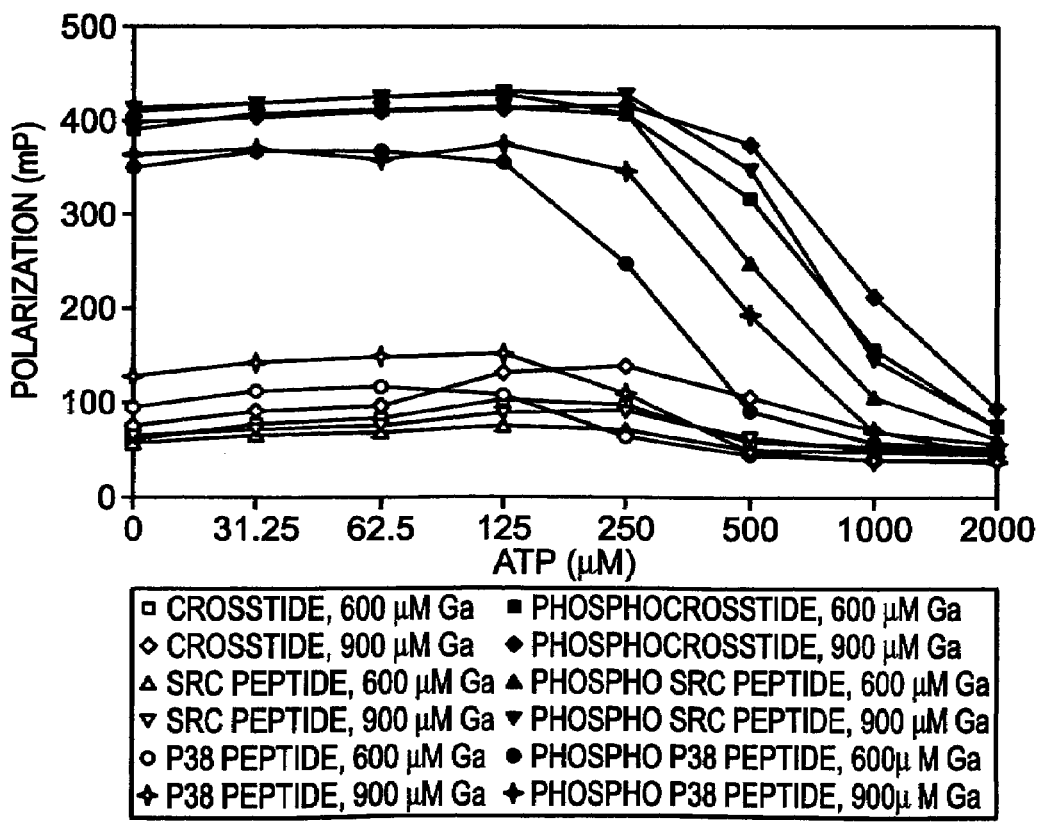

FIG. 36 shows graphs of results from binding reactions performed to address the optimization of the amounts of ATP, acetate, and gallium used. Each graph shows the ATP concentration used in each binding reaction versus the fluorescence polarization signal measured. The data of FIG. 36A were obtained with Crosstide ("peptide") or Phosphocrosstide ("phosphopeptide") in 200 mM acetate with the indicated concentrations of gallium chloride. The data of FIG. 36B were obtained with Src peptide (peptide or phosphopeptide; SEQ ID NOS:17 and 18, respectively) in 200 mM acetate with the indicated concentrations of gallium chloride. The data of FIG. 36C were obtained with Crosstide/Phosphocrosstide, Src peptide or phosphopeptide, and p38 peptide (SEQ ID NO:9) or phosphopeptide in 300 mM acetate with the indicated concentrations of gallium chloride.

These graphs suggest that there may be a maximum recommended gallium concentration even if the background does not increase substantially. In particular, these graphs shows a bell-shaped "hump" that is dependent on the concentration of gallium used, which is worse in peptides with a higher background response to gallium (at n=2), and that it can be diminished (as well as the ATP resistance raised) by elevating the acetate concentration in the binding solution. This "hump" phenomenon is not affected by sodium chloride in the binding solution (data not shown).

Example 30

Figure 37A:
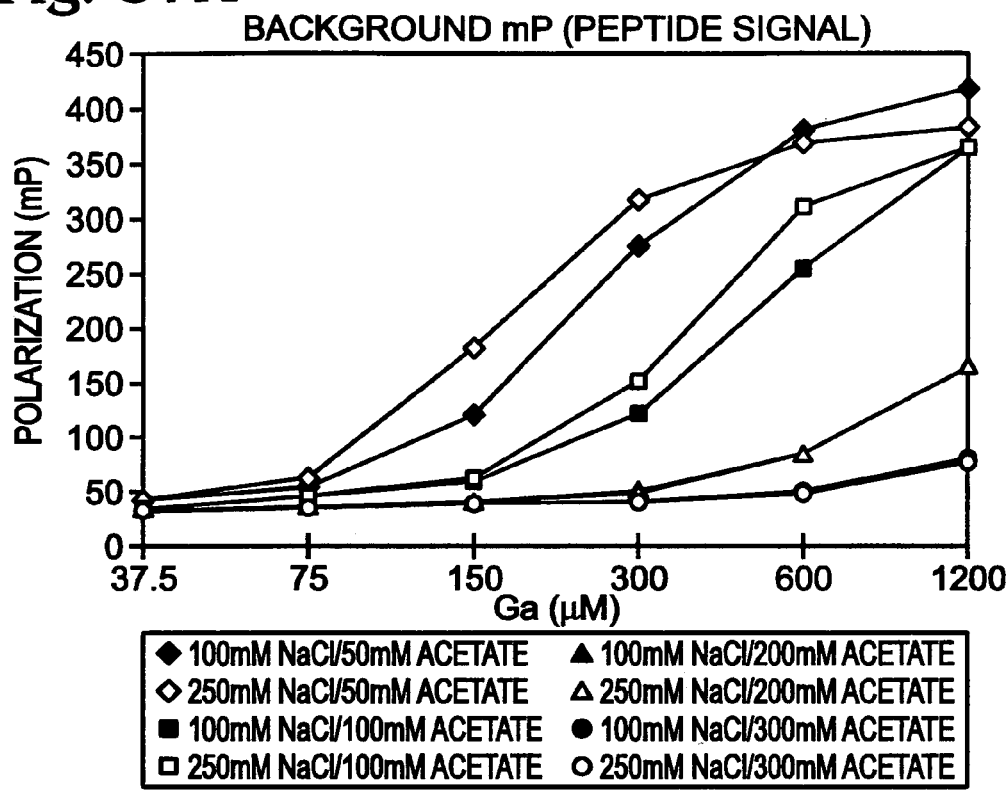
FIG. 37 is a series of graphs showing binding results from binding reactions performed with a p38 substrate peptide (FIG. 36) or a corresponding product phosphopeptide under various gallium concentrations and sodium chloride to acetate ratios, in accordance with aspects of the present teachings.
Figure 37B:
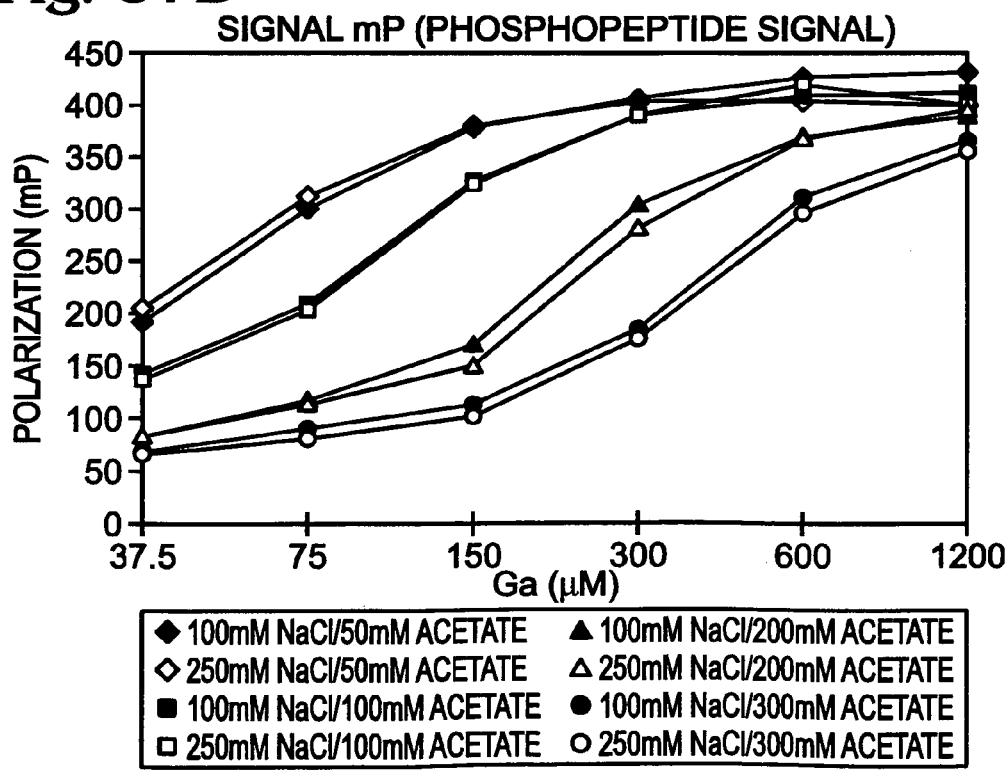

This example describes the influence of various binding solutions on fluorescence polarization in molecular modification assays involving peptide substrates with three carboxy groups; see FIGS. 37 and 38.

Exemplary peptides in this group include the p38 substrate peptide, which is EGF receptor-derived (SEQ ID NO:9). This peptide may be a special case because it is labeled with fluorescein on the epsilon-$NH_2$ group of the C-terminal lysine. This labeling scheme puts the 5FAM (5-carboxyfluorescein) label at the end of a flexible chain, which could increase the "wobble" factor of the fluorophore and thus reduce the maximum achievable fluorescence polarization. The C-terminus of the corresponding calibrator (phosphopeptide) is amidated, while the substrate C-terminus is not. Thus, there is a slight difference in the peptides being compared.

FIG. 37 shows binding results from binding reaction performed with the p38 peptide (panel A), phosphopeptide (panel B), or the net difference in signal between these peptides (panel C). Binding reactions were performed at pH 5.0 with various concentrations of gallium chloride, acetate, and sodium chloride, at pH 5.0, as indicated. The graphs of FIG. 37 show, as expected, greater gallium sensitivity for this 3-carboxy substrate than for the 2-carboxy substrates described above in Example 29. This greater gallium sensitivity can be reduced by raising the acetate concentration. The assay window (signal difference) between substrate (peptide) and calibrator (phosphopeptide) concentration is smaller for this pair, possibly because the binding reactions compare a 2-carboxy phosphopeptide (calibrator) with a 3-carboxy peptide (substrate).

FIG. 38 shows the ATP sensitivity of the binding signal produced by p38 peptide and phosphopeptide with various gallium chloride concentrations. For the ATP resistance at 300 mM acetate, see FIG. 34, panel C.

Example 31

Figure 39A:
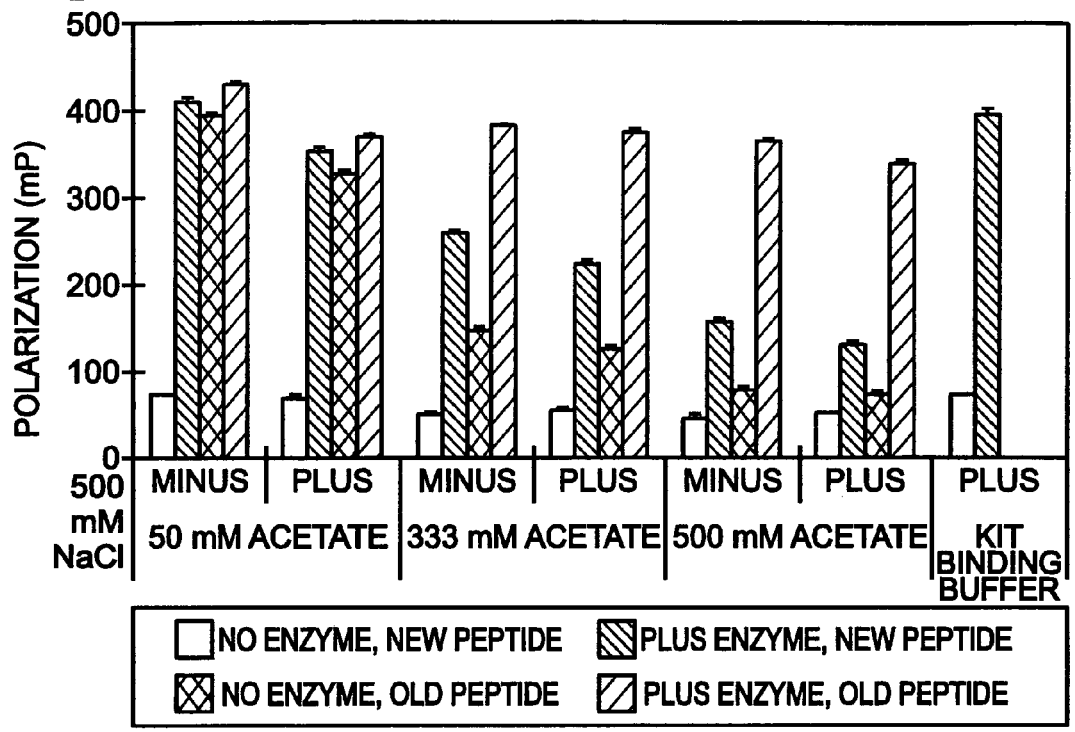
FIG. 39 is a pair of bar graphs showing binding results from binding reactions performed as Syk kinase assays using substrate peptides with different numbers of carboxy groups and under various conditions of acetate buffer and sodium chloride, in accordance with aspects of the present teachings.
Figure 39B:
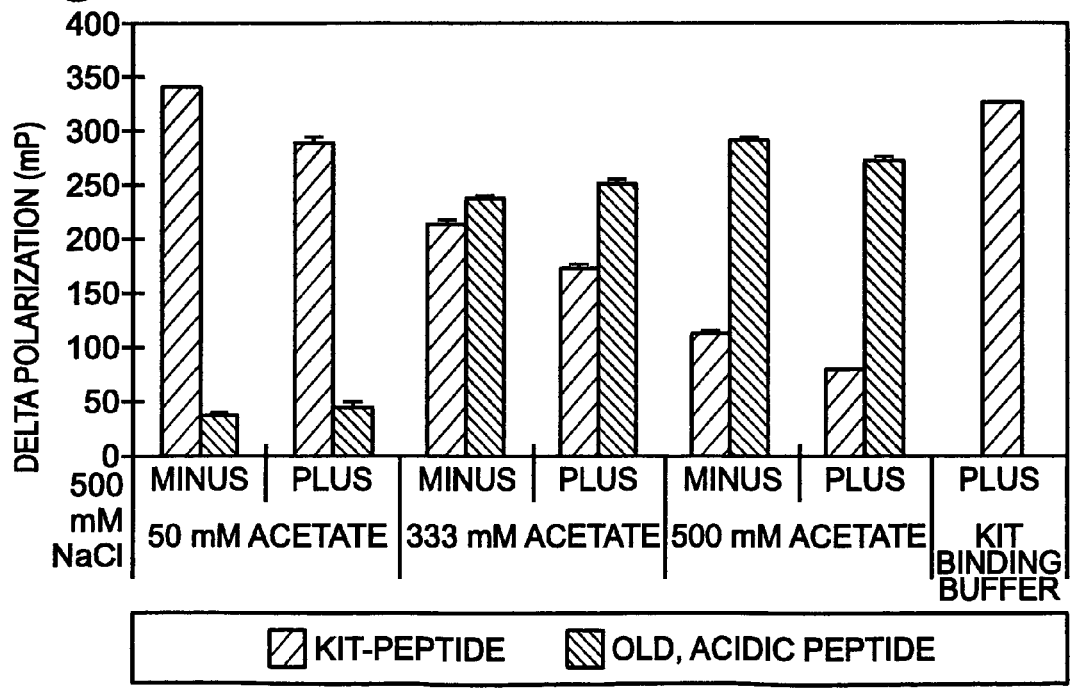
Figure 40A:
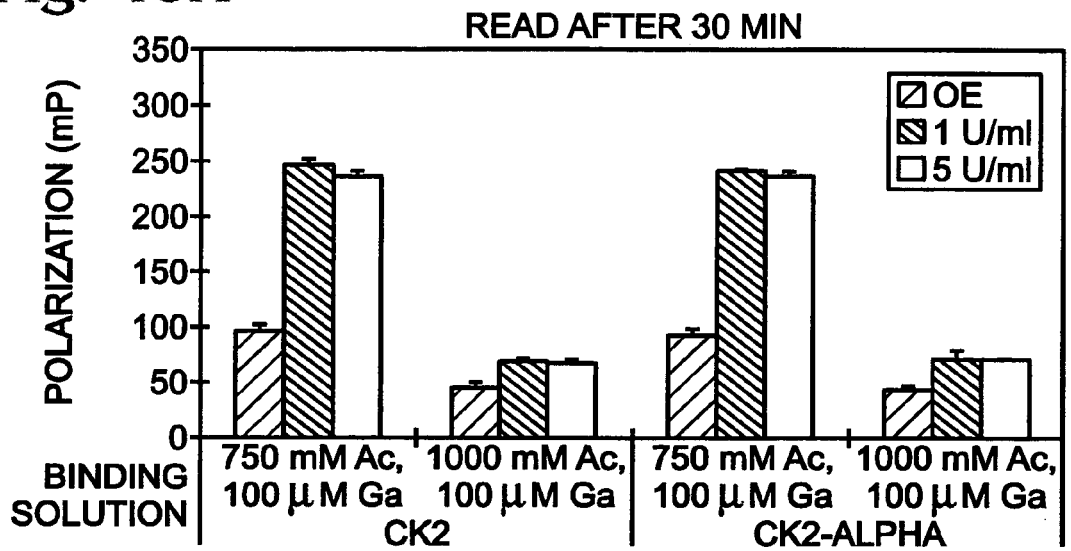
FIG. 40 is a pair of bar graphs showing binding results of binding reactions performed as casein kinase-2 assays with a highly acidic substrate peptide, in accordance with aspects of the present teachings.
Figure 40B:
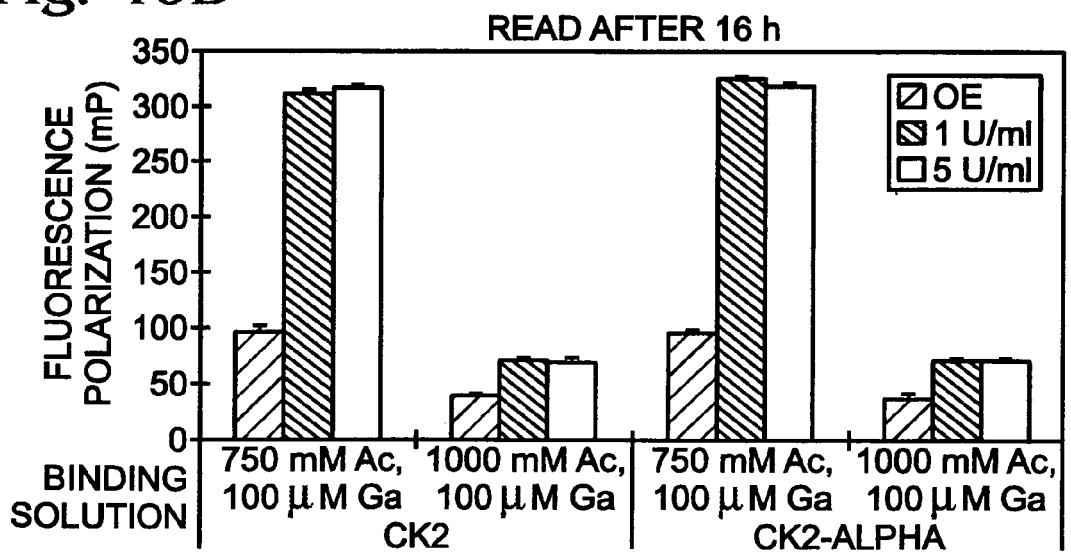

This example describes the influence of various binding solutions on the binding signals produced by peptide substrates with four or more carboxy groups; see FIGS. 39 and 40. Exemplary peptides in this group include a Zap 70 substrate peptide (SEQ ID NO: 24) and a Gastrinic peptide, both of which may exhibit very high backgrounds.

FIG. 39A,B shows graphed results from binding reactions performed on a Syk kinase assay (1U/mL) with the original Zap 70 substrate peptide ("old peptide"; SEQ ID NO:24) in comparison with a modified Zap 70 substrate peptide (SEQ ID NO:23) having only two acidic residues ("new peptide" or "kit peptide"). Binding reactions included the indicated concentrations of acetate, 100 µM gallium chloride (a 1:800 dilution), and the presence or absence of 500 mM NaCl. Alternatively, binding reactions included the "kit" binding buffer (see Example 27). Binding reactions were incubated overnight with substrate peptide or product phosphopeptide and then the fluorescence polarization was measured. By raising the acetate concentration to 500 mM and lowering the gallium concentration to 100 µM, an assay window of 250 mP could be achieved.

FIG. 40 shows another example of binding reactions performed with a very acidic casein kinase-2 (CK2) substrate peptide (SEQ ID NO:25). This CK2 substrate peptide has seven acidic residues, plus a C-terminal carboxy group and 5-carboxyfluorescein, to give a total of nine carboxy groups. Casein kinase-2 assays were performed with either casein kinase 2 ("CK2") or casein kinase 2 alpha ("CK2-alpha"), at the indicated concentrations of 0, 1, or 5 U/mL enzyme. Binding assays were performed subsequently by contacting with binding solution for 30 minutes (panel A) or 16 hours (panel B), using 750 or 1000 mM sodium acetate, pH 5.0, and 100 µM gallium chloride. Both assays used 10 µM ATP. With 750 mM sodium acetate, an assay window of 200 mP was achieved. These results suggest that the molecular modification assays described herein should work with a variety of receptor tyrosine kinases, which often prefer very acidic peptides.

Example 32

Figure 41:
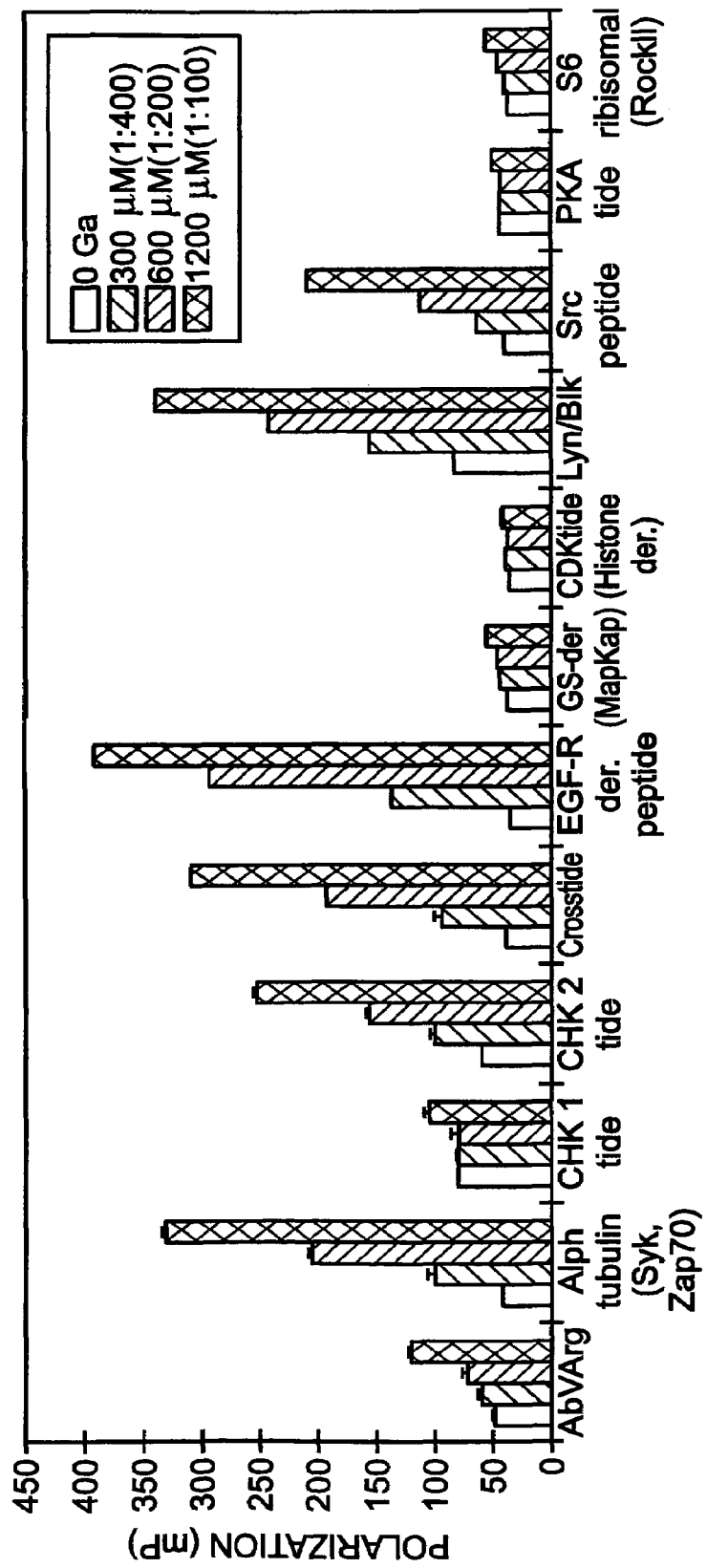
FIG. 41 is a bar graph showing binding results from binding reactions with various nonphosphorylated peptides and at various gallium concentrations, in accordance with aspects of the present teachings.

This example describes binding assays testing the background fluorescence polarization signal for various exemplary peptide substrates as a function of gallium concentration; see FIG. 41.

Binding reactions were performed with the indicated set of gallium concentrations for the following peptides (see Tables 5 and 6 for sequences and additional identifying information): Abl/Arg substrate peptide (SEQ ID NO:2), Alpha tubulin-derived peptide (SEQ ID NO:23), CHK1tide (SEQ ID NO:4), CHK2 tide (SEQ ID NO:5), Crosstide (SEQ ID NO:6), EGF-R der. peptide (SEQ ID NO:9), GS der. peptide (SEQ ID NO:11), CDKtide (SEQ ID NO:13), Lyn/Blk (SEQ ID NO:16), Src (SEQ ID NO:17), PKA tide (SEQ ID NO:20), and S6 ribosomal (SEQ ID NO:21). The background binding signal produced at higher gallium concentrations varied substantially according to peptide sequence. In particular, peptides with two or more carboxy groups tend to give higher background that those with one or fewer carboxy groups.

The following table summarizes correlations between gallium sensitivity and the charge (titrated, theoretical, number of acidic, etc.) of various peptides described herein.

acetic acid, 500 mM NaCl, and titrated to pH 5.0 with NaOH, was used to dilute a stock solution of $GaCl_3$ (0.48M in 0.1 M HCl) 1:400. This binding solution provided good discrimination in binding to 100 nM FL-Phosphocrosstide (SEQ ID NO:7) but not 100 nM FL-Crosstide (SEQ ID NO:6).

This binding solution did not give good results for another peptide/phosphopeptide pair based on the fluorescein-labeled (X-tubulin-derived substrate (SEQ ID NO:23). A modification of the binding buffer provided better results. A 290 mM acetate binding buffer was made by mixing 75 parts of Buffer 1 with 25 parts of a second buffer (Buffer 2, comprising 1 M acetic acid, titrated to pH 5.0 with NaOH). The above-mentioned $GaCl_3$ solution was diluted into this 290 mM acetate buffer 2400 fold. The results demonstrate that the tubulin-derived peptide substrate works much better in this high-acetate system. Accordingly, a ratio of buffers 1 and 2, or a buffer or salt concentration, may be selected according to the sequence and/or charge of the binding target (e.g., peptide).

Example 34

This example summarizes observations on assay components and assay performance from data presented in Examples 26-33.

The influence of a variety of assay components and conditions on assay performance has been evaluated. To facilitate this evaluation, the assay systems sometimes have been char-

TABLE 8

| Sequence Identifier | pI | Titrated charge at pH 5.5 | Predicted charge at pH 5.0 | Aliphatic index | Number acidic | Gallium sensitivity | Acidic amino acids + carboxy | Kinase enzyme |
|---|---|---|---|---|---|---|---|---|
| SEQ ID NO: 2 | 9.84 | 1 | 0 | 66 | 1 | 16.5 | 1 | AbI |
| SEQ ID NO: 4 | 11.6 | 3 | 2 | 130 | 0 | 46 | 0 | CHK1 |
| SEQ ID NO: 5 | 9.84 | 1 | 0 | 63 | 1 | 6 | 2 | CHK2 |
| SEQ ID NO: 6 | 12.6 | 1 | −1 | 43 | 2 | 4.3 | 2 | Akt, |
| SEQ ID NO: 9 | 4.25 | −1 | −1 | 78 | 2 | 3.2 | 2 | p38 |
| SEQ ID NO: 11 | 11.6 | 3 | 1 | 117 | 1 | 71 | 1 | MAPKAP K2 |
| SEQ ID NO: 13 | 10.89 | 4 | 3 | 45 | 0 | 234 | 0 | CDK2/Cyclin A |
| SEQ ID NO: 14 | 7.8 | 1 | −1 | 36 | 2 | | | IKK alpha |
| SEQ ID NO: 16 | 9.84 | 1 | 0 | 68 | 2 | 4.6 | 2 | Blk |
| SEQ ID NO: 17 | 7.12 | 0 | −1 | 96 | 2 | 6.8 | 2 | Fyn |
| SEQ ID NO: 20 | 10.89 | 1 | 2 | 9 | 0 | 156 | 0 | PKA |
| SEQ ID NO: 21 | 12.79 | 5 | 3 | 89 | 0 | 58 | 0 | ROCK II |
| SEQ ID NO: 23 | 4.05 | −1 | −2 | 97.3 | 2 | 4 | 2 | Syk |

Example 33

This example describes data obtained with different acetate concentrations to assay different peptides.

Additional experiments were performed using a third set of buffers based on acetate which differed primarily in acetate concentration. A binding buffer (Buffer 1) comprising 50 mM acterized based on some set of suitable parameters (e.g., related to reaction equilibrium). For example, the peptide/enzyme systems used in kinase/phosphatase assays have been characterized using (1) the Km (Michaelis-Menten constant) of the substrate with a particular kinase, (2) the affinity of the substrate in the nonphosphorylated state to the binding entity ("background"), and (3) the affinity of the substrate in the phosphorylated state to the binding partner (absolute, and in relationship to the amount and affinity of ATP used). The following observations are noted here, based in part on these parameters:

1. Bovine serum albumin (BSA) in the binding solution may (a) enhance precipitation dramatically, and (b) may reduce the concentration of "active" gallium.

2. Binding solution stability may be comparable or the same in each system. Typically, the number of binding sites will decrease over time. However, whether this decrease becomes apparent is a function of the peptide sequence and the ATP concentration used.

3. Gallium concentration is the main contributing factor for the binding capacity of the binding solution.

4. The preferred or usable assay window lies between specific and nonspecific binding of the phosphorylated peptide to the binding entity. This window may be defined by the concentration of gallium, acetate, NaCl, and the number of free carboxy groups in the substrate.

5. Acetate (e.g., in the form of sodium acetate buffer) can be used as a source of carboxy groups to "block" nonspecific binding of acidic residues of peptides to binding partners.

6. The stability of the binding solution may be increased by a decrease in pH from 5.5 to 5.0. This change also puts the pH of the binding solution closer to the pKa of acetate and thus improves the buffering capacity of the system.

7. The peptide substrates roughly can be categorized by counting free carboxy groups (acidic residues +carboxy-terminus). The carboxy-terminus may not be considered free (and thus not counted) if it is modified to remove its negative charge (such as by amidation).

Example 35

This example generalizes the observations of Examples 26-34 to produce general rules for creating binding buffers for molecular modification assays.

These observations have a number of implications for assay construction. These implications may address the stability of the binding solution, the influence of acidic residues of the peptide substrate (or product) on assay results, and the amount of ATP that may be used in assays, among others. These implications may be interpreted using any suitable criteria, including the 24-hour stability of the binding solution and/or the ATP resilience, among others. Selected implications may include:

1. BSA in the binding buffer may be the main reason for the instability and precipitation in the binding solution. Reformulated binding buffer (no BSA; pH 5.0; and varied amounts of gallium (from the binding reagent), NaAc, and NaCl) may result in a more stable binding solution (e.g., as determined 24 hours after preparation at room temperature).

2. The assay window of any given peptide/phosphopeptide pair can be adjusted by changing the concentration of NaAc, NaCl, and gallium in the binding solution. The optimum concentrations are influenced mainly by the total number of carboxy groups in the substrate (on luminophore, number of acidic amino acids, C-terminus (amidated or free), etc.). Secondary considerations include the type of acidic amino acid, positioning of carboxy groups (relative to each other and to the phosphorylation site), and luminophore type. Knowing these features allows the buffer system to be optimized for each application, if desired. These observations and insights virtually remove sequence restrictions on the substrates and vastly improve ATP tolerance, especially for peptides with no or few acidic residues.

3. The reformulated "high" gallium binding reagent makes it possible to have very high gallium concentrations in binding solution and thus further improves ATP tolerance in the system.

4. The change of carrier substance in reaction buffer can be beneficial for inhibitor IC50 determination, depending on the inhibitor. Several proteins and detergents (at least) are compatible.

These findings for different assays can be summarized in tabular form, based on the number of carboxy groups in the peptide substrate.

TABLE 9

| Number of Carboxy Groups On Peptide Substrate | Selected Implications for Binding Buffer |
| --- | --- |
| 0 | NaAc - low (but leaving enough buffering capacity to lower pH) |
| | NaCl - presence (e.g., ~500 mM) boosts signal |
| | Adding a free carboxy terminus boosts affinity |
| 1 | NaAc - ~50 mM is on the safe side) |
| | NaCl - probably optional but should not hurt (except perhaps stability of binding solution) |
| 2 | NaAc - ~200-300 mM (although hardest to predict) |
| | Gallium - may be titrated, but the higher the acetate concentration, the more likely that one gallium concentration will fit more peptides |
| 3 | NaAc - ~300 mM |
| | Gallium - ~600 µM (or titrate in) |
| 4+ | NaAc - ~300-500 mM |
| | Gallium - ~100 µM (or titrate in) |
| | Higher acetate concentrations and/or different gallium concentrations may be helpful with more acidic residues |

The assays more generally can be performed using any suitable components and conditions. Thus, components generally may be replaced by other components capable of performing the same or similar functions. For example, in this context, acetate could be replaced by propionate or other suitable compositions, among others.

Example 36

This example describes further generalizations about adjusting binding solutions in molecular modification assays according the structure and/or charge of the binding target.

The following table summarizes exemplary starting conditions for optimization of binding solutions according to the structure and/or charge of the binding target (such as target peptide). The binding solutions may include the indicated ratios of Buffer 1 (50 mM acetic acid, 500 mM NaCl, titrated to pH 5.0 with NaOH) and Buffer 2 (1M acetic acid, titrated to pH 5.0 with NaOH). The binding solutions also may include the indicated dilutions of a gallium-based binding reagent (such as gallium chloride at 0.48M). Binding reactions may be incubated with binding targets for the indicated times before measuring a binding signal (such as fluorescence polarization). The time of incubation may be selected according to the structure/charge of the target peptide and/or according to the binding solution used in the binding reaction.

TABLE 10

| Number of —COOHs in peptide | Buffer 1 | Buffer 2 | Dilution of Binding Partner | Binding Incubation Time |
|---|---|---|---|---|
| None or 1 | 100% | 0% | 1/400 | 30 minutes |
| 2 or 3 | 75% | 25% | 1/600 | 1 hour |
| 4 | 40% | 60% | 1/1200 | 2 hours |
| 5 or more | 25% | 75% | 1/2500 | 5 hours or more, depending on number of acidic residues in peptide |

Example 37

This example describes aspects of the present teachings relating to resonance energy transfer, including using FRET (Fluorescence Resonance Energy Transfer) and TR-FRET (Time-Resolved Fluorescence Resonance Energy Transfer) as a detection mechanism; see FIGS. 42-49.

Figure 42A:
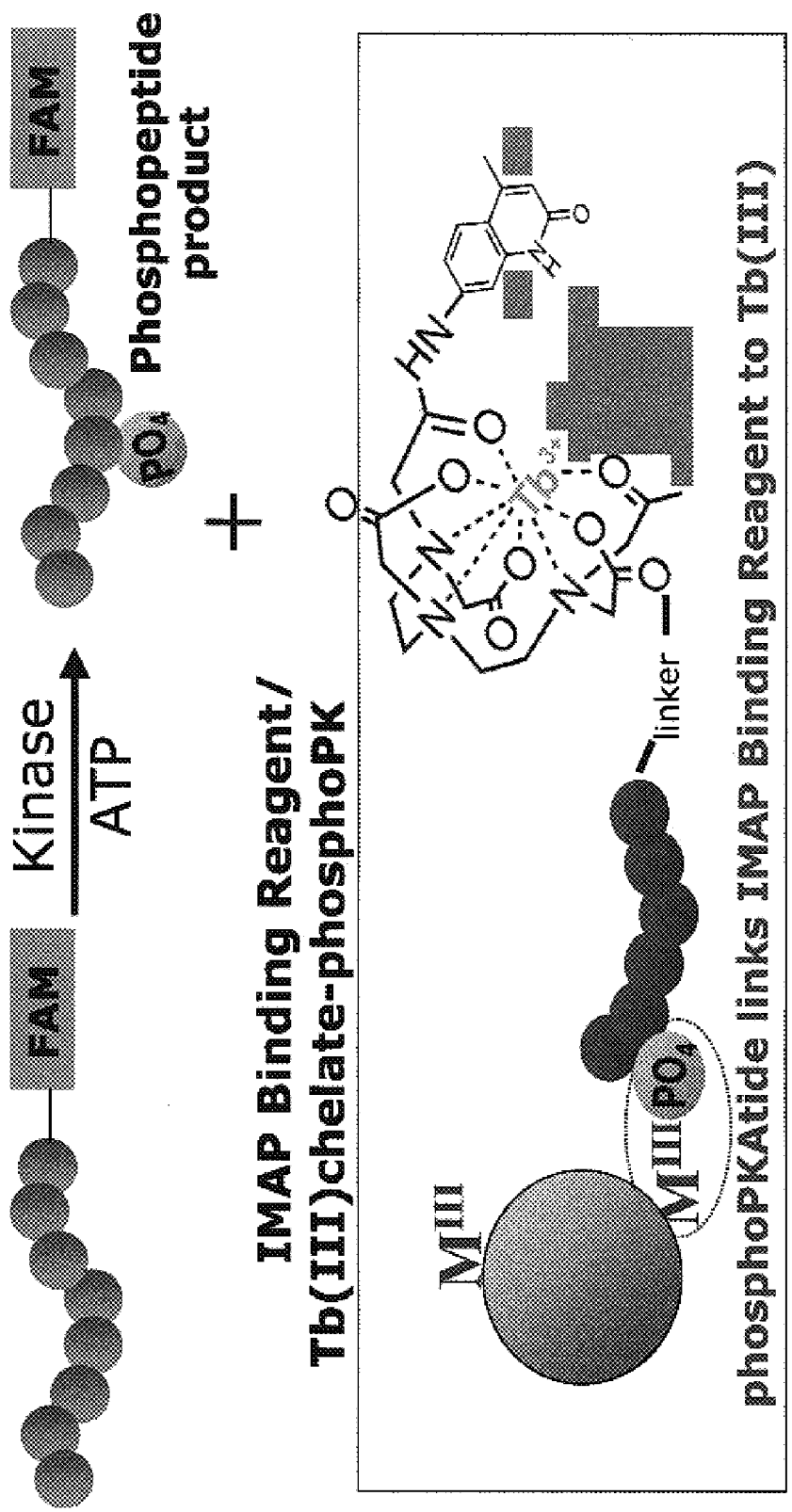
FIG. 42 is a schematic representation of an exemplary FRET (or TR-FRET) kinase assay, in accordance with aspects of the present teachings.
Figure 42B:
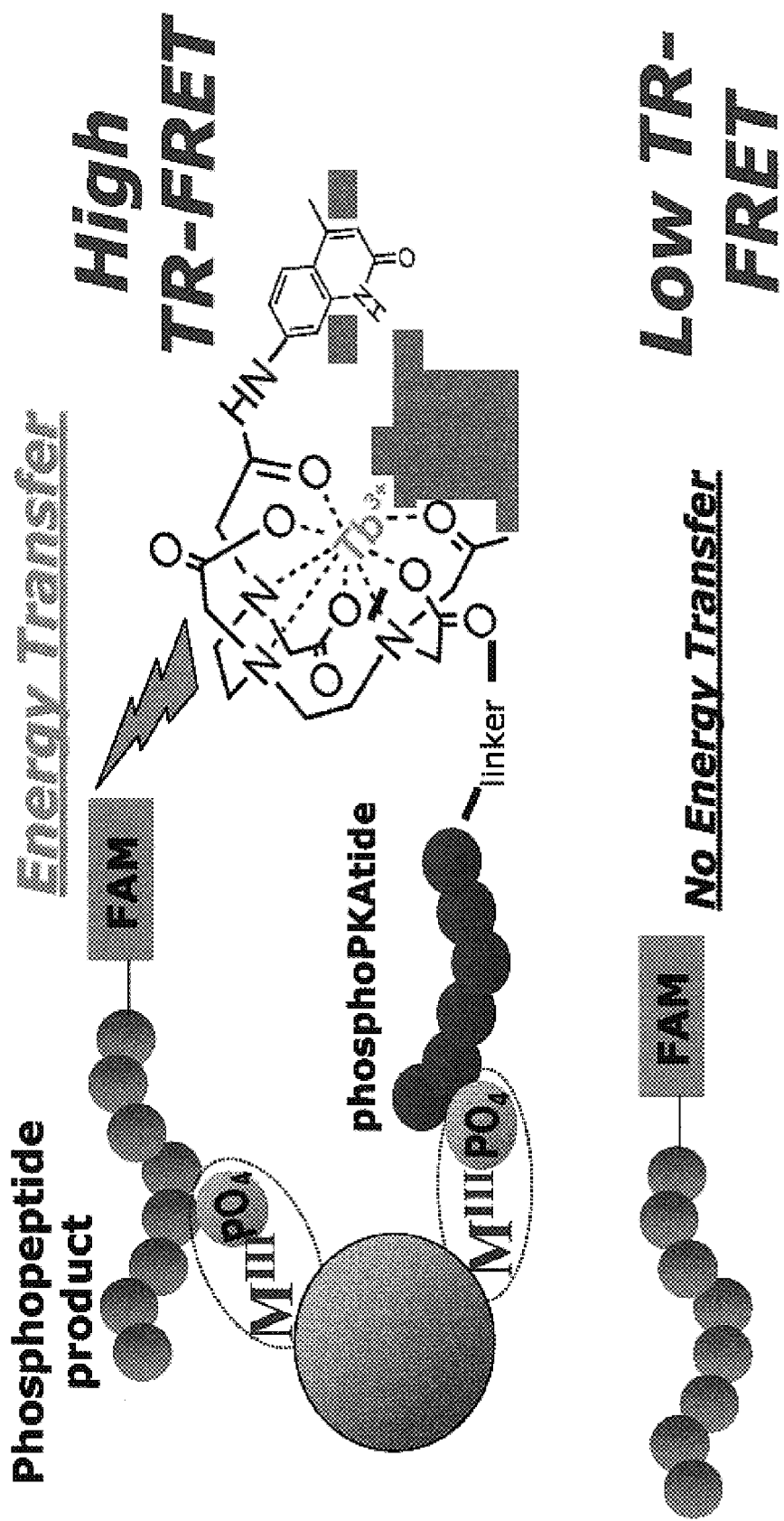

FIG. 42 is a schematic representation of an exemplary FRET (or TR-FRET) kinase assay. In this assay, a peptide substrate is exposed to a kinase enzyme and a source of phosphate groups. The substrate may include a FRET label, specifically, a member of a FRET donor/acceptor pair, for example, a luminescent or dark acceptor such as FAM. The kinase enzyme may phosphorylate the substrate, to produce a phosphopeptide product. In some embodiments, this reaction may be performed in the presence of one or more potential modulators, such as candidate agonists or antagonists, or candidate promoters or inhibitors, and so on, to determine the effect of the potential modulator on the (kinetics and/or endpoint of the) reaction. (In some embodiments, selected assay components may be used to detect the present, concentration, and/or activity of a substrate, without expressly requiring performance of the reaction.) The reaction mixture including the substrate and/or product (optionally including enzyme and (expended and/or unexpended) phosphate source) may be exposed to a suitable binding or association partner, capable of recognizing the phosphorylated product, but not the unphosphorylated substrate. The binding partner may include and/or associate the opposite or conjugate member of the FRET donor/acceptor pair, for example, a luminescent donor such as a terbium chelate. Thus, in this assay, the binding partner will associate with phosphorylated product, but not unphosphorylated substrate. This, in turn, implies that energy transfer will be relatively high in the presence of phosphorylated product, since donor and acceptor will come into proximity via binding, and relatively low in the absence of phosphorylated product, since donor and acceptor will remain relatively separated in the absence of binding. In some embodiments, the positions of the donor and acceptor may be reversed, such that the donor is associated with the substrate/product, and the acceptor is associated with the binding partner. Energy transfer can be monitored using any suitable indicator(s), including a decrease in donor luminescence, an increase in acceptor luminescence, and/or a decrease in donor lifetime, among others.

FRET (or TR-FRET) can be used as a readout or reporter function in any of the assays described herein, including but not limited to kinase assays (as described immediately above), phosphatase assays, cyclase assays, and phosphodiesterase assays, among others. In each case, one member of a FRET donor/acceptor pair may be associated with the substrate and/or product, and one member may be associated with the binding partner. For example, a FRET phosphatase assay may be performed essentially as described above, beginning with a phosphorylated substrate, where phosphatase activity will result in a loss in energy transfer as phosphorylated substrate is converted to nonphosphorylated product (with a resulting loss of affinity for the binding partner). More generally, the donor and acceptor may be positioned on any suitable reaction components, at any suitable point(s) in the reaction, as long as the reaction leads to a detectable change in energy transfer.

The donor and acceptor may be associated with reaction components using any suitable mechanism(s). For example, the association may be covalent or noncovalent, direct or indirect, and so on. In FIG. 42, the donor is indirectly associated with the binding partner, attached via interaction of members of a specific binding pair, namely, a suitable metal on the binding partner, and a phosphate on the donor. Suitable binding pairs may include metal/phosphate, avidin/biotin (or streptavidin/biotin), sugar/lectin, antibody/antigen, and so on. In FIG. 42, the acceptor is directly associated with the substrate/product, attached via a covalent bond.

FIG. 43 are schematics showing exemplary terbium chelates, which may be used as suitable members of a donor/acceptor pair. The synthesis of such chelates is described below, in Example 39. The embodiments are based on DTPA, although any other suitable chelates and/or cryptates may be used. The embodiment depicted at left includes Tb-CS-124 attached to "PKA," where "PKA" represents the peptide PKAtide. This embodiment may be phosphorylated with the kinase PKA. The embodiment depicted at right includes Tb-CS-124 attached to phosphothreonine. These embodiments include one or more phosphate groups covalently attached to a terbium chelate that is sensitized to fluoresce, preferably strongly, in aqueous solution.

Figure 44:
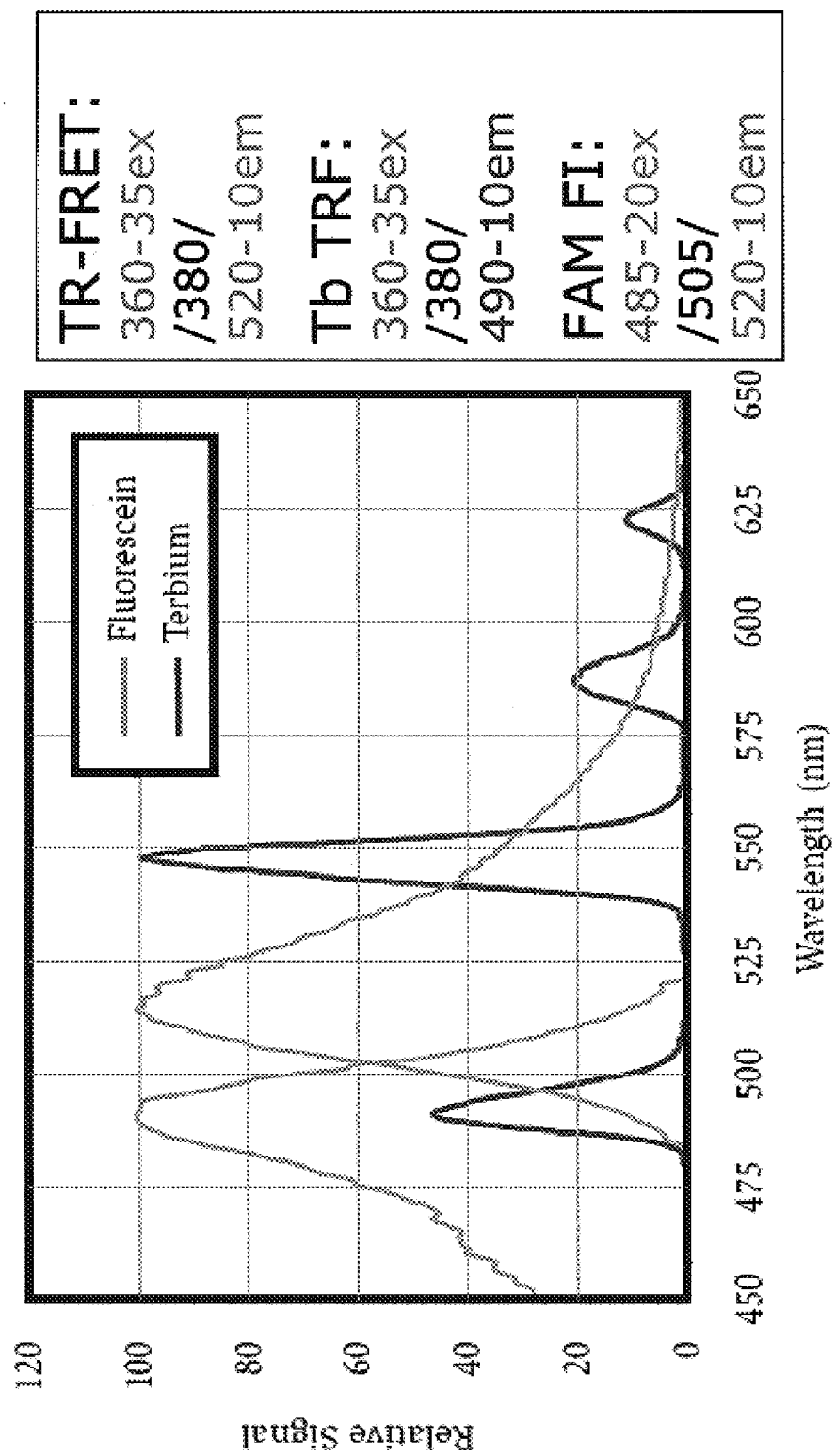
FIGS. 44 and 45 are spectra from (44) terbium and fluorescein, and (45) terbium and rhodamine, in accordance with aspects of the present teachings.
Figure 45:
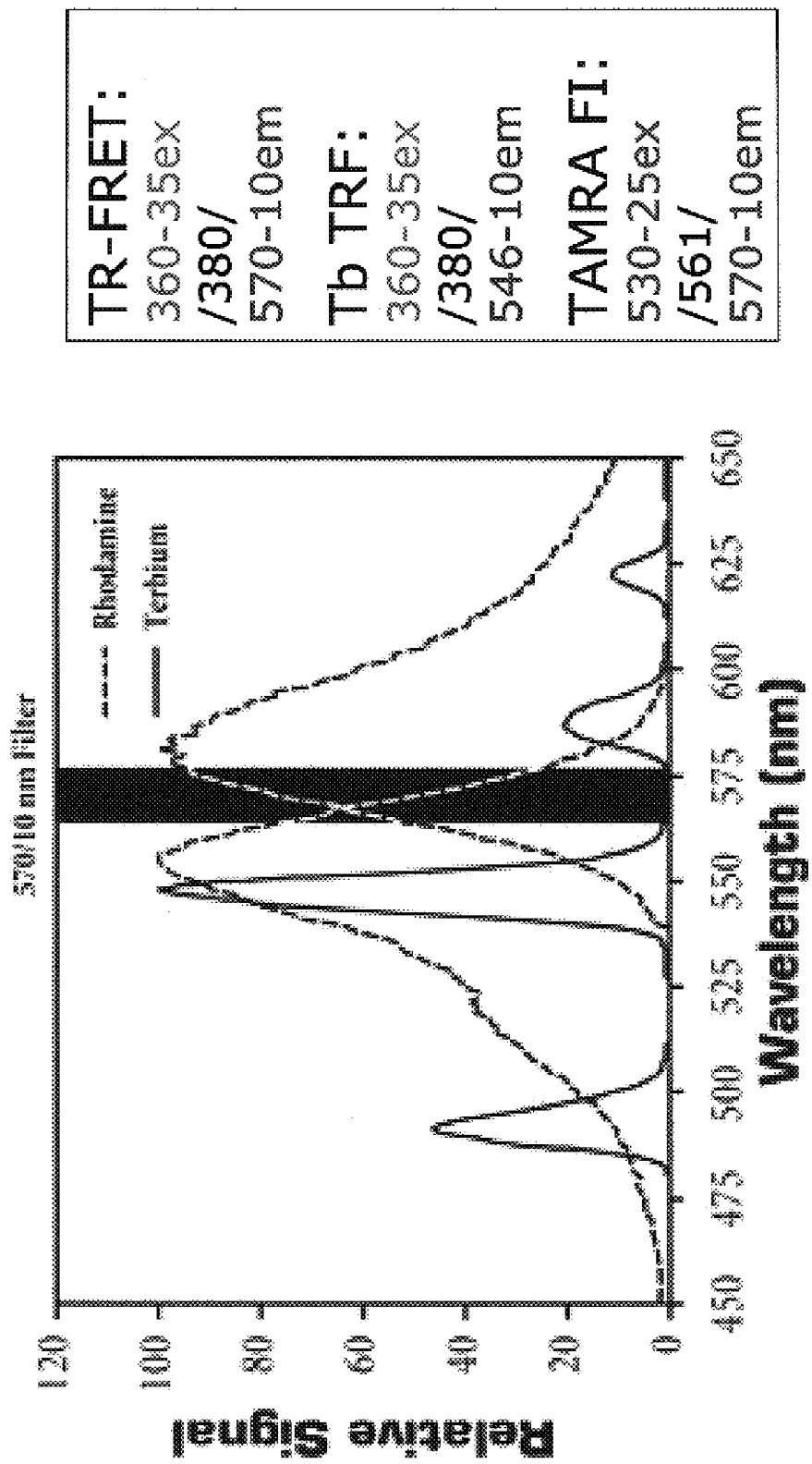

FIGS. 44 and 45 are spectra from (44) terbium and fluorescein, and (45) terbium and rhodamine. More specifically, these figures show emission spectra for terbium, and excitation (left) and emission (right) spectra for fluorescein and rhodamine. These spectra show that these combinations of luminophores are suitable for use as FRET pairs, since the emission spectrum of the terbium overlaps with the excitation spectrum of fluorescein and rhodamine. For example, energy transfer may occur between the 479-nm emission band of terbium and the 490-nm excitation band of fluorescein. Similarly, energy transfer may occur between terbium and phosphopeptides labeled with fluorescein and rhodamine, among others.

Figure 46:
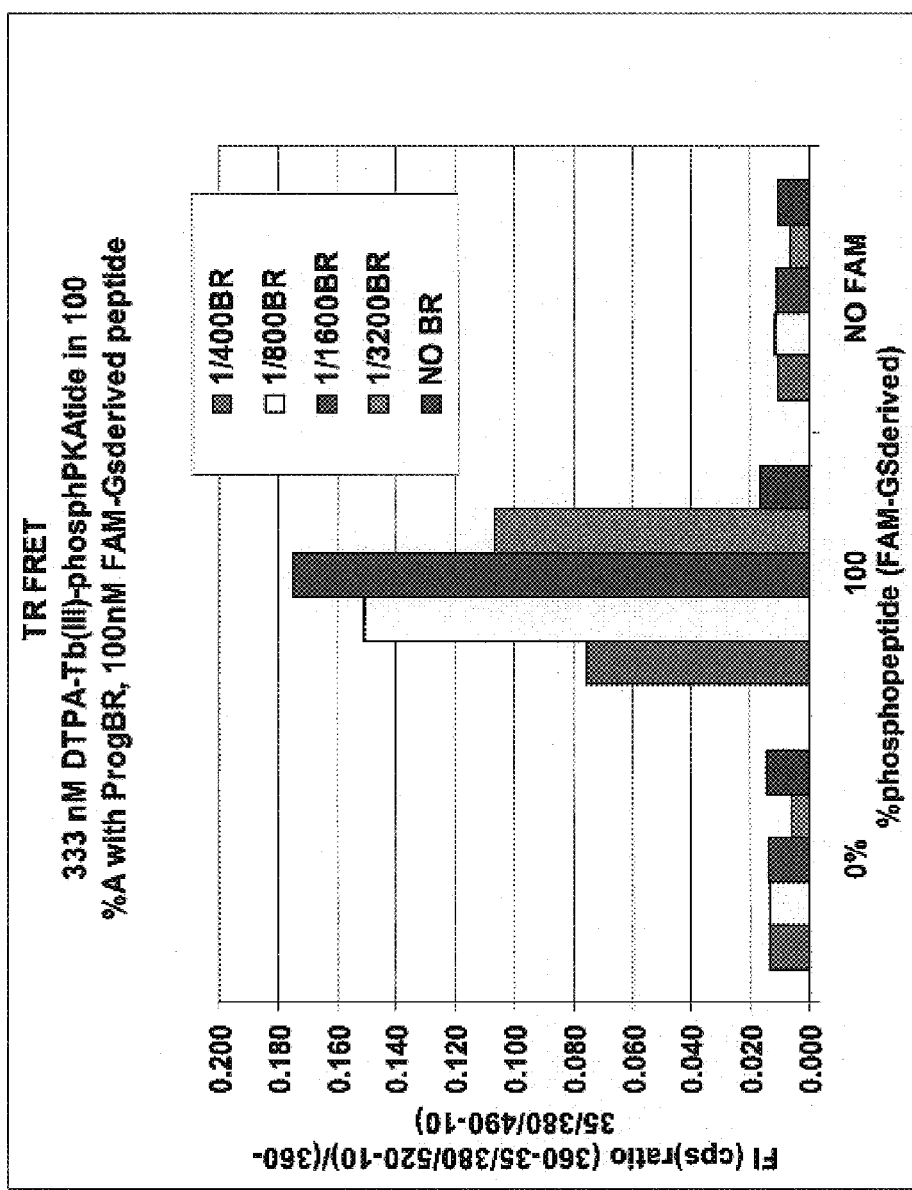
FIG. 46 is a bar graph showing that FRET is suitable for detection of phosphorylated peptide, in accordance with aspects of the present teachings.
Figure 47:
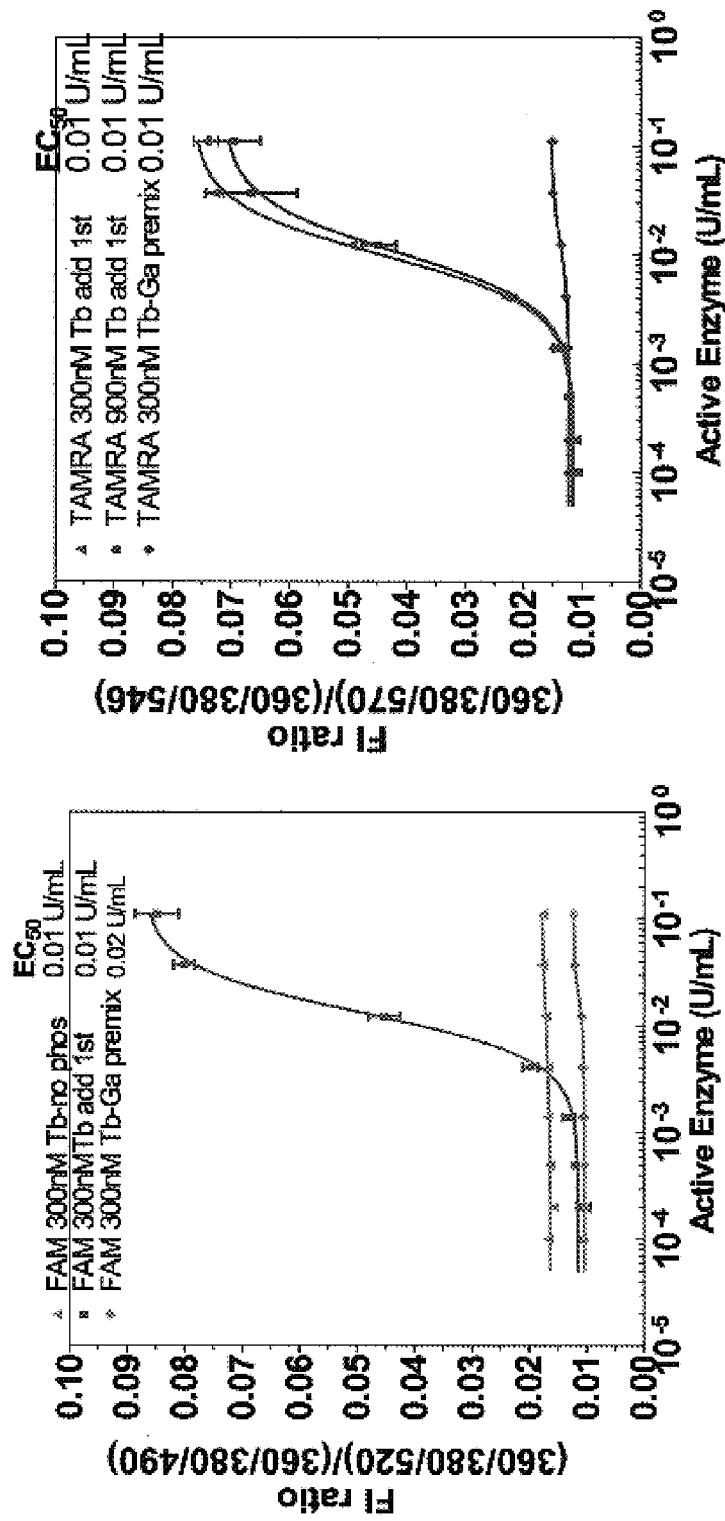
FIG. 47 shows results from a FRET kinase assay for CDK2-cyclin A cyclin-dependent kinase, in accordance with aspects of the present teachings.

FIG. 46 is a bar graph showing that FRET is suitable for detection of phosphorylated peptide. The system studied in these experiments includes a terbium chelate, such as terbium-CS124 (Tb-CS124), covalently attached to a phosphate-bearing species, such as the phosphopeptide "PKAtide." Here, in the presence of a gallium binding reagent, there is no significant FRET signal in the absence of phosphopeptide (labeled "0%") or acceptor (labeled "no FAM"), and there is a significant FRET signal in the presence of phosphopeptide (labeled "100"). Similar results may be seen with other FIG. 47 shows results from a FRET kinase assay for CDK2-cyclin A cyclin-dependent kinase. Comparable results are obtained using FAM acceptor (left) and TAMRA acceptor (right).

Figure 48:
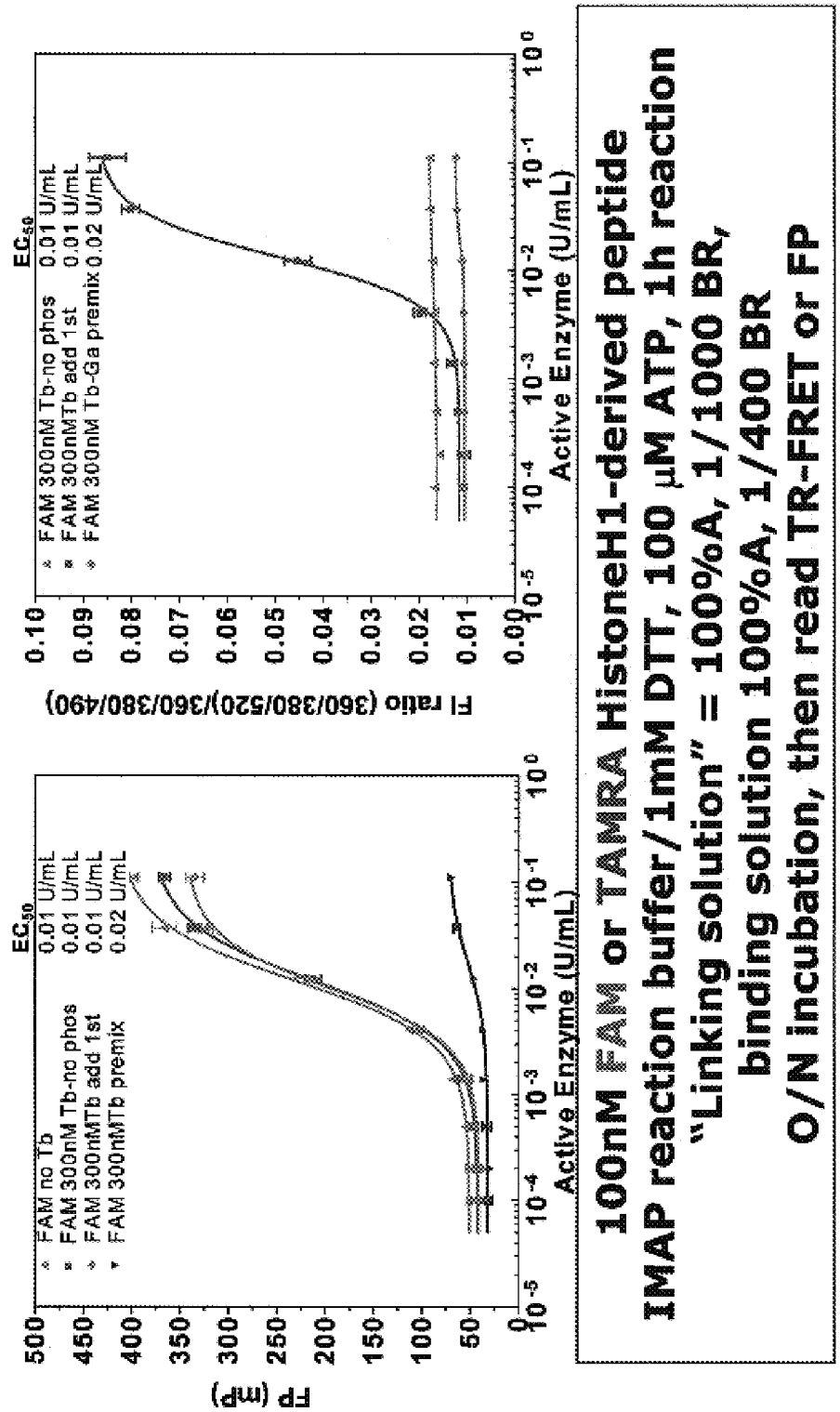
FIGS. 48 and 49 show comparisons between FP (left) and FRET (right) assays, for FAM acceptor (48) and TAMRA acceptor (49), in accordance with aspects of the present teachings.
Figure 49:
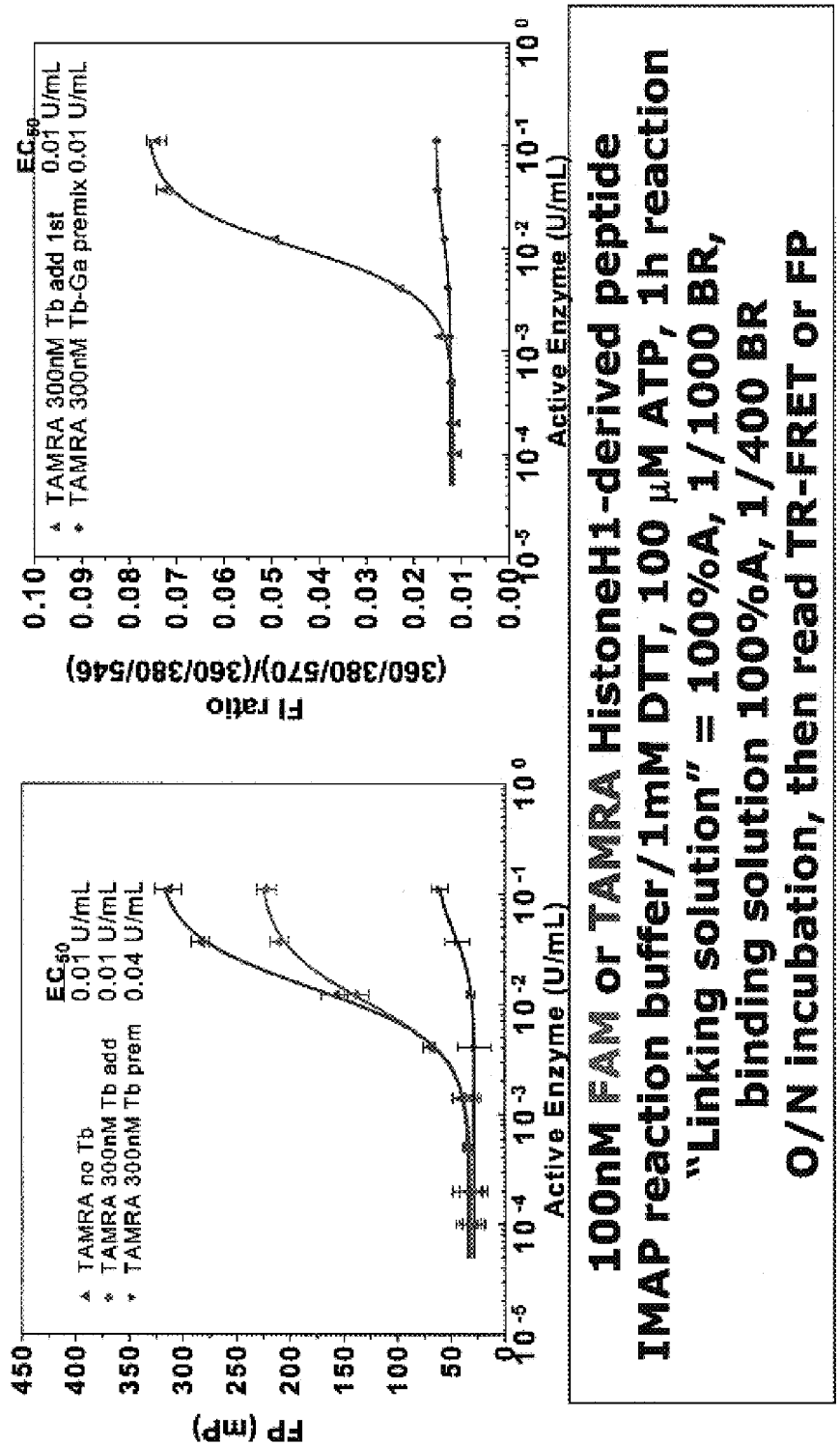

FIGS. 48 and 49 show comparisons between FP (left) and FRET (right) assays, for FAM acceptor (48) and TAMRA acceptor (49). The results show that both assay formats may provide robust readouts.

FRET-based assays may have various advantages over (or in combination with) other assay formats, for example, fluorescence-polarization (FP) based formats. First, FP-based assays may work best with relatively high substrate conversion, which in turn effectively may place an upper limit on usable substrate concentration and/or necessitate use of higher enzyme concentrations. FRET-based assays may overcome these potential limitations. Second, FP-based assays may be limited by the size of the luminescent entity (unless labeled by long lifetime fluorophores). TR-FRET does not have this size limitation. Third, although both IMAP-FP and the TR-FRET assays work well under standard IMAP-FP conditions, TR-FRET will gain in the sensitivity of its response with increasing substrate concentrations (because the assay only responds to product, not substrate; hence, more substrate=more product at any fixed kinase concentration), whereas, in FP, the opposite occurs (because greater product formation is obscured by increasing substrate concentration). Thus, FRET may provide greater flexibility in choice of substrate concentrations, as well as the ability to use lower enzyme concentrations. Moreover, substrates that are too poor to use in IMAP might very well be used in the TR-FRET assay. Fourth, FP and TR-FRET both may be read in the same system. Thus, information from both assays can be combined to enhance precision and reduce interferences, further than either technique can do alone. Fifth, FRET assays may be multiplexed, for example, using multiple acceptors such as TAMRA and fluorescein on separate peptides for separate kinases.

The FRET approach generally involves constructing an assay so that changes in donor-acceptor separation, detectable as changes in energy transfer, are correlated with changes in the assay parameter(s) of interest. These parameters may include the presence or activity of a species of interest, the kinetics and/or endpoint of a reaction of interest, and so on. This change in separation may be effected using any suitable mechanism(s), consistent with these goals. For example, in the metal-based embodiments described herein, a donor (e.g., lanthanide salt) may be brought directly into proximity with gallium (e.g., in mixed clusters), and FRET detected in the presence of an acceptor-labeled phosphorylated entity that interacts with the gallium. Alternatively, or in addition, the donor and acceptor may be brought into (or out of) contact via interaction with a common binding partner. (For example, one member of a donor/acceptor pair may always interact with the common binding partner, and the, second member of the donor/acceptor pair may be brought into (or out of) contact based on the outcome of a reaction.) This indirect approach is the same, in a sense, as the direct approach, in that it allows for proximity between a phosphorylated acceptor-labeled entity, such as a peptide, a lanthanide compound (cryptate), and the gallium binding entity, bringing donor and acceptor together. However, this indirect approach is different, in a sense, in that it allows associating the lanthanide entity in a better-defined way with the gallium binding entities (e.g., onto their surface). In some embodiments, this association may involve a cryptate, and not the metal ion itself, which may increase brightness of the lanthanide and shield the lanthanide from interactions with the gallium itself. Binding of donor and acceptor to a common binding partner may amplify signal, but bringing more than one donor and/or acceptor into proximity, enhancing the avenues for and thus the likelihood of energy transfer. These concepts are illustrated in FIG. 42, among others. Alternatively, the metal of the binding entity itself may take part in an energy transfer pair. Where the metal of the binding entity engages in energy transfer, the metal may be europium, terbium, ruthenium, or iron, among others. Some energy transfer partners that may include the binding entity metal may be quenchers, such as Fe.

In this approach, the number of phosphate binding sites, the concentration of acceptor, and the concentration of donor can be modified independently from each other, which may provide big advantages in FRET (or TR-FRET) assays. This may be especially true for kinase assays, where the phosphate binding capacity must enable the interaction of donor and acceptor, and at the same time be in excess over the amount of ATP added. In addition, this approach may allow modification of the size of the gallium binding entities, and thus the number of gallium binding sites, by modifying pH (and/or other solution properties), and with that possibly enhancing the possibility of proximity between donor and acceptor.

The FRET-based assay approach may includes a variety of embodiments and improvements. For example, a phosphorylated peptide/protein/molecule may be labeled with lanthanide (Eu(III) or Tb(III)) cryptate or chelate to tether it on the surface of a gallium binding entity. Alternatively, or in addition, Tamra (Tb) or Cy5 (Eu) or others may be used as acceptors on an enzyme substrate. Alternatively, or in addition, the lanthanide may be tethered onto the enzyme substrate, and the acceptor onto the gallium binding entity (essentially reversing some of the embodiments described above). The acceptor in this case could be APC (tethered by non-specific interaction) APC is a superior acceptor to Cy5, although nonspecific interaction may not be a good tether mechanism for a general assay principle. Alternatively, or in addition, assays may involve non-lanthanide donors, such as quantum dots (Q-dots), or standard fluorophore pairs, such as fluorescein and TAMRA, although such donors and donor/acceptor pairs may make it more difficult or impossible to reduce background using time-resolved FRET (as possible with lanthanide compounds and other long-lifetime donors).

Example 38

This example describes further selected aspects and embodiments of the present teachings, including experimental setups, results, and related discussion, as set forth in the Appendix of U.S. Provisional Patent Application Ser. No. 60/615,308, filed Sep. 30, 2004, which is incorporated herein by reference.

Example 39

This example describes exemplary lanthanide chelates, suitable for use as members of a resonance energy transfer pair, in accordance with aspects of the present teachings. The chelates optionally may include a reactive group, a member of a specific binding pair, and so on, to facilitate interaction with a substrate, product, binding partner, and/or other reaction component. Here, the chelates include a phosphate group, to facilitate interaction with suitable metals associated with a binding partner. The chelates may function to stabilize the Tb(III) and shield it from deactivation by water. The chelates may include antenna portions, which act as light collecting devices to relay the energy to the Tb(III) core, improving luminescence. Tb and other lanthanides have long fluorescence lifetimes (300 μsec-1 msec) relative to "standard" luminophores such as FAM and TAMRA (nsec). By introducing delay (50 msec) between excitation and measurement of emission, non-FRET acceptor fluorescence and background sample autofluorescence may be reduced or avoided.

The exemplary chelates may be characterized schematically, for example, using three general formulae:

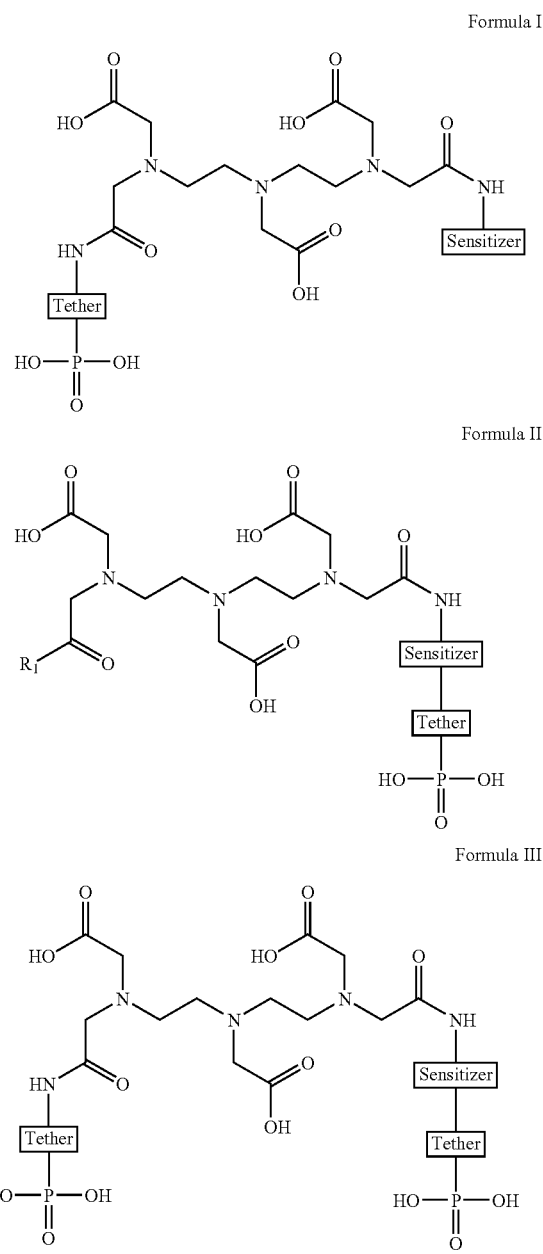

The "sensitizer" generally comprises any structure capable of and/or adapted to enhance light absorption, including but not limited to heterocyclic aromatic compounds, such as 2- or 4-quinolones, 2- or 4-coumarins, phenones, quinolines, and merocyanines, among others. These structures may be selected from the following groups, among others:

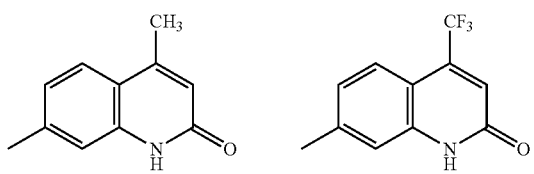

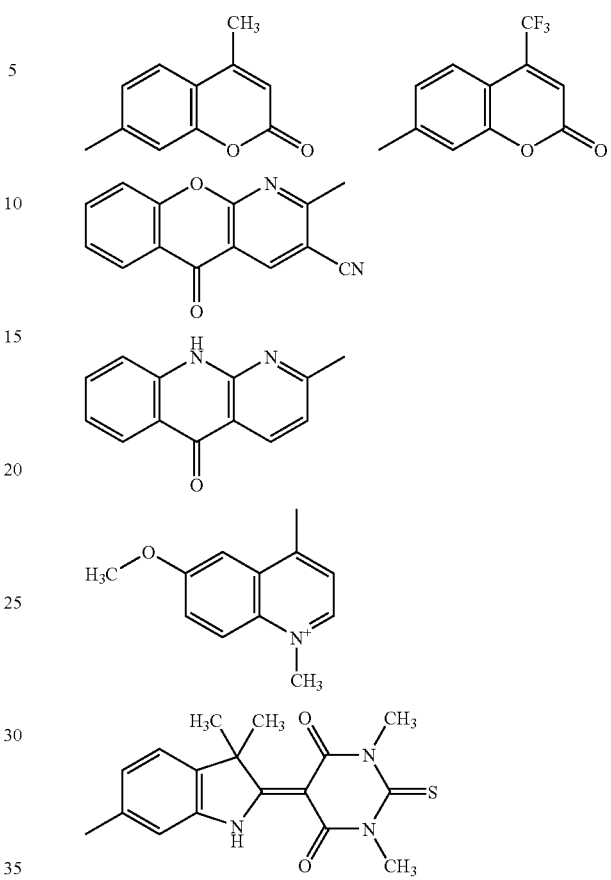

The "tether" generally comprises any structure capable of and/or adapted to join portions of the chelate, including but not limited to $-(CH_2)_nO-$, $-(CH_2)_nPhO-$, $-(CH_2)_nPh(CH_2)_mO-$, carboxyalkoxy, and alkenoxy, among others. Here, n and m are independently 1-12, $R_1$ is independently H or alkyl, and Ph is a phenyl group.

The exemplary chelates may be synthesized via any suitable mechanism, for example, by introducing a phosphate group onto the skeleton of a lanthanide chelate. Thus, in a representative synthetic pathway, the carbostyril 124 residue of cs124-DTPA (diethylene triamine pentaacetate) may be modified, as shown:

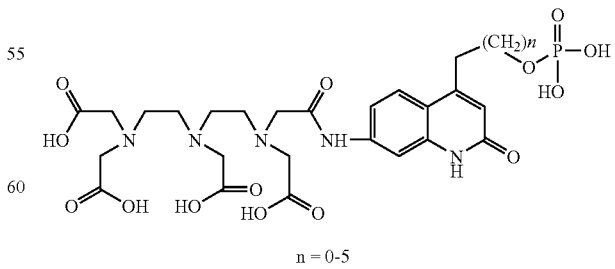

A phosphate group may be introduced onto another portion of cs24-DTPA, via an appropriate linkage.

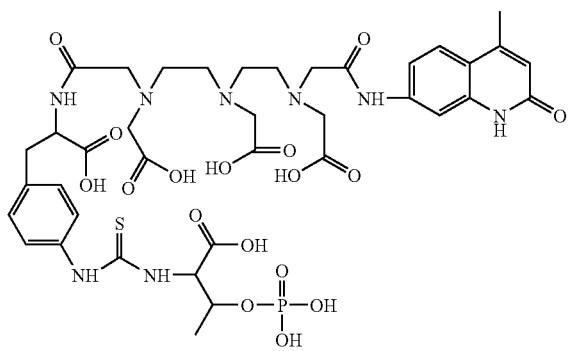

A laser dye, such as merocyanine, may be used as a sensitizer.

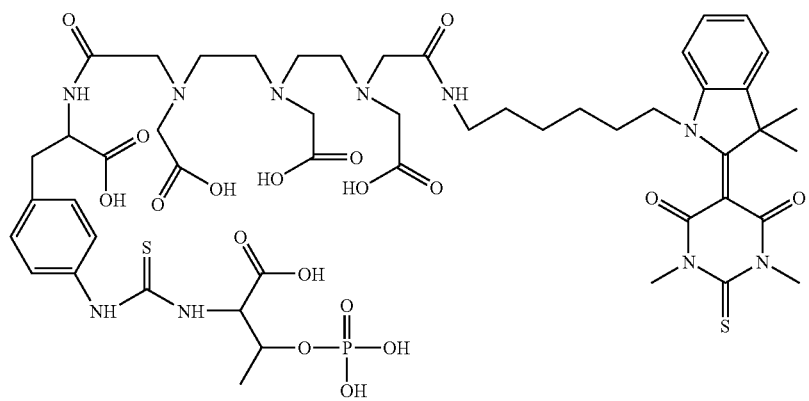

Finally, a linkage may be introduced onto a skeleton of DPTA.

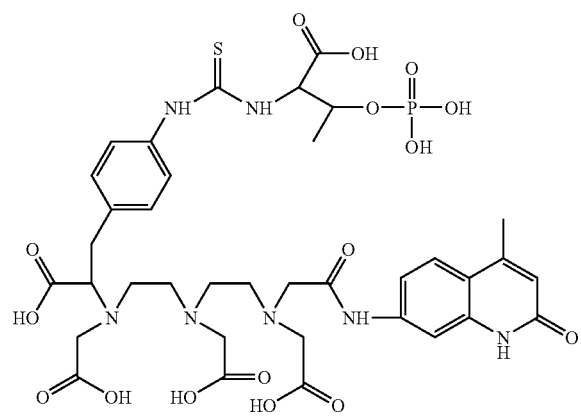

Example 40

This example describes additional exemplary lanthanide chelates, suitable for use as members of a resonance energy transfer pair, in accordance with aspects of the present teachings.

The luminescent lanthanide chelate may be characterized by a number of parameters, including extinction coefficient, quantum yield, and luminescence lifetime. Extinction coefficient is a wavelength-dependent measure of the absorbing power of a luminophore. Quantum yield is a ratio of the number of photons emitted to the number of photons absorbed by a luminophore. Luminescence lifetime is the average time between absorption and re-emission of light by a luminophore. Lanthanide luminescence is typically exceptional for its long luminescence lifetimes, which often are in the microsecond to millisecond range.

Luminescent lanthanide complexes generally include a luminescent trivalent lanthanide atom and an organic chelator bound to the trivalent lanthanide. The organic chelator may be used to fine-tune the spectral properties of the lanthanide and to permit the lanthanide to participate in specific interactions with biological molecules. The chelator may effectively increase the extinction coefficient of the lanthanide by acting as an "antenna" or "sensitizer" that can absorb light and transfer the associated energy to the lanthanide ion. The chelator also may increase the quantum yield of the lanthanide by decreasing luminescence quenching by the solvent.

The spectral properties of photoluminescence may be characterized by excitation spectrum, emission spectrum, and/or Stokes' shift, among others. An excitation spectrum is the dependence of emission intensity upon the excitation wavelength, measured at a single constant emission wavelength. An emission spectrum is the wavelength distribution of the emission, measured after excitation with a single constant excitation wavelength. A Stokes' shift is the difference in wavelengths between the maximum of the emission spectrum and the maximum of the absorption spectrum.

Luminescence-based methods or assays may be influenced by the parameters discussed above—extinction coefficient, quantum yield, luminescence lifetime, excitation and emission spectra, and/or Stokes' shift, among others—and may involve characterizing luminescence intensity (e.g., FLINT), luminescence polarization or anisotropy (e.g., FP), luminescence resonance energy transfer (e.g., FRET), luminescence lifetime (e.g., FLT), total internal reflection luminescence (e.g., TIRF), luminescence correlation spectroscopy (e.g., FCS), and/or luminescence recovery after photobleaching (e.g., FRAP or FPR), among others.

Luminescence methods have several significant potential strengths. For example, luminescence methods may be very sensitive, because modern detectors, such as photomultiplier tubes (PMTs) and charge-coupled devices (CCDs), can detect very low levels of light. In addition, luminescence methods may be very selective, because the luminescence signal may come almost exclusively from the luminophore.

The present teachings provide systems, including compositions, kits, and methods, particularly for photoluminescence applications. The compositions and kits may include organic chelators, luminescent lanthanide complexes that incorporate those chelators for use in certain photoluminescence assays, and/or precursors and derivatives of these chelators and complexes, among others. The methods may involve detecting light emitted by the complex, and using properties of that light to understand properties of the complex and its environment. Thus, in this aspect, the compositions may act as reporter molecules, for example, to report on the activity of an enzyme and/or a modulator, such as an agonist or antagonist, of the enzyme.

The organic chelator may be a derivative of a polyazamacrocyclic chelating group. For example, the organic chelator may be a derivative of a 1,4,7,10-tetraazacyclododecane ring system, for example, having the formula:

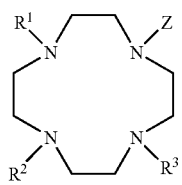

The tetraazacyclododecane chelator may be substituted. For example, the chelator may be substituted at the 1-, 4-, and 7-positions by substituents $R^1$, $R^2$, and $R^3$. The chelator further may be substituted at the 10-position by a sensitizer Z. The sensitizer, as discussed in the Introduction, may act as an antenna that increases luminescence by capturing and transferring light energy to an associated lanthanide. The sensitizer typically comprises a polyheterocyclic ring system.

Substituents $R^1$, $R^2$, and $R^3$, which may be the same or different, may be hydrogen, or may be a substituent selected to facilitate the binding of a lanthanide ion within the tetraazacyclododecane ring. Substituents $R^1$, $R^2$, and $R^3$ typically incorporate functional groups that help complex the selected lanthanide. For example, the $R^1$, $R^2$, and $R^3$ substituents may incorporate substituents that themselves incorporate a carbonyl group, such as a carboxylic acid, ester, or amide. Alternatively or in addition, the $R^1$, $R^2$, and $R^3$ substituents may incorporate a phosphonate moiety.

The $R^1$, $R^2$, and $R^3$ substituents are typically acetic acid derivatives, which may be substituted or unsubstituted, as shown below:

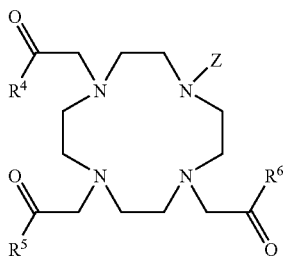

Here, the $R^4$, $R^5$, and $R^6$ substituents may be independently hydroxy, alkyl groups having 1-6 carbons, alkoxy groups having 1-6 carbons, or amine groups, each of which optionally may be further substituted by additional aliphatic groups, aromatic groups, amide groups, and/or heteroatom-substituted aliphatic groups.

The sensitizer Z may comprise a polycyclic heteroaromatic ring system that is bound to the tetraazacyclododecane ring via a covalent linkage. The heteroaromatic ring system may include 2-6 fused aromatic rings, having 1-6 heteroatoms. In some aspects of the chelator, the sensitizer has the formula

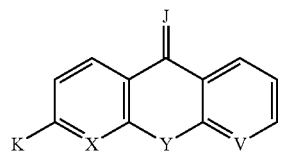

where K is a covalent linkage to the tetraazacyclododecane, and X, Y, V, and J are carbon or a heteroatom that is nitrogen, oxygen, sulfur, or selenium. The sensitizer optionally may be further substituted at one or more positions by additional substituents, such as alkyl, alkoxy, halogen, carboxylic acid, sulfonic acid, and/or phosphonate, among others. Typically, the linkage K is an alkyl linkage, and more typically K is a methylene group. In one particular aspect of the chelator, X is nitrogen, V is an aromatic carbon, and both J and Y are oxygen. Particularly preferred sensitizers have the formula

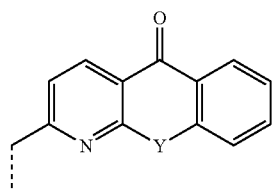

where Y is oxygen, sulfur, or selenium

The chelator typically forms a complex with a lanthanide ion so that at least the nitrogen atoms of the tetraazacyclododecane macrocycle bind to the lanthanide ion. Typically one or more of substituents $R^1$, $R^2$, and $R^3$ also may coordinate with the lanthanide ion, as may a heteroatom present in the sensitizer Z. Where the resulting lanthanide ion is not fully complexed, the remaining coordination sites may be occupied by a solvent molecule, such as water, or by one or more additional ligands that may be strongly coordinated to the lanthanide ion, or may be subject to ligand exchange when the complex is in solution.

The complexed lanthanide ion may be selected from cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), and lutetium (Lu). Typically, the lanthanide ion is terbium, europium, dysprosium, or samarium. More typically, the lanthanide is terbium.

In a particularly preferred embodiment, the lanthanide complex (including chelator, sensitizer, and lanthanide) has the formula

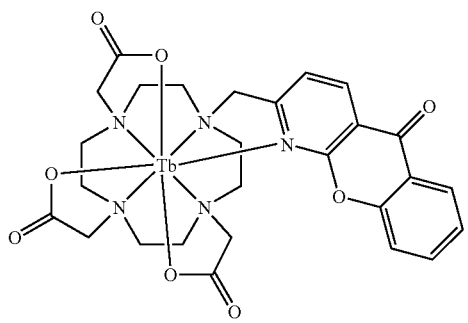

The chelator optionally may be further substituted by one or more reactive functional groups ($R_X$), or conjugated substances ($S_C$), each of which is bound to the chelator via a covalent linking moiety L. The reactive functional group or conjugated substance may be a substituent on the polyazamacrocycle itself, a substituent on $R^1$, $R^2$, or $R^3$, or a substituent on the sensitizer Z. Where the lanthanide complex is substituted by a reactive functional group, it is typically a substituent on the sensitizer moiety.

The covalent linking moiety L is optionally a single covalent bond, such that either the reactive functional group $R_X$ or the conjugated substance $S_C$ is bound directly to the organic chelator. Alternatively, L may incorporate a series of nonhydrogen atoms that form a stable covalent linkage between the reactive functional group or conjugated substance and the chelator. Typically, L may incorporate 1-20 nonhydrogen atoms in a stable conformation. Stable atom conformations include, without limitation, carbon-carbon bonds, amide linkages, ester linkages, sulfonamide linkages, ether linkages, thioether linkages, and/or other covalent bonds. Preferred covalent linkages may include single bonds, carboxamides, sulfonamides, ethers, and carbon-carbon bonds, or a combination thereof.

The reactive functional group $R_X$ may include any functional group that exhibits appropriate reactivity to be conjugated with a desired substance. The choice the reactive group typically depends on the functional groups present on the substance to be conjugated. Typically, functional groups present on such substances include, but are not limited to, alcohols, aldehydes, amines, carboxylic acids, halogens, ketones, phenols, phosphates, and thiols, or a combination thereof. Suitable $R_X$ groups include activated esters of carboxylic acids, aldehydes, alkyl halides, amines, anhydrides, aryl halides, carboxylic acids, haloacetamides, halotriazines, hydrazines (including hydrazides), isocyanates, isothiocyanates, maleimides, phosphoramidites, sulfonyl halides, and thiol groups, or a combination thereof. Typically, $R_X$ is an activated ester of a carboxylic acid, an amine, a haloacetamide, a hydrazine, an isothiocyanate, or a maleimide group. In one aspect of the lanthanide complex, $R_X$ is a succinimidyl ester of a carboxylic acid.

The organic chelators that are substituted with a reactive functional group may be used to prepare a variety of conjugates. The conjugated substance may be a member of a specific binding pair. Alternatively, the conjugated substance may be a molecular carrier. The conjugated substance may include a biomolecule that is an amino acid, a peptide, a protein, a nucleoside, a nucleotide, an oligonucleotide, a nucleic acid polymer, or a carbohydrate. The conjugated substance may include a polar moiety, or a masked polar moiety, or the conjugated substance may include a solid or semi-solid matrix. The conjugated substance may include one or more additional dyes or luminophores.

The conjugated substance Sc may be a naturally occurring or a synthetically modified substance, particularly where it is an amino acid, a peptide, a protein, a nucleoside, a nucleotide, an oligonucleotide, a nucleic acid polymer, or a carbohydrate. For example, the conjugated substance may be a polypeptide or other substance that is naturally or artificially substituted by one or more phosphate functional groups. In this example, the conjugated substance may be substituted by phosphate prior to conjugation with the organic chelator, or the selected conjugated substance may first be conjugated to the organic chelator, and subsequently phosphorylated, for example, by enzymatic phosphorylation.

The conjugated substance $S_C$ also may be a member of a specific binding pair or a molecular carrier. Specific binding pair members typically specifically bind to and are complementary with the complementary member of the specific binding pair. Conjugated members of a specific binding pair can be used to localize compounds of the present teachings to the complementary member of that specific binding pair. Representative specific binding pairs are listed in Table 11.

TABLE 11

| Representative specific binding pair members | |
|---|---|
| antibody | antigen |
| avidin (streptavidin) | biotin |
| DNA | aDNA |
| enzyme | enzyme substrate |
| lectin | carbohydrate |
| receptor | ligand |
| RNA | aRNA |

The conjugated substance $S_C$ may be a biological or artificial polymer, particularly where it is a carrier. Biological polymers include proteins, carbohydrates, and nucleic acid polymers. Artificial polymers include polyethylene glycols and polymeric microparticles composed of polystyrene, latex, or other polymeric material. Preferably, a conjugated carrier is a carbohydrate that is a dextran, or amino-substituted dextran, or a polymer microparticle. The conjugated carrier may be selected so that conjugation of the lanthanide complex to the carrier detectably alters one or more luminescence properties of the complex. In particular, the carrier may be selected so that conjugation of the lanthanide complex to the carrier alters the fluorescence intensity or polarization of the lanthanide complex.

The conjugated substance Sc may be a metal or glass surface, and may be, for example, the sides or bottom of a microwell, or a slide, or the surface of a chip, particularly where the conjugated substance is a solid or semi-solid matrix. The compound of the present teachings is optionally covalently bound to a fiber optic probe, where the probe is composed of glass or functionalized glass (e.g., aminopropyl glass), or the compound is attached to the fiber optic probe via an intermediate polymer, such as polyacrylamide. Incorporation of the compounds of the present teachings on such surfaces permit the remote sensing of sample pH values.

The conjugated substance Sc may include or comprise a dye or luminophore. In such cases, the dye or luminophore may be selected so that energy-transfer occurs between the lanthanide complex and the conjugated dye or luminophore, where the lanthanide complex is optionally the luminescence donor, or the luminescence acceptor.

Example 41

This example describes, without limitation, exemplary prenyl transfer assays, in accordance with aspects of the present teachings. Prenyl transfer activity may include addition (prenylation) or removal (deprenylation) of prenyl groups, such as farnesyl or geranylgeranyl groups, among others. The prenyl groups may be added to (or removed from) any suitable molecules, such as polypeptides, among others, in prenyl transfer assays. In some examples, the prenyl transfer assays may include an acceptor substrate, a donor substrate, a sample, and an association partner. The acceptor substrate may be configured to receive a prenyl group from the donor substrate, to produce a product by action of a prenyl transfer activity, such as a transferase enzyme, in the sample. The association partner may associate selectively with the product relative to at least one of the substrates, or with at least one of the substrates relative to the product. Furthermore, the product, one or more of the substrates, and/or the association partner may include a luminescent label. Accordingly, the extent of selective association with the association partner, and thus the amount of prenyl transfer activity, may be measured in a luminescence assay, such an assay detecting luminescence polarization, luminescence energy transfer, and/or luminescence intensity, among others. In some examples, candidate modulators of prenyl transfer activity may be screened for their ability to affect (e.g., inhibit) prenyl transfer activity. The systems of the present teachings may provide more rapid, sensitive, safe, and/or effective approaches to detecting prenyl transfer activity. These systems thus may be useful in a variety of applications, including, without limitation, life science research, drug research, accelerated drug discovery, assay development, and/or high-throughput screening. Further aspects of prenyl transfer assays are described in U.S. patent application Ser. No. 10/957,332, filed Sep. 30, 2004, which is incorporated herein by reference.

Example 42

This example describes, without limitation, exemplary polypeptide modification assays, in accordance with aspects of the present teachings. These assays may be used for detecting molecular modifications of molecules such as polypeptides, among others, and the presence and/or activity of enzymes and/or other agents involved in facilitating or otherwise regulating such modifications. The molecular modifications may include the cleavage or degradation of molecules such as polypeptides, among others. However, the molecular modifications also may include splicing of two molecules, such as by protein ligases, including ubiquitin-protein conjugations (or ubiquitination), among others. The present teaching may include a method of detecting modification of a polypeptide in a sample, where the method includes contacting the sample with a binding partner that binds specifically to one of the modified and nonmodified forms of the polypeptide, but not both, the binding partner including a metal required for specific binding to the one form; and detecting a response indicative of the extent of binding between the binding partner and the one form. The assays may include luminescence assays, such as luminescence polarization, luminescence resonance energy transfer, and/or luminescence intensity, among others. The assays provided by the present teaching may be useful in a variety of applications, including without limitation life science research, drug research, accelerated drug discovery, assay development, and high-throughput screening. Further aspects of lipid assays are described in U.S. Patent Application Ser. No. 60/554,766, filed Mar. 19, 2004, which is incorporated herein by reference.

Example 43

This example describes, without limitation, exemplary lipid modification assays, in accordance with aspects of the present teachings. These assays may be used for detecting molecular modifications, such as phosphorylation, dephosphorylation, and/or cleavage, among others, of lipids, lipid fragments, and/or lipid precursors. These assays also may be used to detect the presence and/or activity of enzymes and/or other agents, such as drugs, involved in facilitating, inhibiting, or otherwise regulating such lipid modifications. The molecular modifications may include structural changes in lipids, lipid fragments, and/or lipid precursors, such as phosphate addition and/or removal, among others. Alternatively, or in addition, the molecular modifications may include cleavage of a lipid into lipid fragments, such as by a lipase enzyme, and/or joining of two lipid precursors, such as by a lipid ligase enzyme, among others. The present teachings may include a method of detecting modification of a lipid (and/or lipid fragment and/or lipid precursor) in a sample, where the method includes contacting the sample with a binding partner that binds specifically to one of the modified and nonmodified forms of the lipid (and/or fragment and/or precursor), but not both, the binding partner including a metal required for specific binding to the one form; and detecting a response indicative of the extent of binding between the binding partner and the one form. The assays may include luminescence assays, such as luminescence polarization, luminescence resonance energy transfer, and/or luminescence intensity, among others. The assays provided by the present teachings may be useful in a variety of applications, including, without limitation, life science research, drug research, accelerated drug discovery, assay development, and high-throughput screening. Further aspects of lipid assays are described in U.S. patent application Ser. No. 11/146,553, filed Jun. 6, 2005, which is incorporated herein by reference.

Example 44

This example describes selected aspects and embodiments of the present teachings, as a first series of ordered paragraphs.

1. A method of detecting the activity of an enzyme that operates on an enzyme substrate to form an enzyme product in a sample, comprising:

contacting the substrate or product with a binding partner that specifically binds to the substrate or to the product but not to both, where the binding partner includes a metal that is involved in binding between the binding partner and the substrate or product;

contacting the substrate with the enzyme;

exposing the sample to light capable of inducing luminescence from the sample; and measuring a detectable luminescence energy transfer response, without separating the bound substrate or product from the unbound substrate or product, where the detectable luminescence energy transfer response is indicative of the extent of binding between the substrate or product and the binding partner; and correlating the luminescence energy transfer response with the activity of the enzyme.

2. A method of detecting phosphorylation or nonphosphorylation of a polypeptide in a sample, comprising:

contacting the polypeptide with a binding partner that specifically binds to the phosphorylated polypeptide or to the nonphosphorylated polypeptide but not to both, where the binding partner includes a metal that is required for binding between the binding partner and the phosphorylated polypeptide or nonphosphorylated polypeptide;

exposing the sample to light capable of inducing luminescence from the sample; and measuring a detectable luminescence energy transfer, where the luminescence energy transfer is indicative of the extent of binding between the polypeptide and the binding partner without separating the bound polypeptide from the unbound polypeptide; and correlating the luminescence energy transfer with the extent of phosphorylation or nonphosphorylation of the polypeptide, or with the activity of an enzyme that affects phosphorylation or nonphosphorylation of the polypeptide.

3. A method of detecting cyclization or noncyclization of a nucleotide in a sample, comprising:

contacting a nonradioactive nucleotide with a binding partner that specifically binds to a cyclized nucleotide or to a noncyclized nucleotide but not to both, substantially without regard to the nucleoside portion of the nucleotide, where the binding partner includes a metal that is required for binding between the binding partner and the cyclized nucleotide or noncyclized nucleotide;

exposing the sample to capable of inducing luminescence from the sample; and measuring a detectable luminescence energy transfer, where the luminescence energy transfer is indicative of the extent of binding between the nucleotide and the binding partner; and correlating the response with the extent of cyclization or noncyclization of the nucleotide, or with the activity of an enzyme that affects cyclization or noncyclization of the nucleotide.

4. The method of one of paragraphs 1, 2, or 3, where the metal is a tricationic metal ion.

5. The method of paragraphs 1, 2, or 3, where the metal is selected from the group consisting of aluminum, iron, gallium, europium, and terbium.

6 The method of paragraph 5, where the metal is Ga(ill).

7. The method of one of paragraphs 1, 2, or 3, where the binding partner further includes a dicationic metal ion.

8. The method of paragraph 2, where at least one of the phosphorylated polypeptide, nonphosphorylated polypeptide, and the polypeptide is luminescent.

9. The method of paragraph 3, where at least one of the cyclized nucleotide, noncyclized nucleotide, and the nucleotide is luminescent.

10. The method of one of paragraphs 1, 2, or 3 where measuring the detectable luminescence energy transfer response includes measuring luminescence intensity.

11. The method of one of paragraphs 1, 2, or 3, where the detectable luminescence energy transfer is detectable luminescence resonance energy transfer.

12. The method of paragraph 1, where at least one of the substrate and/or product, and the binding partner includes an energy transfer donor, and at least the other of the substrate and/or product, and the binding partner includes an energy transfer acceptor, such that luminescence energy transfer can occur between the donor and the acceptor.

13. The method of paragraph 2, where the binding partner includes a luminescent energy transfer donor, and at least one of the phosphorylated polypeptide, nonphosphorylated polypeptide, and polypeptide, is an energy transfer acceptor, such that luminescence energy transfer can occur between the energy transfer donor and the energy transfer acceptor.

14. The method of paragraph 3 where the binding partner includes a luminescent energy transfer donor, and at least one other of the cyclized nucleotide, noncyclized nucleotide, and nucleotide includes an energy transfer acceptor, such that luminescence energy transfer can occur between the energy transfer donor and the energy transfer acceptor.

15. The method of one of paragraphs 12, 13, and 14, where the binding partner includes an energy transfer donor.

16. The method of paragraph 12, where the binding partner includes an energy transfer donor or acceptor, and that energy transfer donor or acceptor includes the metal that is involved in binding between the binding partner and the substrate or product.

17. The method of paragraph 15, the energy transfer donor having a luminescence lifetime, where the luminescence lifetime is at least about 400 nanoseconds.

18. The method of paragraph 15, where the energy transfer donor comprises a lanthanide.

19. The method of one of paragraphs 12, 13, and 14 where the energy transfer donor is a luminescent lanthanide chelate.

20. The method of one of paragraphs 12, 13, and 14 where the energy transfer donor is a luminescent metal-ligand complex donor.

21. The method of paragraph 20 where the metal-ligand complex is a ruthenium complex, an osmium complex, a rhenium complex, a platinum complex, or an iridium complex.

22. The method of one of paragraphs 12, 13, and 14 where the energy transfer acceptor is a xanthene, a phenoxazine, a phthalocyanine, a cyanine, a porphyrin, a polyazaindacene, or a phycobiliprotein.

23. The method of paragraph 19, where the lanthanide chelate includes an organic chelator and a sensitizer moiety.

24. The method of paragraph 19, where the lanthanide chelate is associated with the binding partner via a metal-binding functional group that binds to the metal.

25. The method of paragraph 24, where the metal-binding functional group is a phosphate, sulfonic acid, or carboxylic acid functional group.

26. The method of paragraph 24, where the metal-binding functional group is a phosphate functional group.

27. The method of paragraph 24, where the metal-binding functional group is bound to the lanthanide chelate via a covalent linkage.

28. The method of paragraph 27, where the metal-binding functional group is bound to the sensitizer portion of the lanthanide chelate.

29. The method of paragraph 27, where the metal-binding functional group is bound to the organic chelate portion of the lanthanide chelate.

30. The method of paragraph 19, where the organic chelator has the structural formula of Formula I, Formula II, or Formula III Formula I

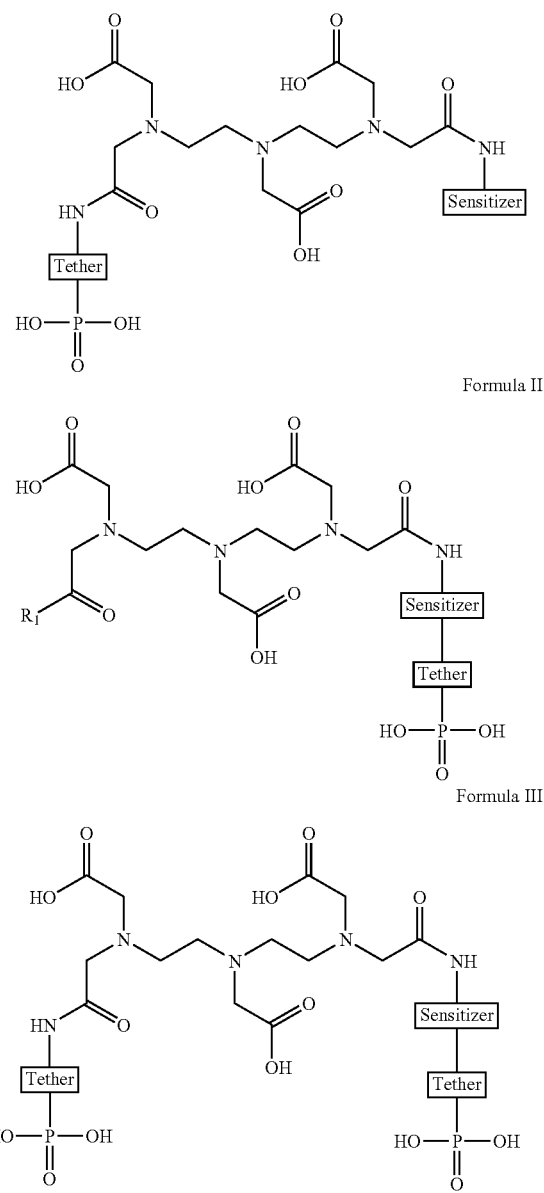

Formula II

Formula III where the sensitizer moiety is a heterocyclic polyaromatic ring structure; and where the tether moiety is a covalent linkage.

31. The method of paragraph 19, where the organic chelator has the formula

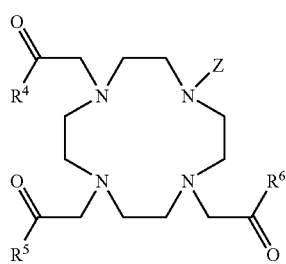

where the $R^4$, $R^5$, and $R^6$ substituents are independently hydroxy, alkyl groups having 1-6 carbons, alkoxy groups having 1-6 carbons, or amine groups, each of which is optionally further substituted by additional aliphatic groups, aromatic groups, amide groups, and heteroatom-substituted aliphatic groups;

Z is a sensitizer moiety that is a polycyclic heteroaromatic ring system that is bound via a covalent linkage;

the lanthanide chelate is substituted by a metal-binding functional group; and the lanthanide chelate is optionally substituted by one or more reactive functional groups or conjugated substances.

32. The method of paragraph 31, where Z is a sensitizer moiety having the formula

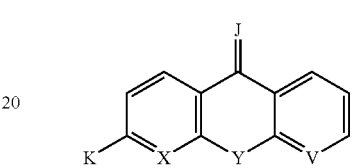

where K is the covalent linkage;

where X, Y, V, and J are carbon or a heteroatom that is nitrogen, oxygen, sulfur, or selenium; and where the sensitizer is optionally further substituted at one or more positions by alkyl, alkoxy, halogen, or a metal-binding functional group.

33. The method of paragraph 19, where the lanthanide chelate includes a complexed lanthanide ion that is selected from cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), and lutetium (Lu).

34. The method of paragraph 19, where the lanthanide chelate includes a complexed lanthanide ion that is selected from terbium, europium, dysprosium, or samarium.

35. The method of paragraph 34, where the lanthanide ion is terbium.

36. The method of paragraph 19, where the lanthanide chelate has the formula

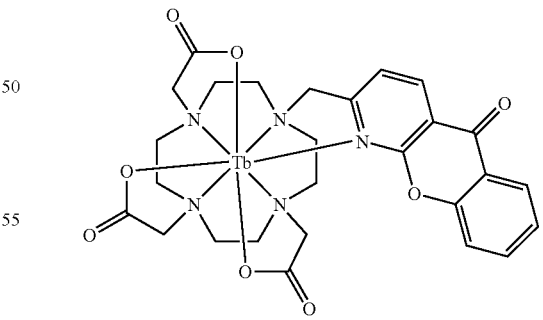

where the lanthanide chelate is associated with the binding partner via a metal-binding functional group, and is optionally further substituted by one or more reactive functional groups or conjugated substances.

37. The method of paragraph 1, where the substrate is a polypeptide, and where the substrate and product are related by a posttranslational modification.

38. The method of paragraph 37, where the posttranslational modification is phosphorylation or dephosphorylation of the polypeptide.

39. The method of paragraph 37, where the posttranslational modification is proteolysis or ligation of the polypeptide.

40. The method of paragraph 37, where the posttranslational modification is prenylation of the polypeptide.

41. The method of paragraph 1, where the substrate is a nucleotide, and where the substrate and product are related by a cyclization or decyclization of the nucleotide.

42. The method of paragraph 1, where the substrate is a lipid, lipid precursor or lipid fragment.

43. The method of paragraph 1, where the enzyme is selected from the group consisting of kinases and phosphatases.

44. The method of paragraph 1, where the enzyme is selected from the group consisting of cyclases and phosphodiesterases.

45. The method of paragraph 1, where the enzyme is selected from the group consisting of proteases and protein ligases.

46. The method of paragraph 1, where the enzyme is selected from the group consisting of prenyl transferases and prenyl detransferases.

47. The method of paragraph 1, where the enzyme is selected from the group of lipases and lipid ligases.

48. The method of paragraph 1, where the substrate includes a phosphorylated polypeptide or a nonphosphorylated polypeptide.

49. The method of paragraph 1, where the substrate includes a cyclized nucleotide or a noncyclized nucleotide.

50. The method of paragraph 1, further comprising:
contacting the substrate and enzyme with a candidate compound; and
determining the ability of the candidate compound to enhance or inhibit enzyme activity by its effects on the response.

51. The method of paragraph 2, where the polypeptide includes fewer than about 50 amino acids.

52. The method of paragraph 2, where the binding partner binds to the phosphorylated polypeptide.

53. The method of paragraph 2, where the binding partner is not a polypeptide.

54. The method of paragraph 2, where the enzyme catalyzes addition or cleavage of a phosphate group to or from a protein, further comprising contacting the polypeptide with the enzyme prior to the steps of contacting, measuring, and correlating.

55. The method of paragraph 2, where the enzyme is a kinase.

56. The method of paragraph 2, where the enzyme is a phosphatase.

57. The method of paragraph 2, further comprising:
contacting the polypeptide and enzyme with a candidate compound; and
determining the ability of the candidate compound to enhance or inhibit phosphorylation or dephosphorylation of the polypeptide by its effects on the response.

58. The method of paragraph 3, where the nucleotide includes an adenine or a guanine.

59. The method of paragraph 3, where the binding partner binds to the cyclized nucleotide.

60. The method of paragraph 3, where the binding partner is not a polypeptide.

61. The method of paragraph 3, where the enzyme catalyzes cyclization or decyclization of a nucleotide, further comprising contacting the nucleotide with the enzyme.

62. The method of paragraph 3, where the enzyme is a phosphodiesterase.

63. The method of paragraph 3, where the enzyme is a cyclase.

64. The method of paragraph 3, further comprising:
contacting the nucleotide and enzyme with a candidate compound; and
determining the ability of the candidate compound to enhance or inhibit cyclization or decyclization of the nucleotide by its effects on the response.

65. The method of paragraph 3, where the step of detecting a response is performed without separating the bound nucleotide from the unbound nucleotide.

66. The method of paragraph 3, further comprising washing the sample to remove any nucleotide not bound to the binding partner prior to the step of measuring the detectable luminescence response.

67. The method of one of paragraphs 1, 2, or 3 further comprising:
providing a sample holder having a plurality of sample sites supporting a corresponding plurality of samples; and
repeating the steps of contacting, detecting, and correlating for the plurality of samples.

68. A method of detecting a phosphorylated form or a nonphosphorylated form of a polypeptide in a sample, comprising: (A) contacting the sample with a binding partner that binds specifically to one of the phosphorylated and nonphosphorylated forms of the polypeptide, but not both, the binding partner including a metal involved in the specific binding to the one form; and (B) exposing the sample to a condition capable of inducing luminescence from the sample; and (C) measuring a detectable luminescence response, where the detectable luminescence response is luminescence energy transfer, and the detectable luminescence response is indicative of the extent of binding between the binding partner and the one form.

69. A method of detecting a cyclized or noncyclized form of a nucleotide in a sample, comprising:
contacting the nucleotide with a binding partner that specifically binds to one of a cyclized form and a noncyclized form of the nucleotide, but not both, the binding partner including a metal required for specific binding of the binding partner to the one form of the nucleotide; and
exposing the nucleotide to a condition capable of producing luminescence, and
detecting a luminescence energy transfer produced by the step of exposing;
where the luminescence energy transfer is indicative of the extent of binding between the one form of the nucleotide and the binding partner.

70. A method of detecting a cyclized or noncyclized form of a nucleotide in a sample, comprising:
contacting the nucleotide with a binding partner that specifically binds to one of a cyclized form and a noncyclized form of the nucleotide, but not both, substantially without regard to the base portion the nucleotide; and
exposing the nucleotide to a condition capable of producing luminescence, and
detecting a luminescence energy transfer produced by the step of exposing;
where the luminescence energy transfer is indicative of the extent of binding between the one form of the nucleotide and the binding partner.

71. The method of one of paragraphs 69 and 70, further comprising a step of contacting the nucleotide with at least one enzyme selected from cyclases and phosphodiesterases.

72. The method of paragraph 71, wherein the step of contacting the nucleotide with at least one enzyme is performed before the step of contacting the nucleotide with a binding partner.

73. The method of paragraph 71, further comprising (1) a step of contacting the at least one enzyme with a candidate compound; and (2) a step of determining the ability of the candidate compound to enhance or inhibit enzyme activity by its effect on the response.

74. The method of paragraph 71, further comprising a step of correlating the response with a cyclization or decyclization activity of the at least one enzyme on the nucleotide.

75. The method of one of paragraphs 69 and 70, where the step of contacting includes (1) a step of placing a metal salt in a liquid, the metal salt including the metal, and (2) a step of contacting the nucleotide with the metal salt after the step of placing.

76. The method of one of paragraphs 69 and 70, where the step of contacting includes a step of contacting the nucleotide with one or more metals selected from the group consisting of aluminum, gallium, and iron ions, and wherein the one or more metals are required for specific binding of the binding partner to the one form of the nucleotide.

77. The method of one of paragraphs 69 and 70, wherein the step of contacting includes a step of contacting the nucleotide with one or more metal ions selected from the group consisting of europium, strontium, terbium, and zirconium ions, and wherein the one or more metals are required for specific binding of the binding partner to the one form of the nucleotide.

78. The method of one of paragraphs 69 and 70, wherein the step of contacting includes a step of contacting with gallium, the gallium being required for specific binding of the binding partner to the one form of the nucleotide.

79. The method of one of paragraphs 69 and 70, wherein the steps of contacting and detecting are performed a plurality of times for a plurality of samples disposed in different wells of a microplate.

80. The method of one of paragraphs 69 and 70, further comprising a step of associating the metal with a distinct solid support that does not include the metal.

81. The method of one of paragraphs 69 and 70, wherein the step of detecting is performed after the step of contacting without separation of bound and unbound species of the nucleotide.

82. The method of one of paragraphs 69 and 70, wherein the steps of contacting and detecting are performed a plurality of times for a plurality of samples disposed in different wells of a microplate.

83. The method of one of paragraphs 69 and 70, wherein the nucleotide is luminescent.

84. A kit for performing the method of paragraph 62, comprising:
a cyclized or noncyclized form of a nucleotide; and
a binding partner that specifically binds to one of the cyclized form and the noncyclized form of the nucleotide, but not both, wherein the binding partner includes a metal required for specific binding of the binding partner to the one form of the nucleotide.

85. The kit of paragraph 84, further comprising an enzyme capable of converting the cyclized form of the nucleotide into the noncyclized form, or vice versa.

86. The kit of paragraph 84, wherein the kit includes a luminescently labeled, cyclized form of the nucleotide and a binding partner that specifically binds to the noncyclized form of the nucleotide.

87. The kit of paragraph 86, further comprising a phosphodiesterase enzyme.

88. The kit of paragraph 84, wherein the kit includes a luminescently labeled, noncyclized form of the nucleotide and a binding partner that specifically binds to the noncyclized form of the nucleotide.

89. The kit of paragraph 88, further comprising a cyclase enzyme.

90. A kit for performing the method of paragraph 70, comprising:
a cyclized or noncyclized form of a nucleotide; and
a binding partner that specifically binds to one of the cyclized form and the noncyclized form of the nucleotide, but not both, substantially without regard to the base portion the nucleotide.

91. A method of detecting the activity of a cyclase or a phosphodiesterase that operates on a nucleotide substrate to form a nucleotide product in a sample, comprising:
contacting the nucleotide substrate with a binding partner that specifically binds to the nucleotide substrate or to the nucleotide product but not to both, where the binding partner includes a metal required for binding between the binding partner and the nucleotide substrate or product;
contacting the nucleotide substrate with at least one of a cyclase and a phosphodiesterase;
detecting a response indicative of the extent of binding between the nucleotide substrate or product and the binding partner without separating bound and unbound fractions of such nucleotide substrate or product; and
correlating the response with the activity of the enzyme.

92. A method of detecting, in a sample, a first analyte or a second analyte related to the first analyte by a molecular modification, comprising:
contacting the sample with a metal that forms a covalent coordination complex with one of the first and second analytes, but not both; and
detecting a response indicative of the extent of binding between metal and the one analyte without separating bound and unbound species of the one analyte produced by the step of contacting.

93. A method of detecting, in a sample, a first analyte or a second analyte related to the first analyte by a molecular modification, comprising:
contacting the sample with gallium, the gallium specifically binding to one of the first and second analytes, but not both; and
detecting a response indicative of the extent of binding between the gallium and the one analyte.

The following claims particularly point out certain combinations and subcombinations regarded as novel and nonobvious and directed to one of the inventions. These claims may refer to "an" element or "a first" element or the equivalent thereof; such claims should be understood to include incorporation of one or more such elements, neither requiring nor excluding two or more such elements. Inventions embodied in other combinations and subcombinations of features, functions, elements, and/or properties may be claimed through amendment of the present claims or through presentation of new claims in this or a related application. Such claims, whether directed to a different invention or to the same invention, and whether broader, narrower, equal, or different in scope to the original claims, also are regarded as included within the subject matter of the inventions of the present disclosure.

We claim:

1. A method of detecting the activity of an enzyme that catalyzes formation of a product from a substrate, the method comprising:

contacting the substrate with the enzyme and with a binding partner to form a sample mixture, the binding partner binding selectively either to the substrate relative to the product or to the product relative to the substrate, the binding partner including at least one metal that is required for selective binding of the binding partner to the substrate or to the product via at least one phosphate moiety of the substrate or product, where the substrate and/or product includes an energy transfer donor and the binding partner includes an energy transfer acceptor, or the substrate and/or product includes an energy transfer acceptor and the binding partner includes an energy transfer donor, such that luminescence energy transfer can occur between the donor and the acceptor when the binding partner binds to the substrate or the product, where the enzyme is selected from the group consisting of kinases, phosphatases, nucleotide cyclases, and nucleotide phosphodiesterases, where the binding partner includes a lanthanide chelate and the metal, where the lanthanide chelate includes an organic chelator and a lanthanide, and where the organic chelator includes at least one metal-binding functional group that associates the lanthanide chelate with the metal;

exposing the sample mixture to light capable of inducing luminescence from the energy transfer donor;

measuring a detectable luminescence energy transfer response from the sample mixture, without separating the bound substrate or product from the unbound substrate or product, where the detectable luminescence energy transfer response is indicative of the extent of binding between the substrate or product and the binding partner; and correlating the response with the activity of the enzyme.

2. The method of claim 1, where the metal is selected from the group consisting of aluminum, iron, gallium, europium, and terbium.

3. The method of claim 2, where the metal is Ga(III).

4. The method of claim 2, where the metal is Fe(III).

5. The method of claim 1, where measuring the detectable luminescence energy transfer response includes measuring luminescence intensity.

6. The method of claim 1, where the energy transfer acceptor is luminescent.

7. The method of claim 1, where the energy transfer acceptor is a quencher.

8. The method of claim 1, where the binding partner includes the energy transfer donor.

9. The method of claim 1, the energy transfer donor having a luminescence lifetime, where the luminescence lifetime is at least about 400 nanoseconds.

10. The method of claim 1, where the energy transfer donor comprises the lanthanide chelate.

11. The method of claim 1, where the metal-binding functional group is a phosphate, sulfonic acid, or carboxylic acid functional group.

12. The method of claim 11, where the metal-binding functional group is a phosphate functional group.

13. The method of claim 1, where the organic chelator includes a sensitizer moiety.

14. The method of claim 13, where the organic chelator has the formula

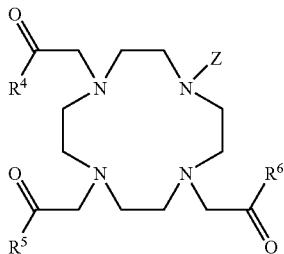

where the $R^4$, $R^5$, and $R^6$ substituents are independently hydroxy, alkyl groups having 1-6 carbons, alkoxy groups having 1-6 carbons, or amine groups, each of which is optionally further substituted by additional aliphatic groups, aromatic groups, amide groups, and heteroatom-substituted aliphatic groups;

where Z is a sensitizer moiety that is a polycyclic heteroaromatic ring system that is bound via a covalent linkage;

where the organic chelator is substituted by the metal-binding functional group; and where the organic chelator is optionally substituted by one or more reactive functional groups or conjugated substances.

15. The method of claim 14, where Z is a sensitizer moiety having the formula

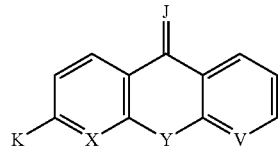

where K is the covalent linkage;

where X, Y, V, and J are carbon or a heteroatom that is nitrogen, oxygen, sulfur, or selenium; and where the sensitizer is optionally further substituted at one or more positions by alkyl, alkoxy, halogen, or a metal-binding functional group.

16. The method of claim 10, where the energy transfer donor includes a complexed lanthanide ion that is selected from terbium, europium, dysprosium, or samarium.

17. The method of claim 1, where the substrate is a polypeptide, and where the substrate and product are related by phosphorylation or dephosphorylation of the polypeptide.

18. The method of claim 1, further comprising:
   contacting the substrate and enzyme with a candidate compound; and
   determining the ability of the candidate compound to enhance or inhibit enzyme activity by its effects on the response.

19. The method of claim 1, further comprising:
   providing a sample holder having a plurality of sample sites supporting a corresponding plurality of sample mixtures; and
   repeating the steps of contacting, exposing, measuring, and correlating for the plurality of sample mixtures.

* * * * *